US012577548B2

(12) United States Patent
Cascao-Pereira et al.

(10) Patent No.: US 12,577,548 B2
(45) Date of Patent: Mar. 17, 2026

(54) ALPHA-AMYLASE COMBINATORIAL VARIANTS

(71) Applicant: DANISCO US INC, Palo Alto, CA (US)

(72) Inventors: Luis G. Cascao-Pereira, Redwood City, CA (US); Dina Finan, Pleasanton, CA (US); David Edward Wildes, San Francisco, CA (US); Pieter Augustinus, Palo Alto, CA (US); Roel Hermant, Palo Alto, CA (US); Monica Ocha Ruiz, Palo Alto, CA (US); Dewy Van Tol, Palo Alto, CA (US); Richard R Bott, Kirkland, WA (US); Marc Kolkman, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 541 days.

(21) Appl. No.: 17/901,168

(22) Filed: Sep. 1, 2022

(65) Prior Publication Data

US 2023/0348879 A1     Nov. 2, 2023

Related U.S. Application Data

(63) Continuation of application No. 16/292,057, filed on Mar. 4, 2019, now abandoned, which is a continuation of application No. 14/775,595, filed as application No. PCT/US2014/023458 on Mar. 11, 2014, now abandoned.

(60) Provisional application No. 61/907,131, filed on Nov. 21, 2013, provisional application No. 61/906,617, filed on Nov. 20, 2013, provisional application No. 61/776,699, filed on Mar. 11, 2013.

(51) Int. Cl.
| | |
|---|---|
| *C12N 15/52* | (2006.01) |
| *A23L 2/38* | (2021.01) |
| *C11D 3/386* | (2006.01) |
| *C12N 9/26* | (2006.01) |
| *C12N 9/28* | (2006.01) |
| *C12P 19/02* | (2006.01) |
| *C12P 19/14* | (2006.01) |

(52) U.S. Cl.
CPC ............ *C12N 9/2414* (2013.01); *A23L 2/382* (2013.01); *C11D 3/386* (2013.01); *C11D 3/38681* (2013.01); *C12N 9/2417* (2013.01); *C12P 19/02* (2013.01); *C12P 19/14* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,989,169 | A | 11/1999 | Svendsen |
| 8,084,240 | B2 | 12/2011 | Cuevas et al. |
| 8,252,573 | B2 | 8/2012 | Svendsen et al. |
| 9,040,278 | B2 | 5/2015 | Carcao-Pereira |
| 2001/0039253 | A1 | 11/2001 | Borchert et al. |
| 2005/0049165 | A1 | 3/2005 | Kottwitz |
| 2007/0190632 | A1 | 8/2007 | Bessler |
| 2007/0212768 | A1 | 9/2007 | Bessler |
| 2010/0021587 | A1 | 1/2010 | Chang et al. |
| 2011/0212876 | A1 | 9/2011 | Meek |
| 2012/0045817 | A1 | 2/2012 | Edward |
| 2012/0172275 | A1* | 7/2012 | Jones ............ C12Y 302/01001 510/109 |
| 2012/0258497 | A1 | 10/2012 | Andersen et al. |
| 2012/0270267 | A1 | 10/2012 | Anderson |
| 2013/0000055 | A1 | 1/2013 | Jackson |
| 2014/0141489 | A1 | 5/2014 | Kaasgaard |
| 2014/0287477 | A1 | 9/2014 | Carcao-Pereira |
| 2017/0037387 | A1 | 2/2017 | Cascao-Pereira et al. |
| 2019/0330610 | A1* | 10/2019 | Babe .............. C12Y 304/21062 |

FOREIGN PATENT DOCUMENTS

| | | | |
|---|---|---|---|
| CN | 102603917 | A | 7/2012 |
| CN | 101679960 | B | 1/2013 |
| CN | 101848986 | B | 12/2014 |
| EP | 1414977 | B1 | 1/2008 |
| EP | 1794293 | B1 | 9/2010 |
| EP | 2428572 | A2 | 3/2012 |
| RU | 2010122896 | A | 12/2011 |
| WO | 9414951 | A1 | 7/1994 |
| WO | 1995010603 | A1 | 4/1995 |
| WO | 1999023211 | A1 | 5/1995 |
| WO | 1995026397 | A1 | 10/1995 |
| WO | 1996023873 | A1 | 8/1996 |
| WO | 1996023874 | A1 | 8/1996 |
| WO | 1997041213 | A1 | 11/1997 |
| WO | 1999019467 | A1 | 4/1999 |
| WO | 2000029560 | A1 | 5/2000 |

(Continued)

OTHER PUBLICATIONS

UniProt Accession No. P00693, 2013.

(Continued)

*Primary Examiner* — Tekchand Saidha

(57) ABSTRACT

Disclosed are compositions and methods relating to variant alpha-amylases. The variant alpha-amylases are useful, for example, for starch liquefaction and saccharification, for cleaning starchy stains in laundry, dishwashing, and other applications, for textile processing (e.g., desizing), in animal feed for improving digestibility, and for baking and brewing.

21 Claims, 31 Drawing Sheets

Specification includes a Sequence Listing.

(56) References Cited

FOREIGN PATENT DOCUMENTS

| WO | 0060058 | A2 | 10/2000 |
|---|---|---|---|
| WO | 2000060059 | A2 | 10/2000 |
| WO | 2000060060 | A2 | 10/2000 |
| WO | 2001066712 | A2 | 9/2001 |
| WO | 2002010355 | A2 | 2/2002 |
| WO | 0231124 | A2 | 4/2002 |
| WO | 2002092797 | A2 | 11/2002 |
| WO | 2006002643 | A2 | 1/2006 |
| WO | 2008153805 | A2 | 12/2008 |
| WO | 2009061379 | A2 | 5/2009 |
| WO | 2009061380 | A2 | 5/2009 |
| WO | 2010115021 | A2 | 10/2010 |
| WO | 2011098531 | A1 | 8/2011 |
| WO | 2011100410 | A2 | 8/2011 |
| WO | 2013057141 | A2 | 4/2013 |
| WO | 2013057143 | A2 | 4/2013 |
| WO | 2013063460 | A2 | 5/2013 |
| WO | 2014099523 | A1 | 6/2014 |

OTHER PUBLICATIONS

UniProt Accession No. 10BPOU4, 2012.

UniProt Accession No. E014J1, Nov. 2, 2010.

Suzuki et al., "Amino Acid Residues Stabilizing a Bacillus alpha-Amylase against Irreversible Thermoinactivation," J. Biol. Chem., 1989, vol. 264, p. 18933-18938.

Sumitami et al., "New type of starch-binding domain: the direct repeat motif in the C-terminal region of Bacillus sp. no. 195 alpha-amylase contributes to starch binding and raw starch degrading," Biochem. J. 2000, vol. 350, pp. 477-484.

Shiau et al., "Improving the Termostability of Raw-Starch-Digesting Amylase from a Cytophago sp. by Site-Directed Mutagenesis," Applied and Environmental Microbiology, 2003, vol. 69, pp. 2383-2385.

Reddy et al., "An overview of the Microbial Alpha-Amylase Family," African Journal of Biotechnology, 2003, vol. 2, No. 12, pp. 645-648, Academic Press, US.

PCT International Search Report and the Written Opinion of the International Searching Authority for International Application No. PCT/US2014/023590, Stoyanov, Borislav, Examiner, ISA/EPO; Sep. 16, 2014.

PCT International Search Report and the Written Opinion of the International Searching Authority for International Application No. PCT/US2014/023515, Stoyanov, Borislav, Examiner, ISA/EPO; Aug. 20, 2014.

PCT International Search Report and the Written Opinion of the International Searching Authority for International Application No. PCT/US2014/023458, Stoyanov, Borislav, Examiner, ISA/EPO; Sep. 3 2014.

PCT International Preliminary Report on Patentability for International Application No. PCT/US2014/023590; Moon, Kiwan, Authorized Officer; WIPO; Sep. 15, 2015.

PCT International Preliminary Report on Patentability for International Application No. PCT/US2014/023515; Becamel, Philippe, Authorized Officer, WIPO; Sep. 15, 2015.

PCT International Preliminary Report on Patentability for International Application No. PCT/US2014/023458; Mohri, Mineko, Authorized Officer, WIPO; Sep. 15, 2015.

PCT International Preliminary Report on Patentability for International Application No. PCT/US2014/065522, Linder, Nora, Authorized Officer, ISA/EP; May 24, 2016.

PCT International Search Report and the Written Opinion of the International Searching Authority for International Application No. PCT/US2014/065522; Stoyanov, Borislav, Examiner, ISA/EP; Mar. 5, 2015.

Liu et al., "Improved heterologous gene expression in Trichoderma reesei by cellobiohydrolase I gene (cbh1) promoter optimization," Acta Biochim. Biophys. Sin., 2008, vol. 40, No. 2, pp. 158-165.

Jeang et al., "Cloning of a Gene Encoding Raw-Starch-Digesting Amylase from a Cytophaga sp. and Its Expression in Escherichia coli," Applied and Environmental Microbiology, 2002, vol. 68, pp. 3651-3654.

Holm et al., Random mutagenesis used to probe structure and function of Bacillus stearothermophilus alpha-amylase, Protein Eng., 1990, 3, 181-91.

Girard, "Molecular cloning of cDNAs encoding a range of digestive enzymes from a phytophagous beetle," Insect Biochemistry and Molecular Biology, 1999, vol. 29, No. 12, pp. 1129-1142.

Collison, "Starch Retrogradation," In Starch and Its Derivatives, Fourth Edition, 1968, Radley, J.A., (Ed.), Chapman and Hall Ltd., London, pp. 194-201.

Christophersen et al., "Enzymatic Characterisation of Novamyl, a Thermostable alpha-Amylase," Starch, 1998, vol. 50, pp. 39-45.

Branden et al. Introduction to Protein Structure, Garland Publishing Inc., New York, p. 247, 1991.

* cited by examiner

CLUSTAL 2.0.10 multiple sequence alignment

```
CspAmy2    --AATNGTMMQYFEWYVPNDGQQWNRLRTDAPYLSSVGITAVWTPPAYKGTSQADVGYGP
PcuAmy1    ---ADNGTIMQYFEWYLPNDGAHWNRLNNDAQNLKNVGITAVWIPPAYKGGSSADVGYGV
BASE       NTAPINETMMQYFEWDLPNDGTLWTKVKNEAANLSSLGITALWLPPAYKGTSQSDVGYGV
           . * *:****** :****  *.::..:*  *..:****:* ***** *.:*****

CspAmy2    YDLYDLGEFNQKGTVRTKYGTKGELKSAVNTLHSNGIQVYGDVVMNHKAGADYTENVTAV
PcuAmy1    YDTYDLGEFNQKGTVRTKYGTKSELISAVNNLHAKGIAVYGDVVLNHRMNADATELVDAV
BASE       YDLYDLGEFNQKGTIRTKYGTKTQYIQAIQAAKAAGMQVYADVVFNHKAGADGTEFVDAV
           ** **********:******* ; .*:: :: *: **.***:**; .** ** * **

CspAmy2    EVNPSNRNQETSGEYNIQAWTGFNFPGRGTTYSNFKWQWFHFDGTDWDQSRSLSRIFKFR
PcuAmy1    EVDPNNRNVETTSTYQIQAWTQYDFPGRGNTYSSFKWRWYHFDGVDWDQSRGLNRIYKLR
BASE       EVDPSNRNQETSGTYQIQAWTKFDFPGRGNTYSSFKWRWYHFDGTDWDESRKLNRIYKFR
           **:*.*** **;. *:***** ;:*****.***.***:*;****.***:** *.**;*:*

CspAmy2    GTGKAWDWEVSSENGNYDYLMYADIDYDHPDVVNEMKKWGVWYANEVGLDGYRLDAVKHI
PcuAmy1    GDGKDWDWEVDSEYGNYDYLMGADLDFNHPDVVNETKTWGKWFVNTVNLDGVRLDAVKHI
BASE       STGKAWDWEVDTENGNYDYLMFADLDMDHPEVVTELKNWGTWYVNTTNIDGFRLDAVKHI
           . ** *****.:* ******* **:* ;**;**.* *.** *;.* ..:** *******

CspAmy2    KFSFLKDWVDNARAATGKEMFTVGEYWQNDLGALNNYLAKVNYNQSLFDAPLHYNFYAAS
PcuAmy1    KFDFMRDWVNNVRSTTGKNLFAVGEYWHYDVNKLNSYITKTNGTMSLFDVPLHFRFYDAS
BASE       KYSFFPDWLTYVRNQTGKNLFAVGEFWSYDVNKLHNYITKTNGSMSLFDAPLHNNFYTAS
           *:.*; **:  .* ***;:*:***;*  *;. *;.*;;*.*  , ****.*** .** **

CspAmy2    TGGGYYDMRNILNNTLVASNPTKAVTLVENHDTQPGQSLESTVQPWFKPLAYAFILTRSG
PcuAmy1    NGGGGYDMRNLLNNTLMSSNPMKAVTFVENHDTQPTQALQSTVQSWFKPLAYATILTREQ
BASE       KSSGYFDMRYLLNNTLMKDQPSLAVTLVDNHDTQPGQSLQSWVEPWFKPLAYAFILTRQE
           ...* ;*** ;*****; .;* ***;*;****** *;*;* *;.******** ****.

CspAmy2    GYPSVFYGDMYGTKGTTTREIPALKSKIEPLLKARKDYAYGTQRDYIDNPDVIGWTREGD
PcuAmy1    GYPCVFYGDYYGT---SDGKISSYKPIMDKLLNARKVYAYGTQRDYFDHPDIVGWTREGD
BASE       GYPCVFYGDYYGI---PKYNIPGLKSKIDPLLIARRDYAYGTQRDYIDHQDIIGWTREGI
           ***.***** **    . ;*.. *. ;; ** **; *********;*; *;:******

CspAmy2    STKAKSGLATVITDGPGGSKRMYVGTSNAGEIWYDLTGNRTDKITIGSDGYATFPVNGGS
PcuAmy1    AAHAGSGLATLITDGPGGSKWMYVGTSKAGQVWTDKTGNRSGTVTIDANGWGNFWVNGGS
BASE       DTKPNSGLAALITDGPGGSKWMYVGKKHAGKVFYDLTGNRSDTVTINADGWGEFKVNGGS
           ::. ****:;********* ****.,;**;;: * ****:..;**.;;*;. * *****

CspAmy2    VSVWVQQ-   (SEQ ID NO: 1)
PcuAmy1    VSVWAK--   (SEQ ID NO: 3)
BASE       VSIWVAKK   (SEQ ID NO: 5)
           **;*.
```

*FIG. 1*

| | pH 4.5 (65°C) | | pH 5.0 (70°C) | | pH 5.7 (85°C) | |
|---|---|---|---|---|---|---|
| Variant | Half-life (Min) | PI | Half-life (Min) | PI | Half-life (Min) | PI |
| C16A | 28.3 | 11.3 | 95.0 | 7.9 | 45.9 | 3.4 |
| C16B | 15.2 | 3.2 | 29.6 | 4.5 | 27.9 | 4.0 |
| C16C | 31.3 | 12.5 | 104.3 | 8.6 | 52.4 | 3.9 |
| C16D | 20.0 | 4.2 | 36.5 | 5.5 | 34.6 | 4.9 |
| C16E | 42.1 | 16.8 | 132.7 | 11.0 | 67.2 | 4.9 |
| C16F | 26.4 | 5.5 | 54.1 | 8.2 | 46.8 | 6.7 |
| C16G | 28.6 | 11.4 | 102.7 | 8.5 | 47.0 | 3.5 |
| C16H | 21.7 | 4.5 | 39.3 | 6.0 | 34.2 | 4.9 |
| C16I | 37.7 | 15.1 | 124.0 | 10.2 | 57.5 | 4.2 |
| C16J | 28.4 | 5.9 | 56.2 | 8.5 | 44.4 | 6.3 |
| S241Q | 4.8 | 1.0 | 6.6 | 1.0 | 7.0 | 1.0 |
| E187P | 2.5 | 1.0 | 12.1 | 1.0 | 13.6 | 1.0 |

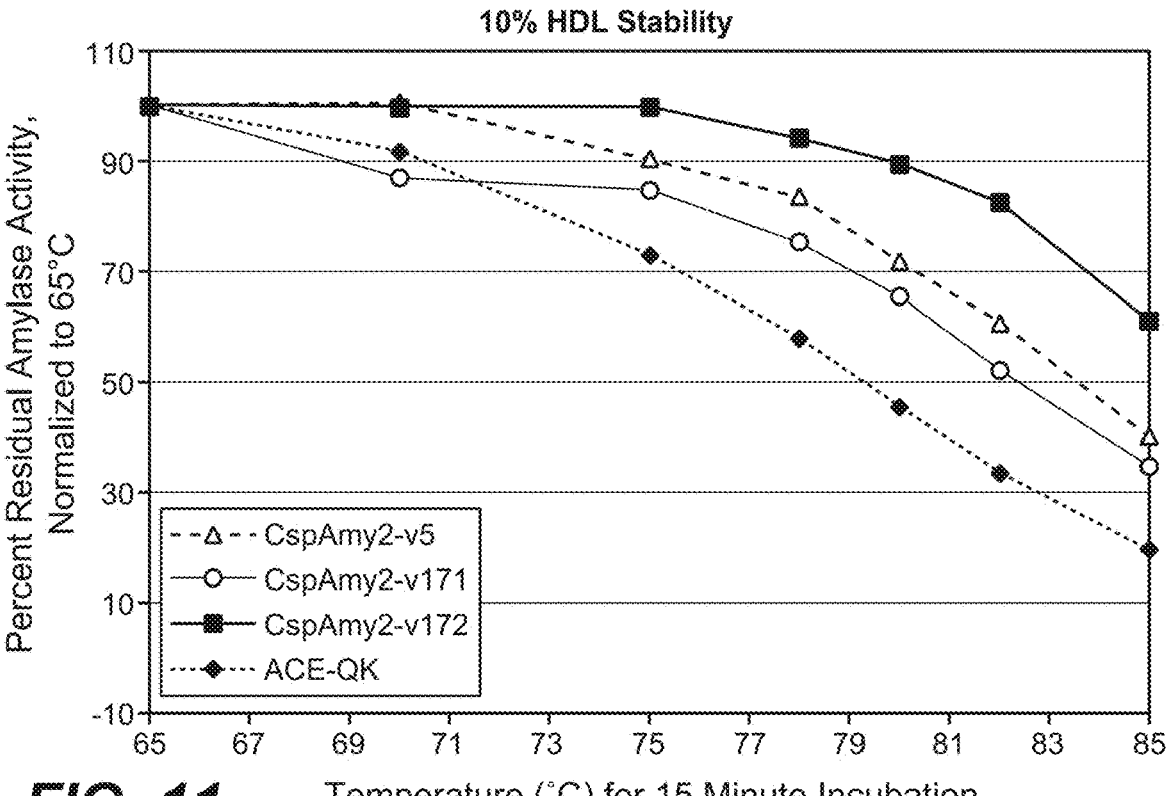
FIG. 11          Temperature (°C) for 15 Minute Incubation
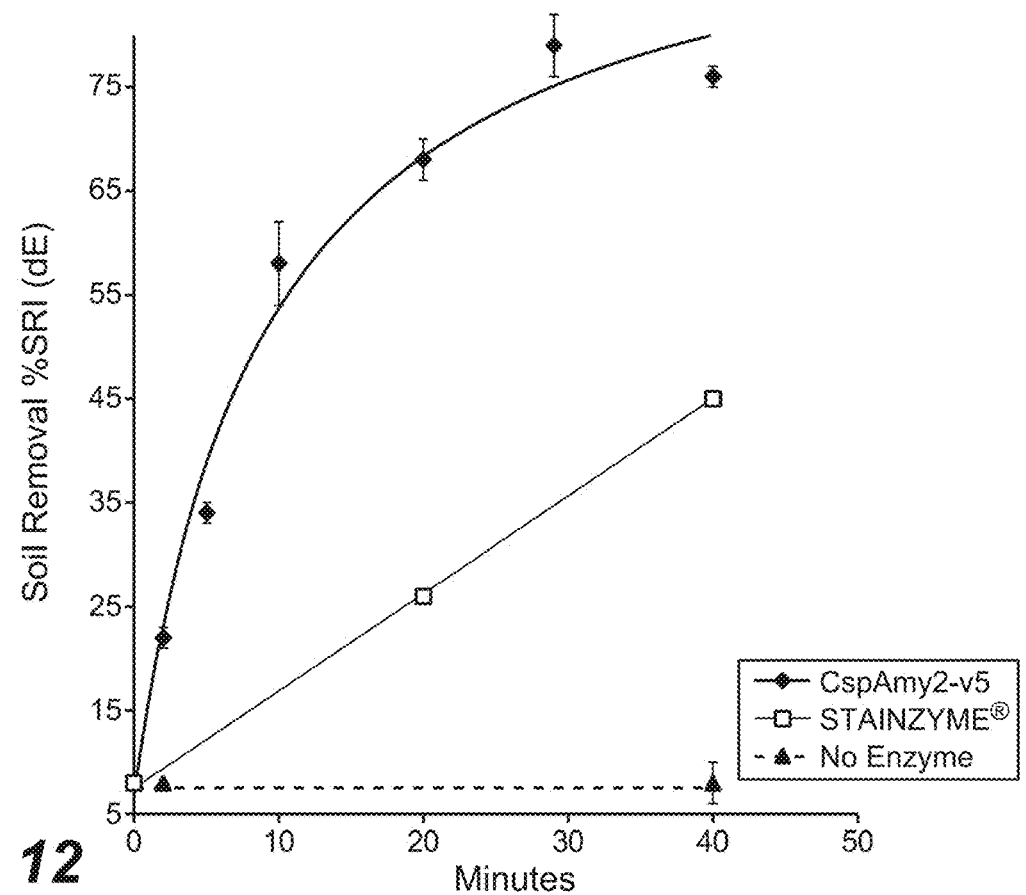
FIG. 12          Minutes

Phosphate-Free Detergent
IEC-60436 WFK Type B (pH=10.4 in 3g/l)

| COMPONENT | WT % | PROPERTIES |
|---|---|---|
| Sodium citrate dihydrate | 30.0 | Builder |
| Maleic Acid/ Acrylic Acid Copolymer Sodium Salt (SOKALAN® CP5; BASF) | 12.0 | Builder |
| Sodium perborate monohydrate | 5.0 | Builder |
| TAED | 2.0 | Bleaching (Source of Active Oxygen) |
| Sodium disilicate: Protil A (Cognis) | 25.0 | Bleaching |
| Linear fatty alcohol ethoxylate | 2.0 | |
| Sodium carbonate anhydrous | add to 100 | Buffering Agent |

*FIG. 13A*

Phosphate Detergent
IEC-60436 WFK Type C (pH=10.3 in 3g/l)

| COMPONENT | WT % | PROPERTIES |
|---|---|---|
| Sodium tripolyphosphate | 23 | Builder |
| Sodium citrate dehydrate | 22.3 | Builder |
| Maleic Acid/ Acrylic Acid Copolymer Sodium Salt | 4 | Builder |
| Sodium perborate monohydrate | 6 | Bleaching (Source of Active Oxygen) |
| TAED | 2 | Bleaching |
| Sodium disilicate: Protil A (Cognis) | 5 | Buffering Agent |

| G476 \ G477 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 1.66 | 2.47 | 1.55 | 1.64 | 1.51 | 1.31 | 1.31 | 1.61 | 1.46 | 1.79 | 1.64 | 1.61 |  |  | 1.3 | 1.68 | 1.73 | 1.61 | 1.56 |  |
| C | 2.24 | 1.91 | 1.62 | 1.58 | 1.93 | 1.87 | 1.71 | 2.2 | 1.64 | 1.74 | 2.43 | 1.7 |  |  | 1.39 | 1.67 | 2.22 | 2.21 | 2.04 | 1.95 |
| D | 1.56 | 3.1 | 1.71 |  | 1.76 |  | 1.51 | 1.76 | 1.56 | 1.6 | 1.75 | 1.65 |  | 1.65 | 1.5 | 1.61 | 1.54 | 1.78 | 1.71 | 1.52 |
| E | 1.6 | 2.39 | 1.65 | 1.51 | 1.58 | 1.55 | 1.49 |  | 1.52 |  | 1.58 | 1.53 |  |  | 1.43 | 1.48 | 1.62 | 1.68 | 1.54 |  |
| F |  | 2.4 | 1.96 | 1.66 | 1.52 | 1.77 | 1.36 |  |  |  | 1.86 | 1.59 |  |  |  | 1.76 | 1.78 | 2.19 | 1.62 | 1.52 |
| G |  | 2.69 | 1.54 | 1.54 | 1.62 | 1.01 | 1.3 | 1.49 |  |  | 1.5 | 1.49 | 2.19 | 1.44 | 1.32 | 1.6 | 1.55 |  | 1.63 |  |
| H |  |  | 1.54 | 1.48 |  | 1.35 | 1.24 |  | 0.97 |  | 1.53 | 1.29 |  | 1.28 | 1.24 |  | 1.43 | 1.57 |  | 1.7 |
| I | 1.72 | 1.98 | 1.7 | 1.67 | 2.08 | 1.72 |  | 2.32 | 1.53 |  | 1.97 | 1.48 |  | 1.83 | 1.55 | 1.59 | 1.81 |  | 2.05 | 1.15 |
| K |  |  | 1.56 | 1.48 |  |  | 1.05 | 1.67 | 1.12 | 1.52 | 1.5 | 1.45 |  |  | 1.02 | 1.42 | 1.58 | 1.42 | 1.1 | 1.15 |
| L | 1.61 | 2.31 |  | 1.84 | 2.18 | 1.54 | 1.47 |  | 1.32 | 1.78 | 1.6 | 1.55 |  | 1.68 | 1.84 | 1.82 | 1.87 | 1.88 |  |  |
| M | 1.77 | 1.93 | 1.55 |  | 1.86 | 1.55 | 1.37 |  |  | 1.84 | 1.76 | 1.68 |  | 1.48 | 1.39 | 1.62 | 1.66 | 2.0 | 1.48 | 1.61 |
| N | 1.58 |  |  |  | 1.52 | 1.4 |  |  | 1.39 | 1.55 | 1.46 | 1.7 |  | 1.55 | 1.39 | 1.64 | 1.51 |  | 1.31 | 1.55 |
| P | 1.5 |  | 1.49 | 1.58 | 1.73 | 1.33 | 1.34 | 1.68 | 1.35 | 1.79 | 1.74 | 1.55 |  | 1.55 | 1.35 | 1.59 | 1.55 | 1.77 | 1.67 | 1.39 |
| Q | 1.55 | 2.46 | 1.49 | 1.55 |  | 1.28 | 0.96 |  |  | 1.39 | 1.59 | 1.36 |  | 1.55 | 1.41 | 1.47 | 1.42 | 1.56 | 1.38 | 1.5 |
| R | 1.31 | 1.87 | 1.42 | 1.56 |  | 1.37 | 1.38 | 1.59 |  | 1.58 | 1.59 | 1.39 | 2.28 | 1.49 |  | 1.6 | 1.63 | 1.82 | 0.98 | 1.47 |
| S | 1.57 | 2.14 |  |  | 1.65 | 1.53 | 1.33 |  |  | 1.82 | 1.62 | 1.64 |  | 1.47 | 1.47 |  | 1.6 | 1.79 | 1.35 | 1.72 |
| T | 1.61 | 1.89 | 1.69 | 1.51 |  | 1.47 | 1.4 | 2.64 | 1.38 | 2.01 | 1.66 | 1.51 |  | 2.01 | 1.42 | 1.75 | 1.67 | 2.11 | 1.66 | 1.49 |
| V |  | 2.14 |  | 1.55 | 1.5 |  | 1.18 | 2.28 | 1.27 | 2.54 | 1.93 | 1.57 |  | 1.56 | 1.4 | 1.79 | 1.79 | 2.33 | 1.15 | 1.56 |
| W | 1.45 | 2.38 | 1.94 |  |  | 1.48 |  |  |  | 1.91 |  |  |  |  |  |  |  |  |  | 1.36 |
| Y |  | 2.67 | 1.6 | 1.62 |  |  | 1.29 | 2.04 | 1.75 |  | 1.61 | 1.63 |  | 1.47 | 1.6 | 1.61 | 1.65 | 1.69 | 1.36 |  |

FIG. 25

| | G477 A | G477 C | G477 D | G477 E | G477 F | G477 G | G477 H | G477 I | G477 K | G477 L | G477 M | G477 N | G477 P | G477 Q | G477 R | G477 S | G477 T | G477 V | G477 W | G477 Y |
|---|---|---|---|---|---|---|---|---|---|---|---|---|---|---|---|---|---|---|---|---|
| G476 A | 1.39 | 2.18 | 1.3 | 1.47 | 1.51 | 1.23 | 1.41 | 1.48 | 1.44 | 1.41 | 1.68 | 1.41 | | | 1.44 | 1.53 | 1.35 | 1.5 | 1.46 | |
| G476 C | 2.13 | 1.95 | 1.37 | 1.41 | 1.82 | 1.88 | 1.47 | 2.35 | 1.46 | 1.55 | 2.17 | 1.47 | | | 1.52 | 1.51 | 2.15 | 2.39 | 1.86 | 1.59 |
| G476 D | 1.42 | 3.43 | 1.28 | | 1.4 | | 1.54 | 1.51 | 1.43 | | 1.56 | 1.37 | | | 1.34 | 1.41 | 1.35 | 1.37 | 1.49 | 1.42 |
| G476 E | 1.33 | 2.48 | 1.37 | 1.26 | 1.52 | 1.37 | 1.3 | | 1.39 | 1.43 | 1.41 | 1.28 | | 1.3 | 1.42 | 1.37 | 1.33 | 1.54 | 1.39 | |
| G476 F | | 2.08 | 1.32 | 1.44 | 1.51 | 1.33 | 1.5 | | | | | 1.22 | | | | 1.61 | 1.42 | 1.55 | 1.71 | |
| G476 G | | 2.22 | 1.5 | 1.31 | 1.43 | 1.0 | 1.36 | | | | 1.39 | 1.38 | 1.55 | 1.34 | 1.6 | 1.32 | 1.47 | | 1.5 | 1.38 |
| G476 H | | 2.29 | 1.51 | 1.29 | | 1.35 | 1.27 | 1.31 | 1.45 | | 1.47 | 1.28 | | 1.26 | 1.77 | 1.14 | 1.49 | 1.45 | | |
| G476 I | 1.48 | | 1.4 | 1.43 | 1.74 | 1.42 | | 1.56 | 1.56 | | 1.69 | 1.45 | | 1.44 | 1.25 | 1.51 | 1.48 | | 1.87 | 1.53 |
| G476 K | | 2.12 | | 1.31 | | | 1.51 | 1.31 | 1.71 | 1.31 | 1.5 | 1.42 | | | 1.6 | 1.49 | 1.58 | 1.64 | 1.49 | 1.51 |
| G476 L | 1.29 | 2.19 | 1.28 | 1.47 | 1.79 | 1.33 | 1.64 | 1.31 | 1.23 | 1.6 | 1.37 | | | 1.47 | 1.76 | | 1.42 | 1.51 | | |
| G476 M | 1.47 | 1.94 | | | 1.76 | 1.51 | 1.43 | | | 1.43 | 1.41 | | | | | | 1.54 | 1.81 | 1.72 | 1.6 |
| G476 N | 1.43 | | | | 1.53 | 1.33 | | | 1.28 | 1.46 | | 1.3 | | 1.42 | 1.41 | | 1.26 | | 1.38 | 1.45 |
| G476 P | 1.54 | | | | | 1.19 | 1.49 | 1.6 | 1.41 | 1.57 | 1.59 | 1.51 | | 1.42 | 1.55 | 1.59 | 1.39 | | 1.34 | 1.45 |
| G476 Q | 1.37 | 2.1 | 1.32 | 1.4 | 1.38 | 1.23 | | | | 1.71 | 1.37 | 1.36 | | 1.3 | 1.36 | | 1.62 | 1.39 | 1.19 | 1.38 |
| G476 R | 1.34 | 2.02 | 1.43 | 1.37 | | 1.37 | 1.48 | | | | | 1.34 | | 1.37 | | 1.59 | 1.45 | 1.63 | 1.44 | 1.27 |
| G476 S | 1.33 | 2.24 | 1.42 | 1.4 | 1.38 | 1.23 | 1.33 | 1.48 | | 1.5 | 1.34 | | 1.55 | | 1.38 | 1.39 | 1.37 | 1.29 | 1.3 | 1.54 |
| G476 T | 1.34 | 1.93 | | 1.37 | 1.48 | | 1.39 | | | 1.33 | 1.47 | 1.37 | | 1.39 | 1.37 | | | 1.68 | | |
| G476 V | | 2.1 | 1.43 | 1.47 | | 1.38 | 1.28 | 1.61 | 1.46 | 1.57 | 1.38 | | | 1.61 | 1.58 | 1.53 | 1.31 | 1.69 | 1.61 | 1.66 |
| G476 W | 1.38 | 2.61 | 1.47 | 1.24 | 1.49 | 1.38 | 1.27 | 1.77 | 1.28 | 2.67 | 1.53 | 1.33 | | 1.47 | | 1.36 | 1.32 | 1.79 | 1.54 | 1.57 |
| G476 Y | | 2.09 | 1.34 | 1.33 | | 1.2 | 1.21 | 1.48 | 1.71 | 1.51 | | 1.43 | | 1.36 | 1.54 | 1.46 | 1.53 | 1.57 | 1.46 | 1.3 |

*FIG. 26*

SEQUENCE LISTING

```
Sequence total quantity: 50
SEQ ID NO: 1            moltype = AA  length = 485
FEATURE                 Location/Qualifiers
REGION                  1..485
                        note = Synthetic amino acid sequence of the mature form of
                        the CspAmy2 alpha-amylase polypeptide
source                  1..485
                        mol_type = protein
                        organism = synthetic construct
SEQUENCE: 1
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRNQETS GEYNIQAWTG FNFPGRGTTY SNFKWQWFHF DGTDWDQSRS LSRIFKFRGT  180
GKAWDWEVSS ENGNYDYLMY ADIDYDHPDV VNEMKKWGVW YANEVGLDGY RLDAVKHIKF  240
SFLKDWVDNA RAATGKEMFT VGEYWQNDLG ALNNYLAKVN YNQSLFDAPL HYNFYAASTG  300
GGYYDMRNIL NNTLVASNPT KAVTLVENHD TQPGQSLEST VQPWFKPLAY AFILTRSGGY  360
PSVFYGDMYG TKGTTTREIP ALKSKIEPLL KARKDYAYGT QRDYIDNPDV IGWTREGDST  420
KAKSGLATVI TDGPGGSKRM YVGTSNAGEI WYDLTGNRTD KITIGSDGYA TFPVNGGSVS  480
VWVQQ                                                              485

SEQ ID NO: 2            moltype = AA  length = 483
FEATURE                 Location/Qualifiers
REGION                  1..483
                        note = Synthetic amino acid sequence of the mature
                        CspAmy2-v1 a-amylase polypeptide
source                  1..483
                        mol_type = protein
                        organism = synthetic construct
SEQUENCE: 2
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRNQETS GEYNIQAWTG FNFPGRGTTY SNFKWQWFHF DGTDWDQSRS LSRIFKFTGK  180
AWDWEVSSEN GNYDYLMYAD IDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                                483

SEQ ID NO: 3            moltype = AA  length = 480
FEATURE                 Location/Qualifiers
REGION                  1..480
                        note = Synthetic amino acid sequence of the mature form of
                        the PcuAmy1 alpha-amylase polypeptide
source                  1..480
                        mol_type = protein
                        organism = synthetic construct
SEQUENCE: 3
ADNGTIMQYF EWYLPNDGAH WNRLNNDAQN LKNVGITAVW IPPAYKGGSS ADVGYGVYDT  60
YDLGEFNQKG TVRTKYGTKS ELISAVNNLH AKGIAVYGDV VLNHRMNADA TELVDAVEVD  120
PNNRNVETTS TYQIQAWTQY DFPGRGNTYS SFKWRWYHFD GVDWDQSRGL NRIYKLRGDG  180
KDWDWEVDSE YGNYDYLMGA DLDFNHPDVV NETKTWGKWF VNTVNLDGVR LDAVKHIKFD  240
FMRDWVNNVR STTGKNLFAV GEYWHYDVNK LNSYITKTNG TMSLFDVPLH FRFYDASNGG  300
GGYDMRNLLN NTLMSSNPMK AVTFVENHDT QPTQALQSTV QSWFKPLAYA TILTREQGYP  360
```

```
CVFYGDYYGT SDGKISSYKP IMDKLLNARK VYAYGTQRDY FDHPDIVGWT REGDAAHAGS  420
GLATLITDGP GGSKWMYVGT SKAGQVWTDK TGNRSGTVTI DANGWGNFWV NGGSVSVWAK  480

SEQ ID NO: 4              moltype = AA  length = 478
FEATURE                   Location/Qualifiers
REGION                    1..478
                          note = Synthetic amino acid sequence of a variant form of
                           PcuAmy1 alpha-amylase having a deletion of both R177 and
                           R178
source                    1..478
                          mol_type = protein
                          organism = synthetic construct
SEQUENCE: 4
ADNGTIMQYF EWYLPNDGAH WNRLNNDAQN LKNVGITAVW IPPAYKGGSS ADVGYGVYDT  60
YDLGEFNQKG TVRTKYGTKS ELISAVNNLH AKGIAVYGDV VLNHRMNADA TELVDAVEVD  120
PNNRNVETTS TYQIQAWTQY DFPGRGNTYS SFKWRWYHFD GVDWDQSRGL NRIYKLDGKD  180
WDWEVDSEYG NYDYLMGADL DFNHPDVVNE TKTWGKWFVN TVNLDGVRLD AVKHIKFDFM  240
RDWVNNVRST TGKNLFAVGE YWHYDVNKLN SYITKTNGTM SLFDVPLHFR FYDASNGGGG  300
YDMRNLLNNT LMSSNPMKAV TFVENHDTQP TQALQSTVQS WFKPLAYATI LTREQGYPCV  360
FYGDYYGTSD GKISSYKPIM DKLLNARKVY AYGTQRDYFD HPDIVGWTRE GDAAHAGSGL  420
ATLITDGPGG SKWMYVGTSK AGQVWTDKTG NRSGTVTIDA NGWGNFWVNG GSVSVWAK    478

SEQ ID NO: 5              moltype = AA  length = 484
FEATURE                   Location/Qualifiers
REGION                    1..484
                          note = Synthetic amino acid sequence of a
                           C-terminal-truncated version of the Bacillus sp. TS-23
                           alpha-amylase
source                    1..484
                          mol_type = protein
                          organism = synthetic construct
SEQUENCE: 5
NTAPINETMM QYFEWDLPND GTLWTKVKNE AANLSSLGIT ALWLPPAYKG TSQSDVGYGV  60
YDLYDLGEFN QKGTIRTKYG TKTQYIQAIQ AAKAAGMQVY ADVVFNHKAG ADGTEFVDAV  120
EVDPSNRNQE TSGTYQIQAW TKFDFPGRGN TYSSFKWRWY HFDGTDWDES RKLNRIYKFR  180
STGKAWDWEV DTENGNYDYL MFADLDMDHP EVVTELKNWG TWYVNTTNID GFRLDAVKHI  240
KYSFFPDWLT YVRNQTGKNL FAVGEFWSYD VNKLHNYITK TNGSMSLFDA PLHNNFYTAS  300
KSSGYFDMRY LLNNTLMKDQ PSLAVTLVDN HDTQPGQSLQ SWVEPWFKPL AYAFILTRQE  360
GYPCVFYGDY YGIPKYNIPG LKSKIDPLLI ARRDYAYGTQ RDYIDHQDII GWTREGIDTK  420
PNSGLAALIT DGPGGSKWMY VGKKHAGKVF YDLTGNRSDT VTINADGWGE FKVNGGSVSI  480
WVAK                                                              484

SEQ ID NO: 6              moltype = AA  length = 482
FEATURE                   Location/Qualifiers
REGION                    1..482
                          note = Synthetic amino acid sequence of a variant form of
                           BASE alpha-amylase having a deletion of both R180 and S181
source                    1..482
                          mol_type = protein
                          organism = synthetic construct
SEQUENCE: 6
NTAPINETMM QYFEWDLPND GTLWTKVKNE AANLSSLGIT ALWLPPAYKG TSQSDVGYGV  60
YDLYDLGEFN QKGTIRTKYG TKTQYIQAIQ AAKAAGMQVY ADVVFNHKAG ADGTEFVDAV  120
EVDPSNRNQE TSGTYQIQAW TKFDFPGRGN TYSSFKWRWY HFDGTDWDES RKLNRIYKFT  180
GKAWDWEVDT ENGNYDYLMF ADLDMDHPEV VTELKNWGTW YVNTTNIDGF RLDAVKHIKY  240
SFFPDWLTYV RNQTGKNLFA VGEFWSYDVN KLHNYITKTN GSMSLFDAPL HNNFYTASKS  300
SGYFDMRYLL NNTLMKDQPS LAVTLVDNHD TQPGQSLQSW VEPWFKPLAY AFILTRQEGY  360
PCVFYGDYYG IPKYNIPGLK SKIDPLLIAR RDYAYGTQRD YIDHQDIIGW TREGIDTKPN  420
SGLAALITDG PGGSKWMYVG KKHAGKVFYD LTGNRSDTVT INADGWGEFK VNGGSVSIWV  480
AK                                                                482

SEQ ID NO: 7              moltype = DNA  length = 1536
FEATURE                   Location/Qualifiers
misc_feature              1..1536
                          note = Synthetic DNA fragment encoding CspAmy2-v1
source                    1..1536
                          mol_type = other DNA
                          organism = synthetic construct
SEQUENCE: 7
atgaaacaac aaaaacggct ttacgcccga ttgctgacgc tgttatttgc gctcatcttc  60
ttgctgcctc attctgcagc tagcgcagca gcgacaaacg gaacaatgat gcagtatttc  120
gagtggtatg tacctaacga cggccagcaa tggaacagac tgagaacaga tgccccttac  180
ttgtcatctg ttggtattac agcagtatgg acaccgccgg cttataaggg cacgtctcaa  240
gcagatgtgg ggtacggccc gtacgatctg tatgatttag gcagatttaa tcaaaaaggt  300
acagtcagaa cgaagtatgg cacaaaagga gaacttaaat ctgctgttaa cacgctgcat  360
tcaaatggaa tccaagtgta tggtgatgtc gtgatgaatc ataaagcagg tgctgattat  420
acagaaaacg taacgcggt ggaggtgaat ccgtctaata gaaatcagga aacgagcggc  480
gaatataata ttcaggcatg gacaggcttc aactttccgg gcagaggaac aacgtattct  540
aacttcaaat ggcagtggtt ccattttgat ggaacggatt gggaccagag cagaagcctc  600
```

-continued

```
tctagaatct tcaaattcac gggaaaggcg tgggactggg aggtttcttc agaaaacgga    660
aattatgact atctgatgta cgcggacatt gattatgacc atccggatgt cgtgaatgaa    720
atgaaaaagt ggggcgtctg gtatgccaac gaagttgggt tagatggata cagacttgac    780
gcggtcaaac atattaaatt tagctttctc aaagactggg tggataacgc aagagcagcg    840
acgggaaaag aaatgtttac ggttggcgaa tattggcaaa atgatttagg ggccctgaat    900
aactacctgg caaaggtaaa ttacaaccaa tctctttttg atgcgccgtt gcattacaac    960
ttttacgctg cctcaacagg gggtggatat tacgatatga gaaatattct taataacacg    1020
ttagtcgcaa gcaatccgac aaaggctgtt acgttagttg agaatcatga cacacagcct    1080
ggacaatcac tggaatcaac agtccaaccg tggtttaaac cgttagccta cgcgtttatt    1140
ctcacgagaa gcggaggcta tccttctgta ttttatggag atatgtacgg tacaaaagga    1200
acgacaacaa gagagatccc tgctcttaaa tctaaaatcg aacctttgct taaggctaga    1260
aaagactatg cttatggaac acagagagac tatattgata acccggatgt cattggctgg    1320
acgagagaag gggactcaac gaaagccaag agcggtctgg ccacagtgat tacagatggg    1380
ccgggcggtt caaaaagaat gtatgttggc acgagcaagg ggggtgaaat ctggtatgat    1440
ttgacaggga atagaacaga taaaatcacg attggaagcg atggctatgc aacatttcct    1500
gtcaatgggg gctcagtttc agtatgggtg cagcaa                              1536
```

SEQ ID NO: 8              moltype = AA  length = 483
FEATURE                   Location/Qualifiers
REGION                    1..483
                          note = Synthetic amino acid sequence of the mature form of
                           CspAmy2-v5
source                    1..483
                          mol_type = protein
                          organism = synthetic construct
SEQUENCE: 8
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV    120
NPSNRNQETS GEYNIQAWTG FNFPGRGTTY SNFKWQWFHF DGTDWDQSRS LSRIFKFTGK    180
AWDWPVSSEN GNYDYLMYAD YDYDHPDVVN EMKKWGVWYA NEVGLDGYRL DAVKHIKFSF    240
LKDWVDNARA ATGKEMFTVG EYWQNDLGAL NNYLAKVNYN QSLFDAPLHY NFYAASTGGG    300
YYDMRNILNN TLVASNPTKA VTLVENHDTQ PGQSLESTVQ PWFKPLAYAF ILTRSGGYPS    360
VFYGDMYGTK GTTTREIPAL KSKIEPLLKA RKDYAYGTQR DYIDNPDVIG WTREGDSTKA    420
KSGLATVITD GPGGSKRMYV GTSNAGEIWY DLTGNRTDKI TIGSDGYATF PVNKGSVSVW    480
VQQ                                                                  483

SEQ ID NO: 9              moltype = AA  length = 483
FEATURE                   Location/Qualifiers
REGION                    1..483
                          note = Synthetic amino acid sequence of the mature form of
                           CspAmy2-v6
source                    1..483
                          mol_type = protein
                          organism = synthetic construct
SEQUENCE: 9
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV    120
NPSNRNQETS GEYNIQAWTG FNFPGRGTTY SNFKWQWFHF DGTDWDQSRS LSRIFKFTGK    180
AWDWPVSSEN GNYDYLMYAD YDYDHPDVVN EMKKWGVWYA NEVGLDGYRL DAVKHIKFSF    240
LKDWVDNARA ATGKEMFTVG EYWQNDLGAL NNYLAKVNYN QSLFDAPLHY NFYAASTGGG    300
YYDMRNILNN TLVASNPTKA VTLVENHDTQ PGQSLESTVQ PWFKPLAYAF ILTRSGGYPS    360
VFYGDMYGTK GTTTREIPAL KSKIEPLLKA RKDYAYGTQR DYIDNPDVIG WTREGDSTKA    420
KSGLATVITD GPGGSKRMYV GTSNAGEIWY DLTGNNSTKI TIGSDGYATF PVNKGSVSVW    480
VQQ                                                                  483

SEQ ID NO: 10             moltype = AA  length = 483
FEATURE                   Location/Qualifiers
REGION                    1..483
                          note = Synthetic amino acid sequence of mature CspAmy2-16A
source                    1..483
                          mol_type = protein
                          organism = synthetic construct
SEQUENCE: 10
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV    120
NPSNRYQETS GEYNIQAWTG FNFPGRGTTY SNFKWQWFHF DGTDWDQSRS LSRIFKFTGK    180
AWDWPVSSEN GNYDYLMYAD YDYDHPDVVN EMKKWGVWYA NEVGLDGYRL DAVKHIKFSF    240
LKDWVDNARA ATGKEMFTVG EYWQNDLGAL NNYLAKVNYN QSLFDAPLHY NFYAASTGGG    300
YYDMRNILNN TLVASNPTKA VTLVENHDTQ PGQSLESTVQ PWFKPLAYAF ILTRSGGYPS    360
VFYGDMYGTK GTTTREIPAL KSKIEPLLKA RKDYAYGTQR DYIDNPDVIG WTREGDSTKA    420
KSGLATVITD GPGGSKRMYV GTSNAGEIWY DLTGNRTDKI TIGSDGYATF PVNGGSVSVW    480
VQQ                                                                  483

SEQ ID NO: 11             moltype = AA  length = 483
FEATURE                   Location/Qualifiers
REGION                    1..483
                          note = Synthetic amino acid sequence of mature CspAmy2-16B
source                    1..483
                          mol_type = protein
```

```
                                organism = synthetic construct
SEQUENCE: 11
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNFKWQWFHF DGTDWDQSRS LSRIFKFTGK  180
AWDWEVSSEN GNYDYLMYAD YDYDHPDVVN EMKKWGVWYA NEVGLDGYRL DAVKHIKFQF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                               483

SEQ ID NO: 12              moltype = AA  length = 483
FEATURE                    Location/Qualifiers
REGION                     1..483
                           note = Synthetic amino acid sequence of mature CspAmy2-16C
source                     1..483
                           mol_type = protein
                           organism = synthetic construct
SEQUENCE: 12
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNWKWQWFHF DGTDWDQSRS LSRIFKFTGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                               483

SEQ ID NO: 13              moltype = AA  length = 483
FEATURE                    Location/Qualifiers
REGION                     1..483
                           note = Synthetic amino acid sequence of mature CspAmy2-16D
source                     1..483
                           mol_type = protein
                           organism = synthetic construct
SEQUENCE: 13
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNWKWQWFHF DGTDWDQSRS LSRIFKFTGK  180
AWDWEVSSEN GNYDYLMYAD YDYDHPDVVN EMKKWGVWYA NEVGLDGYRL DAVKHIKFQF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                               483

SEQ ID NO: 14              moltype = AA  length = 483
FEATURE                    Location/Qualifiers
REGION                     1..483
                           note = Synthetic amino acid sequence of the mature
                            CspAmy2-16E
source                     1..483
                           mol_type = protein
                           organism = synthetic construct
SEQUENCE: 14
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNWKWQWFHF DGTDWDQSRS LSRIFKFHGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNGGSVSVW  480
VQQ                                                               483

SEQ ID NO: 15              moltype = AA  length = 483
FEATURE                    Location/Qualifiers
REGION                     1..483
                           note = Synthetic amino acid sequence of mature CspAmy2-16F
source                     1..483
                           mol_type = protein
                           organism = synthetic construct
SEQUENCE: 15
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNWKWQWFHF DGTDWDQSRS LSRIFKFHGK  180
AWDWEVSSEN GNYDYLMYAD YDYDHPDVVN EMKKWGVWYA NEVGLDGYRL DAVKHIKFQF  240
```

```
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 16            moltype = AA   length = 483
FEATURE                  Location/Qualifiers
REGION                   1..483
                         note = Synthetic amino acid sequence of mature CspAmy2-16G
source                   1..483
                         mol_type = protein
                         organism = synthetic construct
SEQUENCE: 16
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTH SNWKWQWFHF DGTDWDQSRS NSRIFKFTGK   180
AWDWPVSSEN GNYDYLMYAD YDYDHPDVVN EMKKWGVWYA NEVGLDGYRL DAVKHIKFSF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 17            moltype = AA   length = 483
FEATURE                  Location/Qualifiers
REGION                   1..483
                         note = Synthetic amino acid sequence of mature CspAmy2-16H
source                   1..483
                         mol_type = protein
                         organism = synthetic construct
SEQUENCE: 17
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTH SNWKWQWFHF DGTDWDQSRS NSRIFKFTGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 18            moltype = AA   length = 483
FEATURE                  Location/Qualifiers
REGION                   1..483
                         note = Synthetic amino acid sequence of mature CspAmy2-16I
source                   1..483
                         mol_type = protein
                         organism = synthetic construct
SEQUENCE: 18
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTH SNWKWQWFHF DGTDWDQSRS NSRIFKFHGK   180
AWDWPVSSEN GNYDYLMYAD YDYDHPDVVN EMKKWGVWYA NEVGLDGYRL DAVKHIKFSF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 19            moltype = AA   length = 483
FEATURE                  Location/Qualifiers
REGION                   1..483
                         note = Synthetic amino acid sequence of mature CspAmy2-16J
source                   1..483
                         mol_type = protein
                         organism = synthetic construct
SEQUENCE: 19
AATNGTMMQY FEWYVPNDGQ QWNRLRTDAP YLSSVGITAV WTPPAYKGTS QADVGYGPYD   60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTH SNWKWQWFHF DGTDWDQSRS NSRIFKFHGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 20            moltype = AA   length = 483
```

```
FEATURE             Location/Qualifiers
REGION              1..483
                    note = Synthetic amino acid sequence of mature
                    CspAmy2-v1-E187P
source              1..483
                    mol_type = protein
                    organism = synthetic construct
SEQUENCE: 20
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRNQETS GEYNIQAWTG FNFPGRGTTY SNFKWQWFHF DGTDWDQSRS LSRIFKFTGK   180
AWDWPVSSEN GNYDYLMYAD IDYDHPDVVN EMKKWGVWYA NEVGLDGYRL DAVKHIKFSF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 21         moltype = AA   length = 483
FEATURE             Location/Qualifiers
REGION              1..483
                    note = Synthetic amino acid sequence of mature
                    CspAmy2-v1-S241Q
source              1..483
                    mol_type = protein
                    organism = synthetic construct
SEQUENCE: 21
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRNQETS GEYNIQAWTG FNFPGRGTTY SNFKWQWFHF DGTDWDQSRS LSRIFKFTGK   180
AWDWEVSSEN GNYDYLMYAD IDYDHPDVVN EMKKWGVWYA NEVGLDGYRL DAVKHIKFQF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 22         moltype = AA   length = 483
FEATURE             Location/Qualifiers
REGION              1..483
                    note = Synthetic amino acid sequence of mature CspAmy2-v171
source              1..483
                    mol_type = protein
                    organism = synthetic construct
SEQUENCE: 22
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRNQETS GEYNIQAWTG FNFPGRGTTY SNFKWQWFHF DGTDWDQSRS LSRIFKFDGK   180
AWDWPVSSEN GNYDYLMYAD YDYDHPDVVN EMKKWGVWYA NEVGLDGYRL DAVKHIKFSF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNKGSVSVW   480
VQQ                                                                483

SEQ ID NO: 23         moltype = AA   length = 483
FEATURE             Location/Qualifiers
REGION              1..483
                    note = Synthetic amino acid sequence of mature CspAmy2-v172
source              1..483
                    mol_type = protein
                    organism = synthetic construct
SEQUENCE: 23
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTY SNFKWQWFHF DGTDWDQSRS LSRIFKFDGK   180
AWDWPVSSEN GNYDYLMYAD YDYDHPDVVN EMKKWGVWYA NEVGLDGYRL DAVKHIKFSF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNKGSVSVW   480
VQQ                                                                483

SEQ ID NO: 24         moltype = AA   length = 483
FEATURE             Location/Qualifiers
REGION              1..483
                    note = Synthetic amino acid sequence of the mature
                    CspAmy2-C18P amylase polypeptide
source              1..483
```

```
                         mol_type = protein
                         organism = synthetic construct
SEQUENCE: 24
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRYQETS GEYNIQAWTG FNFPGRGTTY SNWKWQWFHF DGTDWDQSRS LSRIFKFDGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLAKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 25            moltype = AA  length = 483
FEATURE                  Location/Qualifiers
REGION                   1..483
                         note = Synthetic amino acid sequence of the mature
                          CspAmy2-C25A amylase polypeptide
source                   1..483
                         mol_type = protein
                         organism = synthetic construct
SEQUENCE: 25
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRYQETS GHYNIQAWTG FNFPGRGTTY SNWKWQWFHF DGTDWDESRS LSRIFKFDGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLFKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGKQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 26            moltype = AA  length = 483
FEATURE                  Location/Qualifiers
REGION                   1..483
                         note = Synthetic amino acid sequence of the mature
                          CspAmy2-C25B amylase polypeptide
source                   1..483
                         mol_type = protein
                         organism = synthetic construct
SEQUENCE: 26
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRYQETS GHYNIQAWTG FNFPGRGTTY SNWKWQWFHF DGTDWDESRS LSRIFKFDGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLFKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 27            moltype = AA  length = 483
FEATURE                  Location/Qualifiers
REGION                   1..483
                         note = Synthetic amino acid sequence of the mature
                          CspAmy2-C25F amylase polypeptide
source                   1..483
                         mol_type = protein
                         organism = synthetic construct
SEQUENCE: 27
AATNGTMMQY FEWYVPNDGQ QWNRLRTDAP YLSSVGITAV WTPPAYKGTS QADVGYGPYD    60
LYDLGEFNQK GTVRTKYGTK GELKSAVNTL HSNGIQVYGD VVMNHKAGAD YTENVTAVEV   120
NPSNRYQETS GHYNIQAWTG FNFPGRGTTY SNWKWQWFHF DGTDWDQSRS LSRIFKFDGK   180
AWDWEVSSEN GNYDYLMYAD YDYDHPDVVN EMKKWGVWYA NEVGLDGYRL DAVKHIKFQF   240
LKDWVDNARA ATGKEMFTVG EYWQNDLGAL NNYLFKVNYN QSLFDAPLHY NFYAASTGGG   300
YYDMRNILNN TLVASNPTKA VTLVENHDTQ PGQSLESTVQ PWFKPLAYAF ILTRSGGYPS   360
VFYGDMYGTK GTTTREIPAL KSKIEPLLKA RKDYAYGTQR DYIDNPDVIG WTREGDSTKA   420
KSGLATVITD GPGGSKRMYV GTSNAGEIWY DLTGNRTDKI TIGSDGYATF PVNGGSVSVW   480
VQQ                                                                483

SEQ ID NO: 28            moltype = AA  length = 483
FEATURE                  Location/Qualifiers
REGION                   1..483
                         note = Synthetic amino acid sequence of mature CspAmy2-v179
source                   1..483
                         mol_type = protein
                         organism = synthetic construct
SEQUENCE: 28
AATNGTMMQY FEWYVPNDGQ QWNRLRTDAP YLSSVGITAV WTPPAYKGTS QADVGYGPYD    60
```

```
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNFKWQWFHF DGTDWDQSRS LSRIFKFDGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
DYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNTESVSVW  480
VQQ                                                                483
```

```
SEQ ID NO: 29            moltype = AA  length = 483
FEATURE                  Location/Qualifiers
REGION                   1..483
                         note = Synthetic amino acid sequence of mature CspAmy2-v180
source                   1..483
                         mol_type = protein
                         organism = synthetic construct
SEQUENCE: 29
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNFKWQWFHF DGTDWDQSRS LSRIFKFDGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
DYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVEGQSVSVW  480
VQQ                                                                483
```

```
SEQ ID NO: 30            moltype = AA  length = 483
FEATURE                  Location/Qualifiers
REGION                   1..483
                         note = Synthetic amino acid sequence of mature CspAmy2-v181
source                   1..483
                         mol_type = protein
                         organism = synthetic construct
SEQUENCE: 30
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRYQETS GEYNIQAWTG FNFPGRGTTY SNFKWQWFHF DGTDWDQSRS LSRIFKFDGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
DYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVETRSVSVW  480
VQQ                                                                483
```

```
SEQ ID NO: 31            moltype = AA  length = 483
FEATURE                  Location/Qualifiers
REGION                   1..483
                         note = Synthetic amino acid sequence of mature CspAmy2-v186
source                   1..483
                         mol_type = protein
                         organism = synthetic construct
SEQUENCE: 31
AATNGTMMQY FEWYVPNDGQ QWNRLRTDAP YLSSVGINAV WTPPAYKGTS QADVGYGPYD  60
LYDLGEFNQK GTVRTKYGTK GELKSAVHTL HSNGIQVYGD VVMNHKAGAD YTENVTAVEV  120
NPSNRYQEIS GEYMIQAWTG FNFPGRGTTY SNWKWQWFHF DGTDWDQSRS RSRIFKFDGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
YYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNKESVSVW  480
VQQ                                                                483
```

```
SEQ ID NO: 32            moltype = AA  length = 483
FEATURE                  Location/Qualifiers
REGION                   1..483
                         note = Synthetic amino acid sequence of mature CspAmy2-v191
source                   1..483
                         mol_type = protein
                         organism = synthetic construct
SEQUENCE: 32
AATNGTMMQY FEWYVPNDGQ QWNRLRTDAP YLSSVGITAV WTPPAYKGTS QADVGYGPYD  60
LYDLGEFNQK GTVRTKYGTK GELKSAVNTL HSNGIQVYGD VVMNHKAGAD YTENVTAVEV  120
NPSNRYQETS GHYNIQAWTG FNFPGRGTTY SNFKWQWFHF DGTDWDQSRS LSRIFKFDGK  180
AWDWPVSSEN GNYDYLMYAD YDYDHPDVVN EMKKWGVWYA NEVGLDGYRL DAVKHIKFSF  240
LKDWVDNARA ATGKEMFTVG EYWQNDLGAL NNYLAKVNYN QSLFDAPLHY NFYAASTGGG  300
DYDMRNILNN TLVASNPTKA VTLVENHDTQ PGQSLESTVQ PWFKPLAYAF ILTRSGGYPS  360
VFYGDMYGTK GTTTREIPAL KSKIEPLLKA RKDYAYGTQR DYIDNPDVIG WTREGDSTKA  420
KSGLATVITD GPGGSKRMYV GTSNAGEIWY DLTGNRTDKI TIGSDGYATF PVNTESVSVW  480
```

VQQ                                                                      483

```
SEQ ID NO: 33         moltype = DNA   length = 1443
FEATURE               Location/Qualifiers
misc_feature          1..1443
                      note = Synthetic codon-optimized nucleotide sequence of the
                      PcuAmy1 gene
source                1..1443
                      mol_type = other DNA
                      organism = synthetic construct SEQUENCE: 33
gccgacaacg gcacaatcat gcagtatttc gagtggtacc tgccgaacga cggagcgcac   60
tggaacagac ttaataacga cgcacaaaac ctgaaaaatg tgggcatcac ggcagtgtgg  120
attcctccgg catacaaggg cggcagctca gcagtgtcgg gctacggagt ttacgataca  180
tacgacctgg gcgagttcaa tcagaaaggc acggtcagaa caaagtacgg aacgaagagc  240
gaactgattt cagcggtcaa caatcttcac gcaaagggca ttgcggttta cggcgacgtg  300
gtcctgaacc atagaatgaa tgcggatgca acggagcttg tggatgcggt tgaggtggat  360
ccgaacaaca gaaacgtcga gacgacaagc acgtatcgaa tccaggcatg gacgcaatac  420
gatttcccgg gcagaggcaa cacgtacagc agctttaaat ggagatggta tcacttcgac  480
ggcgtcgact gggaccagag cagaggcctg aacagaatct ataagctgag aggcgatggc  540
aaggattggg actgggaggt cgacagcgag tacggcaact acgattacct gatgggagcg  600
gacctggact tcaaccaccc ggatgtggtt aacgaaacaa agacatgggg caaatggttt  660
gtgaacacgg tgaacctgga tggcgtcaga ctggacgcgg ttaagcacat caagttcgac  720
ttcatgagag actgggtgaa caacgtgaga agcacgacgg gcaagaacct tttcgcagtt  780
ggcgagtatt ggcactacga cgtgaacaaa ctgaacagct acatcacgaa gacgaatggc  840
acgatgagcc tgttcgacgt gccgctgcac tttagatttt atgatgcaag caacggcggg  900
ggcggctacg acatgagaaa cctgctgaat aacacgctga tgagcagcaa cccgatgaag  960
gcggttacat tcgttgagaa ccatgacaca caaccgacgc aggccctgca atcaacggtc 1020
caaagctggt ttaagccgct tgcgtatgct acaatcctga cgagagagca aggctacccg 1080
tgcgttttct acggcgacta ttatggaaca agcacgacgg aaattagcag ctacaagccg 1140
atcatggata agcttcttaa cgcgagaaag gtgtacgcct acggcacgca gagagattac 1200
ttcgatcatc cggacatcgt tggctggaca agagaaggcg atgcagcaca tgctggctca 1260
ggactggcaa cgcttatcac agatggccct ggcggaagca gtggatgta tgttggaacg 1320
tcaaaggcag gccaggtctg acggataaaa acaggaaaca gaagcggaac ggtgacgatt 1380
gatgccaatg gctggggaaa cttttgggtt aatggcggat cagttagcgt ttgggcaaaa 1440
taa                                                                 1443
```

```
SEQ ID NO: 34         moltype = AA   length = 478
FEATURE               Location/Qualifiers
REGION                1..478
                      note = Synthetic amino acid sequence of the mature of
                      PcuAmy1-v1A polypeptide
source                1..478
                      mol_type = protein
                      organism = synthetic construct SEQUENCE: 34
ADNGTIMQYF EWYLPNDGAH WNRLNNDAQN LKNVGITAVW IPPAYKGGSS ADVGYGVYDT   60
YDLGEFNQKG TVRTKYGTKS ELISAVNNLH AKGIAVYGDV VLNHRMNADA TELVDAVEVD  120
PNNRYVETTS TYQIQAWTQY DFPGRGNTYS SFKWRWYHFD GVDWDQSRGL NRIYKLDGKD  180
WDWPVDSEYG NYDYLMGADL DFNHPDVVNE TKTWGKWFVN TVNLDGVRLD AVKHIKFDFM  240
RDWVNNVRST TGKNLFAVGE YWHYDVNKLN SYITKTNGTM SLFDVPLHFR FYDASNGGGG  300
YDMRNLLNNT LMSSNPMKAV TFVENHDTQP GQSLESTVQS WFKPLAYATI LTREQGYPCV  360
FYGDYYGTSD GKISSYKPIM DKLLNARKVY AYGTQRDYFD HPDIVGWTRE GDAAHAGSGL  420
ATLITDGPGG SKWMYVGTSK AGQVWTDKTG NRSGTVTIDA NGWGNFWVNK GSVSVWAK    478
```

```
SEQ ID NO: 35         moltype = AA   length = 478
FEATURE               Location/Qualifiers
REGION                1..478
                      note = Synthetic amino acid sequence of the mature of
                      PcuAmy1-v6 polypeptide
source                1..478
                      mol_type = protein
                      organism = synthetic construct SEQUENCE: 35
ADNGTIMQYF EWYLPNDGAH WNRLNNDAQN LKNVGITAVW IPPAYKGGSS ADVGYGVYDT   60
YDLGEFNQKG TVRTKYGTKS ELISAVNNLH AKGIAVYGDV VLNHRMNADA TELVDAVEVD  120
PNNRYVETTS TYQIQAWTQY DFPGRGNTYS SWKWRWYHFD GVDWDQSRGL NRIYKLDGKD  180
WDWPVDSEYG NYDYLMGADL DFNHPDVVNE TKTWGKWFVN TVNLDGVRLD AVKHIKFDFM  240
RDWVNNVRST TGKNLFAVGE YWHYDVNKLN SYITKTNGTM SLFDVPLHFR FYDASNGGGG  300
YDMRNLLNNT LMSSNPMKAV TFVENHDTQP GQSLESTVQS WFKPLAYATI LTREQGYPCV  360
FYGDYYGTSD GKISSYKPIM DKLLNARKVY AYGTQRDYFD HPDIVGWTRE GDAAHAGSGL  420
ATLITDGPGG SKWMYVGTSK AGQVWTDKTG NRSGTVTIDA NGWGNFWVNK GSVSVWAK    478
```

```
SEQ ID NO: 36         moltype = AA   length = 478
FEATURE               Location/Qualifiers
REGION                1..478
                      note = Synthetic amino acid sequence of the mature of
                      PcuAmy1-v8 polypeptide
source                1..478
```

```
                        mol_type = protein
                        organism = synthetic construct
SEQUENCE: 36
ADNGTIMQYF EWYLPNDGAH WNRLNNDAQN LKNVGITAVW IPPAYKGGSS ADVGYGVYDT    60
YDLGEFNQKG TVRTKYGTKS ELISAVNNLH AKGIAVYGDV VLNHRMNADA TELVDAVEVD   120
PNNRYVETTS TYQIQAWTQY DFPGRGNTYS SWKWRWYHFD GVDWDQSRGL NRIYKLDGKD   180
WDWPVDSEYG NYDYLMGADL DFNHPDVVNE TKTWGKWFVN TVNLDGVRLD AVKHIKFDFM   240
RDWVNNVRST TGKNLFAVGE YWHYDVNKLN SYITKTNGTM SLFDVPLHFR FYDASNGGGG   300
YDMRNLLNNT LMSSNPMKAV TFVENHDTQP GQSLESTVQS WFKPLAYATI LTREQGYPCV   360
FYGDYYGTSD GKISSYKPIM DKLLNARKVY AYGTQRDYFD HPDIVGWTRE GDAAHAGSGL   420
ATLITDGPGG SKWMYVGTSK AGQVWTDKTG NRSGTVTIDA NGWGNFWVNR RSVSVWAK    478

SEQ ID NO: 37           moltype = AA  length = 478
FEATURE                 Location/Qualifiers
REGION                  1..478
                        note = Synthetic amino acid sequence of the mature of
                         PcuAmy1-v16 polypeptide
source                  1..478
                        mol_type = protein
                        organism = synthetic construct
SEQUENCE: 37
ADNGTIMQYF EWYLPNDGAH WNRLNNDAQN LKNVGITAVW IPPAYKGGSS ADVGYGVYDT    60
YDLGEFNQKG TVRTKYGTKS ELISAVNNLH AKGIAVYGDV VLNHRMNADA TELVDAVEVD   120
PNNRYVETTS TYQIQAWTQY DFPGRGNTYS SWKWRWYHFD GVDWDQSRGL NRIYKLDGKD   180
WDWPVDSEYG NYDYLMGADL DFDHPDVVNE TKTWGKWFVN TVNLDGVRLD AVKHIKFDFM   240
RDWVNNVRST TGKNLFAVGE YWHYDVNKLN SYITKTNGTM SLFDVPLHFR FYDASNGGGG   300
YDMRNLLNNT LMSSNPMKAV TFVENHDTQP GQSLESTVQS WFKPLAYATI LTREQGYPCV   360
FYGDYYGTSD GKISSYKPIM DKLLNARKVY AYGTQRDYFD HPDIVGWTRE GDAAHAGSGL   420
ATLITDGPGG SKWMYVGTSK AGQVWTDKTG NRSGTVTIDA NGWGNFWVNK GSVSVWAK    478

SEQ ID NO: 38           moltype = DNA  length = 1479
FEATURE                 Location/Qualifiers
misc_feature            1..1479
                        note = Synthetic codon-modified nucleic acid sequence
                         encoding the mature form of BASE
source                  1..1479
                        mol_type = other DNA
                        organism = synthetic construct
SEQUENCE: 38
tctgcagctt cagcaaacac cgcgccgatt aacgaaacca tgatgcagta tttcgaatgg    60
gatctgccga acgatggcac cctgtggacc aaagtgaaaa acgaagcggc gaacctgagc   120
agcctgggca ttaccgcgct gtggctgccg ccggcatata aaggcaccag ccagagcgat   180
gtgggctatg gcgtgtatga tctgtacgat ctgggcgaat ttaaccagaa aggcaccatt   240
cgtaccaaat atggcaccaa aacccagtat attcaggcga tccaggcggc gaaagcggcg   300
ggtatgcagg tgtatgcgga tgtggtgttt aaccataaag cgggtgcgga tggcaccgaa   360
tttgtggatg cggtggaagt ggatccgagc aaccgtaacc aggaaaccag cggcacctat   420
cagattcagg cgtggaccaa atttgatttt cccggccgtg gcaacaccta tagcagcttt   480
aaatggcgct ggtatcattt tgatggcacc gattgggatg aaagccgtaa actgaaccgc   540
atctataaat ttcgtagcac cggcaaagcg tgggattggg aagtggatac cgaaaacggc   600
aactatgatt acctgatgtt cgcagacctg gatatggatc atccggaagt ggtgaccgaa   660
ctgaaaaact ggggcacctg gtatgtgaac accaccaaca ttgatggctt tcgtctgatt   720
gcggtgaaac acatcaaata cagctttttt ccggattggc tgacctatgt gcgtaaccag   780
accggcaaaa acctgtttgc ggtgggcgaa ttttggagct atgatgtgaa caaactgcac   840
aactacatca ccaaaaccaa cggcagcatg agcctgtttg atgcgccgct gcataacaac   900
ttttataccg cgagcaaaag cagcggctat tttgatatgc gttatctgct gaacaacacc   960
ctgatgaaag atcagccgag cctgcccgtg accctggtgg ataaccatga tacccagccg  1020
ggccagagcc tgcaaagctg ggtggaaccg tggtttaaac cgctggccta cgcgtttatt  1080
ctgacccgtc aagagggcta tccgtgcgtt ttttatggcg attattacgg catcccgaaa  1140
tataacattc cgggcctgaa aagcaaaatt gatccgctgc tgattgcgcg tcgtgattat  1200
gcgtatggca cccagcgtga ttatattgat caccaggata ttattggctg gacccgtgaa  1260
ggcattgata ccaaaccgaa cagcggcctg gccgcgctga ttaccgatgg cccgggtggc  1320
agcaaatgga tgtatgtggg caaaaaacat gcgggcaaag tgtttttatga tctgaccggc  1380
aaccgtagcg ataccgtgac cattaacgcg gatggctggg gtgagtttaa agtgaacggc  1440
ggcagcgtga gcatttgggt ggcgaaataa gttaacaga                         1479

SEQ ID NO: 39           moltype = AA  length = 482
FEATURE                 Location/Qualifiers
REGION                  1..482
                        note = Synthetic amino acid sequence of BASE-V28
source                  1..482
                        mol_type = protein
                        organism = synthetic construct
SEQUENCE: 39
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGTYQIAW TKFDPGRGN TYSSFKWRWY HFDGTDWDES RKLNRIYKFT   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
```

-continued

```
PCVFYGDYYG IPKYNIPGLK SKIDPLLIAR RDYAYGTQRD YIDHQDIIGW TREGIDTKPN    420
SGLAALITDG PGGSKWMYVG KKHAGKVFYD LTGNRSDTVT INADGWGEFK VNRGSVSIWV    480
AK                                                                  482

SEQ ID NO: 40           moltype = AA  length = 482
FEATURE                 Location/Qualifiers
REGION                  1..482
                        note = Synthetic amino acid sequence of BASE-V29
source                  1..482
                        mol_type = protein
                        organism = synthetic construct
SEQUENCE: 40
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRNQE TSGTYQIQAW TKFDFPGRGN TYSSWKWRWY HFDGTDWDES RKLNRIYKFT   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 41           moltype = AA  length = 482
FEATURE                 Location/Qualifiers
REGION                  1..482
                        note = Synthetic amino acid sequence of BASE-V30
source                  1..482
                        mol_type = protein
                        organism = synthetic construct
SEQUENCE: 41
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRNQE TSGEYQIQAW TKFDFPGRGN TYSSFKWRWY HFDGTDWDES RKLNRIYKFH   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 42           moltype = AA  length = 482
FEATURE                 Location/Qualifiers
REGION                  1..482
                        note = Synthetic amino acid sequence of BASE-V31
source                  1..482
                        mol_type = protein
                        organism = synthetic construct
SEQUENCE: 42
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGEYQIQAW TKFDFPGRGN TYSSFKWRWY HFDGTDWDES RKLNRIYKFH   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 43           moltype = AA  length = 482
FEATURE                 Location/Qualifiers
REGION                  1..482
                        note = Synthetic amino acid sequence of BASE-V32
source                  1..482
                        mol_type = protein
                        organism = synthetic construct
SEQUENCE: 43
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGTYQIQAW TKFDFPGRGN TYSSWKWRWY HFDGTDWDES RKLNRIYKFT   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 44           moltype = AA  length = 482
FEATURE                 Location/Qualifiers
REGION                  1..482
```

-continued

```
                              note = Synthetic amino acid sequence of BASE-V33
source                        1..482
                              mol_type = protein
                              organism = synthetic construct
SEQUENCE: 44
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRNQE TSGEYQIQAW TKFDFPGRGN TYSSWKWRWY HFDGTDWDES RKLNRIYKFH   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 45                 moltype = AA  length = 482
FEATURE                       Location/Qualifiers
REGION                        1..482
                              note = Synthetic amino acid sequence of BASE-V34
source                        1..482
                              mol_type = protein
                              organism = synthetic construct
SEQUENCE: 45
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGEYQIQAW TKFDFPGRGN TYSSWKWRWY HFDGTDWDES RKLNRIYKFH   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 46                 moltype = AA  length = 482
FEATURE                       Location/Qualifiers
REGION                        1..482
                              note = Synthetic amino acid sequence of BASE-V35
source                        1..482
                              mol_type = protein
                              organism = synthetic construct
SEQUENCE: 46
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGHYQIQAW TKFDFPGRGN TYSSWKWRWY HFDGTDWDES RKLNRIYKFD   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 47                 moltype = AA  length = 482
FEATURE                       Location/Qualifiers
REGION                        1..482
                              note = Synthetic amino acid sequence of BASE-V36
source                        1..482
                              mol_type = protein
                              organism = synthetic construct
SEQUENCE: 47
NTAPINETMM QYFEWDLPND GTLWTKVKNE AANLSSLGIT ALWLPPAYKG TSQSDVGYGV    60
YDLYDLGEFN QKGTIRTKYG TKTQYIQAIQ AAKAAGMQVY ADVVFNHKAG ADGTEFVDAV   120
EVDPSNRYQE TSGEYQIQAW TKFDFPGRGN TYSSWKWRWY HFDGTDWDES RKLNRIYKFG   180
GKAWDWPVDT ENGNYDYLMF ADLDMDHPEV VTELKNWGTW YVNTTNIDGF RLDAVKHIKY   240
SFFPDWLTYV RNQTGKNLFA VGEFWSYDVN KLHNYITKTN GSMSLFDAPL HNNFYTASKS   300
SGYFDMRYLL NNTLMKDQPS LAVTLVDNHD TQPGQSLQSW VEPWFKPLAY AFILTRQEGY   360
PCVFYGDYYG IPKYNIPGLK SKIDPLLIAR RDYAYGTQRD YIDHQDIIGW TREGIDTKPN   420
SGLAALITDG PGGSKWMYVG KKHAGKVFYD LTGNRSDTVT INADGWGEFK VNRGSVSIWV   480
AK                                                                 482

SEQ ID NO: 48                 moltype =   length =
SEQUENCE: 48
000

SEQ ID NO: 49                 moltype = AA  length = 4
FEATURE                       Location/Qualifiers
REGION                        1..4
                              note = Synthetic peptide
source                        1..4
                              mol_type = protein
```

-continued

```
                        organism = synthetic construct
SEQUENCE: 49
RGTG                                                                    4

SEQ ID NO: 50           moltype = AA   length = 478
FEATURE                 Location/Qualifiers
REGION                  1..478
                        note = Synthetic mature form of PcuAmy1-v3
source                  1..478
                        mol_type = protein
                        organism = synthetic construct
SEQUENCE: 50
ADNGTIMQYF EWYLPNDGAH WNRLNNDAQN LKNVGITAVW IPPAYKGGSS ADVGYGVYDT   60
YDLGEFNQKG TVRTKYGTKS ELISAVNNLH AKGIAVYGDV VLNHRMNADA TELVDAVEVD  120
PNNRNVETTS TYQIQAWTQY DFPGRGNTYS SFKWRWYHFD GVDWDQSRGL NRIYKLDGKD  180
WDWPVDSEYG NYDYLMGADL DFNHPDVVNE TKTWGKWFVN TVNLDGVRLD AVKHIKFDFM  240
RDWVNNVRST TGKNLFAVGE YWHYDVNKLN SYITKTNGTM SLFDVPLHFR FYDASNGGGG  300
YDMRNLLNNT LMSSNPMKAV TFVENHDTQP TQALQSTVQS WFKPLAYATI LTREQGYPCV  360
FYGDYYGTSD GKISSYKPIM DKLLNARKVY AYGTQRDYFD HPDIVGWTRE GDAAHAGSGL  420
ATLITDGPGG SKWMYVGTSK AGQVWTDKTG NRSGTVTIDA NGWGNFWVNK GSVSVWAK    478
```

ALPHA-AMYLASE COMBINATORIAL VARIANTS

CROSS REFERENCE TO RELATED APPLICATIONS

This application is a continuation of U.S. patent application Ser. No. 16/292,057, filed Mar. 4, 2019, which is a continuation of U.S. patent application Ser. No. 14/775,595, filed Sep. 11, 2015, which is a U.S. National Stage Application of International Patent Application No. PCT/US2014/023458 under 37 U.S.C. § 371, filed Mar. 11, 2014, which claims benefit of priority from U.S. Provisional Patent Application Nos. 61/776,699, filed Mar. 11, 2013, 61/906, 617, filed Nov. 20, 2013, and 61/907,131, filed Nov. 21, 2013, and are each incorporated herein by reference in their entirety.

REFERENCE TO A SEQUENCE LISTING

The contents of the electronic submission of the text file Sequence Listing, named 20230508_NB40387-US-PCN2_sequencelisting.xml" was created on May 8, 2023 and is 88 KB in size, which is hereby incorporated by reference in its entirety.

FIELD OF THE INVENTION

Disclosed are compositions and methods relating to variant α-amylases containing a plurality of combinable mutations. The variant α-amylases are useful, for example, for starch liquefaction and saccharification, cleaning starchy stains, textile desizing, baking, and brewing.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

α-amylases hydrolyze starch, glycogen, and related polysaccharides by cleaving internal α-1,4-glucosidic bonds at random. α-amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestibility. These enzymes can also be used to remove starchy soils and stains during dishwashing and laundry washing.

Numerous publications have described mutations in α-amylases. However, not all mutations produce the same effect in different molecules and not all mutation can be combined. In addition, many mutations produce molecules that have certain desirable qualities at the expense of other properties. The need exists for robust engineered α-amylases molecules.

SUMMARY

The present compositions and methods relate to variant amylase polypeptides, and methods of use, thereof. Aspects and embodiments of the present compositions and methods are summarized in the following separately-numbered paragraphs:

1. In one aspect, a recombinant variant of a parent α-amylase is provided, comprising: a mutation at an amino acid residue corresponding to E187 or S241; and at least one mutation at an amino acid residue corresponding to an amino acid residue selected from the group consisting of N126, Y150, F153, L171, T180, and, I203; wherein the variant α-amylase or the parent α-amylase has at least 60% amino acid sequence identity relative to SEQ ID NO: 1, which is used for numbering; and wherein the variant has increased thermostability, detergent stability, starch liquefaction activity, and/or cleaning performance compared to the parent α-amylase or a reference α-amylase differing from the variant α-amylase only by the absence of the mutations.

2. In some embodiments, the variant α-amylase of paragraph 1 comprises at least two mutations at amino acid residues corresponding N126, Y150, F153, L171, and, I203, using SEQ ID NO: 1 for numbering.

3. In some embodiments, the variant α-amylase of any of the preceding paragraphs further comprises a deletion of at least one amino acid residue corresponding to R178, G179, T180, and G181, using SEQ ID NO: 1 for numbering.

4. In some embodiments, the variant α-amylase of any of the preceding paragraphs further comprise deletions of amino acid residues corresponding to R178 and G179, or T180 and G181.

5. In some embodiments, the variant α-amylase of any of the preceding paragraphs further comprises a mutation at an amino acid residue corresponding to G476 and/or G477, using SEQ ID NO: 1 for numbering.

6. In some embodiments, the variant α-amylase of any of the preceding paragraphs further comprises a mutation in an amino acid residue corresponding to an amino acid residue selected from the group consisting of E132, Q167, T180, and A277, using SEQ ID NO: 1 for numbering.

7. In some embodiments, the variant α-amylase of any of the preceding paragraphs further comprises a mutation in an amino acid residue corresponding to an amino acid residue selected from the group consisting of R458, T459, and D460, using SEQ ID NO: 1 for numbering.

8. In some embodiments, the variant α-amylase of any of the preceding paragraphs further comprises a mutation in an amino acid residue corresponding to T180, using SEQ ID NO: 1 for numbering.

9. In some embodiments, the variant α-amylase of any of the preceding paragraphs further comprises a mutation in an amino acid residue corresponding to N205, using SEQ ID NO: 3 for numbering.

10. In some embodiments, the variant α-amylase of any of the preceding paragraphs further comprises a mutation in an amino acid residue corresponding to an amino acid residue selected from the group consisting of T333G, A335S, and Q337E, using SEQ ID NO: 3 for numbering.

11. In some embodiments, the variant α-amylase of any of the preceding paragraphs further comprises a mutation in an amino acid residue corresponding to an amino acid residue position selected from the group consisting of 6, 7, 8, 11, 14, 15, 20, 21, 23, 26, 27, 28, 37, 38, 39, 40, 42, 45, 46, 48, 49, 50, 51, 52, 53, 54, 58, 61, 62, 68, 70, 71, 72, 73, 79, 80, 81, 82, 84, 85, 87, 88, 89, 92, 93, 94, 95, 96, 97, 98, 101, 108, 111, 112, 113, 114, 115, 116, 117, 118, 120, 122, 123, 124, 126, 127, 129, 130, 131, 132, 133, 134, 136, 137, 138, 140, 142, 143, 144, 147, 148, 149, 150, 151, 152, 153, 154, 155, 156, 158, 159, 165, 167, 168, 170, 171, 172, 175, 176, 177, 180, 181, 182, 187, 190, 191, 193, 199, 200, 201, 203, 206, 208, 210, 211, 212, 214, 215, 216, 219, 221, 223, 225, 226, 227, 235, 238, 239, 240, 241, 242, 243, 245, 246, 247, 248, 249, 250, 252, 253, 254, 256, 257, 258, 260, 261, 262, 266, 267, 268, 269, 270, 271, 273, 276, 277, 279, 280, 282, 284, 285, 286, 288, 296, 299, 300, 301, 302, 303, 304, 307, 308, 310, 311, 312, 313, 316, 317, 318, 320, 321, 325, 327, 335, 338, 342, 348, 349, 352, 356, 357, 360, 362, 363, 368, 369, 377, 381, 382, 383, 384, 385, 388, 390, 392, 394, 395, 396, 397, 398, 400, 401, 402, 403, 404, 405, 407, 408, 410, 414, 415, 416, 418, 419, 420, 421, 422, 423, 424, 426, 428, 429, 430, 431, 434, 435, 436, 439, 441, 442, 444, 445, 446, 447, 448, 449, 450, 451, 454, 455, 457, 460, 461, 462, 463, 464, 465, 466, 467, 469, 470, 471, 473, 474, 475, 476, 477, 479, 480, 481, 482, 483, and 484, using SEQ ID NO: 1 for numbering.

12. In some embodiments, the variant α-amylase of any of the preceding paragraphs comprises a combinations of mutations corresponding to mutations selected from the group consisting of:

$$E187P + I203Y + G476K,$$

$$E187P + I203Y + G476K + R458N + T459S + D460T,$$

$$T180D + E187P + I203Y + G476K,$$

$$N126Y + T180D + E187P + I203Y + G476K,$$

$$N126Y + T180D + E187P + I203Y + Y303D + G476T + G477E,$$

$$N126Y + T180D + E187P + I203Y + Y303D + N475E + G477Q,$$

$$N126Y + T180D + E187P + I203Y + Y303R + N475E + G476T + G477R,$$

$$T038N + N088H + N126Y + T129I + N134M + F153W +$$
$$L171R + T180D + E187P + I203Y + G476K + G477E,$$

$$N126Y + E132H + T180D + E187P + I203Y + Y303D + G476T + G477E,$$

$$N126Y + E187P + G476K,$$

$$N126Y + F153W + E187P + G476K,$$

$$N126Y + F153W + E187P + G4726 + G477R,$$

$$N126Y + E187P + I203Y,$$

$$N126Y + I203Y + S241Q,$$

$$N126Y + T180H + E187P + I203Y,$$

-continued $$N126Y + T180H + I203Y + S241Q,$$

$$N126Y + F153W + T180H + E187P + I203Y,$$

$$N126Y + F153W + T180H + I203Y + S241Q,$$

$$N126Y + Y150H + F153W + L171N + E187P + I203Y,$$

$$N126Y + Y150H + F153W + L171N + I203Y + S241Q,$$

$$N126Y + Y150H + F153W + L171N + T180H + E187P + I203Y,$$

$$N126Y + Y150H + F153W + L171N + T180H + I203Y + S241Q, \text{ and}$$

$$N126Y + F153W + T180D + I203Y + S241Q;$$

wherein the variant has increased thermostability, detergent stability, stability starch liquefaction activity, or cleaning performance compared to the parent; and wherein the variant or the parent has at least 60% amino acid sequence identity relative to SEQ ID NO: 1, which is used for numbering.

13. In some embodiments, the variant amylase of any of paragraphs 1-12 comprises the combinations of mutations corresponding to N126Y+F153W+T180D+I203Y+S241Q and one or more mutations corresponding to mutations selected from the group consisting of E132H, Q167E, A277F, and T400K.

14. In some embodiments, the variant amylase of paragraph 13 comprises the combinations of mutations corresponding to mutations selected from the group consisting of:

$$N126Y + E132H + F153W + T180D + I203Y + S241Q + A277F,$$

$$N126Y + E132H + F153W +$$
$$Q167E + T180D + I203Y + S241Q + A277F, \text{ and}$$

$$N126Y + E132H + F153W + Q167E +$$
$$T180D + I203Y + S241Q + A277F + T400K.$$

15. In some embodiments, the variant amylase of any of the preceding paragraphs is from a *Cytophaga* species.

16. In some embodiments, the variant amylase of any of the preceding paragraphs is from a *Paenibacillus* species.

17. In some embodiments, the variant amylase of any of the preceding paragraphs is not from a *Bacillus* species.

18. In some embodiments, the variant amylase of any of the preceding paragraphs has at least 70% amino acid sequence identity to the amino acid sequence of SEQ ID NO: 1, SEQ ID NO: 3, or SEQ ID NO: 5.

19. In some embodiments, the variant amylase of any of the preceding paragraphs has at least 70% amino acid sequence identity to the amino acid sequence of SEQ ID NO: 1 or SEQ ID NO: 3.

20. In some embodiments, the variant amylase of any of paragraphs 1-18 has at least 80% amino acid sequence identity to the amino acid sequence of SEQ ID NO: 1, SEQ ID NO: 3, or SEQ ID NO: 5.

21 In some embodiments, the variant amylase of any of paragraphs 1-18 has at least 90% amino acid sequence identity to the amino acid sequence of SEQ ID NO: 1, SEQ ID NO: 3, or SEQ ID NO: 5.

22. In another aspect, a composition comprising the variant α-amylase of any of the preceding paragraphs is provided.

23. In some embodiments, the composition of paragraph 22 is effective for removing starchy stains from laundry, dishes, or textiles.

24. In some embodiments, the composition of paragraph 22 or 23 further comprises a surfactant.

25. In some embodiments, the composition of any of paragraphs 22-24 is a detergent composition.

26. In some embodiments, the composition of any of paragraphs 22-24 is a laundry detergent or a laundry detergent additive.

27. In some embodiments, the composition of any of paragraphs 22-24 is a manual or automatic dishwashing detergent.

28. In some embodiments, the composition of any of paragraphs 22-24 further comprises one or more additional enzymes selected from the group consiting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, ß-glucanase, arabinosidase, hyaluronidase, chondroitinase, laccase, metalloproteinase, amadoriase, glucoamylase, arabinofuranosidase, phytase, isomerase, transferase, and an amylase other than the amylase of any one of paragraphs 1-21.

29. In some embodiments, the composition of paragraph 21 is for liquifying starch.

30. In some embodiments, the composition of paragraph 21 is for saccharifying a composition comprising starch, for SSF post liquefaction, or for direct SSF without prior liquefaction.

31. In some embodiments, the composition of paragraph 21 is for producing a fermented beverage.

32. In some embodiments, the composition of paragraph 21 is for producing a baked food product.

33. In some embodiments, the composition of paragraph 21 is for textile desizing.

34. In another aspect, a method for removing a starchy stain or soil from a surface is provided, comprising: contacting the surface in the presence of a composition comprising an effective amount of the variant amylase of any of the paragraphs 1-21, and allowing the polypeptide to hydrolyze starch components present in the starchy stain to produce smaller starch-derived molecules that dissolve in the aqueous composition, thereby removing the starchy stain from the surface.

35. In some embodiments of the method of paragraph 34 the aqueous composition further comprises a surfactant.

36. In some embodiments of the method of any of paragraphs 34 or 35 the surface is a textile surface or a surface on dishes.

37. In some embodiments of the method of any of paragraphs 34-36 the composition further comprises at least one additional enzymes selected from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, ß-glucanase, arabinosidase, hyaluronidase, chondroitinase, laccase, metalloproteinase, amadoriase, glucoamylase, arabinofuranosidase, phytase, isomerase, transferase, and an amylase other than the amylase of any one of paragraphs 1-21.

38. In another aspect, a method for saccharifying a composition comprising starch to produce a composition comprising glucose is provided, wherein the method comprises:

(i) contacting the solution comprising starch with effective amount of the variant amylase of any of the paragraphs 1-21; and (ii) saccharifying the solution comprising starch to produce the composition comprising glucose; wherein the variant amylase catalyzes the saccharification of the starch solution to glucose or other enriched carbohydrate syrups.

39. In some embodiments of the method of paragraph 38 the composition comprising starch comprises liquefied starch, gelatinized starch, granular starch, or starch heat-treated below its gelatinization temperature.

40. In some embodiments of the method of paragraph 38 or 39 the fermentation is a simultaneous saccharification and fermentation (SSF) reaction.

41. In some embodiments of the method of any of paragraphs 38-40 the method further comprises contacting a mash and/or a wort with an amylase.

42. In some embodiments, the method of any one of paragraphs 38-41 further comprises adding glucoamylase, hexokinase, xylanase, glucose isomerase, xylose isomerase, phosphatase, phytase, pullulanase, β-amylase, α-amylase that is not the variant α-amylase, protease, cellulase, hemicellulase, lipase, cutinase, isoamylase, redox enzyme, esterase, transferase, pectinase, alpha-glucosidase, beta-glucosidase, or a combination thereof, to the starch solution.

43. In some embodiments of the method of any one of paragraphs 38-42 the amylase is expressed and secreted by a host cell.

44. In some embodiments of the method of paragraph 43 the composition comprising starch is contacted with the host cell.

45. In some embodiments of the method of paragraph 43 or 44 the host cell further expresses and secretes one or more enzymes selected from the group consisting of glucoamylase, hexokinase, xylanase, glucose isomerase, xylose isomerase, phosphatase, phytase, pullulanase, β-amylase, α-amylase that is not the variant α-amylase, protease, cellulase, hemicellulase, lipase, cutinase, isoamylase, redox enzyme, esterase, transferase, pectinase, alpha-glucosidase, and beta-glucosidase.

46. In some embodiments of the method of any one of paragraphs 43-45 the host cell further expresses and secretes a glucoamylase.

47. In some embodiments of the method of any one of paragraphs 43-46 the host cell is capable of fermenting the composition.

48. In another aspect, a composition comprising glucose produced by the method of any one of paragraphs 38-47 is provided.

49. In another aspect, a liquefied starch produced by the method of any one of paragraphs 38-47 is provided.

50. In another aspect, a fermented beverage produced by the method of any one of paragraphs 38-47 is provided.

51. In another aspect, use of an amylase of any of paragraphs 1-21 in the production of a composition comprising glucose, in the production of a liquefied starch, in the production of a fermented beverage, in cleaning starchy stains, or in textile desizing, is provided.

52. In another aspect, a method of desizing a textile is provided, comprising contacting a desizing composition with a sized textile for a time sufficient to desire the textile, wherein the desizing composition comprises a variant α-amylase of any one of paragraphs 1-21.

53. In another aspect, an isolated polynucleotide encoding a polypeptide of any of paragraphs 1-21 is provided.

54. In another aspect, an expression vector comprising the polynucleotide of paragraph 53 is provided.

55. In another aspect, a host cell comprising the expression vector of paragraph 54 is provided 56. In another aspect, a polypeptide according to any one of paragraphs 1-21 encoded by a polynucleotide that hybridizes under stringent conditions to a polynucleotide complementary to the full-length of the polynucleotide of SEQ ID NO: 7, SEQ ID NO: 33, or SEQ ID NO: 38 is provided.

These and other aspects and embodiments of the compositions and methods will be apparent from the present description and drawings.

BRIEF DESCRIPTION OF THE DRAWINGS

FIG. 1 shows an amino acid sequence alignment of CspAmy2 α-amylase (SEQ ID NO: 1), PcuAmy1 α-amylase (SEQ ID NO: 3), and BASE α-amylase, using Clustal W with default parameters.

FIG. 11 is a graph showing the detergent stability of CspAmy2-v5, CspAmy2-v171, CspAmy2-v172, and ACE-QK.

FIG. 12 is a graph showing the relative cleaning performance of CspAmy2-v5 and STAINZYME® in a hand dishwashing application.

FIGS. 13A and 13B, are tables showing the compositions of WfK B citrate-based detergent (FIG. 13A) and WfK C phosphate-based detergent (FIG. 13B).

FIGS. 18 and 19 show the cleaning performance of CspAmy2-v6 (squares) compared to POWERASE® (diamonds), dosed at 0, 1, 2, 4, or 8 ppm in WfK C detergent against the mixed starch stain (FIG. 18) and the pasta stain (FIG. 19). CspAmy2-v6 clearly outperformed POWERASE® against both stains.

FIG. 25 is a table showing the PI values for C16F variants having different pairwise combinations of mutations at positions G476 and G477, relative to a C16F control, in a corn starch microswatch assay. PI values for revertants (i.e., G476G and G477G) are empirically determined.

FIG. 26 is a table showing the PI values for C16F variants having different pairwise combinations of mutations at positions G476 and G477, relative to a C16F control, in a corn amylose hydrolysis assay. PI values for revertants (i.e., G476G and G477G) are empirically determined.

DETAILED DESCRIPTION

Figure 2:
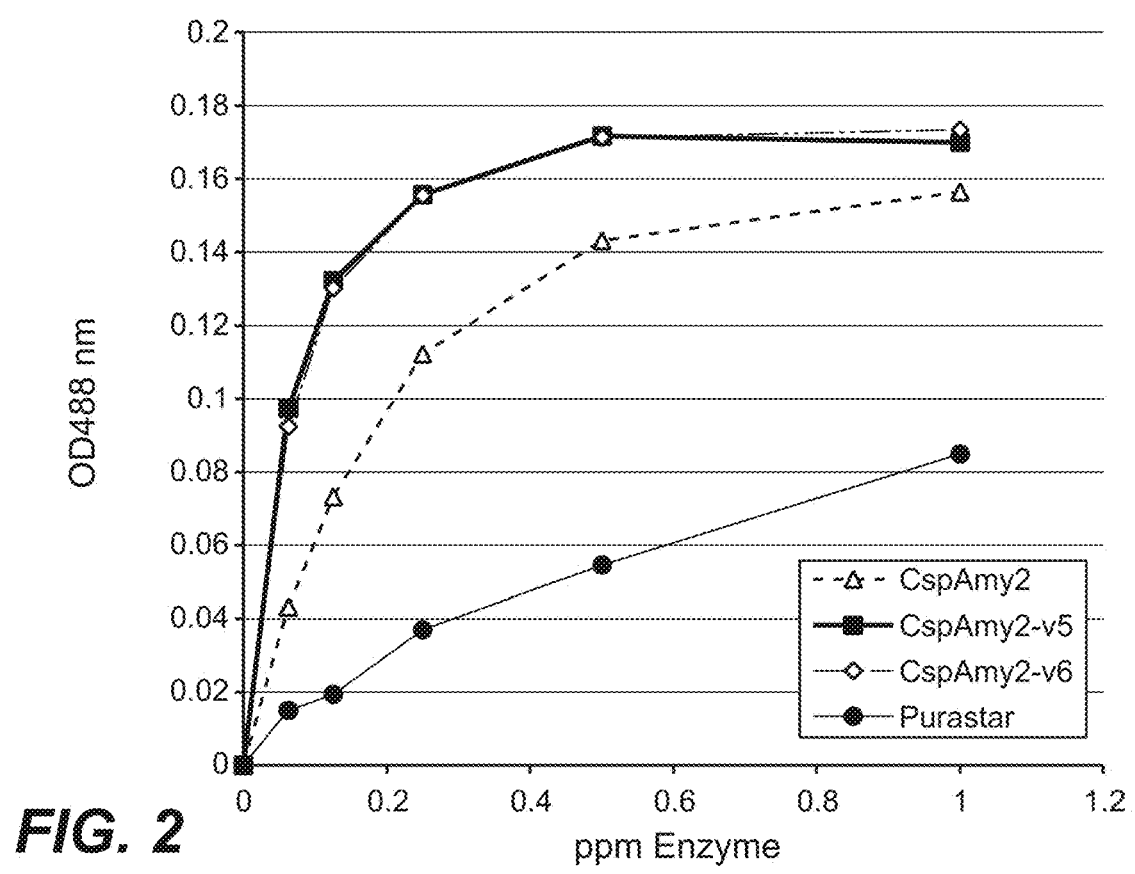
FIG. 2 is a graph showing the cleaning benefit of different doses of CspAmy2-v5 and CspAmy2-v6 on CS-28 rice starch at pH 8.

Described are compositions and methods relating to variant amylase enzymes. The variants were discovered by a combination of experimental approaches, as detailed in the appended Examples. The approaches include the use of site evaluation libraries (SELs) and structure-based analysis. Exemplary applications for the variant amylase enzymes are for starch liquefaction and saccharification, for cleaning starchy stains in laundry, dishwashing, and other applications, for textile processing (e.g., desizing), in animal feed for improving digestibility, and and for baking and brewing. These and other aspects of the compositions and methods are described in detail, below.

Prior to describing the various aspects and embodiments of the present compositions and methods, the following definitions and abbreviations are described.

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

| | |
|---|---|
| ABTS | 2,2-azino-bis-3-ethylbenzothiazoline-6-sulfonic acid |
| AE or AEO | alcohol ethoxylate |
| AES or AEOS | alcohol ethoxysulfate |
| AkAA | *Aspergillus kawachii* α-amylase |
| AnGA | *Aspergillus niger* glucoamylase |
| AOS | α-olefinsulfonate |
| AS | alkyl sulfate |
| cDNA | complementary DNA |
| ct/kg | cents/kg (US currency) |
| CMC | carboxymethylcellulose |
| DE | dextrose equivalent |
| DNA | deoxyribonucleic acid |
| DPn | degree of saccharide polymerization having n subunits |
| ds or DS | dry solids |
| DTMPA | diethylenetriaminepentaacetic acid |
| EC | Enzyme Commission |
| EDTA | ethylenediaminetetraacetic acid |
| EO | ethylene oxide (polymer fragment) |
| EOF | end of fermentation |
| FH | French hardness |
| GA | glucoamylase |
| GAU/g ds | glucoamylase activity unit/gram dry solids |
| GH | general hardness |
| HDL | high density liquid detergent |
| HDD | heavy duty powder detergent |
| HSG | high suds granular detergent |

-continued

| HFCS | high fructose corn syrup |
| HgGA | *Humicola grisea* glucoamylase |
| IPTG | isopropyl β-D-thiogalactoside |
| IRS | insoluble residual starch |
| kDa | kiloDalton |
| LAS | linear alkylbenzenesulfonate |
| LAT, BLA | *B. licheniformis* amylase |
| MW | molecular weight |
| MWU | modified Wohlgemuth unit; $1.6 \times 10^{-5}$ mg/MWU = unit of activity |
| NCBI | National Center for Biotechnology Information |
| NOBS | nonanoyloxybenzenesulfonate |
| NTA | nitriloacetic acid |
| OxAm | Purastar HPAM 5000L (Danisco US Inc.) |
| PAHBAH | p-hydroxybenzoic acid hydrazide |
| PEG | polyethyleneglycol |
| pI | isoelectric point |
| PI | performance index |
| ppm | parts per million, e.g., μg protein per gram dry solid |
| PVA | poly(vinyl alcohol) |
| PVP | poly(vinylpyrrolidone) |
| RCF | relative centrifugal/centripetal force (i.e., x gravity) |
| RNA | ribonucleic acid |
| SAS | alkanesulfonate |
| SDS-PAGE | sodium dodecyl sulfate polyacrylamide gel electrophoresis |
| SSF | simultaneous saccharification and fermentation |
| SSU/g solid | soluble starch unit/gram dry solids |
| sp. | species |
| TAED | tetraacetylethylenediamine |
| Tm | melting temperature |
| TrGA | *Trichoderma reesei* glucoamylase |
| w/v | weight/volume |
| w/w | weight/weight |
| v/v | volume/volume |
| wt % | weight percent |
| ° C. | degrees Centigrade |
| H$_2$O | water |
| dH$_2$O or DI | deionized water |
| dIH$_2$O | deionized water, Milli-Q filtration |
| g or gm | grams |
| μg | micrograms |
| mg | milligrams |
| kg | kilograms |
| μL and μl | microliters |
| mL and ml | milliliters |
| mm | millimeters |
| μm | micrometer |
| M | molar |
| mM | millimolar |
| μM | micromolar |
| U | units |
| sec | seconds |
| min(s) | minute/minutes |
| hr(s) | hour/hours |
| DO | dissolved oxygen |
| Ncm | Newton centimeter |
| ETOH | ethanol |
| eq. | equivalents |
| N | normal |
| uPWA | variant α-amylase derived from *Pyrococcus woesei* |
| PWA | α-amylase from *Pyrococcus woesei* |
| MWCO | molecular weight cut-off |
| SSRL | Stanford Synchrotron Radiation Lightsource |
| PDB | Protein Database |
| CAZy | Carbohydrate-Active Enzymes database |
| Tris-HCl | tris(hydroxymethyl)aminomethane hydrochloride |
| HEPES | 4-(2-hydroxyethyl)-1-piperazineethanesulfonic acid |

1.2. Definitions

The terms "amylase" or "amylolytic enzyme" refer to an enzyme that is, among other things, capable of catalyzing the degradation of starch. α-Amylases are hydrolases that cleave the α-D-(1→4) O-glycosidic linkages in starch. Generally, α-amylases (EC 3.2.1.1; α-D-(1→4)-glucan glucano-hydrolase) are defined as endo-acting enzymes cleaving α-D-(1→4) O-glycosidic linkages within the starch molecule in a random fashion yielding polysaccharides containing three or more (1-4)-α-linked D-glucose units. In contrast, the exo-acting amylolytic enzymes, such as 0-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

"Enzyme units" herein refer to the amount of product formed per time under the specified conditions of the assay. For example, a "glucoamylase activity unit" (GAU) is defined as the amount of enzyme that produces 1 g of glucose per hour from soluble starch substrate (4% DS) at 60° C., pH 4.2. A "soluble starch unit" (SSU) is the amount of enzyme that produces 1 mg of glucose per minute from soluble starch substrate (4% DS) at pH 4.5, 50° C. DS refers to "dry solids."

The term "starch" refers to any material comprised of the complex polysaccharide carbohydrates of plants, comprised of amylose and amylopectin with the formula (C6H10O5)x, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The term "starch" includes granular starch. The term "granular starch" refers to raw, i.e., uncooked starch, e.g., starch that has not been subject to gelatinization.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present α-amylases, "activity" refers to α-amylase activity, which can be measured as described, herein.

The term "performance benefit" refers to an improvement in a desirable property of a molecule. Exemplary performance benefits include, but are not limited to, increased hydrolysis of a starch substrate, increased grain, cereal or other starch substrate liquefaction performance, increased cleaning performance, increased thermal stability, increased detergent stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

The terms "protease" and "proteinase" refer to an enzyme protein that has the ability to perform "proteolysis" or "proteolytic cleavage" which refers to hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450, both of which are incorporated herein by reference). The pNA assay (See e.g., Del Mar et al., Anal. Biochem. 99:316-320 [1979]) also finds use in determining the active enzyme concentration for fractions collected during gradient elution. This assay measures the rate at which p-nitroaniline is released as the enzyme hydrolyzes a soluble synthetic peptide substrate, such as succinyl-alanine-alanine-proline-phenylalanine-p-nitroanilide (suc-AAPF-pNA), and cleavage occurs between the C-terminal amino acid (phenylalanine) and the p-NA, causing the production of yellow color from the hydrolysis reaction, which is measured at 410 nm on a spectrophotometer and is proportional to the active enzyme concentration. Measurement of the color change allows calculation of the rate of the reaction. In addition, absorbance measurements at 280 nanometers (nm) can be used to determine the total protein concentration. The active enzyme/total protein ratio gives the enzyme purity when a reference standard is used.

The terms "serine protease" refers to enzymes that cleave peptide bonds in proteins, in which enzymes serine serves as the nucleophilic amino acid at the enzyme active site. Serine proteases fall into two broad categories based on their structure: chymotrypsin-like (trypsin-like) or subtilisin-like. Most commonly used in laundry and dishwashing detergents are serine protease, particularly subtilisins.

The term "TIM barrel" refers to a three dimensional polypeptide structure that include eight α-helices and eight parallel β-strands that alternate along the peptide backbone.

The term "surface-exposed" with respect to an amino acid residue in a polypeptide refers to a residue that is on the exterior surface of a polypeptide when the polypeptide is intact and properly folded, i.e., not denatured or fragmented. In the case of an α-amylase, the structure is referred to as a TIM barrel.

The term "non-canonical" with reference to an amino acid residue in a polypeptide refers to a residue that is not normally found at a given position based on amino acid sequence alignments of similar molecules using Clustal W with default parameter. In some cases, the particular residue is found at a given position in only 1 in 10, 1 in 20, 1 in 30, 1 in 50, or even 1 in 100 similar molecules.

"Combinatorial variants" are variants comprising two or more mutations, e.g., 2, 3, 4, 5, 6, 7, 8, 9, 10, or more, substitutions, deletions, and/or insertions.

"Combinable mutations" are mutations at any amino acid position that can be used to make combinatorial variants. Combinable mutations improve at least one desired property of the molecule (in this case, an amylase), while not significantly decreasing either expression, activity, or stability.

Terms, such as "a remaining non-G residue in the calcium-binding loop," "a non-G amino acid residue remaining in the calcium-binding loop," and similar terms, refer to an amino acid residue in the calcium-binding loop of a variant α-amylase, which remains in the variant following a deletion of at least one amino acid residue in the calcium-binding loop of a parent α-amylases, and which is not a glycine residue. The non-G residue may be a member of an "XG" pair, of which there are two in most α-amylases, and may be the remaining non-G residue following a pair-wise deletion of one of the two XG residue pairs in the calcium binding loop of a parent α-amylase.

A "stabilizing interaction" between the residue at position 132 (using SEQ ID NO: 1 for numbering) and the remaining non-G residue in the $X_1G/S_1X_2G_2$ motif (corresponding to residues at positions 178-181 of SEQ ID NO: 1) refers to a hydrogen bond or a salt bridge formed between the side chains of the subject amino acid residues. The stabilization can result from charge balancing the interacting residues, such that if one residue is positively charged at a preselected pH, the other is negatively charged, and the overall charge is zero.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an amylase is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life (t1/2) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na3 citrate, pH 7.0). Hybridized, duplex nucleic acids are characterized by a melting temperature (Tm), where one half of the hybridized nucleic acids are unpaired with the complementary strand. Mismatched nucleotides within the duplex lower the Tm. A nucleic acid encoding a variant α-amylase may have a Tm reduced by 1° C.-3° C. or more compared to a duplex formed between the nucleotide of SEQ ID NO: 2 and its identical complement.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/ mg of protein.

As used herein, "water hardness" is a measure of the minerals (e.g., calcium and magnesium) present in water.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric 5/8" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

"A cultured cell material comprising an amylase" or similar language, refers to a cell lysate or supernatant (including media) that includes an amylase as a component. The cell material may be from a heterologous host that is grown in culture for the purpose of producing the amylase.

"Percent sequence identity" means that a particular sequence has at least a certain percentage of amino acid residues identical to those in a specified reference sequence, when aligned using the CLUSTAL W algorithm with default parameters. See Thompson et al. (1994) Nucleic Acids Res. 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDOEKR |
| Use negative matrix: | OFF |
| Toggle Residue specific penalties: | ON |
| Toggle hydrophilic penalties: | ON |
| Toggle end gap separation penalty | OFF. |

Deletions are counted as non-identical residues, compared to a reference sequence. Deletions occurring at either termini are included. For example, a variant with five amino acid deletions of the C-terminus of the mature CspAmy2 polypeptide of SEQ ID NO: 1 would have a percent sequence identity of 99% (612/617 identical residues×100, rounded to the nearest whole number) relative to the mature polypeptide. Such a variant would be encompassed by a variant having "at least 99% sequence identity" to a mature amylase polypeptide.

"Fused" polypeptide sequences are connected, i.e., operably linked, via a peptide bond between two subject polypeptide sequences.

The term "filamentous fungi" refers to all filamentous forms of the subdivision Eumycotina, particularly Pezizomycotina species.

The term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

The term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

An "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, India pale ale, lager, pilsner, bitter, Happoshu (second beer), third beer, dry beer, near beer, light beer, low alcohol beer, low calorie beer, porter, bock, dopplebock, stout, porter, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% to the referenced value.

2. α-Amylase Variants

An aspect of the present compositions and methods is variant amylase enzymes that include combinations of mutations that improve their performance in industrial applications. The combinatorial variants were initially discovered using an α-amylase from *Cytophaga* sp. (herein, "CspAmy2 amylase"), which was previously described by Jeang, C-L et al. ((2002) *Applied and Environmental Microbiology,* 68:3651-54). The amino acid sequence of the mature form of the CspAmy2 α-amylase polypeptide is shown below as SEQ ID NO: 1:

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRNQETS GEYNIQAWTG FNFPGRGTTY SNFKWQWFHF

DGTDWDQSRS LSRIFKFRGT GKAWDWEVSS ENGNYDYLMY

ADIDYDHPDV VNEMKKWGVW YANEVGLDGY RLDAVKHIKF

SFLKDWVDNA RAATGKEMFT VGEYWQNDLG ALNNYLAKVN

YNQSLFDAPL HYNFYAASTG GGYYDMRNIL NNTLVASNPT

KAVTLVENHD TQPGQSLEST VQPWFKPLAY AFILTRSGGY

PSVFYGDMYG TKGTTTREIP ALKSKIEPLL KARKDYAYGT

QRDYIDNPDV IGWTREGDST KAKSGLATVI TDGPGGSKRM

YVGTSNAGEI WYDLTGNRTD KITIGSDGYA TFPVNGGSVS

VWVQQ
```

In SEQ ID NO: 1, R178 and G179 are underlined. A variant of the *Cytophaga* sp. α-amylase having a deletion of both R178 and G179 (herein, "CspAmy2-v1") has also been described (Shiau, R-J. et al. (2003) *Applied and Environmental Microbiology,* 69:2383-85). The amino acid sequence of the mature CspAmy2-v1 α-amylase polypeptide is shown below as SEQ ID NO: 2:

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRNQETS GEYNIQAWTG FNFPGRGTTY SNFKWQWFHF

DGTDWDQSRS LSRIFKFTGK AWDWEVSSEN GNYDYLMYAD

IDYDHPDVVN EMKKWGVWYA NEVGLDGYRL DAVKHIKFSF

LKDWVDNARA ATGKEMFTVG EYWQNDLGAL NNYLAKVNYN

QSLFDAPLHY NFYAASTGGG YYDMRNILNN TLVASNPTKA

VTLVENHDTQ PGQSLESTVQ PWFKPLAYAF ILTRSGGYPS
```

```
                        -continued
VFYGDMYGTK GTTTREIPAL KSKIEPLLKA RKDYAYGTQR

DYIDNPDVIG WTREGDSTKA KSGLATVITD GPGGSKRMYV

GTSNAGEIWY DLTGNRTDKI TIGSDGYATF PVNGGSVSVW

VQQ
```

Using SEQ ID NO: 2 as a starting point, a number of combinatorial CspAmy2 variants were initially made and tested as described in the Examples section. The best performing variants generally included a stabilizing mutation at an amino acid position corresponding to either E187 or S241, but not both positions, and at least one additional performance-enhancing mutation at amino acid position selected from the group consisting of N126, Y150, F153, L171, T180, and, I203 (using SEQ ID NO: 1 for numbering).

It is known that many bacterial (and other) α-amylases share the same fold, often share significant amino acid sequence identity, and sometimes benefit from the same mutations. In the present case, corresponding amino acid positions were identified by amino acid sequence alignment in an α-amylase from *Paenibacillus curdlanolyticus* (i.e., PcuAmy1; SEQ ID NO: 3) and a C-terminal-truncated version of the *Bacillus* sp. TS-23 α-amylase (i.e., "BASE;" SEQ ID NO: 5; see, e.g., US20120045817 and WO2010/ 115028).

The amino acid sequence of the mature form of the PcuAmy1 α-amylase polypeptide is shown below as SEQ ID NO: 3:

```
ADNGTIMQYF EWYLPNDGAH WNRLNNDAQN LKNVGITAVW

IPPAYKGGSS ADVGYGVYDT YDLGEFNQKG TVRTKYGTKS

ELISAVNNLH AKGIAVYGDV VLNHRMNADA TELVDAVEVD

PNNRNVETTS TYQIQAWTQY DFPGRGNTYS SFKWRWYHFD

GVDWDQSRGL NRIYKLRGDG KDWDWEVDSE YGNYDYLMGA

DLDFNHPDVV NETKTWGKWF VNTVNLDGVR LDAVKHIKFD

FMRDWVNNVR STTGKNLFAV GEYWHYDVNK LNSYITKTNG

TMSLFDVPLH FRFYDASNGG GGYDMRNLLN NTLMSSNPMK

AVTFVENHDT QPTQALQSTV QSWFKPLAYA TILTREQGYP

CVFYGDYYGT SDGKISSYKP IMDKLLNARK VYAYGTQRDY

FDHPDIVGWT REGDAAHAGS GLATLITDGP GGSKWMYVGT

SKAGQVWTDK TGNRSGTVTI DANGWGNFWV NGGSVSVWAK
```

In SEQ ID NO: 3, R177 and R178 are underlined. The amino acid sequence of a variant form of PcuAmy1 α-amylase having a deletion of both R177 and R178 (herein, "PcuAmy1-v1") is shown below as SEQ ID NO: 4:

```
ADNGTIMQYF EWYLPNDGAH WNRLNNDAQN LKNVGITAVW

IPPAYKGGSS ADVGYGVYDT YDLGEFNQKG TVRTKYGTKS

ELISAVNNLH AKGIAVYGDV VLNHRMNADA TELVDAVEVD

PNNRNVETTS TYQIQAWTQY DFPGRGNTYS SFKWRWYHFD

GVDWDQSRGL NRIYKLDGKD WDWEVDSEYG NYDYLMGADL
```

```
                     -continued
DFNHPDVVNE TKTWGKWFVN TVNLDGVRLD AVKHIKFDFM

RDWVNNVRST TGKNLFAVGE YWHYDVNKLN SYITKTNGTM

SLFDVPLHFR FYDASNGGGG YDMRNLLNNT LMSSNPMKAV

TFVENHDTQP TQALQSTVQS WFKPLAYATI LTREQGYPCV

FYGDYYGTSD GKISSYKPIM DKLLNARKVY AYGTQRDYFD

HPDIVGWTRE GDAAHAGSGL ATLITDGPGG SKWMYVGTSK

AGQVWTDKTG NRSGTVTIDA NGWGNFWVNG GSVSVWAK
```

The amino acid sequence of a C-terminal-truncated version of the *Bacillus* sp. TS-23 α-amylase (herein, "BASE;" see, e.g., US20120045817 and WO2010/115028) is shown, below as SEQ ID NO: 5:

```
NTAPINETMM QYFEWDLPND GTLWTKVKNE AANLSSLGIT

ALWLPPAYKG TSQSDVGYGV YDLYDLGEFN QKGTIRTKYG

TKTQYIQAIQ AAKAAGMQVY ADVVFNHKAG ADGTEFVDAV

EVDPSNRNQE TSGTYQIQAW TKFDFPGRGN TYSSFKWRWY

HFDGTDWDES RKLNRIYKFR STGKAWDWEV DTENGNYDYL

MFADLDMDHP EVVTELKNWG TWYVNTTNID GFRLDAVKHI

KYSFFPDWLT YVRNQTGKNL FAVGEFWSYD VNKLHNYITK

TNGSMSLFDA PLHNNFYTAS KSSGYFDMRY LLNNTLMKDQ

PSLAVTLVDN HDTQPGQSLQ SWVEPWFKPL AYAFILTRQE

GYPCVFYGDY YGIPKYNIPG LKSKIDPLLI ARRDYAYGTQ

RDYIDHQDII GWTREGIDTK PNSGLAALIT DGPGGSKWMY

VGKKHAGKVF YDLTGNRSDT VTINADGWGE FKVNGGSVSI

WVAK
```

In SEQ ID NO: 5, R180 and S181 are underlined. The amino acid sequence of a variant form of BASE α-amylase having a deletion of both R180 and S181 (herein, "ACE") is shown, below as SEQ ID NO: 6:

```
NTAPINETMM QYFEWDLPND GTLWTKVKNE AANLSSLGIT

ALWLPPAYKG TSQSDVGYGV YDLYDLGEFN QKGTIRTKYG

TKTQYIQAIQ AAKAAGMQVY ADVVFNHKAG ADGTEFVDAV

EVDPSNRNQE TSGTYQIQAW TKFDFPGRGN TYSSFKWRWY

HFDGTDWDES RKLNRIYKFT GKAWDWEVDT ENGNYDYLMF

ADLDMDHPEV VTELKNWGTW YVNTTNIDGF RLDAVKHIKY

SFFPDWLTYV RNQTGKNLFA VGEFWSYDVN KLHNYITKTN

GSMSLFDAPL HNNFYTASKS SGYFDMRYLL NNTLMKDQPS

LAVTLVDNHD TQPGQSLQSW VEPWFKPLAY AFILTRQEGY

PCVFYGDYYG IPKYNIPGLK SKIDPLLIAR RDYAYGTQRD

YIDHQDIIGW TREGIDTKPN SGLAALITDG PGGSKWMYVG

KKHAGKVFYD LTGNRSDTVT INADGWGEFK VNGGSVSIWV

AK
```

An amino acid sequence alignment of CspAmy2 (SEQ ID NO: 1), PcuAmy1 (SEQ ID NO: 3), and BASE (SEQ ID NO: 5), using Clustal W with default parameters, is shown in FIG. 1. Positions N126, Y150, F153, L171, R178, G179, T180, E187, 1203, and S241 in CspAmy2 correspond to positions N125, Y149, F152, L170, R177, G178, D179, E186, L202, and D240 in PcuAmy1, respectively, and positions N128, Y152, F155, L173, R180, S181, T182, E189, L205, and S243, respectively in BASE. Numbering for other positions through out the molecules can be determined using the alignment and information, herein.

Based on experimental data obtained using the aforementioned three parent α-amylases, embodiments of the present variant α-amylases include variants having a mutation at an amino acid position corresponding to E187 or S241 in combination with at least one mutation at an amino acid position corresponding to a position selected from N126, Y150, F153, L171, T180, and 1203 (using SEQ ID NO: 1 for numbering), wherein the mutations provide at least one performance benefit to the resulting variant.

Referring to SEQ ID NO: 1 for numbering, exemplary mutations at amino acid position E187 include E187V and E187P. Exemplary mutations at amino acid position S241 include S241Q and S241A. In some embodiments, mutations are made in only one of these positions. Exemplary mutations at amino acid position N126 includes N126Y. Exemplary mutations at amino acid position Y150 include Y150F, Y150H, and Y150W. Exemplary mutations at amino acid position F153 include F153H, F153W, and F153Y. Exemplary mutations at amino acid position L171 include L171F, L171G, L171I, L171M, L171R, L171V, L171W, L171Y, L171H, L171K, L171N, L171Q, and L171S. Exemplary mutations at amino acid position T180 include T180D and T180H. Exemplary mutations at amino acid position 1203 includes 1203C, 1203V, 1203F, 1203L, 1203M, and 1203Y.

In some embodiments, the variant α-amylases further include a mutation in amino acid residues corresponding to E132, Q167, A277, and/or T400, using SEQ ID NO: 1 for numbering. Exemplary mutations at amino acid position E132 include E132A, E132C, E132D, E132F, E132G, E132H, E132I, E132K, E132L, E132M, E132N, E132P, E132Q, E132R, E132V, and E132W. Exemplary mutations at amino acid position Q167 include Q167A, Q167D, Q167E, Q167G, Q167H, Q167K, Q167M, Q167N, Q167P, Q167S, Q167T, and Q167V. Exemplary mutations at amino acid position A277 include A277C, A277D, A277E, A277F, A277G, A277I, A277K, A277L, A277M, A277N, A277Q, A277R, A277S, A277T, A277V, A277W, and A277Y. Exemplary mutations at amino acid position T400 include T400A, T400C, T400D, T400F, T400G, T400I, T400K, T400L, T400M, T400N, T400Q, T400R, T400W, and T400Y.

In some embodiments, the variant α-amylases further include a mutation in an amino acid residue corresponding to G476, using SEQ ID NO: 1 for numbering. Exemplary mutations at amino acid position G476 include G476A, G476C, G476H, G476K, G476N, G476P, G476Q, G476R, G476S, G476T, G476V, and G476Y.

In some embodiments, the variant α-amylases are those that include, or further include, mutations in both amino acid residues corresponding to G476 and G477, using SEQ ID NO: 1 for numbering. Surprisingly, experimental evidence suggests that any combination of residues at these positions, other than two adjacent glycines as are present in many naturally occurring α-amylases, increases improve starch hydrolysis activity, particularly in cleaning applications.

In some embodiments, the variant α-amylases further include mutations in amino acid residues corresponding to R458, T459, and/or D460. Exemplary mutations are R458N, T459S, and D460T, respectively.

In some embodiments, the variant α-amylases further include a deletion in the $X_1G/S_1X_2G_2$ motif adjacent to the calcium-binding loop corresponding to R178, G179, T180, and G181, using SEQ ID NO: 1 for numbering. In some embodiments, the variant α-amylases include adjacent, pairwise deletions of amino acid residues corresponding to R178 and G179, or T180 and G181. A deletion in amino acid residues corresponding to R178 and G179 may be referred to as "ΔRG," while a deletion in amino acid residues corresponding to T180 and G181 "ΔTG." This nomenclature will naturally change depending on the amino acid residues originally present in the parent molecule.

In some embodiments, the variant α-amylases include mutations at positions corresponding to E132 and/or T180 (using SEQ ID NO: 1 for numbering), in combination with an RG-deletion or a TG-deletion (or equivalent deletion based on the sequence of the parent α-amylases), such that a stabilizing interaction can occur between the remaining non-G residue in the $X_1G/S_1X_2G_2$ motif and the residue at position 132. In some embodiments, the residue at position 132 is negatively charged (i.e., D or E) and the remaining non-G residue is positively charged (i.e., H, R, or K). In some embodiments, the residue at position 132 is positively charged (i.e., H, R, or K) and the remaining non-G residue is negatively charged (i.e., D or E).

Exemplary combinations of mutation (using SEQ ID NO: 1 for numbering) are shown, below:

$E187P + I203Y + G476K$(i.e., $CspAmy2$-$v$ 5);

$E187P + I203Y + G476K + R458N + T459S + D460T$(i.e., $CspAmy2$-$v$ 6);

$T180D + E187P + I203Y + G476K$(i.e., $CspAmy2$ $v$ 171);

$N126Y + T180D + E187P + I203Y + G476K$(i.e., $CspAmy2v$ 172);

$N126Y + T180D + E187P + I203Y + Y303D + G476T + G477E$, (i.e., $CspAmy2v$ 179);

$N126Y + T180D + E187P + I203Y + Y303D + N475E + G477Q$, (i.e., $CspAmy2v$ 180);

$N126Y + T180D + E187P + I203Y + Y303R + N475E + G476T + G477R$, (i.e., $CspAmy2v$ 181);

$T038N + N88H + N126Y + T129I + N134M + F153W + L171R + T180D + E187P + I203Y + G476K + G477E$, (i.e., $CspAmy2v$ 186);

$N126Y + E132H + T180D + E187P + I203Y + Y303D + G476T + G477E$, (i.e., $CspAmy2v$ 191);

$N126Y + E187P + I203Y$(i.e., $CspAmy2$-$v$ C16A);

$N126Y + I203Y + S241Q$(i.e., $CspAmy2$-$v$ C16B);

$N126Y + T180H + E187P + I203Y$(i.e., $CspAmy2$-$v$ C16C);

$N126Y + T180H + I203Y + S241Q$(i.e., $CspAmy2$-$v$ C16D);

$N126Y + F153W + T180H + E187P + I203Y$(i.e., $CspAmy2$-$v$ C16E);

$N126Y + F153W + T180H + I203Y + S241Q$(i.e., $CspAmy2$-$v$ C16F);

$N126Y + Y150H + F153W + L171N + E187P + I203Y$(i.e., $CspAmy2$-$v$ C16G);

$N126Y + Y150H + F153W + L171N + I203Y + S241Q$(i.e., $CspAmy2$-$v$ C16H);

$N126Y + Y150H + F153W + L171N + T180H + E187P + I203Y$(i.e., $CspAmy2$-$v$ C16I);

-continued $N126Y + Y150H + F153W + L171N + T180H + I203Y + S241Q$(i.e., $CspAmy2$-$v$ C16J);

$N126Y + F153W + T180D + I203Y + S241Q$(i.e., $CspAmy2$-$v$ C18P);

$N126Y + E132H + F153W + T180D + I203Y + S241Q + A277F$(i.e., $CspAmy2$-$v$ C25F);

$N126Y + E132H + F153W + Q167E + T180D + I203Y + S241Q + A277F$(i.e., $CspAmy2$-$v$ C25B); and $N126Y + E132H + F153W + Q167E + T180D + I203Y + S241Q + A277F + T400K$(i.e., $CspAmy2$-$vC25A$).

All the above combinations of mutation are contemplated for use in conjunction with the aforementioned deletions at positions corresponding to R178, G179, T180, and/or G181. Such deletions may be naturally occurring, as in the case of *Bacillus lichemformis* α-amylase.

In addition to the aforementioned mutations, the PcuAmy1 variants may further include mutations at position T333, A335, and Q337E (using SEQ ID NO: 3 numbering). These positions are in a surface-exposed loop and mutations at these positions, particularly at T333, impart protease resistance to PcuAmy1 but do not otherwise affect performance. These mutations also appear to be fully compatible with other mutations. A further mutation in PcuAmy1 variants is N205, which mutation changes the wild-type N residue to D. D is the residue that typically occupies this position in α-amylases.

Accordingly, the present α-amylases include the all the exemplary combinations of mutations shown above in the context of CspAmy2, as well as the following exemplary combinations (using SEQ ID NO: 3 numbering) are shown, below:

$N125Y + E186P + T333G + A335S + Q337E + G472K$(i.e., $PcuAmy1$-$v$ 1A);

$N125Y + F152W + E186P + T333G + A335S + Q337E + G472K$(i.e., $PcuAmy1$-$v6$);

$N125Y + F152W + E186P + T333G + A335S + Q337E + G472R + G473R$(i.e., $PcuAmy1$-$v8$); and $N125Y + F152W + E186P + N205D + T333G + A335S + Q337E + G472K$(i.e., $PcuAmy1$-$v16$).

All the above combinations of mutations are contemplated for use in conjunction with deletions at positions corresponding to R177, G178, D179, and/or G180, and such deletions may be naturally occurring, as in the case of *Bacillus licheniformis* α-amylase.

The present variants can also be described in terms of BASE numbering (i.e., SEQ ID NO: 5), for example, $N128Y + E189P + G475R$(i.e., BASE-$V28$);

$F155W + E189P + G475R$(i.e., BASE-$V29$);

$T134E + T182H + E189P + G475R$(i.e., BASE-$V30$);

$N128Y + T134E + T182H + E189P + G475R$(i.e., BASE-$V31$);

$N128Y + F155W + E189P + G475R$(i.e., BASE-$V32$);

-continued

T134E + F155W + T182H + E189P + G475R(i.e., BASE-V33);

N128Y + T134E + F155W + T182H + E189P + G475R(i.e., BASE-V34);

N128Y + T134H + F155W +

T182D + E189P + G475R(i.e., BASE-V35); and

N128Y + T134E + F155W + T182G + E189P + G457R(i.e., BASE-V36).

All the above combinations of mutations are contemplated for use in conjunction with deletions at positions corresponding to R180, S181, T182, and/or G183, and such deletions may be naturally occurring, as in the case of *Bacillus licheniformis* α-amylase.

Corresponding amino acid positions in other α-amylases be identified by amino acid sequence alignment using CspAmy2 (SEQ ID NO: 1), PcuAmy1 (SEQ ID NO: 3), or BASE (SEQ ID NO: 5), using Clustal W with default parameters. α-amylases in which the foregoing mutations are likely to produce a performance benefit include those having a similar fold and/or having 60% or greater amino acid sequence identity to any of the well-known *Bacillus* amylases (e.g., from *B. licheniformis* (i.e., BLA and LAT), *B. stearothermophilus* (i.e., BSG), and *B. amyloliquifaciens* (i.e., P00692, BACAM, and BAA)), Carbohydrate-Active Enzymes database (CAZy) Family 13 amylases, or any amylase that has heretofore been referred to by the descriptive term, "Termamyl-like." Exemplary α-amylases include but are not limited to those from *Bacillus* sp. SG-1, *Bacillus* sp. 707, *Bacillus* sp. DSM12368 (i.e., A7-7), *Bacillus* sp. DSM 12649 (i.e., AA560), *Bacillus* sp. SP722, *Bacillus megaterium* (DSM90 14), and KSM AP1378.

The reader will appreciate that where an α-amylase naturally has a mutation listed above (i.e., where the wild-type α-amylase already comprised a residue identified as a mutation), then that particular mutation does not apply to that α-amylase. However, other described mutations may work in combination with the naturally occurring residue at that position.

In some embodiments, the present α-amylase variants have the indicated combinations of mutations and a defined degree of amino acid sequence homology/identity to SEQ ID NO: 1, SEQ ID NO: 3, or SEQ ID NO: 5, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity.

In some embodiments, the present α-amylase variants have the indicated combinations of mutations and are derived from a parental amylase having a defined degree of amino acid sequence homology/identity to SEQ ID NO: 1, SEQ ID NO: 3, or SEQ ID NO: 5, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity.

In some embodiments, in addition to the mutations described above, the present α-amylases further include one or more mutations that provide a further performance benefit. Additional mutations that were experimentally determined to provide at least one performance advantage when combined with the aforementioned combinatorial variants include mutations at positions corresponding to 6, 7, 8, 11, 14, 15, 20, 21, 23, 26, 27, 28, 37, 38, 39, 40, 42, 45, 46, 48, 49, 50, 51, 52, 53, 54, 58, 61, 62, 68, 70, 71, 72, 73, 79, 80, 81, 82, 84, 85, 87, 88, 89, 92, 93, 94, 95, 96, 97, 98, 101, 108, 111, 112, 113, 114, 115, 116, 117, 118, 120, 122, 123, 124, 126, 127, 129, 130, 131, 132, 133, 134, 136, 137, 138, 140, 142, 143, 144, 147, 148, 149, 150, 151, 152, 153, 154, 155, 156, 158, 159, 165, 167, 168, 170, 171, 172, 175, 176, 177, 180, 181, 182, 187, 190, 191, 193, 199, 200, 201, 203, 206, 208, 210, 211, 212, 214, 215, 216, 219, 221, 223, 225, 226, 227, 235, 238, 239, 240, 241, 242, 243, 245, 246, 247, 248, 249, 250, 252, 253, 254, 256, 257, 258, 260, 261, 262, 266, 267, 268, 269, 270, 271, 273, 276, 277, 279, 280, 282, 284, 285, 286, 288, 296, 299, 300, 301, 302, 303, 304, 307, 308, 310, 311, 312, 313, 316, 317, 318, 320, 321, 325, 327, 335, 338, 342, 348, 349, 352, 356, 357, 360, 362, 363, 368, 369, 377, 381, 382, 383, 384, 385, 388, 390, 392, 394, 395, 396, 397, 398, 400, 401, 402, 403, 404, 405, 407, 408, 410, 414, 415, 416, 418, 419, 420, 421, 422, 423, 424, 426, 428, 429, 430, 431, 434, 435, 436, 439, 441, 442, 444, 445, 446, 447, 448, 449, 450, 451, 454, 455, 457, 460, 461, 462, 463, 464, 465, 466, 467, 469, 470, 471, 473, 474, 475, 476, 477, 479, 480, 481, 482, 483, and 484, using SEQ ID NO: 1 for numbering. Specific mutations are T6A, T6D, T6E, T6G, T6K, T6M, T6N, T6Q, T6S, M7A, M7V, M8C, M8F, M8I, M8L, M8Y, F11V, Y14A, Y14I, Y14Q, Y14T, Y14V, V15C, V15D, V15I, V15N, V15T, Q20A, Q20C, Q20D, Q20H, Q20K, Q20M, Q20N, Q20R, Q20S, Q20Y, Q21F, Q21W, N23A, N23C, N23D, N23E, N23H, N23K, N23Q, N23R, N23S, N23T, N23V, R26C, R26E, R26G, R26K, R26M, R26S, R26T, T27A, T27C, T27D, T27E, T27F, T27H, T27I, T27K, T27L, T27M, T27N, T27Q, T27R, T27S, T27V, T27Y, D28A, D28C, D28T, I37F, I37V, T38D, T38N, A39L, V40A, V40C, V40D, V40G, V40H, V40I, V40K, V40M, V40P, V40Q, V40R, V40S, V40T, V40W, V40Y, T42A, T42C, T42I, T42M, T42V, A45C, A45G, Y46F, G48A, T49I, S50A, S50C, S50E, S50G, S50K, S50M, S50N, S50Q, S50R, S50T, S50Y, Q51C, Q51D, Q51E, Q51S, Q51V, A52C, A52D, A52E, A52F, A52G, A52H, A52K, A52L, A52M, A52R, A52S, A52T, A52V, A52Y, D53E, V54N, V54T, P58A, P58C, P58H, P58I, P58S, P58T, P58V, L61M, L61V, Y62A, Y62C, Y62D, Y62F, Y62G, Y62H, Y62I, Y62K, Y62L, Y62M, Y62N, Y62P, Y62Q, Y62R, Y62S, Y62V, N68C, N68D, N68E, N68F, N68H, N68L, N68P, N68Q, N68R, N68S, N68V, N68W, N68Y, K70R, G71A, G71C, G71D, G71E, G71K, G71R, G71S, T72G, T72S, V73S, T79F, T79I, T79L, T79M, T79N, T79S, T79Y, K80A, K80C, K80D, K80F, K80H, K80I, K80M, K80N, K80Q, K80R, K80S, K80T, K80V, K80Y, G81A, G81D, G81E, G81F, G81H, G81I, G81K, G81N, G81P, G81R, G81S, G81T, E82A, E82D, E82M, E82Q, K84A, K84C, K84E, K84I, K84Q, K84R, K84S, K84T, K84Y, S85A, S85C, S85D, S85E, S85G, S85H, S85I, S85L, S85M, S85N, S85Q, S85R, S85T, S85V, S85Y, V87I, V87T, N88C, N88D, N88E, N88G, N88H, N88I, N88K, N88L, N88M, N88Q, N88R, N88S, N88T, N88V, N88W, N88Y, T89A, T89D, T89E, T89F, T89H, T89I, T89K, T89L, T89M, T89N, T89Q, T89R, T89S, T89Y, S92A, S92C, S92D, S92E, S92F, S92G, S92H, S92L, S92M, S92N, S92Q, S92R, S92T, S92W, S92Y, N93A, N93C, N93E, N93F, N93H, N93I, N93K, N93L, N93Q, N93S, N93T, N93Y, G94A, G94C, G94N, I95M, Q96A, Q96E, Q96H, Q96I, Q96K, Q96L, Q96M, Q96N, Q96R, Q96V, Q96Y, V97I, V97T, Y98F, Y98I, Y98L, Y98V, V101C, V101T, G108A, G108S, Y111D, Y111E, Y111L, Y111N, Y111S, Y111T, Y111V, T112A,
T112F, T112H, T112I, T112K, T112L, T112M, T112N,
T112P, T112R, T112V, T112W, E113D, E113N, E113Q,
E113T, N114A, N114C, N114D, N114E, N114F, N114G,
N114H, N114I, N114L, N114P, N114Q, N114R, N114S,
N114T, N114V, N114W, N114Y, V115A, V15I, T116A,
T116C, T116D, T116G, T116H, T1161, T116K, T116N,
T116P, T116Q, T116R, T116S, A117C, A1171, A117S,
A117V, V118A, V118C, V118E, V118F, V118H, V1181,
V118L, V118M, V118N, V118Q, V118R, V118S, V118W,
V118Y, V120A, V120C, V1201, V120M, V120T, P122A,
P122D, P122E, P122G, P122H, P122N, P122R, P122S,
P122T, P122W, S123A, S123C, S123G, S123K, S123L,
N124A, N124D, N124F, N124G, N124L, N124R, N124S,
N124V, Y126A, Y126C, Y126D, Y126E, Y126G, Y126H,
Y126I, Y126K, Y126L, Y126M, Y126N, Y126Q, Y126R,
Y126S, Y126T, Y126V, Y126W, Q127A, Q127C, Q127D,
Q127E, Q127F, Q127H, Q1271, Q127K, Q127L, Q127M,
Q127N, Q127R, Q127S, Q127T, Q127V, Q127W, Q127Y,
T129A, T129C, T129D, T129E, T129F, T129G, T129I,
T129K, T129L, T129M, T129N, T129Q, T129R, T129S,
T129V, T129W, T129Y, S130A, S130G, S1301, S130K,
S130L, S130M, S130N, S130P, S130R, S130T, S130V,
S130W, G131A, G131C, G131D, G131F, G131H, G131I,
G131K, G131L, G131M, G131P, G131Q, G131V, G131W,
G131Y, E132A, E132C, E132D, E132F, E132G, E132H,
E132I, E132K, E132L, E132M, E132N, E132P, E132Q,
E132R, E132V, E132W, Y133A, Y133D, Y133E, Y133G,
Y133K, Y133L, Y133M, Y133R, Y133S, Y133T, Y133W,
N134A, N134D, N134F, N134G, N134H, N134I, N134K,
N134L, N134M, N134R, N134S, N134V, N134W, N134Y,
Q136A, Q136C, Q136D, Q136E, Q136F, Q136H, Q136K,
Q136L, Q136M, Q136N, Q136R, Q136S, Q136T, Q136V,
Q136W, Q136Y, A137S, A137T, A137V, W138F, W138Y,
G140A, G140M, N142F, N142K, N142L, N142M, N142P,
N142V, N142W, N142Y, F143H, F143Y, P144C, P144D,
P144E, P144G, P144H, P144I, P144K, P144L, P144M,
P144N, P144Q, P144S, P144T, P144Y, G147A, G147C,
G147H, G147K, G147L, G147M, G147N, G147Q, G147R,
T148A, T148D, T148E, T148F, T1481, T148K, T148L,
T148R, T148S, T148V, T148W, T149A, T149C, T149D,
T149E, T149F, T149H, T149K, T149L, T149M, T149N,
T149Q, T149V, T149W, T149Y, Y150H, S151A, S151E,
S151F, S151H, S1511, S151K, S151L, S151M, S151Q,
S151R, S151V, N152A, N152C, N152D, N152E, N152G,
N152H, N152K, N152M, N152P, N152Q, N152R, N152S,
N152T, W153F, W153H, W153Q, W153R, W153T, W153Y,
K154A, K154C, K154D, K154E, K154G, K154I, K154L,
K154M, K154N, K154R, K154T, K154Y, W155P, Q156A,
Q156D, Q156E, Q156F, Q156G, Q156H, Q156I, Q156L,
Q156M, Q156N, Q156R, Q156S, Q156Y, F158C, F158D,
F158K, F158L, F158M, F158N, F158P, F158Q, F158R,
F158S, F158V, H159M, H159Y, W165C, W165D, W165E,
W165F, W165H, W165I, W165K, W165L, W165M,
W165Q, W165R, W165T, W165Y, Q167A, Q167D, Q167E,
Q167G, Q167H, Q167K, Q167M, Q167N, Q167P, Q167S,
Q167T, Q167V, S168A, S168D, S168F, S168H, S168I,
S168K, S168M, S168N, S168Q, S168R, S168T, S168V,
S168W, S168Y, S170A, S170C, S170D, S170E, S170F,
S170L, S170M, S170N, S170Q, S170R, S170T, L171A,
L171C, L171F, L171G, L171H, L1711, L171N, L171Q,
L171R, L171T, L171V, L171W, L171Y, S172A, S172D,
S172H, S172R, S172T, F175M, F175Y, K176I, K176T,
F177L, F177V, F177W, D180A, D180C, D180F, D180G,
D180H, D180I, D180L, D180N, D180Q, D180R,
D180S, D180T, D180V, D180W, D180Y, G181A, G181C,
G181D, G181E, G181F, G181H, G181K, G181L, G181M, G181N, G181Q, G181R, G181S, G181T, G181V, G181Y,
K182A, K182P, E187D, E187I, E187K, E187M, E187N,
E187P, E187R, E187S, E187T, E187V, E187Y, S190A,
S190C, S190D, S190F, S190L, S190N, S190P, S190Q,
E191A, E191C, E191F, E191G, E191H, E1911, E191K,
E191N, E191Q, E191R, E191S, E191T, E191W, E191Y,
G193A, G193C, G193D, G193E, G193F, G193H, G193K,
G193L, G193M, G193N, G193Q, G193R, G193S, G193T,
G193V, G193W, M199L, Y200F, A201M, Y203I, Y203L,
Y203V, D206A, D206E, D206G, D206H, D206M, D206N,
D206Q, D206R, D206S, D206T, P208A, P208E, P208F,
P208I, P208K, P208L, P208T, P208V, P208Y, V210A,
V210E, V210H, V210K, V210N, V210Q, V210R, V210S,
V210T, V211A, V211E, V211H, V2111, V211Q, V211R,
N212E, N212F, N212G, N212L, N212M, N212R, N212V,
M214I, M214L, K215C, K215E, K215F, K215M, K215N,
K215R, K215Y, K216F, V219I, V219T, Y221F, Y2211,
Y221L, N223C, N223E, N2231, N223K, N223Q, N223R,
N223S, N223T, N223V, N223W, N223Y, V225A, V2251,
V225L, V225M, G226D, G226M, G226Q, G226R, G226S,
L227F, L2271, L227W, L227Y, V235A, I238A, I238L,
I238M, K239D, K239E, K239P, K239Q, K239R, K239S,
K239T, F240K, F240L, F240M, F240Q, F240R, Q241A,
Q241C, Q241D, Q241E, Q241G, Q241H, Q241K, Q241L,
Q241M, Q241N, Q241P, Q241R, Q241S, Q241T, Q241V,
Q241W, Q241Y, F242V, L243C, L243Y, D245A, D245C,
D245E, D245G, D245L, D245M, D245N, W246F, V247I,
V247L, D248E, D248H, D248N, D248T, D248V, N249A,
N249E, N249G, N249H, N249Q, N249Y, A250M, A250S,
A250V, A252C, A252D, A252E, A252G, A252H, A2521,
A252K, A252L, A252M, A252N, A252Q, A252S, A252V,
A252W, A252Y, A253E, A2531, A253K, A253L, A253M,
A253Q, A253S, A253T, A253V, A253Y, T254F, T254K,
T254S, K256A, K256M, K256N, K256S, E257Q, E257S,
M258L, T260A, T260C, T260S, T260V, V2611, V261W,
G262A, Q266A, Q266D, Q266E, Q266H, Q2661, Q266M,
Q266N, Q266S, Q266T, Q266V, Q266Y, N267H, N2671,
N267Q, N267R, N267S, N267T, N267V, N267Y, D268G,
D268N, L269C, L269D, L2691, L269K, L269Q, L269S,
L269T, L269Y, G270A, G270D, G270E, G270F, G270H,
G270I, G270L, G270M, G270Q, G270T, G270V, G270Y,
A271C, A271D, A271E, A271H, A271K, A271M, A271Q,
A271R, A271S, A271T, A271V, A271Y, N273C, N273G,
N273H, N273I, N273K, N273R, L276I, L276M, A277C,
A277D, A277E, A277F, A277G, A2771, A277K, A277L,
A277M, A277N, A277Q, A277R, A277S, A277T, A277V,
A277W, A277Y, V279C, V279T, N280A, N282S, N282T,
S284T, S284Y, L285A, L285C, L285I, L285V, F286M,
A288C, A296C, A296D, A296E, A296F, A296G, A296H,
A296I, A296L, A296M, A296N, A296Q, A296R, A296S,
A296V, A296W, A296Y, T299A, T299D, T299E, T299F,
T299G, T299K, T299L, T299M, T299R, T299S, T299V,
T299W, G300A, G300C, G300D, G300E, G300F, G300H,
G300K, G300M, G300Q, G300R, G300V, G300W, G301A,
G301C, G301D, G301E, G301F, G301H, G301K, G301L,
G301M, G301Q, G301R, G301S, G301T, G301V, G301W,
G301Y, G302S, Y303A, Y303C, Y303D, Y303E, Y303F,
Y303G, Y303H, Y303I, Y303K, Y303L, Y303M, Y303N,
Y303Q, Y303R, Y303S, Y303T, Y303V, Y303W, Y304F,
Y304K, Y304W, R307A, R307C, R307E, R307G, R307H,
R307K, R307M, R307N, R307Q, R307S, R307T, N308C,
N308D, N308E, N308G, N308L, N308M, N308T, N308V,
L310A, L310C, L310D, L310E, L310H, L310I, L310M,
L310P, L310W, L310Y, N311C, N311E, N311G, N311H,
N311K, N311Q, N311R, N311S, N311V, N311W, N311Y,
N312D, N312F, N312G, N312H, N312K, N312Q, N312R,
T313A, T313S, A316D, A316E, A316G, A316H, A316K, A316Q, A316R, A316Y, S317C, S317D, S317G, S317H, S317K, S317L, S317N, S317Q, S317R, S317T, S317W, S317Y, N318A, N318C, N318F, N318G, N318I, N318K, N318L, N318M, N318Q, N318R, N318S, N318T, N318V, N318W, T320A, T320C, T320D, T320E, T320G, T320H, T320I, T320K, T320N, T320P, T320Q, T320R, T320V, T320W, T320Y, K321C, K321F, K321H, K321N, K321S, K321Y, L325A, L325C, L325F, L325I, L325M, L325Q, L325V, E327D, E327L, Q335C, Q335E, E338A, E338D, E338F, E338G, E338H, E338I, E338K, E338P, E338Q, E338R, E338T, E338V, E338Y, Q342A, Q342C, Q342G, Q342L, Q342M, Q342R, Q342S, Q342T, Q342V, Q342W, L348A, L348C, L348H, L348I, L348M, L348Q, L348S, L348T, A349G, A349R, F352I, F352L, F352M, F352T, F352V, R356Q, S357A, S357C, S357D, S357E, S357F, S357H, S357I, S357K, S357L, S357N, S357Q, S357T, S357V, S357W, S357Y, Y360F, Y360I, Y360L, Y360M, Y360V, S362A, S362C, S362E, S362I, S362T, S362V, V363I, V363L, M368F, M368I, M368L, M368Y, Y369A, Y369E, Y369I, Y369L, Y369N, Y369V, R377A, R377C, R377D, R377E, R377F, R377G, R377H, R377I, R377K, R377L, R377N, R377Q, R377S, R377T, R377V, R377W, R377Y, A381C, A381E, A381G, A381H, A381K, A381L, A381M, A381N, A381P, A381Q, A381V, A381W, A381Y, L382F, L382H, L382Q, L382S, K383A, K383C, K383D, K383E, K383H, K383I, K383L, K383M, K383N, K383Q, K383R, K383S, K383W, K383Y, S384A, S384C, S384D, S384F, S384G, S384H, S384I, S384L, S384N, S384R, S384V, S384Y, K385A, K385D, K385E, K385F, K385G, K385H, K385L, K385M, K385Q, K385R, K385T, K385V, K385Y, P388A, P388C, P388D, P388I, P388L, P388N, P388R, P388S, P388T, P388V, L390M, L390V, A392C, A392S, K394A, K394C, K394E, K394F, K394G, K394H, K394I, K394L, K394Q, K394R, K394S, K394T, K394V, K394W, K394Y, D395A, D395E, D395N, D395S, D395T, Y396A, Y396D, Y396F, Y396K, Y396M, Y396N, Y396Q, Y396T, Y396V, Y396W, A397D, A397E, A397H, A397K, A397M, A397N, A397Q, A397V, Y398A, Y398C, Y398F, Y398H, Y398I, Y398L, Y398W, T400A, T400C, T400D, T400F, T400G, T400I, T400K, T400L, T400M, T400N, T400Q, T400R, T400W, T400Y, Q401A, Q401C, Q401F, Q401H, Q401I, Q401L, Q401M, Q401N, R402C, R402D, R402F, R402K, R402L, R402M, R402N, R402Q, R402S, R402W, D403E, D403N, D403S, Y404E, Y404G, Y404K, Y404M, Y404N, Y404R, Y404W, I405C, I405F, I405L, I405M, I405V, N407A, N407C, N407D, N407E, N407G, N407K, N407M, N407Q, N407R, P408A, P408C, P408D, P408I, P408K, P408L, P408M, P408N, P408Q, P408V, P408W, V410A, V410C, V410D, V410E, V410F, V410H, V410I, V410L, V410M, V410N, V410Q, V410S, V410T, T414A, T414I, T414S, T414V, R415M, E416C, E416D, E416F, E416H, E416I, E416K, E416L, E416M, E416N, E416Q, E416R, E416T, E416V, E416W, E416Y, D418A, D418E, D418G, D418H, D418I, D418K, D418L, D418M, D418N, D418Q, D418S, D418T, D418V, D418W, S419A, S419C, S419E, S419G, S419L, S419M, S419N, S419R, S419V, S419W, S419Y, T420A, T420C, T420D, T420E, T420G, T420H, T420I, T420K, T420M, T420P, T420S, T420V, T420W, T420Y, K421A, K421D, K421E, K421H, K421I, K421L, K421M, K421N, K421P, K421Q, K421R, K421T, K421V, K421W, K421Y, A422C, A422D, A422E, A422F, A422G, A422I, A422L, A422N, A422P, A422Q, A422R, A422S, A422Y, K423A, K423D, K423E, K423F, K423H, K423I, K423L, K423M, K423N, K423Q, K423R, K423S, K423T, K423V, K423W, K423Y, S424A, S424C, S424G, S424K, S424N, S424Q, S424R, S424T, L426S, L426T, L426V, T428G, T428V, V429A, V429C, V429I, V429L, I430C, I430G, I430L, I430M, I430Q, I430V, T431A, T431C, T431S, P434A, P434C, P434D, P434E, P434F, P434H, P434I, P434K, P434L, P434M, P434N, P434Q, P434R, P434S, P434V, P434Y, G435A, G435C, G435D, G435E, G435F, G435H, G435I, G435K, G435M, G435N, G435P, G435Q, G435R, G435S, G435T, G435W, G436F, G436I, G436M, G436N, G436Q, G436S, G436V, R439A, R439D, R439G, R439H, R439K, R439M, R439N, R439P, R439Q, R439S, R439V, R439W, R439Y, Y441A, Y441C, Y441D, Y441F, Y441G, Y441H, Y441K, Y441L, Y441M, Y441N, Y441P, Y441R, Y441S, Y441T, Y441W, V442A, V442C, V442I, V442T, T444C, T444D, T444E, T444F, T444G, T444H, T444I, T444K, T444L, T444M, T444N, T444P, T444R, T444S, T444W, S445A, S445C, S445E, S445G, S445H, S445K, S445L, S445M, S445N, S445T, S445V, N446A, N446C, N446H, N446K, A447C, A447D, A447F, A447H, A447L, A447M, A447N, A447Q, A447R, A447S, A447Y, G448A, G448C, G448D, G448E, G448H, G448K, G448L, G448M, G448N, G448Q, G448R, G448S, G448T, G448W, E449D, E449H, E449K, E449T, I450A, I450C, I450D, I450E, I450G, I450K, I450L, I450M, I450N, I450Q, I450S, I450T, I450W, I450Y, W451Y, L454A, L454I, L454K, L454M, L454W, T455A, T455I, T455L, T455S, N457H, N457K, N457R, N457T, N457V, N457Y, D460A, D460E, D460G, D460M, D460N, D460Q, D460S, D460V, K461C, K461H, K461L, K461M, K461N, K461Q, K461T, K461Y, I462A, I462L, I462M, I462Q, I462T, I462V, T463D, T463E, T463H, T463P, T463Q, T463R, T463V, T463Y, I464P, I464T, G465A, G465C, G465D, G465E, G465K, G465L, G465M, G465N, G465Q, G465W, G465Y, S466A, S466C, S466D, S466G, S466H, S466K, S466L, S466M, S466N, S466T, S466W, S466Y, D467E, D467G, D467L, Y469A, Y469D, Y469E, Y469I, Y469M, Y469N, Y469R, Y469S, Y469T, Y469V, Y469W, A470S, A470V, T471A, T471C, T471E, T471G, T471H, T471I, T471L, T471M, T471N, T471S, T471V, T471W, P473C, P473D, P473E, P473G, P473I, P473K, P473L, P473R, P473T, P473W, V474A, V474C, V474L, V474S, N475A, N475C, N475E, N475F, N475H, N475K, N475L, N475M, N475P, N475Q, N475R, N475S, N475T, N475V, G476A, G476D, G476E, G476F, G476H, G476I, G476L, G476M, G476N, G476P, G476Q, G476R, G476S, G476T, G476V, G476W, G476Y, G477A, G477D, G477F, G477H, G477I, G477K, G477L, G477M, G477Q, G477S, G477T, G477V, G477W, G477Y, V479C, V479D, V479E, V479F, V479H, V479I, V479N, V479P, V479Y, S480A, S480C, S480H, V481A, V481C, V481N, W482Y, V483A, V483G, V483I, V483K, V483L, V483M, V483R, V483Y, Q484A, Q484C, Q484F, Q484G, Q484H, Q484K, Q484L, Q484M, Q484P, Q484R, Q484T, and Q484Y.

Furthermore, the present amylases may include any number of conservative amino acid substitutions. Exemplary conservative amino acid substitutions are listed in Table 1Table 1. Conservative amino acid substitutions

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |

-continued

| For Amino Acid | Code | Replace with any of |
|---|---|---|
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The reader will appreciate that some of the above mentioned conservative mutations can be produced by genetic manipulation, while others are produced by introducing synthetic amino acids into a polypeptide by genetic or other means.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides. The present amylase polypeptides may also be truncated to remove the N or C-termini, so long as the resulting polypeptides retain amylase activity.

The present amylase may be a "chimeric" or "hybrid" polypeptide, in that it includes at least a portion of a first amylase polypeptide, and at least a portion of a second amylase polypeptide (such chimeric amylases have recently been "rediscovered" as domain-swap amylases). The present amylases may further include heterologous signal sequence, an epitope to allow tracking or purification, or the like. Exemplary heterologous signal sequences are from *B. licheniformis* amylase (LAT), *B. subtilis* (AmyE or AprE), and *Streptomyces* CelA.

2.5. Nucleotides Encoding Variant Amylase Polypeptides

In another aspect, nucleic acids encoding a variant amylase polypeptide are provided. The nucleic acid may encode a particular amylase polypeptide, or an amylase having a specified degree of amino acid sequence identity to the particular amylase.

In one example, the nucleic acid encodes an amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1, SEQ ID NO: 3, or SEQ ID NO: 5 (excluding the portion of the nucleic acid that encodes the signal sequence). It will be appreciated that due to the degeneracy of the genetic code, a plurality of nucleic acids may encode the same polypeptide.

In another example, the nucleic acid hybridizes under stringent or very stringent conditions to a nucleic acid encoding (or complementary to a nucleic acid encoding) an amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1, SEQ ID NO: 3, or SEQ ID NO: 5 (excluding the portion of the nucleic acid that encodes the signal sequence).

In some embodiments, the nucleic acid hybridizes under stringent or very stringent conditions to the nucleic acid of SEQ ID NO: 7, SEQ ID NO: 33, or SEQ ID NO: 38, or to a nucleic acid complementary to these nucleic acids.

Nucleic acids may encode a "full-length" ("fl" or "FL") amylase, which includes a signal sequence, only the mature form of an amylase, which lacks the signal sequence, or a truncated form of an amylase, which lacks the N or C-terminus of the mature form.

A nucleic acid that encodes a α-amylase can be operably linked to various promoters and regulators in a vector suitable for expressing the α-amylase in host cells. Exemplary promoters are from *B. licheniformis* amylase (LAT), *B. subtilis* (AmyE or AprE), and *Streptomyces* CelA. Such a nucleic acid can also be linked to other coding sequences, e.g., to encode a chimeric polypeptide.

3. Production of Variant Amylases

The present variant amylases can be produced in host cells, for example, by secretion or intracellular expression. A cultured cell material (e.g., a whole-cell broth) comprising a variant amylase can be obtained following secretion of the variant amylase into the cell medium. Optionally, the variant amylase can be isolated from the host cells, or even isolated from the cell broth, depending on the desired purity of the final variant amylase. A gene encoding a variant amylase can be cloned and expressed according to methods well known in the art. Suitable host cells include bacterial, fungal (including yeast and filamentous fungi), and plant cells (including algae). Particularly useful host cells include *Aspergillus niger, Aspergillus oryzae* or *Trichoderma reesei*. Other host cells include bacterial cells, e.g., *Bacillus subtilis* or *B. licheniformis*, as well as *Streptomyces*.

The host cell further may express a nucleic acid encoding a homologous or heterologous glucoamylase, i.e., a glucoamylase that is not the same species as the host cell, or one or more other enzymes. The glucoamylase may be a variant glucoamylase, such as one of the glucoamylase variants disclosed in U.S. Pat. No. 8,058,033 (Danisco US Inc.), for example. Additionally, the host may express one or more accessory enzymes, proteins, peptides. These may benefit liquefaction, saccharification, fermentation, SSF, etc processes. Furthermore, the host cell may produce biochemicals in addition to enzymes used to digest the various feedstock (s). Such host cells may be useful for fermentation or simultaneous saccharification and fermentation processes to reduce or eliminate the need to add enzymes.

3.1. Vectors

A DNA construct comprising a nucleic acid encoding variant amylases can be constructed to be expressed in a host cell. Representative nucleic acids that encode variant amylases include SEQ ID NO: 4. Because of the well-known degeneracy in the genetic code, variant polynucleotides that encode an identical amino acid sequence can be designed and made with routine skill. It is also well-known in the art to optimize codon use for a particular host cell. Nucleic acids encoding variant amylases can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding a variant amylase can be transformed and replicated in a bacterial host cell as a means of propagating and amplifying the vector. The vector also may be transformed into an expression host, so that the encoding nucleic acids can be expressed as a functional amylase. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). A representative vector is pJG153, a promoterless Cre expression vector that can be replicated in a bacterial host. See Harrison et al. (June 2011) *Applied Environ. Microbiol.* 77: 3916-22. pJG153 can be modified with routine skill to comprise and express a nucleic acid encoding an amylase variant.

A nucleic acid encoding a variant amylase can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding a variant amylase, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an amylase is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. cbh1 is an endogenous, inducible promoter from *T. reesei*. See Liu et al. (2008) "Improved heterologous gene expression in *Trichoderma reesei* by cellobiohydrolase I gene (cbh1) promoter optimization," *Acta Biochim. Biophys. Sin (Shanghai)* 40(2): 158-65.

The coding sequence can be operably linked to a signal sequence. The DNA encoding the signal sequence may be the DNA sequence naturally associated with the amylase gene to be expressed or from a different Genus or species. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding a variant amylase. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of amylase for subsequent enrichment or purification. Extracellular secretion of amylase into the culture medium can also be used to make a cultured cell material comprising the isolated amylase.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the amylase to a host cell organelle such as a peroxisome, or to a particular host cell compartment. Such a targeting sequence includes but is not limited to the sequence, SKL. For expression under the direction of control sequences, the nucleic acid sequence of the amylase is operably linked to the control sequences in proper manner with respect to expression.

The procedures used to ligate the DNA construct encoding an amylase, the promoter, terminator and other elements, respectively, and to insert them into suitable vectors containing the information necessary for replication, are well known to persons skilled in the art (see, e.g., Sambrook et al., Molecular Cloning: A Laboratory Manual, 2$^{nd}$ ed., Cold Spring Harbor, 1989, and 3$^{rd}$ ed., 2001).

3.2. Transformation and Culture of Host Cells

An isolated cell, either comprising a DNA construct or an expression vector, is advantageously used as a host cell in the recombinant production of an amylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium,* and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe*. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* sp., e.g., *Fusarium oxysporum* or of a *Rhizomucor* sp. such as *Rhizomucor miehei* can be used as the host organism. Other suitable strains include *Thermomyces* and *Mucor* sp. In addition, *Trichoderma* sp. can be used as a host. A suitable procedure for transformation of *Aspergillus* host cells includes, for example, that described in EP238023. An amylase expressed by a fungal host cell can be glycosylated, i.e., will comprise a glycosyl moiety. The glycosylation pattern can be the same or different as present in the wild-type amylase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) Science 9:991-1001 for transformation of *Aspergillus* strains. Genetically stable transformants can be constructed with vector systems whereby the nucleic acid encoding an amylase is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$) is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2 \times 10^6$/mL. A volume of 100 μL of these protoplasts or cells in an appropriate solution (e.g., 1.2 M sorbitol and 50 mM $CaCl_2$)) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an amylase may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an amylase. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of an α-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

The polynucleotide encoding an amylase in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of an amylase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired variant amylase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an amylase.

3.4. Identification of Amylase Activity

To evaluate the expression of an amylase in a host cell, assays can measure the expressed protein, corresponding mRNA, or α-amylase activity. For example, suitable assays include Northern blotting, reverse transcriptase polymerase chain reaction, and in situ hybridization, using an appropriately labeled hybridizing probe. Suitable assays also include measuring amylase activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. α-amylase activity also may be measured by any known method, such as the PAHBAH or ABTS assays, described below.

3.5. Methods for Enriching and Purifying Variants Amylases

Fermentation, separation, and concentration techniques are well known in the art and conventional methods can be used in order to prepare a concentrated a variant α-amylase polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate a variant α-amylase polypeptide-containing solution in order to optimize recovery. Use of unconcentrated solutions requires increased incubation time in order to collect the enriched or purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

The enzyme solution is concentrated into a concentrated enzyme solution until the enzyme activity of the concentrated variant α-amylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate an amylase. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific variant α-amylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, variant amylase concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

During fermentation, a variant α-amylase polypeptide accumulates in the culture broth. For the isolation, enrichment, or purification of the desired variant α-amylase, the culture broth is centrifuged or filtered to eliminate cells, and the resulting cell-free liquid is used for enzyme enrichment or purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further enrichment or purification, a conventional procedure such as ion exchange chromatography may be used.

Enriched or purified enzymes are useful for laundry and cleaning applications. For example, they can be used in laundry detergents and spot removers. They can be made into a final product that is either liquid (solution, slurry) or solid (granular, powder).

A more specific example of enrichment or purification, is described in Sumitani et al. (2000) "New type of starch-binding domain: the direct repeat motif in the C-terminal region of *Bacillus* sp. 195 α-amylase contributes to starch binding and raw starch degrading," Biochem. J. 350: 477-484, and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$), and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, PA; Cat. No. 19812) was equilibrated with 20 mM Tris/HCl buffer (pH 7.0) containing 5 mM $CaCl_2$) and 1.5 M (NH4)2SO4. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See, e.g., Sumitani et al. (2000) *Biochem. J.* 350: 477-484, for general discussion of the method and variations thereon.

For production scale recovery, variant α-amylase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Compositions and Uses of Variant Amylases

Variants amylases are useful for a variety of industrial applications. For example, variant amylases are useful in a starch conversion process, particularly in a saccharification process of a starch that has undergone liquefaction. The desired end-product may be any product that may be produced by the enzymatic conversion of the starch substrate. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gulonic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation conditions that may be used in the production of these end-products. Variant amylases are also useful in compositions and methods of food preparation. These various uses of variant amylases are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may also be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling or grinding, whole kernels are ground into a fine powder and often processed without fractionating the grain into its component parts. In some cases, oils from the kernels are recovered. Dry ground grain thus will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-amylase may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 5.5-6.5 and about 1 mM of calcium (about 40 ppm free calcium ions) can also be added. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. Gelatinization occurs rapidly under these conditions, and the enzymatic activity, combined with the significant shear forces, begins the hydrolysis of the starch substrate. The residence time in the jet cooker is brief. The partly gelatinized starch may be passed into a series of holding tubes maintained at 105-110° C. and held for 5-8 min. to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g., 90 minutes to 120 minutes. The liquefied starch typically is in the form of a slurry having a dry solids content (w/w) of about 10-50%; about 10-45%; about 15-40%; about 20-40%; about 25-40%; or about 25-35%.

Liquefaction with variant amylases advantageously can be conducted at low pH, eliminating the requirement to adjust the pH to about pH 5.5-6.5. Variants amylases can be used for liquefaction at a pH range of 2 to 7, e.g., pH 3.0-7.5, pH 4.0-6.0, or pH 4.5-5.8. Variant amylases can maintain liquefying activity at a temperature range of about 85° C.-95° C., e.g., 85° C., 90° C., or 95° C. For example, liquefaction can be conducted with 800 μg an amylase in a solution of 25% DS corn starch for 10 min at pH 5.8 and 85° C., or pH 4.5 and 95° C., for example. Liquefying activity can be assayed using any of a number of known viscosity assays in the art.

In particular embodiments using the present amylase variants, starch liquefaction is performed at a temperature range of 90-115° C., for the purpose of producing high-purity glucose syrups, HFCS, maltodextrins, etc.

4.3. Saccharification

The liquefied starch can be saccharified into a syrup rich in lower DP (e.g., DP1+DP2) saccharides, using variant amylases, optionally in the presence of another enzyme(s). The exact composition of the products of saccharification depends on the combination of enzymes used, as well as the type of granular starch processed. Advantageously, the syrup obtainable using the provided variant amylases may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. The present amylases also produce a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. Saccharification may be performed, for example, at a temperature between about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an amylase, saccharification optimally is conducted at a temperature range of about 30° C. to about 75° C., e.g., 45° C.-75° C. or 47° C.-74° C. The saccharifying may be conducted over a pH range of about pH 3 to about pH 7, e.g., pH 3.0-pH 7.5, pH 3.5-pH 5.5, pH 3.5, pH 3.8, or pH 4.5.

An α-amylase may be added to the slurry in the form of a composition. An α-amylase can be added to a slurry of a granular starch substrate in an amount of about 0.6-10 ppm ds, e.g., 2 ppm ds. An α-amylase can be added as a whole broth, clarified, enriched, partially purified, or purified enzyme. The specific activity of the amylase may be about 300 U/mg of enzyme, for example, measured with the PAHBAH assay. The α-amylase also can be added as a whole broth product.

An α-amylase may be added to the slurry as an isolated enzyme solution. For example, an α-amylase can be added in the form of a cultured cell material produced by host cells expressing an amylase. An α-amylase may also be secreted by a host cell into the reaction medium during the fermentation or SSF process, such that the enzyme is provided continuously into the reaction. The host cell producing and secreting amylase may also express an additional enzyme, such as a glucoamylase. For example, U.S. Pat. No. 5,422,267 discloses the use of a glucoamylase in yeast for production of alcoholic beverages. For example, a host cell, e.g., *Trichoderma reesei* or *Aspergillus niger*, may be engineered to co-express an α-amylase and a glucoamylase, e.g., HgGA, TrGA, or a TrGA variant, during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanase, an isoamylase, and/or an isopullulanase. See, e.g., WO 2011/153516 A2.

4.4. Isomerization

The soluble starch hydrolysate produced by treatment with amylase can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5 (depending on the isomerase), and Ca$^{2+}$ is removed by ion exchange. Suitable isomerases include SWEETZYME®, IT (Novozymes A/S); G-ZYME® IMGI, and G-ZYME® G993, KETOMAX®, G-ZYME® G993, G-ZYME® G993 liquid, and GENSWEET® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. for alcohol-producing yeast. The temperature and pH of the fermentation will depend upon the fermenting organism. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) Sheng Wu Gong Cheng Xue Bao 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," Biotechnol. Adv. 25(3): 244-63; John et al. (2009) "Direct lactic acid fermentation: focus on simultaneous saccharification and lactic acid production," Biotechnol. Adv. 27(2): 145-52.

The saccharification and fermentation processes may be carried out as an SSF process. Fermentation may comprise subsequent enrichment, purification, and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, CO2 generated by fermentation may be collected with a CO2 scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete amylase continuously throughout SSF. The fungal cells expressing amylase also can be the fermenting microorganism, e.g., an ethanologenic microorganism. Ethanol production thus can be carried out using a fungal cell that expresses sufficient amylase so that less or no enzyme has to be added exogenously. The fungal host cell can be from an appropriately engineered fungal strain. Fungal host cells that express and secrete other enzymes, in addition to amylase, also can be used. Such cells may express glucoamylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as CO2. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising Variants Amylases

Variant amylases may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S. Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. Variant amylases advantageously increase the yield of glucose produced in a saccharification process catalyzed by TrGA.

Alternatively, the glucoamylase may be another glucoamylase derived from plants (including algae), fungi, or bacteria. For example, the glucoamylases may be *Aspergillus niger* G1 or G2 glucoamylase or its variants (e.g., Boel et al. (1984) EMBO J. 3: 1097-1102; WO 92/00381; WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al. (1996) Prot. Eng. 9: 499-505); D257E and D293E/Q (Chen et al. (1995) Prot. Eng. 8: 575-582); N182 (Chen et al. (1994) Biochem. J. 301: 275-281); A246C (Fierobe et al. (1996) Biochemistry, 35: 8698-8704); and variants with Pro residues in positions A435 and S436 (Li et al. (1997) Protein Eng. 10: 1199-1204). Other contemplated glucoamylases include *Talaromyces* glucoamylases, in particular derived from *T. emersonii* (e.g., WO 99/28448 (Novo Nordisk A/S), *T. leycettanus* (e.g., U.S. Patent No. RE 32,153 (CPC International, Inc.)), *T. duponti*, or *T. thermophilus* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase shown in SEQ ID NO:2 in WO 00/04136 (Novo Nordisk A/S). Also suitable are commercial glucoamylases, such as AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR (*A. niger* glucoamylase with a low protease content). Still other suitable glucoamylases include *Aspergillus fumigatus* glucoamylase, *Talaromyces* glucoamylase, *Thielavia* glucoamylase, *Trametes* glucoamylase, *Thermomyces* glucoamylase, *Athelia* glucoamylase, or *Humicola* glucoamylase (e.g., HgGA). Glucoamylases typically are added in an amount of about 0.1-2 glucoamylase units (GAU)/g ds, e.g., about 0.16 GAU/g ds, 0.23 GAU/g ds, or 0.33 GAU/g ds.

Other suitable enzymes that can be used with amylase include a phytase, protease, pullulanase, β-amylase, isoamylase, a different α-amylase, alpha-glucosidase, cellulase, xylanase, other hemicellulases, beta-glucosidase, transferase, pectinase, lipase, cutinase, esterase, redox enzymes, or a combination thereof. For example, a debranching enzyme, such as an isoamylase (EC 3.2.1.68), may be added in effective amounts well known to the person skilled in the art. A pullulanase (EC 3.2.1.41), e.g., PROMOZYME®, is also suitable. Pullulanase typically is added at 100 U/kg ds. Further suitable enzymes include proteases, such as fungal and bacterial proteases. Fungal proteases include those obtained from *Aspergillus*, such as *A. niger, A. awamori, A. oryzae; Mucor* (e.g., *M. miehei*); *Rhizopus*; and *Trichoderma*.

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in Progress in Industrial Microbiology, Vol. 15, pp. 112-115. These β-Amylases have optimum temperatures in the range from 40° C. to 65° C. and optimum pH in the range from about 4.5 to about 7.0. Contemplated 0-amylases include, but are not limited to, 0-amylases from barley SPEZYME® BBA 1500, SPEZYME® DBA, OPTI-MALT™ ME, OPTIMALT™ BBA (Danisco US Inc.); and NOVOZYM™ WBA (Novozymes A/S).

Compositions comprising the present amylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc, for example, endogenous plant (including algal) enzymes, residual enzymes from a prior processing step, and the like.

5. Compositions and Methods for Baking and Food Preparation

The present invention also relates to a "food composition," including but not limited to a food product, animal feed and/or food/feed additives, comprising an amylase, and methods for preparing such a food composition comprising mixing variant amylase with one or more food ingredients, or uses thereof.

Furthermore, the present invention relates to the use of an amylase in the preparation of a food composition, wherein the food composition is baked subsequent to the addition of the polypeptide of the invention. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, an amylase, by itself or in combination with another α-amylase(s), may be added to the flour to augment the level of endogenous α-amylase activity in flour.

An amylase can further be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an amylase include an endo-amylase, e.g., a bacterial endo-amylase from *Bacillus*. The additional amylase can be another maltogenic α-amylase (EC 3.2.1.133), e.g., from *Bacillus*. NOVAMYL® is an exemplary maltogenic α-amylase from *B. stearothermophilus* strain NCIB 11837 and is described in Christophersen et al. (1997) Starch 50: 39-45. Other examples of anti-staling endo-amylases include bacterial α-amylases derived from *Bacillus*, such as *B. licheniformis* or *B. amyloliquefaciens*. The anti-staling amylase may be an exo-amylase, such as 0-amylase, e.g., from plant sources, such as soy bean, or from microbial sources, such as *Bacillus*.

The baking composition comprising an amylase further can comprise a phospholipase or enzyme with phospholipase activity. An enzyme with phospholipase activity has an activity that can be measured in Lipase Units (LU). The phospholipase may have A1 or A2 activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, an amadoriase, a metalloproteinase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*. Xylanases include PENTOPAN® and NOVOZYM 384®, for example, which are commercially available xylanase preparations produced from *Trichoderma reesei*. The amyloglucosidase may be an *A. niger* amyloglucosidase (such as AMG®). Other useful amylase products include GRINDAMYL® A 1000 or A 5000 (Grindsted Products, Denmark) and AMYLASE H™ or AMYLASE P™ (DSM). The glucose oxidase may be a fungal glucose oxidase, in particular an *Aspergillus niger* glucose oxidase (such as GLUZYME®). An exemplary protease is NEUTRASE®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

An amylase may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. An amylase can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying an amylase onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., α-amylase particles, can comprise an amylase. To prepare enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results can generally be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

In a further aspect of the invention, the food composition is an oil, meat, lard, composition comprising an amylase. In this context the term "[oil/meat/lard] composition" means any composition, based on, made from and/or containing oil, meat or lard, respectively. Another aspect the invention relates to a method of preparing an oil or meat or lard composition and/or additive comprising an amylase, comprising mixing the polypeptide of the invention with a oil/meat/lard composition and/or additive ingredients.

In a further aspect of the invention, the food composition is an animal feed composition, animal feed additive and/or pet food comprising an amylase and variants thereof. The present invention further relates to a method for preparing such an animal feed composition, animal feed additive composition and/or pet food comprising mixing an amylase and variants thereof with one or more animal feed ingredients and/or animal feed additive ingredients and/or pet food ingredients. Furthermore, the present invention relates to the use of an amylase in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

6. Textile Desizing Compositions and Use

Also contemplated are compositions and methods of treating fabrics (e.g., to desize a textile) using an amylase. Fabric-treating methods are well known in the art (see, e.g., U.S. Pat. No. 6,077,316). For example, the feel and appearance of a fabric can be improved by a method comprising contacting the fabric with an amylase in a solution. The fabric can be treated with the solution under pressure.

An amylase can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An amylase can be applied during or after the weaving to remove these sizing starch or starch derivatives. After weaving, an amylase can be used to remove the size coating before further processing the fabric to ensure a homogeneous and wash-proof result.

An amylase can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An amylase can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an amylase as a component. An amylase polypeptide can be used as a component in detergent compositions for, e.g., hand washing, laundry washing, dishwashing, and other hard-surface cleaning. Such compositions include heavy duty liquid (HDL), heavy duty dry (HDD), and hand (manual) laundry detergent compositions, including unit dose format laundry detergent compositions, and automatic dishwashing (ADW) and hand (manual) dishwashing compositions, including unit dose format dishwashing compositions.

7.1. Overview

Preferably, an amylase is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, bars, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a H2O2 source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present α-amylase are described, below. Many of these composition can be provided in unit dose format for ease of use. Unit dose formulations and packaging are described in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a C8-C18 alkyl ethoxylated alcohol and/or C6-C12 alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixures thereof) and polymeric carboxylate (such as maleate/acrylate random copolymer or polyacrylate homopolymer).

The composition may further include saturated or unsaturated fatty acid, preferably saturated or unsaturated C12-C24 fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted C8-C18 alkyl ethoxylates, and/or C6-C12 alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C. I. Fluorescent brighteners), flocculating agents, chelating agents, alkoxylated polyamines, fabric deposition aids, and/or cyclodextrin. 7.4. Automatic Dishwashing (ADW) Detergent Composition Exemplary ADW detergent composition includes non-ionic surfactants, including ethoxylated non-ionic surfactants, alcohol alkoxylated surfactants, epoxy-capped poly (oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., C12-18 alcohol, 1-2 ethylene oxide (EO)) or alkyl sulfate (e.g., C16-18) about 1% to about 4%; alcohol ethoxylate (e.g., C14-15 alcohol, 7 EO) about 5% to about 9%; sodium carbonate (e.g., Na2CO3) about 14% to about 20%; soluble silicate (e.g., Na2O, 2SiO2) about 2 to about 6%; zeolite (e.g., NaAlSiO4) about 15% to about 22%; sodium sulfate (e.g., Na2SO4) 0% to about 6%; sodium citrate/citric acid (e.g., C6H5Na3O7/C6H8O7) about 0% to about 15%; sodium perborate (e.g., NaBO3H2O) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., C12-18 alcohol, 1-2 EO) or alkyl sulfate (e.g., C16-18) about 1% to about 3%; alcohol ethoxylate (e.g., C14-15 alcohol, 7 EO) about 5% to about 9%; sodium carbonate (e.g., Na2CO3) about 15% to about 21%; soluble silicate (e.g., Na2O, 2SiO2) about 1% to about 4%; zeolite (e.g., NaAlSiO4) about 24% to about 34%; sodium sulfate (e.g., Na2SO4) about 4% to about 10%; sodium citrate/citric acid (e.g., C6H5Na3O7/C6H8O7) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., C12-15 alcohol, 7 EO) about 7% to about 14%; Soap as fatty acid (e.g., C16-22 fatty acid) about 1 to about 3%; sodium carbonate (as Na2CO3) about 10% to about 17%; soluble silicate (e.g., Na2O, 2SiO2) about 3% to about 9%; zeolite (as NaAlSiO4) about 23% to about 33%; sodium sulfate (e.g., Na2SO4) 0% to about 4%; sodium perborate (e.g., NaBO3H2O) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., C12-15 alcohol, 7 EO) about 10% to about 25%; sodium carbonate (as Na2CO3) about 14% to about 22%; soluble silicate (e.g., Na2O, 2SiO2) about 1% to about 5%; zeolite (e.g., NaAlSiO4) about 25% to about 35%; sodium sulfate (e.g., Na2SO4) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., C12-15 alcohol, 7 EO or C12-15 alcohol, 5 EO) about 12% to about 18%; soap as fatty acid (e.g., oleic acid) about 3% to about 13%; alkenylsuccinic acid (C12-14) 0% to about 13%; aminoethanol about 8% to about 18%; citric acid about 2% to about 8%; phosphonate 0% to about 3%; polymers (e.g., PVP, PEG) 0% to about 3%; borate (e.g., B4O7) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., C12-15 alcohol, 7 EO, or C12-15 alcohol, 5 EO) 3-9%; soap as fatty acid (e.g., oleic acid) about 3% to about 10%; zeolite (as NaAlSiO4) about 14% to about 22%; potassium citrate about 9% to about 18%; borate (e.g., B4O7) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., Na2CO3) about 5% to about 10%; Soluble silicate (e.g., Na2O, 2SiO2) about 1% to about 4%; zeolite (e.g., NaAlSiO4) about 20% to about 40%; Sodium sulfate (e.g., Na2SO4) about 2% to about 8%; sodium perborate (e.g., NaBO3H2O) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., Na2CO3) about 4% to about 10%; soluble silicate (Na2O, 2SiO2) about 1% to about 4%; zeolite (e.g., NaAlSiO4) about 30% to about 50%; sodium sulfate (e.g., Na2SO4) about 3% to about 11%; sodium citrate (e.g., C6H5Na3O7) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., Na2CO3) about 14% to about 22%; zeolite (e.g., NaAlSiO4) about 18% to about 32%; sodium sulfate (e.g., Na2SO4) about 5% to about 20%; sodium citrate (e.g., C6H5Na3O7) about 3% to about 8%; sodium perborate (e.g., NaBO3H2O) about 4% to about 9%; bleach activator (e.g., NOBS or TAED) about 1% to about 5%; carboxymethyl-cellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., C12-15 alcohol, 2-3 EO) about 8% to about 15%; alcohol ethoxylate (e.g., C12-15 alcohol, 7 EO, or C12-15 alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., B4O7) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., C12-15 alcohol, 7 EO, or C12-15 alcohol, 5 EO) 6-12%; aminoethanol about 2% to about 6%; citric acid about 8% to about 14%; borate (e.g., B4O7) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., Na2CO3) about 8% to about 25%; soluble silicates (e.g., Na2O, 2SiO2) about 5% to about 15%; sodium sulfate (e.g., Na2SO4) 0% to about 5%; zeolite (NaAlSiO4) about 15% to about 28%; sodium perborate (e.g., NaBO3.4H2O) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by (C12-C18) alkyl sulfate.

14) A detergent composition formulated as a granulate having a bulk density of at least 600 g/L comprising (C12-C18) alkyl sulfate about 9% to about 15%; alcohol ethoxylate about 3% to about 6%; polyhydroxy alkyl fatty acid amide about 1% to about 5%; zeolite (e.g., NaAlSiO4) about 10% to about 20%; layered disilicate (e.g., SK56 from Hoechst) about 10% to about 20%; sodium carbonate (e.g., Na2CO3) about 3% to about 12%; soluble silicate (e.g., Na2O, 2SiO2) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising (C12-C18) alkyl sulfate about 4% to about 8%; alcohol ethoxylate about 11% to about 15%; soap about 1% to about 4%; zeolite MAP or zeolite A about 35% to about 45%; sodium carbonate (as Na2CO3) about 2% to about 8%; soluble silicate (e.g., Na2O, 2SiO2) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases: Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Additional examples include those mutant proteases described in U.S. Pat. Nos. RE 34,606, 5,955,340, 5,700,676, 6,312,936, and 6,482,628, all of which are incorporated herein by reference. Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: Alcalase®, Savinase®, Primase™, Duralase™, Esperase®, BLAZE™ POLARZYME®, OVOZYME®, KANNASE®, LIQUANASE®, NEUTRASE®, RELASE®, and ESPER-ASE® (Novo Nordisk A/S and Novozymes A/S), Max-atase®, Maxacal™ Maxapem™, Properase®, Purafect®, Purafect OxP™, Purafect Prime™, FNA™, FN2™ FN3™, OPTICLEAN®, OPTIMASE®, PURAMAX™, EXCEL-LASE™, and PURAFAST™ (Danisco US Inc./DuPont Industrial Biosciences, Palo Alto, California, USA), BLAP™ and BLAP™ variants (Henkel Kommanditgesellschaft auf Aktien, Duesseldorf, Germany), and KAP (*B. alkalophilus* subtilisin; Kao Corp., Tokyo, Japan). Another exemplary proteases NprE from *Bacillus* amyloliquifaciens and ASP from Cellulomonas sp. strain 69B4 (Danisco US Inc./DuPont Industrial Biosciences, Palo Alto, California, USA). Various proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500, 364, 5,855,625, US RE 34,606, 5,955,340, 5,700,676, 6,312, 936, and 6,482,628, and various other patents. In some further embodiments, metalloproteases find use in the present invention, including but not limited to the neutral metalloprotease described in WO 07/044993. Suitable proteases include naturally occurring proteases or engineered variants specifically selected or engineered to work at relatively low temperatures.

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al.

Biochemica et Biophysica Acta, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase Ultra™ (Novo Nordisk A/S and Novozymes A/S).

Polyesterases: Suitable polyesterases can be included in the composition, such as those described in, for example, WO 01/34899, WO 01/14629, and U.S. Pat. No. 6,933,140.

Amylases: The present compositions can be combined with other amylases, including other α-amylases. Such a combination is particularly desirable when different α-amylases demonstrate different performance characteristics and the combination of a plurality of different α-amylases results in a composition that provides the benefits of the different α-amylases. Other amylases include commercially available amylases, such as but not limited to STAINZYME®, NATA-LASE®, DURAMYL®, TERMAMYL®, FUNGAMYL® and BAN™ (Novo Nordisk A/S and Novozymes A/S); RAPIDASE®, POWERASE®, PURASTAR®, and PREF-ERENZ™ (from DuPont Industrial Biosciences.).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAR-EZYME® (Novo Nordisk A/S and Novozymes A/S); CLAZINASE® and PURADAX HA® (DuPont Industrial Biosciences); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-O-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., poly-acrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Numerous exemplary detergent formulations to which the present amylases can be added (or is in some cases are identified as a component of) are described in WO2013063460. These include commercially available unit dose detergent formulations/packages such as PUREX® UltraPacks (Henkel), FINISH® Quantum (Reckitt Benckiser), CLOROX™ 2 Packs (Clorox), OxiClean Max Force Power Paks (Church & Dwight), TIDE® Stain Release, CASCADE® ActionPacs, and TIDE® Pods™ (Procter & Gamble), PS.

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

The present variant amylase may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. an amylase, in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops act as protein precipitants, establish preservative agents and aid in foam formation and stabilization.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. an amylase, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt is mixed with water and held for a period of time under controlled temperatures to permit the enzymes present in the malt to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast flocculates and is removed. Finally, the beer is cooled and stored for a period of time, during which the beer clarifies and its flavor develops, and any material that might impair the appearance, flavor and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising an amylase, in combination with a glucoamylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

A fermented beverage, such as a beer, can be produced by one of the methods above. The fermented beverage can be a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

9. Reduction of Iodine-Positive Starch

Variant amylases may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., Starch and its Derivatives 194-201 (Chapman and Hall, London (1968)).

The presence of IPS in saccharide liquor negatively affects final product quality and represents a major issue with downstream processing. IPS plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of variant amylases is expected to improve overall process performance by reducing the amount of IPS.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1

Assays

Various assays used herein are set forth, below, for ease in reading. Any deviations from the protocols in later Examples are indicated in the relevant sections. In these experiments, a spectrophotometer was used to measure the absorbance of the products formed after the completion of the reactions.

A. Chelex Bead Treatment of Culture Supernatants 96-well microtiter plates (MTPs) containing growing cultures were removed from incubators and Enzyscreen lids were replaced with disposable plastic sealers (Nunc cat. #236366; Rochester, NY, USA). Cells were separated from culture supernatant via centrifugation (1118 RCF, 5 minutes). 150 μL supernatant was removed from each well and transferred to filter plates (Millipore Multiscreen HTS, Billerica, MA, USA) containing Chelex beads prepared as described below. Plates were shaken vigorously for 5 minutes and supernatant from 3 replicate growth plates were collected into a single deep-well microtiter plate (Axygen, PDW-11-C) using a vacuum manifold device. Plates containing supernatants were sealed and stored at 4° C.

Chelex-100 beads, 200-400 mesh (BioRad, Hercules, CA, USA) were washed twice with 2 bed-volumes of 1 M HCl followed by 5 bed-volumes of ultrapure water on a sintered glass filter apparatus. 2 bed-volumes of 1 M KOH were used to wash the beads followed by another 5 bed-volume wash with ultrapure water. Filtered beads were transferred to a beaker and suspended with enough ultrapure water to produce slurry capable of mixing. The pH of the slurry was adjusted to 8-8.5 using HCl. The liquid was removed and the beads were dried using a scintered glass filter. A slurry of beads (40% w/v) was prepared in ultra pure water and its pH was adjusted to 8.0 using KOH/HCl. A slurry having a constant consistency was maintained by vigorous mixing. A bubble paddle reservoir device (V&P Scientific, San Diego, CA, USA) was used to transfer 100 μL of slurry to all wells of filter plates. Liquid was removed using a vacuum manifold device.

B. Protein Purification

*Bacillus* strains expressing amylase variants were grown in 2.5 L flasks in cultivation medium (enriched semi-defined media based on MOPs buffer, with urea as the major nitrogen source, glucose as the main carbon source, and supplemented with 1% soytone for robust cell growth) for 60-72 hours at 37° C. or in 14 L tanks using a fed batch fermentation process with a medium of corn steep and soy flour supplemented with mineral salts and glucose as carbon source for 100 hours at 36° C. Following incubation, the cells were separated from the fermentation medium by centrifugation and the supernatants were concentrated by ultra-filtration. Ammonium sulphate was added to the concentrate to a final concentration of 0.5M. The proteins were purified using hydrophobic interaction chromatography using a phenyl sepharose column on the AKTA Explorer FPLC system (GE Healthcare). The column was equilibrated with 50 mM HEPES, pH 8, with 2 mM $CaCl_2$ and 0.5 M ammonium sulfate, and the proteins were eluted with 50 mM HEPES, pH 8, with 2 mM $CaCl_2$ and 50% propylene glycol. After each HPLC run, liquid fractions associated with the peak of interest were pooled, and absorbance measurements of the pooled fractions were taken to estimate initial concentrations. Protein concentration of concentrated samples was determined by averaging the result from three different measurements: absorbance measurements at 280 nm, SDS-PAGE densitometry of acid-treated samples compared to a known standard, and by running the proteins on an HPLC system and taking absorbance measurements at 215 nm and 280 nm.

C. Protein Determination Assay

Protein determination assays were performed using chelex bead-treated culture supernatant from cultures grown in 96-well micro-titer plates (MTPs) over 3 days at 37° C. with shaking at 300 rpm and 80% humidity. A fresh 96-well round-bottom MTP containing 25 μL supernatant per well was used for the High Performance Liquid Chromatography (HPLC) protein determination method. Supernatants were diluted four fold into 25 mM sodium acetate pH 5.5, and 10 μL of each diluted sample was analyzed. An Agilent 1200 (Hewlett Packard) HPLC equipped with a Poroshell 300SB-C8 (Agilent Technologies Santa Clara, CA, USA) column was used. Sample was bound to the column using 25 mM sodium acetate pH 5.5 and eluted over a gradient up to 70% acetonitrile. Absorbance was measured at 220 nm, integrated using ChemStation software (Agilent Technologies) and the protein concentration of samples was determined based on a standard curve of purified CspAmy2-v1 protein.

D. Ceralpha α-Amylase Activity Assay

The Ceralpha α-amylase assay was performed using the Ceralpha Kit (Megazyme, Wicklow, Ireland). The assay involves incubating culture supernatant with a substrate mixture under defined conditions, and the reaction is terminated (and color developed) by the addition of borate buffer (200 mM Boric acid/NaOH buffer, pH 10). The substrate is a mixture of the defined oligosaccharide "nonreducing-end blocked p-nitrophenyl maltoheptaoside" (BPNPG7) and excess levels of α-glucosidase (which has no action on the native substrate due to the presence of the "blocking group"). On hydrolysis of the oligosaccharide by endoacting α-amylase, the excess quantities of α-glucosidase present in the mixture give instantaneous and quantitative hydrolysis of the p-nitrophenyl maltosaccharide fragment to glucose and free p-nitrophenol. The absorbance at 405 nm was measured, which relates directly to the level of amylase in the sample analyzed.

The equipment used for this assay included a Biomek FX Robot (Beckman Coulter Brea, CA, USA); a SpectraMAX MTP Reader (type 340-Molecular Devices, Sunnyvale, CA, USA) and iEMS incubator/shaker (Thermo Scientific, Rockford, IL, USA). The reagent and solutions used were:

1) p-nitrophenyl maltoheptaoside (BPNPG7) substrate (Megazyme Ceralpha HR kit);
2) 50 mM Malate buffer, 0.005% TWEEN® 80, pH 5.6 or 50 mM MOPS, 0.005% TWEEN® 80, pH 7 (dilution buffers); and
3) 200 mM Boric acid/NaOH buffer, pH 10 (STOP buffer).

A vial containing 54.5 mg BPNPG7 substrate was dissolved in 10 mL of MilliQ water and then diluted into 30 mL of dilution buffer to make up 40 mL of the working substrate (1.36 mg/mL). The amylase samples (fermentation supernatant) were diluted 40× with dilution buffer. The assay was performed by adding 5 μL of diluted amylase solution into the wells of a MTP followed by the addition of 55 μL of diluted BPNPG7 working substrate solution. The solutions were mixed and the MTP was sealed with a plate seal and placed in an incubator/shaker (iEMS-Thermo Scientific) for 4 minutes at 25° C. The reaction was terminated by adding 70 μL STOP buffer and the absorbance was read at wavelength 400 nm in an MTP-Reader. A non-enzyme control was used to correct for background absorbance values.

E. Thermostability Assay

The thermostability of CspAmy2-v1 and variants was measured by determining the amylase activity using the Ceralpha α-amylase assay. The equipment used for this assay included a Biomek FX Robot (Beckman Coulter); a SpectraMAX MTP Reader (type 340-Molecular Devices), a Tetrad2DNA Engine PCR machine (Biorad), and iEMS incubator/shaker (Thermo Scientific). The reagent solutions used were (* not in all assays):

1) Heat stress buffers
   a) 50 mM KOAc pH 4.5 (5 ppm $CaCl_2$, 50 ppm NaCl)*,
   b) 50 mM KOAc pH 5.0 (10 ppm $CaCl_2$, 10 mM NaCl)
   c) 50 mM KOAc pH 5.7 (5 ppm $CaCl_2$, 50 ppm NaCl),
   d) 50 mM KOAc pH 5.7 (no salt condition)*,
2) p-nitrophenyl maltoheptaoside (BPNPG7) substrate (Megazyme Ceralpha HR kit):
3) 50 mM Malate buffer, 0.005% TWEEN® 80, pH 5.6 (dilution buffer); and
4) 200 mM Boric acid/NaOH, pH 10 (STOP buffer).

5) Amylase culture supernatant: 1:10 master dilution enzyme plates were diluted 1:10 in each of the four heat stress buffers in a PCR plate 5 μL of the diluted enzyme samples were added to a 96-well PCR plate containing 55 μL of diluted BPNPG7 working substrate solution and the initial amylase activity of the samples was determined using the Ceralpha α-amylase assay as described in Section C. The samples were subjected to heat stress for 3-6 minutes in a PCR thermocycler as follows: Buffers (a) 50° C., (b) 59°-60° C., (c) 65°-70° C., and (d) 65° C. The heat stressed samples were cooled immediately to room temperature and 5 μL aliquots were assayed for amylase activity using the Ceralpha α-amylase assay as described in Section C. For each variant, the ratio of the initial and residual amylase activities was used to calculate the thermostability as follows: Thermostability= $[t_{resiaual}$ value]/$[t_{initial}$ value], so the heat stability activity ratio was calculated based on enzyme activity after heat incubation divided by enzyme activity before heat incubation. For each sample (variants) the performance index (PI) is calculated. The performance index for thermostability stability is determined by comparing the thermostability of the variant enzyme with that of a similarly treated reference enzyme.

F. Starch Hydrolysis Assays (Corn Flour and Corn Starch Application Assays)

Starch hydrolysis of corn flour and corn starch were used to measure specific activity of CspAmy2-v1 and variants. Activity was measured as reducing ends generated by the enzymatic breakdown of corn flour or corn starch. The reducing ends generated during the incubation with either substrate were quantified using a PAHBAH (p-hydroxyben-zoic acid hydrazide) assay. The equipment used for the assay included a Biomek FX Robot (Beckman Coulter); a Spec-traMAX MTP Reader (type 340-Molecular Devices), a Tetrad2DNA Engine PCR machine (Biorad), and iEMS incubator/shaker (Thermo Scientific), and a Bubble Paddle Reservoir.

Azure Farms Organic Corn Flour (Norco, CA) was ground to a fine powder using a consumer coffee grinder and then sifted to obtain a<250 micron fraction. The sifted corn flour was washed extensively with MilliQ water by repeated suspension and centrifugation. Cargill Farms Organic Corn Starch material was also washed extensively with MilliQ water by repeated suspension and centrifugation.

Both corn flour and corn starch washed fractions were suspended in MilliQ water containing 0.005% sodium azide as 20% (w/w) stock solutions. The stock solutions were further diluted with a 20× stock buffer solution to 10.9% w/v corn flour and corn starch solutions (final buffer concentra-tion: 55 mM KOAc, pH 5).

55 μL of the diluted corn flour and corn starch substrates were added to PCR microtiter plates along with 5 μL of 1:10 diluted enzyme samples using a bubble paddle reservoir. The plates were sealed and placed at 83° C. for 5 minutes followed by a ramp down to 45° C. The starch hydrolysis reaction was terminated by addition of 70 μL 0.1 N NaOH. The plates were sealed and centrifuged for 3 minutes at 1610 RCF. The starch hydrolysis reaction products from both reactions were analyzed by the PAHBAH assay as described below.

PAHBAH assay: Aliquots of 80 μL of 0.5 N NaOH were added to all wells of an empty PCR plate (a "PAHBAH reaction plate"), followed by 20 μL of PAHBAH reagent (5% w/v p-hydroxybenzoic acid hydrazide (Sigma #H9882, St. Luois, MO), dissolved in 0.5 N HCl). The solutions were mixed by pipetting up and down. 20 μL of the starch hydrolysis reaction supernatants were added to each well of the PAHBAH reaction plate. The plates were sealed and placed in a thermocycler, programmed for 2 minutes at 95° C. to develop color, and then cooled to 20° C. Samples of 80 μL of the developed PAHBAH reaction mixtures were transferred to a fresh plate, and absorbance was measured at 450 nm in a spectrophotometer.

G. CS-28 Rice Starch Microswatch Assay

The principle of this amylase assay is the liberation of an orange dye due to the hydrolysis of rice starch incorporated in a cotton microswatch. The absorbance at 488 nm of the wash liquid is measured and this relates to the level of amylase activity in the sample analyzed at the desired conditions (pH, temperature, and buffer).

The equipment used for this assay included a Biomek FX Robot (Beckman Coulter), a SpectraMAX MTP Reader (type 340-Molecular Devices) and iEMS incubator/shaker (Thermo Scientific). The reagent and solutions used were:

1) CS-28 Microswatches (rice starch, colored);
2) 10 mM HEPES, 2 mM $CaCl_2$, 0.005% TWEEN 80 buffer, pH 8.0, conductivity 1 mS/cm;
3) 25 mM CAPS, 2 mM $CaCl_2$, 0.005% TWEEN 80 buffer, pH 10.0; conductivity 5 mS/cm (adjusted with 5M NaCl); and
4) 10 mM NaCl, 0.1 mM $CaCl_2$, 0.005% TWEEN 80.
5) 50 mM MOPS pH7.15, 0.1 mM $CaCl_2$.

CS-28 microswatches of 5.5 mm circular diameter were provided by the Center for Testmaterials (CFT, Vlaardingen, The Netherlands). Two microswatches were placed in each well of a 96-well Corning 9017 flat bottomed polystyrene MTP. The culture supernatants were diluted eight fold in 50 mM MOPS pH7.15, 0.1 mM $CaCl_2$), and subsequently in 10 mM NaCl, 0.1 mM $CaCl_2$, 0.005% TWEEN©80 solution to approximately 1 ppm, final enzyme concentration.

The incubator/shaker was set at the desired temperature, 25° C. (ambient temperature) or 50° C. 174 μL or 177 μL of either HEPES or CAPS buffer, respectively, was added to each well of microswatch containing MTP and subsequently 6 μL or 3 μL of diluted enzyme solution was added to each well resulting in a total volume of 180 μL/well. The MTP was sealed with a plate seal and placed in the iEMS incubator/shaker and incubated for 15 minutes at 1150 rpm at 25° C. for cleaning at pH 8, low conductivity (1 mS/cm), or 15 minutes at 1150 rpm at 50° C. for cleaning at pH 10, high conductivity (5 mS/cm). Following incubation under the appropriate conditions, 100 μL of solution from each well was transferred to a new MTP, and the absorbance at 488 nm was measured using a MTP-spectrophotometer. Controls containing two microswatches and buffer but no enzyme were included for subtraction of background clean-ing performance.

Each absorbance value was corrected by subtracting the blank (obtained after incubation of microswatches in the absence of enzyme), and the resulting absorbance provided a measure of the hydrolytic activity. A performance index (PI) was calculated for each sample.

For calculation of the wash performance indices (PI), the Langmuir equation was used to fit the data based on the reference enzyme control. Using the protein concentration of the variants, the expected performance based on the curve-fit was calculated. The observed performance was divided by the calculated performance. This value was then divided by the performance of the reference enzyme.

H. Detergent Stability Assay

The stability of the reference amylase and variants thereof was determined by measuring their activity after incubation under defined conditions, in the presence of a 10% detergent mixture (commercially purchased Persil Color Gel deter-gent, Henkel (Dusseldorf, Germany), purchased in 2011). The detergent was heat-inactivated before use, and the initial and residual amylase activities were determined using the Ceralpha α-amylase assay as described in section C, above.

The equipment used for this assay included a Biomek FX Robot (Beckman Coulter); a SpectraMAX MTP Reader (type 340-Molecular Devices), a Tetrad2DNA Engine PCR machine (Biorad), and iEMS incubator/shaker (Thermo Sci-entific). The reagent solutions used were:

1) p-nitrophenyl maltoheptaoside (BPNPG7) substrate (Megazyme Ceralpha HR kit):
2) Liquid detergent (Persil color gel, enzyme inactivated by heating for 4 hrs at 90° C.);
3) 50 mM MOPS, 0.1 mM CaCl$_2$), 0.005% TWEEN®80 buffer, pH 7 (dilution buffer);
4) 10% detergent solution diluted in dilution buffer;
5) 200 mM Boric acid/NaOH buffer, pH 10 (STOP buffer); and
6) Amylase culture supernatants diluted eight fold in 50 mM MOPS pH 7.15, 0.1 mM CaCl$_2$ containing 0-100 µg/mL protein.

85 µL of a 10% detergent solution was added to a 96-well PCR plate and mixed with 15 µL of the diluted culture supernatant. A sample from the PCR plate was diluted 3× in dilution buffer and a 5 µL aliquot of this dilution was used to determine initial amylase activity. The PCR plate was incubated in a Tetrad PCR block at 80.5° C. for 5 minutes. After incubation, detergent-enzyme mix was diluted 3× in dilution buffer and residual activity was measured. Initial ($t_{initial}$) and residual ($t_{residual}$) amylase activity was deter-mined by the Ceralpha α-amylase assay as described above in Section C using a 5 µL sample.

For each variant, the ratio of the residual and initial amylase activities was used to calculate the detergent sta-bility as follows: Detergent stability=[$t_{residual}$ value]/[$t_{initial}$ value].

For each sample (variants) the performance index (PI) was calculated. The performance index for detergent stabil-ity is determined by comparing the detergent stability of the variant enzyme with that of the similarly treated reference enzyme.

I. Performance index

The performance index (PI) compares the performance or stability of the variant and the reference enzyme at the same protein concentration. In addition, the theoretical values can be calculated, using the parameters of the Langmuir equa-tion of the standard enzyme. A performance index (PI) that is greater than 1 (PI>1) indicates improved performance by a variant as compared to the reference enzyme, while a PI of 1 (PI=1) identifies a variant that performs the same as the reference enzyme, and a PI that is less than 1 (PI<1) identifies a variant that performs worse than the reference enzyme.

Example 2

Generation of *Bacillus* Strains Expressing CspAmy2-v1

In this example, the construction of *Bacillus subtilis* strains expressing CspAmy2-v1 (SEQ ID NO: 2) amylase and variants, thereof, is described. CspAmy2-v1 amylase is a variant of CspAmy2 (SEQ ID NO: 1) amylase having a deletion of both R178 and G179 (i.e., ΔRG). CspAmy2 is an amylase from a *Cytophaga* sp., for which the nucleotide sequence was described by Chii-Ling et al. (2002) *Appl.*

*Environ. Microbiol.* 68: 3651-3654. CspAmy2-v1 was described as having increased thermostability over the CspAmy2 by Rong-Jen et al. (2003) *Appl. Environ. Micro-biol.* 69: 2383-85.

A synthetic DNA fragment (SEQ ID NO: 7) encoding CspAmy2-v1 was produced by GeneArt AG (Regensburg, Germany) and served as template DNA for the construction of *Bacillus subtilis* strains expressing CspAmy2-v1 amylase and variants, thereof. The DNA fragment includes a codon-modified nucleotide sequence encoding the mature form of CspAmy2-v1 amylase adjacent to a sequence encoding the LAT signal peptide (underlined):

ATGAAACAACAAAAACGGCTTTACGCCCGATTGCTGACGCTGTTATTTGC

GCTCATCTTCTTGCTGCCTCATTCTGCAGCTAGCGCAGCAGCGACAAACG

GAACAATGATGCAGTATTTCGAGTGGTATGTACCTAACGACGGCCAGCAA

TGGAACAGACTGAGAACAGATGCCCCTTACTTGTCATCTGTTGGTATTAC

AGCAGTATGGACACCGCCGGCTTATAAGGGCACGTCTCAAGCAGATGTGG

GGTACGGCCCGTACGATCTGTATGATTTAGGCGAGTTTAATCAAAAAGGT

ACAGTCAGAACGAAGTATGGCACAAAAGGAGAACTTAAATCTGCTGTTAA

CACGCTGCATTCAAATGGAATCCAAGTGTATGGTGATGTCGTGATGAATC

ATAAAGCAGGTGCTGATTATACAGAAAACGTAACGGCGGTGGAGGTGAAT

CCGTCTAATAGAAATCAGGAAACGAGCGGCGAATATAATATTCAGGCATG

GACAGGCTTCAACTTTCCGGGCAGAGGAACAACGTATTCTAACTTCAAAT

GGCAGTGGTTCCATTTTGATGGAACGGATTGGGACCAGAGCAGAAGCCTC

TCTAGAATCTTCAAATTCACGGGAAAGGCGTGGGACTGGGAGGTTTCTTC

AGAAAACGGAAATTATGACTATCTGATGTACGCGGACATTGATTATGACC

ATCCGGATGTCGTGAATGAAATGAAAAAGTGGGGCGTCTGGTATGCCAAC

GAAGTTGGGTTAGATGGATACAGACTTGACGCGGTCAAACATATTAAATT

TAGCTTTCTCAAAGACTGGGTGGATAACGCAAGAGCAGCGACGGGAAAAG

AAATGTTTACGGTTGGCGAATATTGGCAAAATGATTTAGGGGCCCTGAAT

AACTACCTGGCAAAGGTAAATTACAACCAATCTCTTTTTGATGCGCCGTT

GCATTACAACTTTTACGCTGCCTCAACAGGGGGTGGATATTACGATATGA

GAAATATTCTTAATAACACGTTAGTCGCAAGCAATCCGACAAAGGCTGTT

ACGTTAGTTGAGAATCATGACACACAGCCTGGACAATCACTGGAATCAAC

AGTCCAACCGTGGTTTAAACCGTTAGCCTACGCGTTTATTCTCACGAGAA

GCGGAGGCTATCCTTCTGTATTTTATGGAGATATGTACGGTACAAAAGGA

ACGACAACAAGAGAGATCCCTGCTCTTAAATCTAAAATCGAACCTTTGCT

TAAGGCTAGAAAAGACTATGCTTATGGAACACAGAGAGACTATATTGATA

ACCCGGATGTCATTGGCTGGACGAGAGAAGGGGACTCAACGAAAGCCAAG

AGCGGTCTGGCCACAGTGATTACAGATGGGCCGGGCGGTTCAAAAAGAAT

GTATGTTGGCACGAGCAATGCGGGTGAAATCTGGTATGATTTGACAGGGA

ATAGAACAGATAAAATCACGATTGGAAGCGATGGCTATGCAACATTTCCT

GTCAATGGGGGCTCAGTTTCAGTATGGGTGCAGCAA

The mature form of the CspAmy2-v1 polypeptide pro-duced from the pHPLT02-CspAmy2-v1 vector is shown, below, as SEQ ID NO: 2.

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWEVSSENGNYDYLMYAD

IDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

To express CspAmy2-v1, the CspAmy2-v1-encoding DNA fragment was cloned into the pHPLT02 vector, a modified version of the pHPLT vector (Solingen et al. (2001) Extremophiles 5:333-341) by GeneArt and fused in-frame to the AmyL (LAT) signal peptide using the unique NheI and XhoI restriction sites, resulting in plasmid pHPLT02-CspAmy2-v1. The pHPLT expression vector contains the *B. licheniformis* LAT promoter (Plat) and additional elements from pUB110 (McKenzie et al. (1986) *Plasmid*, 15: 93-103) including a replicase gene (reppUB), a neomycin/kanamycin resistance gene (neo) and a bleomycin resistance marker (bleo). Site-directed mutagenesis (Stratagene) was used to change the nucleotides 5'-TCA-3' of Serine 28 of the AmyL signal peptide to nucleotides 5'-AGC-3' in order to introduce the unique NheI restriction site.

A suitable *B. subtilis* strain was transformed with pHPLT02-CspAmy2-v1 plasmid DNA using a method known in the art (WO 02/14490). The *B. subtilis* transformants were selected on agar plates containing heart infusion agar (Difco, Catalog No. 244400, Lawrence, KS, USA and 10 mg/L neomycin sulfate (Sigma, Catalog No. N-1876; contains 732 g neomycin per mg, St. Louis, Missouri, USA). Selective growth of *B. subtilis* transformants harboring the pHPLT02-CspAmy2-v1 plasmid was performed in shake flasks at 37° C. for ~65h in MBD medium (enriched semi-defined medium based on MOPs buffer, with urea as major nitrogen source, glucose as the main carbon source, and supplemented with 1% soytone for robust cell growth) containing 5 mM CaCl₂ and 10 ppm neomycin. Growth resulted in the production of secreted CspAmy2-v1 amylase with starch hydrolyzing activity.

Example 3

Generation of *Bacillus* Strains Expressing CspAmy2 Combinatorial Variants

In this example, the construction of *Bacillus subtilis* and *Bacillus licheniformis* strains expressing two combinatorial CspAmy2 variants (CspAmy2-v5 and CspAmy2-v6) is described. CspAmy2-v5 is a variant of CspAmy2 with the mutations E187P, I203Y, G476K, and lacking R178 and G179. CspAmy2-v6 is a variant of CspAmy2 with the mutations E187P, I203Y, G476K, R458N, T459S, D460T, and lacking R178 and G179. For expression of CspAmy2-v5 and CspAmy2-v6, expression constructs were created by a combination of gene synthesis and fusion PCR, using standard techniques.

The CspAmy2-v5 and CspAmy2-v6 expression constructs were ligated into vector pICatH (described in, e.g., EP2428572 and U.S. Pat. No. 7,968,691) and transformed into competent *B. subtilis* cells (amyE negative) as known in the art (WO 2002/014490). In these clones, the DNA fragments encoding CspAmy2-v5 and CspAmy2-v6 are fused in-frame to a sequence encoding the *B. licheniformis* amylase (amyL) signal peptide which leads to secretion of the amylase variants into the growth medium. Expression of CspAmy2-v5 and CspAmy2-v6 in these clones is driven by the *B. licheniformis* amylase (amyL) promoter (FIGS. 1A and 1B).

*B. subtilis* transformants were selected on agar plates containing heart infusion agar (Difco) and 10 mg/L neomycin sulfate, 5 mg/L chloramphenicol and starch azure (Sigma). For each construct, one transformant with starch hydrolyzing activity was selected and the amylase expression constructs in pICatH were sequence verified by DNA sequencing (BaseClear, the Netherlands). The resulting plasmids, pICatH-CspAmy2-v5 and pICatH-CspAmy2-v6, were isolated from the *B. subtilis* clones and transformed into *B. licheniformis* cells (amyL and catH negative) and integrated into the genome as described in EP2428572 and U.S. Pat. No. 7,968,691. After excision of vector sequences, expression constructs were amplified by subjecting the strains to a stepwise increase in chloramphenicol concentration up to 50 μg/ml. The *B. licheniformis* strains showed halos on starch azure plates, indicating secretion of active CspAmy2-v5 and CspAmy2-v6 amylase.

The amino acid sequence of the mature form of CspAmy2-v5 is shown, below, as SEQ ID NO: 8:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNKGSVSVWVQQ
```

The amino acid sequence of the mature form of CspAmy2-v6 is shown, below, as SEQ ID NO: 9:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNNSTKITIGSDGYATFPVNKGSVSVWVQQ
```

Example 4

Cleaning Performance of CspAmy2 Combinatorial Variants

The cleaning performance of purified CspAmy2-v5 and CspAmy2-v6 was analyzed in a microswatch cleaning assay. CFT CS-28 rice starch on cotton swatches or EMPA 161 maize starch on cotton cretonne (Center for Testmaterials, BV, Vlaardingen, Netherlands) containing an indicator dye bound to the starch were punched to form discs measuring 5.5 mm in diameter. Two discs were placed in each well of 3 flat-bottom non-binding 96-well assay plates.

Both variants (i.e., CspAmy2-v5 and CspAmy2-v6), the parent molecule (CspAmy2), and a commercially-available benchmark detergent α-amylase, i.e., PURASTAR® (AmyL; *B. licheniformis* α-amylase; Danisco US Inc.), were diluted to 0.5 mg/mL in dilution buffer (50 mM MOPS, pH 7.2, 0.005% Tween), and then further diluted to 2 ppm in a microtiter plate. 200 µL of these samples were transferred into the first row of each of the swatch plates. 100 µL of HEPES buffer (25 mM HEPES, pH 8.0, with 2 mM CaCl₂ and 0.005% Tween-80) was then added to each well of the next 5 rows of the swatch plates. 100 µL of the diluted enzyme samples were then transferred from the first row into the next row, mixed well, and serial dilutions were continued until before the last row, which served as blanks. Once all rows contained 100 µL of solution, 100 µL of buffer were added to each well of the plate to result in final volumes of 200 µL per well, and final enzyme concentrations of 1, 0.5, 0.25, 0.125, 0.0625, and 0 ppm.

Plates were incubated at 25° C. with agitation at 1150 rpm for 15 minutes. Enzyme performance was assessed by the amount of color released into the wash liquor, which was quantified spectrophotometrically at 488 nm by the transfer of 150 µL of the final wash solution to fresh medium-binding microtiter plates. Triplicate reads were blank-subtracted and averaged. The results of the soil removal assay are shown in FIG. 2. CspAmy2-v5 and CspAmy2-v6 demonstrated similar performance to each other and are significantly better than the parent molecule, CspAmy2, and much better than PURASTAR®.

Example 5

Thermostability Assessment of CspAmy2 Combinatorial Variants

Figure 3:
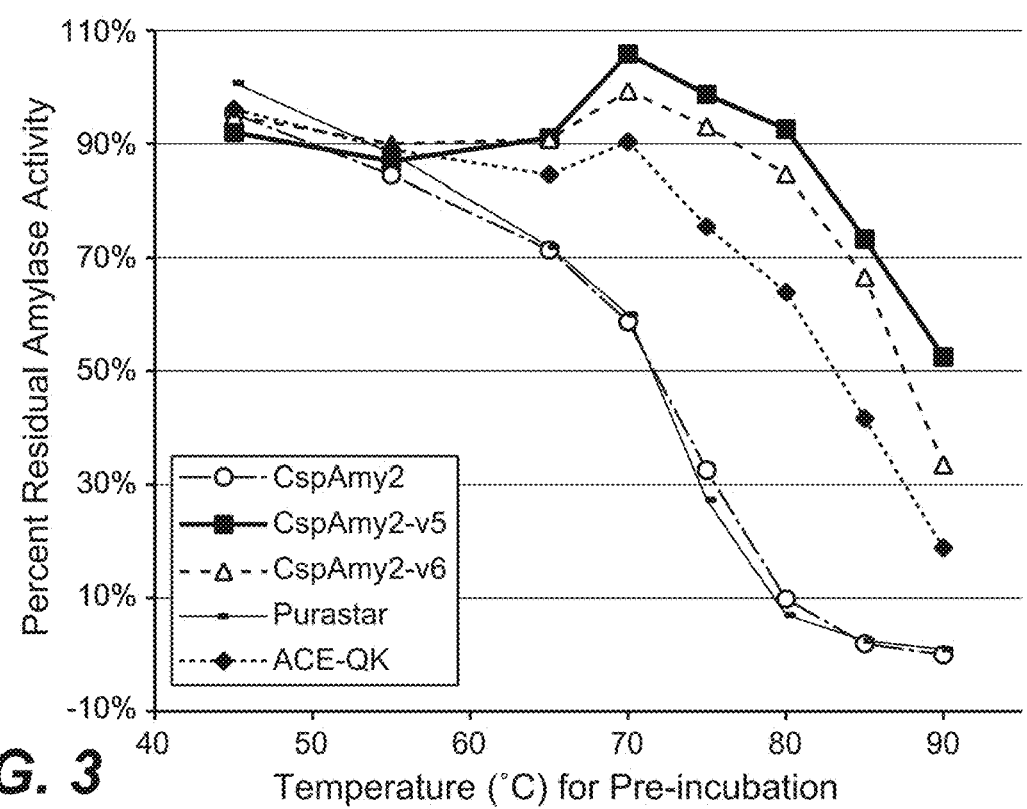
FIG. 3 is a graph showing the thermal stability of CspAmy2-v5 and CspAmy2-v6 in buffer.

A. Thermostability in Buffer 0.5 mg/mL stocks of purified enzymes (i.e., CspAmy2-v5, CspAmy2-v6, CspAmy2), PURASTAR® (*Bacillus licheniformis* α-amylase), and ACE-QK (variant of *Bacillus* sp. TS-23 α-amylase described in US20120045817 and WO2010/115028) were further diluted to 5 ppm in dilution buffer (50 mM MOPS, pH 7.2, 0.005% Tween). 50 µL of each enzyme were added to each of 9 strips of PCR tubes and sealed. One "unstressed" sample of each enzyme was incubated at room temperature throughout the duration of the experiment. The other 8 samples were incubated in a thermocycler at 45, 55, 65, 70, 75, 80, 85, or 90° C. for 15 minutes. The samples were then transferred to microtiter plates in triplicate, and α-amylase activity was for the unstressed and stressed samples using the Ceralpha reagent (Megazyme, Inc.). Residual activity was calculated by dividing the activity of each amylase after the thermal stress by the activity of that unstressed amylase. The results are shown in FIG. 3. CspAmy2-v5 and CspAmy2-v6 demonstrated increased thermostability at low calcium concentrations compared to all other tested enzymes.

B. Thermostability in Buffer with Added Calcium

Figure 4:
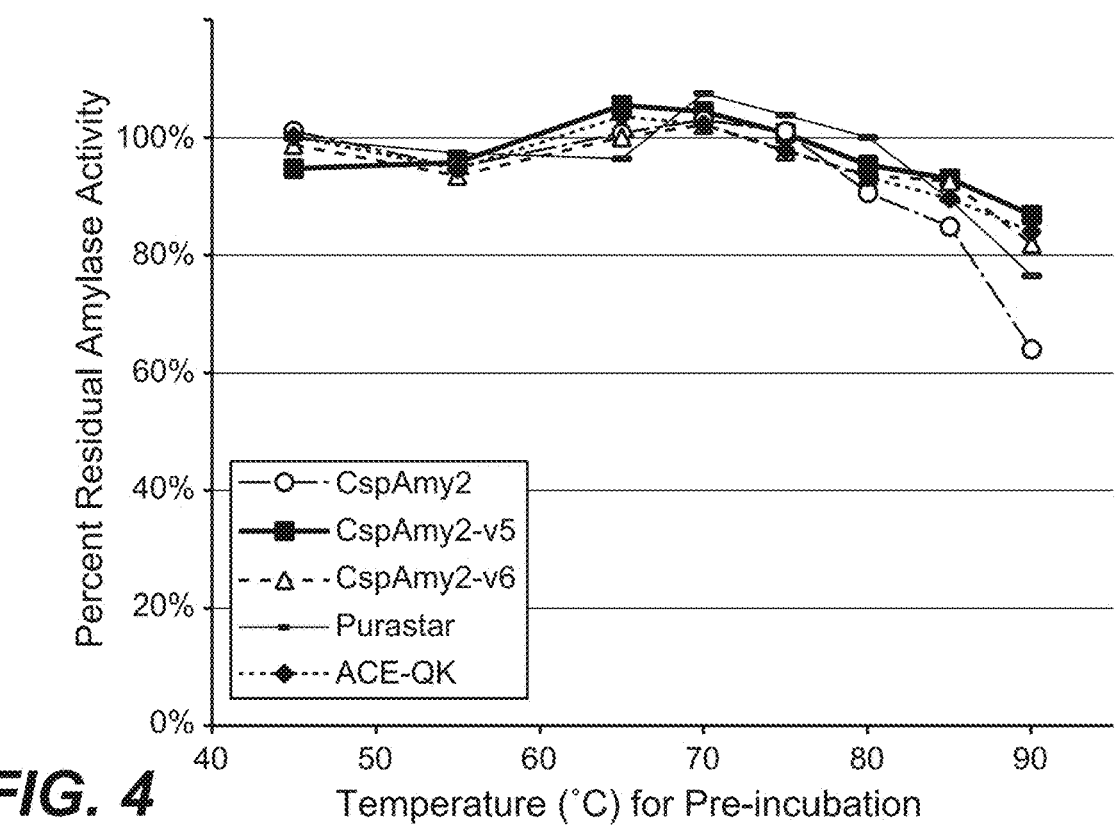
FIG. 4 is a graph showing the thermal stability of CspAmy2-v5 and CspAmy2-v6 in buffer with calcium.

As above, 0.5 mg/mL stocks of purified enzymes were further diluted to 5 ppm in dilution buffer, in this case supplemented with 5 mM calcium chloride (i.e., 50 mM MOPS, pH 7.2, 0.005% Tween, 5 mM calcium chloride). The experiment was carried out as described above. The results are shown in FIG. 4. CspAmy2-v5 and CspAmy2-v6 demonstrated similar thermostability compared to the other tested enzymes.

C. Thermostability in Liquid Detergent

Commercial detergents EPSIL™ Perfect (McBride) and OMO™ Color (Unilever) were heat inactivated at 90° C. for 4 hours to eliminate existing enzyme activities. Following inactivation, the activity CspAmy2-v5, CspAmy2-v6, CspAmy2, PURASTAR®, and ACE-QK in the heat-inactivated detergents was measured using the Suc-AAPF-pNA and Ceralpha assays to ensure that any protease and amylase activities, respectively, had been abolished. 10% solutions of both of these liquid detergents were made in water.

Figure 5:
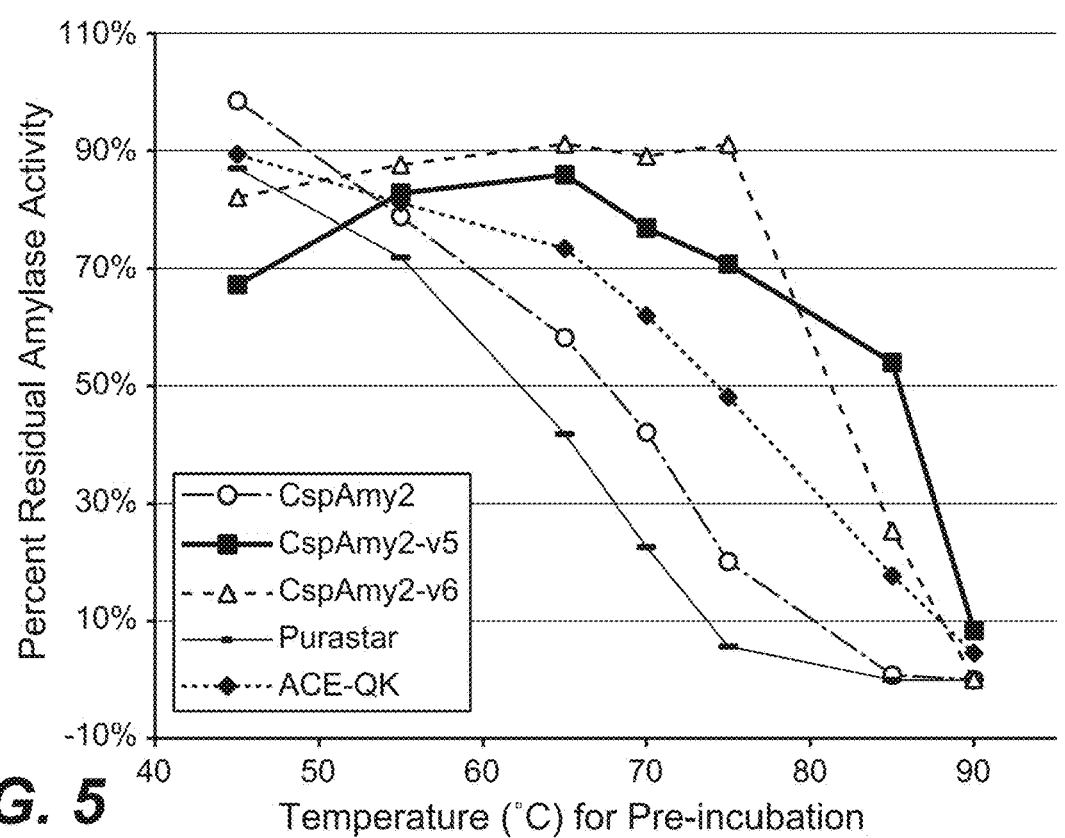
FIG. 5 is a graph showing the detergent stability of CspAmy2-v5 and CspAmy2-v6 in OMO™ Color detergent.
Figures 6, 7:
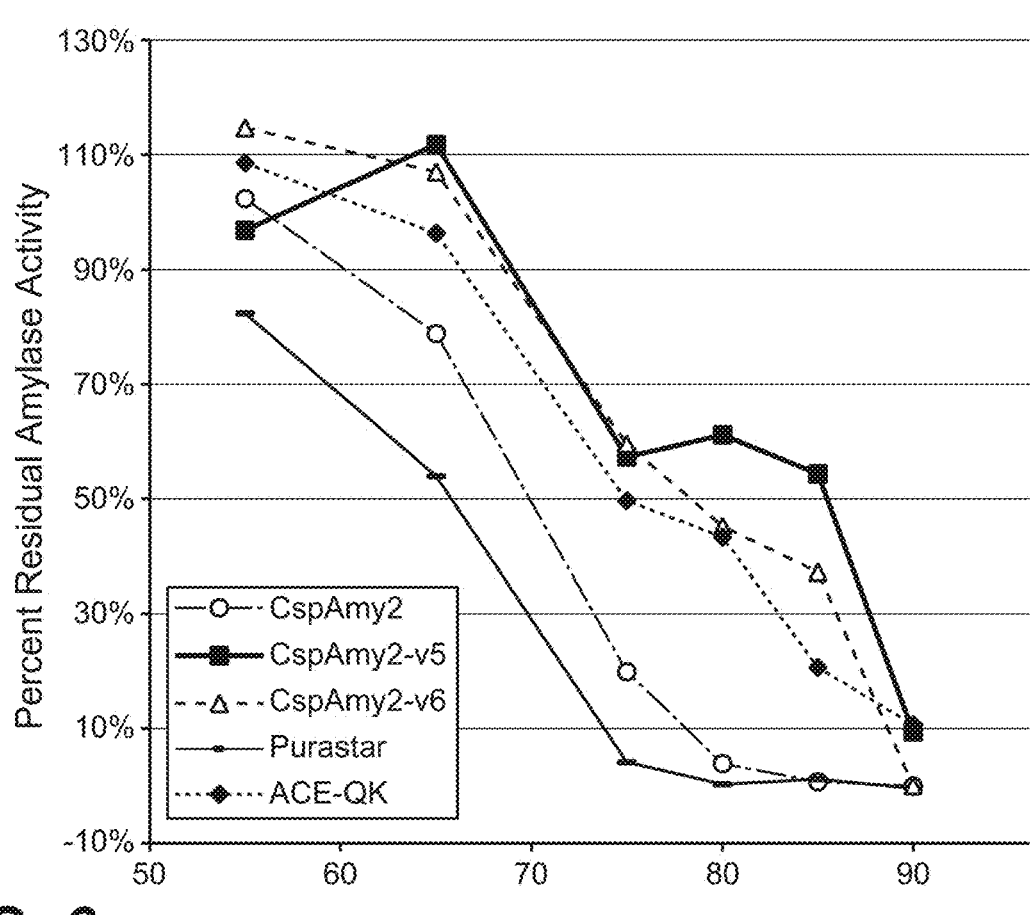
FIG. 6 is a graph showing the detergent stability of CspAmy2-v5 and CspAmy2-v6 in EPSIL™ Perfect detergent.
FIG. 7 is a table showing the relative half-lives and performance indexes of the C16 variants and reference molecules CspAmy2-v1-E187P and CspAmy2-v1-S241Q.

100 µL of each of the 0.5 mg/mL purified enzyme stocks at were added to 400 µL of the 10% detergent solutions. 50 µL of these samples were added to strips of PCR tubes and incubated at the aforementioned temperatures for 15 minutes each, as described above. When samples were removed from the thermocycler, and before α-amylase activity was measured, an additional 1:20 dilution was made in dilution buffer. As above, residual activity was calculated by dividing the activity of each amylase after the detergent and thermal stress by the activity of that unstressed amylase. The results are shown in FIG. 5 (OMO™) and FIG. 6 (EPSIL™) CspAmy2-v5 and CspAmy2-v6 demonstrated superior thermostability compared to the parent enzyme and other tested enzymes.

Example 6

Generation of *Bacillus* Strains Expressing CspAmy2 Combinatorial Variants

A. Design of Combinatorial Variants

Synthetic DNA encoding CspAmy2-v1 variants having various combinations of substitutions at positions N126, Y150, F153, L171, T180, E187, I203, and S241 (referring to SEQ ID NO: 1) were constructed by GeneArt and delivered as plasmids transformed in a *B. subtilis* host, as described for CspAmy2-v5 and CspAmy2-v6 in Example 2. With single substitutions at each of eight sites, 256 combinations were possible. The specific substitutions N126Y, Y150H, F153W, L171N, T180H, E187P, I203Y, and S241Q, were selected, and ten of the possible combinations were made and tested. The names of the variants, and the amino acid residues present at each of the eight positions, is shown in Table 2. For clarity, the full names of the variants in the Table are CspAmy2-C16A-CspAmy2-C16J. In some table and figure the names of the variants are abbreviated but always clear from the description. Further variants of CspAmy2-v1 additionally having the mutations E187P or S241Q were made, and designated CspAmy2-v1-E187P or CspAmy2-v1-S241Q, respectively.

TABLE 2

| | | | Combinations of mutations tested | | | | |
|---|---|---|---|---|---|---|---|
| Name | N126 | Y150 | F153 | L171 | T180 | E187 | I203 | S241 |
| C16A | Y | Y | F | L | T | P | Y | S |
| C16B | Y | Y | F | L | T | E | Y | Q |
| C16C | Y | Y | W | L | T | P | Y | S |
| C16D | Y | Y | W | L | T | E | Y | Q |
| C16E | Y | Y | W | L | H | P | Y | S |
| C16F | Y | Y | W | L | H | E | Y | Q |
| C16G | Y | H | W | N | T | P | Y | S |
| C16H | Y | H | W | N | T | E | Y | Q |
| C16I | Y | H | W | N | H | P | Y | S |
| C16J | Y | H | W | N | H | E | Y | Q |

B. Construction of *Bacillus* Strains Expressing CspAmy2 Combinatorial Variants

The pHPLT02-CspAmy2-v1 plasmid DNA (encoding CspAmy2-v1, see Example 2) served as template to produce the additional combinatorial libraries at pre-selected sites in the mature region. The pHPLT02 expression vector was derived from the pHPLT vector. The pHPLT expression vector contains the *B. licheniformis* LAT promoter (Plat) and additional elements from pUB110 (McKenzie et al. (1986) *Plasmid,* 15: 93-103) including a replicase gene (reppUB), a neomycin/kanamycin resistance gene (neo) and a bleomycin resistance marker (bleo). GeneArt AG (Regensburg, Germany) created combinatorial libraries at the positions described using their standard protocols. The corresponding codons for each site of interest were substituted with codons for at least one non-wild-type amino acid. The codon-mutagenized pHPLT02-CspAmy2-v1 mixes were used to transform competent *B. subtilis* cells as known in the art (WO 2002/014490) to generate the CspAmy2-v1 combinatorial libraries. Transformation mixes were plated on Heart Infusion (HI) agar plates containing 10 mg/L neomycin sulfate. For each library, single bacterial colonies were picked and grown in TSB (tryptone and soy-based broth) liquid medium with 10 mg/ml neomycin selection for subsequent DNA isolation and gene sequence analysis. Variants were generated and identified as members of this combinatorial library. Selective growth of the variants was performed in 96-well MTPs at 37° C. for 68 hours in MBD medium (enriched semi-defined medium based on MOPs buffer, with urea as major nitrogen source, glucose as the main carbon source, and supplemented with 1% soytone for robust cell growth).

The amino acid sequence of mature CspAmy2-16A is shown, below, as SEQ ID NO: 10:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNFKWQWFHFDGTDWDQSRSLSRIFKFTGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

The amino acid sequence of mature CspAmy2-16B is shown, below, as SEQ ID NO: 11:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNFKWQWFHFDGTDWDQSRSLSRIFKFTGKAWDWEVSSENGNYDYLMYAD

YDYDHPDVVNEMKKWGVWYANEVGLDGYRLDAVKHIKFQFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

The amino acid sequence of mature CspAmy2-16C is shown, below, as SEQ ID NO: 12:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNWKWQWFHFDGTDWDQSRSLSRIFKFTGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

The amino acid sequence of mature CspAmy2-16D is shown, below, as SEQ ID NO: 13:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNWKWQWFHFDGTDWDQSRSLSRIFKFTGKAWDWEVSSENGNYDYLMYAD

YDYDHPDVVNEMKKWGVWYANEVGLDGYRLDAVKHIKFQFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

The amino acid sequence of the mature CspAmy2-16E is shown, below, as SEQ ID NO: 14:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD
```

-continued

VVMNHKAGADYTENVTAVEVNPSNRYQETSGEYNIQAWTGFNFPGRGTTY

SNWKWQWFHFDGTDWDQSRSLSRIFKFHGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-16F is shown, below, as SEQ ID NO: 15:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNWKWQWFHFDGTDWDQSRSLSRIFKFHGKAWDWEVSSENGNYDYLMYAD

YDYDHPDVVNEMKKWGVWYANEVGLDGYRLDAVKHIKFQFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-16G is shown, below, as SEQ ID NO: 16:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTH

SNWKWQWFHFDGTDWDQSRSNSRIFKFTGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-16H is shown, below, as SEQ ID NO: 17:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTH

SNWKWQWFHFDGTDWDQSRSNSRIFKFTGKAWDWEVSSENGNYDYLMYAD

YDYDHPDVVNEMKKWGVWYANEVGLDGYRLDAVKHIKFQFLKDWVDNARA

-continued

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-16I is shown, below, as SEQ ID NO: 18:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTH

SNWKWQWFHFDGTDWDQSRSNSRIFKFHGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-16J is shown, below, as SEQ ID NO: 19:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTH

SNWKWQWFHFDGTDWDQSRSNSRIFKFHGKAWDWEVSSENGNYDYLMYAD

YDYDHPDVVNEMKKWGVWYANEVGLDGYRLDAVKHIKFQFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ

The amino acid sequence of mature CspAmy2-v1-E187P is shown, below, as SEQ ID NO: 20:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWPVSSENGNYDYLMYAD

IDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

-continued

```
ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

The amino acid sequence of mature CspAmy2-v1-S241Q is shown, below, as SEQ ID NO: 21:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFTGKAWDWEVSSENGNYDYLMYAD

IDYDHPDVVNEMKKWGVWYANEVGLDGYRLDAVKHIKFQFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNGGSVSVWVQQ
```

Example 7

Thermostability Assessment of CspAmy2 Variants

Combination variants CspAmy2-C16A-CspAmy2-C16J from Example 5 (i.e., "C16A"-"C16G" or "16A-16G," respectively) were tested for thermal stability under the following conditions:
1. 50 mM potassium acetate, pH 5.7, 0.125 mM $CaCl_2$, 2.2 mM NaCl, 85° C.
2. 50 mM potassium acetate, pH 5.0, 0.125 mM $CaCl_2$, 2.2 mM NaCl, 70° C.
3. 50 mM potassium acetate, pH 4.5, 0.125 mM $CaCl_2$, 2.2 mM NaCl, 65° C.

Stock solutions of each variant were prepared by diluting purified variants to a final protein concentration of 1 mg/mL in milli-Q water, then each variant was further diluted (200-fold) in each of the above buffers (final enzyme dose is 5 µg/mL). The diluted enzyme solutions were pre-heated to appropriate temperature for two minutes and then cooled on ice to disrupt any protein aggregates. 50 µL of each enzyme solution was transferred to 0.2 mL PCR strip tubes, which were heated to the appropriate temperature (based on buffer pH) and allowed to incubate over a two-hour period. The samples were then placed in an ice-water bath to end the heat-stress period.

Once all time points were collected for each buffer, residual activity was determined using the Ceralpha assay, as described in Example 1. Two independent inactivation time-course experiments were performed for each variant. Plots of residual activity vs. time were modeled with a single exponential decay equation to determine a rate constant (k) for decay. The half-life of decay was defined as $\ln(2)/k$. These experiments were performed in duplicate for each variant.

Figure 8:
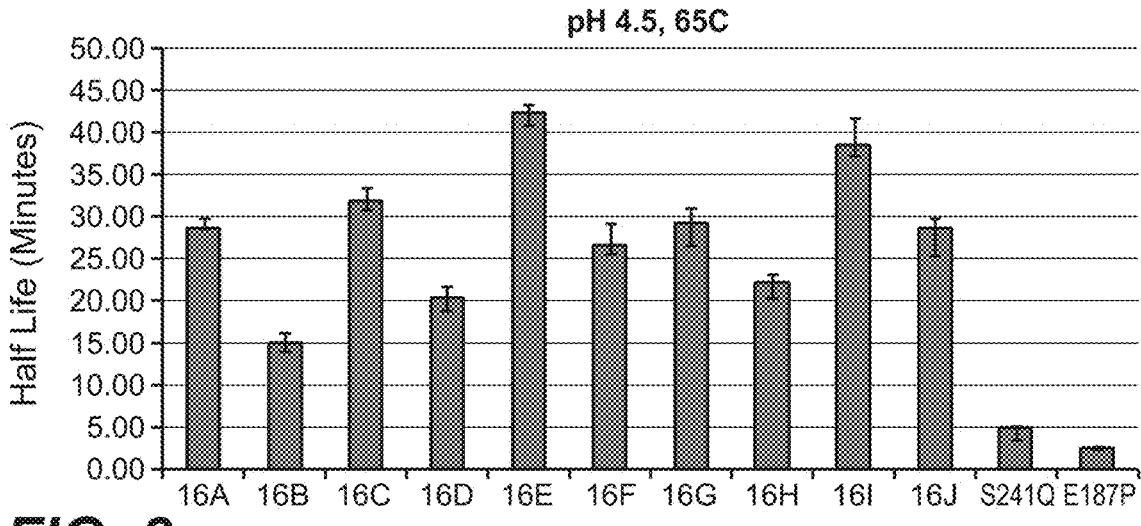
FIG. 8 is a graph showing the thermal stability of the C16 variants and reference molecules CspAmy2-v1-E187P and CspAmy2-v1-S241Q at pH 4.5 and 65° C.
Figure 9:
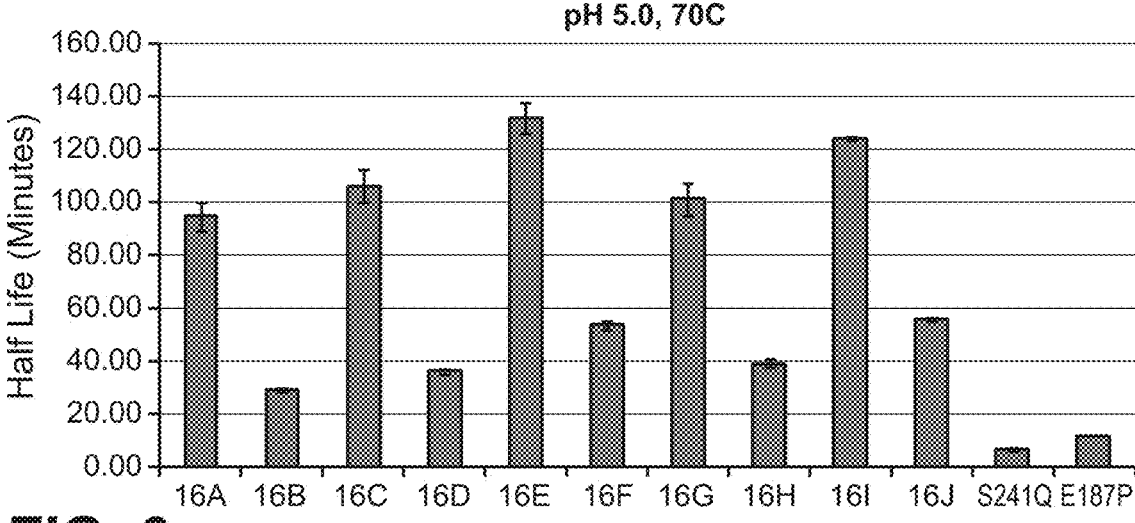
FIG. 9 is a graph showing the thermal stability of the C16 variants and reference molecules CspAmy2-v1-E187P and CspAmy2-v1-S241Q at pH 5.0 and 70° C.
Figure 10:
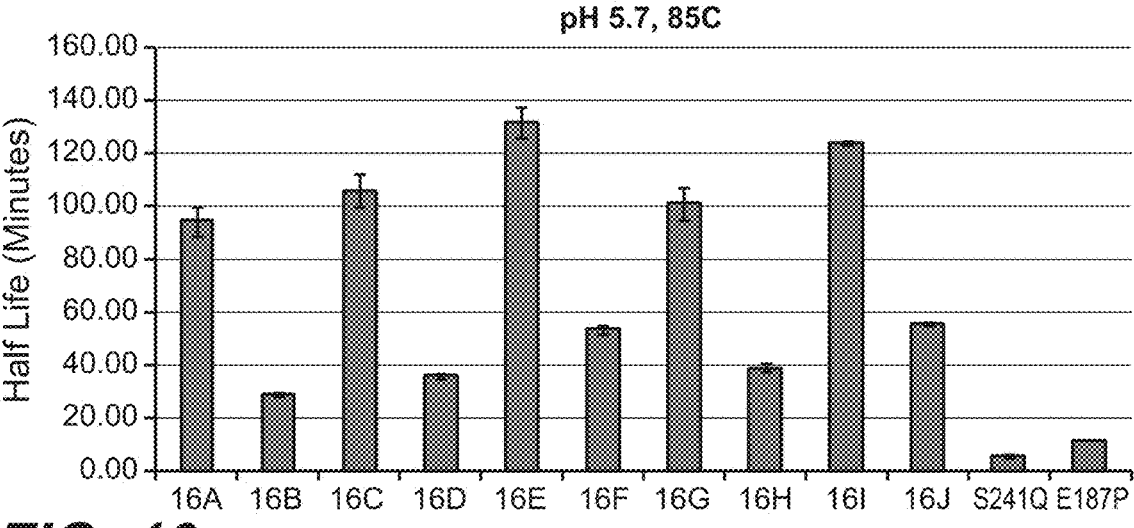
FIG. 10 is a graph showing the thermal stability of the C16 variants and reference molecules CspAmy2-v1-E187P and CspAmy2-v1-S241Q at pH 5.7 and 85° C.

The performance index (PI) for each variant was defined as the ratio of the variant half-life to the half-life of a reference parent molecule. For variants C16A, C16C, C16E, C16G, and C16I, the reference molecule was CspAmy2-v1-E187P. For variants C16B, C16D, C16F, C16H, and C16J, the reference molecule was CspAmy2-v1-S241Q. The relative half-lives and performance indexes are shown in the Table in FIG. 7. Other experiments demonstrated that the stability of C16D was similar to that of STAINZYME®, while the stability of C16F was greater than that of STAIN-ZYME® (not shown). The relative performance of the combination variants at pH 4.5 and 65° C., pH 5.0 at 70° C., and pH 5.7 ay 85° C., is shown graphically in FIGS. 8-10, respectively. All C16A-J variants were more stable than their respective parent molecules.

Example 8

Viscosity Reduction Using CspAmy2 Variants

Combination variants CspAmy2-C16A-CspAmy2-C16J from Example 5 were tested for their ability to reduce the viscosity of a starch solution, as a measure of starch hydrolysis activity. Viscosity experiments were performed using a Rapid Visco Analyser (Newport Scientific; herein "RVA") with 38 mm×68 mm plain washed cans (Part No. AA0384001) and a double-skirted paddle (Part No. NS101783). Data acquisition and analysis was performed with Thermocline for Windows (version 3.11; (Newport Scientific)). Immediately before each run, 33 g of 25% dry solids (ds) corn flour slurry was prepared in an RVA can as follows: 9.17 g corn flour (11.8% moisture content) was weighed out on an analytical balance and mixed with 23.83 g deionized water. Sample pH was adjusted with 0.0828 ml 1N sulfuric acid (for pH 5.8) or 0.285 ml 1N sulfuric acid (for pH 5.0). Enzyme was added at appropriate dose, and the can was placed in the viscometer. All runs were 10 minutes in length, with a temperature ramp to 85° C. over 80 seconds followed by a temperature hold at 85° C. for the remainder of the run. Each enzyme was assessed at three doses. Dose responses were calculated for two parts of the viscosity curve. Peak viscosity is defined as the maximum viscosity reached during the experiment, and final viscosity is defined as the viscosity reading at the end of the experiment. Because viscosity has a reciprocal relationship with enzyme dose, dose response curves were linearized by plotting 1/viscosity (also called fluidity) vs. enzyme dose. Slopes of these curves were used as a quantitative measure of the specific activity of each variant. The performance index (PI) for each variant is defined as the ratio of the variant specific activity to the specific activity of a reference parent molecule. For variants CspAmy2-C16A, CspAmy2-C16C, CspAmy2-C16E, CspAmy2-C16G, and CspAmy2-C16I, the reference is CspAmy2-v1-E187P. For variants CspAmy2-C16B, CspAmy2-C16D, CspAmy2-C16F, CspAmy2-C16H, and CspAmy2-C16J, the reference is CspAmy2-v1-S241Q. Viscosity reduction performance is shown in Tables 3 and 4.

TABLE 3

| Improvements in viscosity reduction at pH 5.8 | | | |
|---|---|---|---|
| | Peak Fluidity/mg enzyme | Peak PI | Final Fluidity/mg enzyme | Final PI |
| C16A | 0.0044 | 1.10 | 0.17 | 1.99 |
| C16B | 0.0047 | 1.18 | 0.17 | 1.47 |
| C16C | 0.0048 | 1.20 | 0.17 | 1.96 |
| C16D | 0.0049 | 1.22 | 0.18 | 1.53 |
| C16E | 0.0043 | 1.08 | 0.18 | 2.12 |
| C16F | 0.0044 | 1.10 | 0.18 | 1.56 |

TABLE 3-continued

| Improvements in viscosity reduction at pH 5.8 | | | |
| --- | --- | --- | --- |
| | Peak Fluidity/mg enzyme | Peak PI | Final Fluidity/mg enzyme | Final PI |
| C16G | 0.0051 | 1.28 | 0.17 | 1.99 |
| C16H | 0.0045 | 1.11 | 0.17 | 1.44 |
| C16I | 0.0047 | 1.19 | 0.19 | 2.16 |
| C16J | 0.0050 | 1.25 | 0.19 | 1.65 |
| E187P | 0.0040 | 1.00 | 0.09 | 1.00 |
| S241Q | 0.0040 | 1.00 | 0.12 | 1.00 |

TABLE 4

| Improvements in viscosity reduction at pH 5.0 | | | |
| --- | --- | --- | --- |
| | Peak Fluidity/mg enzyme | Peak PI | Final Fluidity/mg enzyme | Final PI |
| C16A | 0.0180 | 1.27 | 0.17 | 1.96 |
| C16B | 0.0065 | 1.27 | 0.14 | 1.80 |
| C16C | 0.0061 | 1.24 | 0.19 | 2.08 |
| C16D | 0.0062 | 1.20 | 0.16 | 1.97 |
| C16E | 0.0065 | 1.33 | 0.19 | 2.16 |
| C16F | 0.0061 | 1.18 | 0.17 | 2.16 |
| C16G | 0.0072 | 1.46 | 0.19 | 2.10 |
| C16H | 0.0063 | 1.23 | 0.16 | 1.98 |
| C16I | 0.0067 | 1.35 | 0.20 | 2.23 |
| C16J | 0.0069 | 1.35 | 0.19 | 2.36 |
| E187P | 0.0049 | 1.00 | 0.09 | 1.00 |
| S241Q | 0.0051 | 1.00 | 0.08 | 1.00 |

Example 9

Cleaning Performance and Detergent Stability of CspAmy2 Variants

A. Cleaning Performance of CspAmy2 Variants

The cleaning performance of combination variants CspAmy2-C16A-CspAmy2-C16J from Example 5 was analyzed in a microswatch cleaning assay using CFT CS-28 rice starch on cotton swatches. The assay was performed using culture supernatants. Protein concentration for the supernatants was quantified using HPLC. The equipment used for this assay included a Biomek FX Robot (Beckman Coulter), a SpectraMAX MTP Reader (type 340-Molecular Devices) and iEMS incubator/shaker (Thermo Scientific). The reagent and solutions used were:

1) CS-28 Microswatches (rice starch, colored);
2) 10 mM HEPES, 2 mM $CaCl_2$, 0.005% TWEEN 80 buffer, pH 8.0, conductivity 1 mS/cm;
3) 50 mM MOPS pH7.15, 0.005% TWEEN 80.

CS-28 microswatches of 5.5 mm circular diameter were provided by the Center for Testmaterials (CFT, Vlaardingen, The Netherlands). Two microswatches were placed in each well of a 96-well Corning 9017 flat bottomed polystyrene MTP. The culture supernatants were diluted twenty-fold in 50 mM MOPS pH7.15, 0.005% TWEEN 80.

The incubator/shaker was set at 25° C. (ambient temperature). 178.5 µL of HEPES buffer, respectively, was added to each well of microswatch containing MTP and subsequently 1.5 µL of diluted enzyme solution was added to each well resulting in a total volume of 180 µL/well. The MTP was sealed with a plate seal and placed in the iEMS incubator/shaker and incubated for 15 minutes at 1150 rpm at 25° C. Following incubation under the appropriate conditions, 100

µL of solution from each well was transferred to a new MTP, and the absorbance at 488 nm was measured using a MTP-spectrophotometer. Controls containing two microswatches and buffer but no enzyme were included for subtraction of background cleaning performance.

Each absorbance value was corrected by subtracting the blank (obtained after incubation of microswatches in the absence of enzyme), and the resulting absorbance provided a measure of the hydrolytic activity. A performance index (PI) was calculated for each sample compared to CspAmy2-v1, assuming a linear response in the range of the assay used. The results are shown in Table 4.1.

B. Detergent Stability of CspAmy2 Variants

The detergent stability of the additional CspAmy2 variants was determined by measuring their activity after incubation under defined conditions, in the presence of a 10% detergent mixture (commercially purchased Persil Color Gel detergent, Henkel (Dusseldorf, Germany), purchased in 2011). The detergent was heat-inactivated before use, and the initial and residual amylase activities were determined using the Ceralpha α-amylase assay. The equipment used for this assay included a Biomek FX Robot (Beckman Coulter); a SpectraMAX MTP Reader (type 340-Molecular Devices), a Tetrad2DNA Engine PCR machine (Biorad), and iEMS incubator/shaker (Thermo Scientific). The reagent solutions used were as follows:

1) p-nitrophenyl maltoheptaoside (BPNPG7) substrate (Megazyme Ceralpha HR kit):
2) Liquid detergent (Persil color gel, enzyme inactivated by heating for 4 hrs at 90° C.);
3) 50 mM MOPS, 0.1 mM $CaCl_2$, 0.005% TWEEN®80 buffer, pH 7 (dilution buffer);
4) 10% detergent solution diluted in dilution buffer;
5) 200 mM Boric acid/NaOH buffer, pH 10 (STOP buffer)
6) Amylase culture supernatants diluted eight fold in 50 mM MOPS pH7.15, 0.1 mM $CaCl_2$ containing 0-100 µg/mL protein 80 µL of a 10% detergent solution was added to a 96-well PCR plate and mixed with 20 µL of the diluted culture supernatant. A sample from the PCR plate was diluted 10× in dilution buffer and a 5 µL aliquot of this dilution was used to determine initial amylase activity. The PCR plate was incubated in a Tetrad PCR block at 80.5° C. for 5 minutes. After incubation, detergent-enzyme mix was diluted 10× in dilution buffer and residual activity was measured. Initial ($t_{initial}$) and residual ($t_{residual}$) amylase activity was determined in triplicate by the Ceralpha α-amylase assay using 5 µL samples.

For each variant, the ratio of the residual and initial amylase activities was used to calculate the detergent stability as follows: Detergent stability=[$t_{residual}$ value]/[$t_{initial}$ value]. For each sample (variants) the performance index (PI) was calculated. The performance index for detergent stability is determined by comparing the detergent stability of the variant enzyme with that of the similarly treated CspAmy2-v1 enzyme. The results are shown in Table 5.

TABLE 5

| Cleaning performance and stability of CspAmy2 variants | | |
| --- | --- | --- |
| | Performance Index | |
| Variant | Cleaning | Stability |
| CspAmy2-v1 | 1 | 1 |
| CspAmy2-C16B | 1.02 | 2.51 |
| CspAmy2-C16D | 1.32 | 2.37 |

TABLE 5-continued

| Cleaning performance and stability of CspAmy2 variants | | |
|---|---|---|
| | Performance Index | |
| Variant | Cleaning | Stability |
| CspAmy2-C16F | 1.25 | 2.41 |
| CspAmy2-C16H | 1.2 | 1.17 |
| CspAmy2-C16J | 1.06 | 0.83 |

Example 10

Generation of *Bacillus* Strains Expressing CspAmy2 Combinatorial Variants

A. Design of Combinatorial Variants

Synthetic DNA encoding two additional CspAmy2 variants were constructed by GeneArt and delivered as plasmids transformed in a *B. subtilis* host, as described for CspAmy2-v5 and CspAmy2-v6 in Example 2. CspAmy2 v171 is a variant of CspAmy2 having the mutations T180D, E187P, I203Y, G476K, and lacking R178 and G179. CspAmy2 v172 is a variant of CspAmy2 having the mutations N126Y, T180D, E187P, I203Y, G476K, and lacking R178 and G179.

The amino acid sequence of mature CspAmy2-v171 is shown, below, as SEQ ID NO: 22:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRNQETSGEYNIQAWTGFNFPGRGTTY

SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNKGSVSVWVQQ

The amino acid sequence of mature CspAmy2-v172 is shown, below, as SEQ ID NO: 23:

AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNKGSVSVWVQQ

Example 11

Thermostability Assessment of CspAmy2 Combinatorial Variants

The cleaning detergent stability of purified CspAmy2-v171 and CspAmy2-v172 was compared to that of CspAmy2-v5, and ACE-QK, as described in Example 5. The results are shown in FIG. 11. The stability of CspAmy2-v172 was greater than all other tested enzymes.

Example 12

Cleaning Benefit of a CspAmy2 Combinatorial Variant in Hand Dishwashing

The cleaning benefit of a CspAmy2 variant was compared to that of a commercially-available α-amylase [STAIN-ZYME® (Novozymes A/S)] in a hand dishwashing application. In an assay intended to simulate hand washing, 0.01% (wt/wt) active enzyme (CspAmy2-v6, STAIN-ZYME®, or no enzyme as a control) was added to European Dreft laundry detergent (1 g/L in water; Procter & Gamble, Cincinnati, Ohio, USA) and incubated in the presence of DM77 starch monitor (i.e., ADW melamine tiles from Center for Test Materials CFT BV in Vlaardingen, the Netherlands) at 40° C. with agitation in Laundr-o-meter. The results are shown in FIG. 12. CspAmy2-v5 was far superior to STAINZYME® in cleaning performance in terms of the rate of cleaning observed and the end point reached. Importantly, the rate of cleaning achieved by CspAmy2-v5 was so rapid that benefits were observed within a period of time relevant to hand dishwashing applications (i.e., about 30 seconds). These results indicate that CspAmy2 variants have potential as additives for hand dishwashing compositions.

Example 13

Cleaning Benefit of a CspAmy2 Combinatorial Variant in Automatic Dishwashing

The cleaning benefit of a CspAmy2 variant was compared to that of two benchmark α-amylases (i.e., STAINZYME® and POWERASE®) in an automatic dishwashing (ADW) application. The cleaning assays were performed in a standard Miele 6382 dishwasher using a normal cycle (50° C. and 60 minutes) with water having a hardness of 21 GH and 37.5 FH. 20 g of ADW powder detergent was used for each dishwashing cycle. The detergent was either WfK Type B or Type C (Testgewebe GmbH, Brüggen, Deutschland), which are described in Tables A and B, respectively of FIG. 13.

The test samples were either pasta or mixed-starch stained dishes. The pasta samples were prepared by mixing 150 g of strained pasta cooked in 17 GH water with 200 mL distilled water in a blender for 5 minutes to obtain a chewing gum-like suspension. About 3 g of the suspension was brushed onto the surface of each dish to be included in the cleaning assay, allowed to dry for 24 hours, baked onto the dishes at 120° C. for 2 hours, and allowed to cool. Cleaning performance was evaluated by adding iodine to the washed dishes and using a photo scale rating of 1-10. The mixed starch samples were prepared by mixing 26 g each of potato, corn, rice, and wheat starch in about 4 L g 16 GH water and heating to 95° C. for 10 minutes. After cooling to room temperature, about 30 mL of the mixture was applied to the surface of each dish to be included in the cleaning assay, allowed to dry on the surface of the dishes for 48 hours at room temperature, baked onto the dishes at 80° C. for 1 hour, and allowed to cool. Cleaning performance was determined by weighing the dishes before and after the cleaning assay to determine the amount of starch removed.

Figure 14:
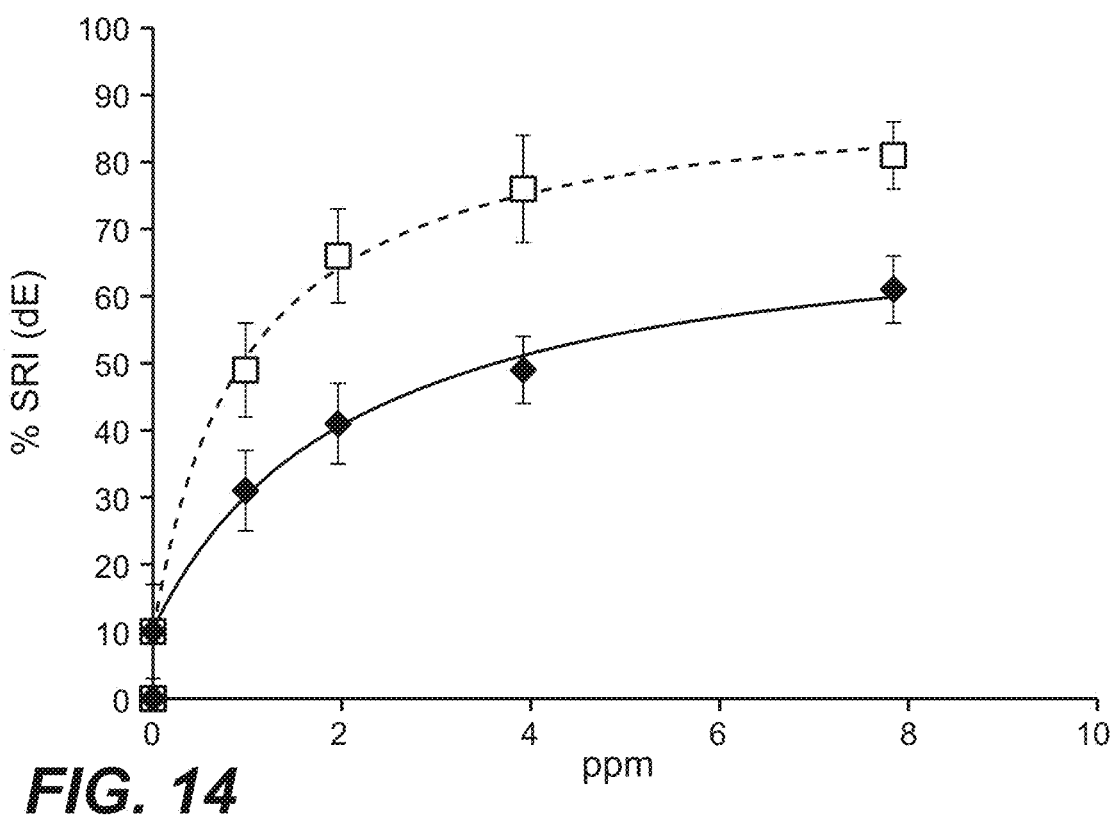
FIGS. 14 and 15 show the cleaning performance of CspAmy2-v6 (squares) compared to POWERASE® (diamonds), dosed at 0, 1, 2, 4, or 8 ppm in WfK B detergent against the mixed starch stain (FIG. 14) and the pasta stain (FIG. 15).
Figure 15:
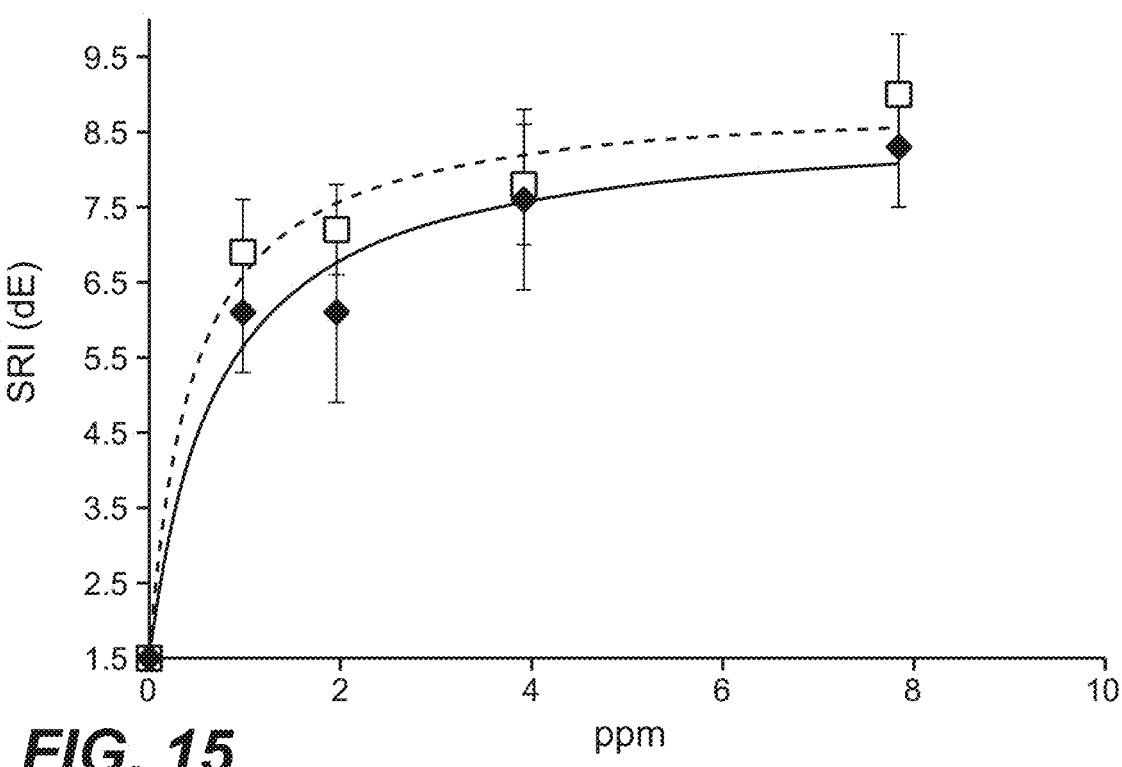
Figure 16:
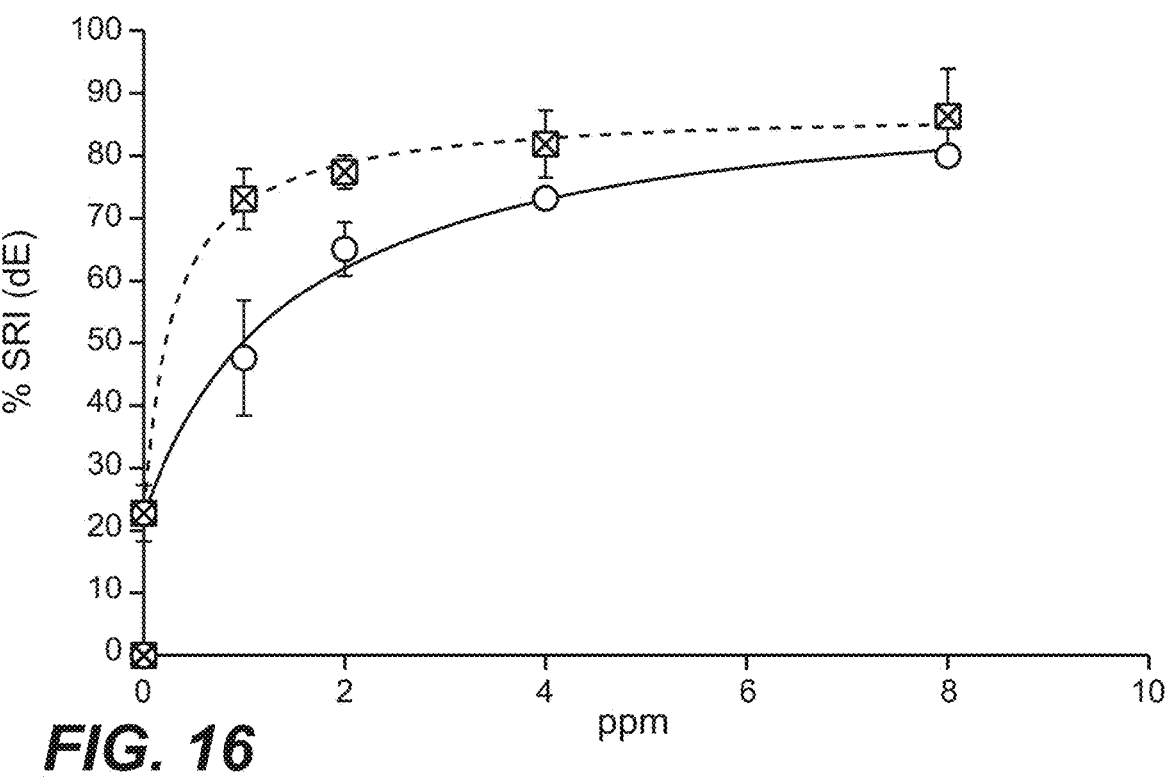
FIGS. 16 and 17 show the cleaning performance of CspAmy2-v6 (squares) compared to STAINZYME® (circles), dosed at 0, 1, 2, 4, or 8 ppm WfK B detergent against the mixed starch stain (FIG. 16) and the pasta stain (FIG. 17).
Figure 17:
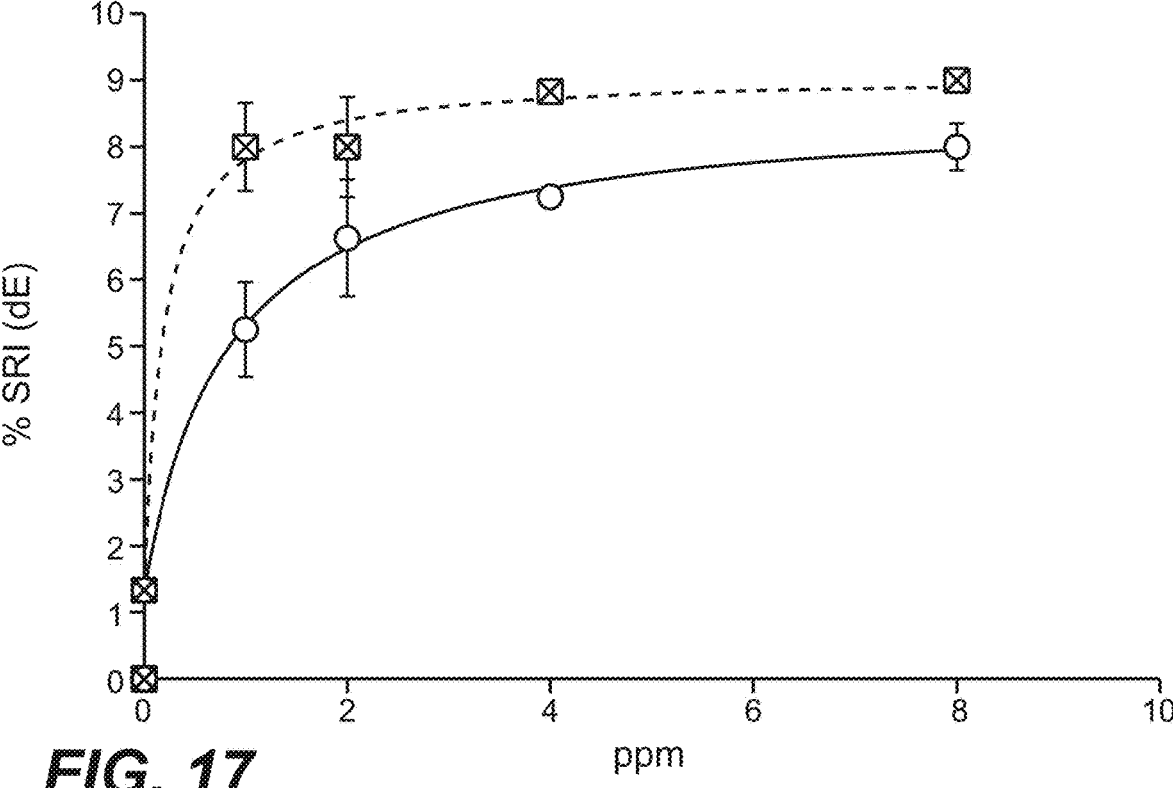

FIGS. 14 and 15 show the cleaning performance of CspAmy2-v6 (squares) compared to POWERASE® (diamonds), dosed at 0, 1, 2, 4, or 8 ppm in about 2.5 cents/kg (ct/kg) WfK B detergent against the mixed starch stain (FIG. 14) and the pasta stain (FIG. 15). CspAmy2-v6 clearly outperformed POWERASE®, particularly against the mixed starch stain. FIGS. 16 and 17 show the cleaning performance of CspAmy2-v6 (squares) compared to STAINZYME® (circles), dosed at 0, 1, 2, 4, or 8 ppm in about 2.5 ct/kg WfK B detergent against the mixed starch stain (FIG. 16) and the pasta stain (FIG. 17). CspAmy2-v6 clearly outperformed STAINZYME®, especially at low doses. FIGS. 18 and 19 show the cleaning performance of CspAmy2-v6 (squares) compared to POWERASE® (diamonds), dosed at 0, 1, 2, 4, or 8 ppm in about 2.5 ct/kg WfK C detergent against the mixed starch stain (FIG. 18) and the pasta stain (FIG. 19). CspAmy2-v6 clearly outperformed POWERASE® against both stains.

Example 14

Site Evaluation Library Screen of C18P and Identification of Activity-Enhancing Mutations Site evaluation libraries (SELs) were constructed and screened at 283 of 485 positions in variant CspAmy2-C18P (i.e., CspAmy2 with the mutations N126Y, F153W, T180D, I203Y, and S241Q, and lacking R178 and G179 (referring to SEQ ID NO: 1 for numbering) to identify additional variants with enhanced activity on one or more of the following substrates: corn amylopectin, swelled corn starch, granular corn starch, and corn starch-stained microswatches. Mutations were discovered throughout the molecule that improved activity. A subset of these variants was re-tested at different dose responses to confirm enhanced activity.

The amino acid sequence of the mature CspAmy2-C18P amylase polypeptide is shown, below, as SEQ ID NO: 24 (the substitutions are underlined):

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRYQETS GEYNIQAWTG FNFPGRGTTY SNWKWQWFHF

DGTDWDQSRS LSRIFKFDGK AWDWEVSSEN GNYDYLMYAD

YDYDHPDVVN EMKKWGVWYA NEVGLDGYRL DAVKHIKFQF

LKDWVDNARA ATGKEMFTVG EYWQNDLGAL NNYLAKVNYN

QSLFDAPLHY NFYAASTGGG YYDMRNILNN TLVASNPTKA

VTLVENHDTQ PGQSLESTVQ PWFKPLAYAF ILTRSGGYPS

VFYGDMYGTK GTTTREIPAL KSKIEPLLKA RKDYAYGTQR

DYIDNPDVIG WTREGDSTKA KSGLATVITD GPGGSKRMYV

GTSNAGEIWY DLTGNRTDKI TIGSDGYATF PVNGGSVSVW

VQQ
```

Corn Amylopectin Assay

Hydrolysis of soluble corn amylopectin was used to measure specific activity of amylase variants. Activity was measured as reducing ends generated by the enzymatic hydrolysis of amylopectin polymers as quantified using a bicinchoninic acid (BCA) assay. The equipment used for the assay included a Biomek FX Robot (Beckman Coulter), a SpectraMAX MTP Reader (type 340-Molecular Devices), and a Tetrad2DNA Engine PCR machine (Biorad).

Purified corn amylopectin (MP Biomedicals, LLC, cat. #195048) was solubilized by boiling for 5 minutes while stirring as a 1.5% (w/w) suspension in water. The material was allowed to cool to room temperature and water and concentrated stock solutions were added to obtain a final amylopectin substrate with 1.25% (w/w) amylopectin, 6.25 ppm calcium, 62.5 ppm sodium, 62.5 mM potassium acetate (pH 5.0), and 0.005% (v/v) Tween 80.

40 µl of the amylopectin substrate was added to 3 PCR microtiter plates. 10 µl of culture supernatant diluted 1:2000 in water/0.005% tween 80 was added to plates followed by through mixing by up and down pipetting. The plates were sealed and placed at 70° C. for 5 minutes followed by a ramp down to 25° C. Amylopectin hydrolysis was terminated by immediate addition/mixing of 10 µL 0.5 N NaOH.

The starch hydrolysis reaction products were analyzed by the BCA assay. Briefly, a reagent provided in a commercial kit (Pierce Chemical, cat. no. 23225) was prepared as per manufacturer's instructions. 90 µl was aliquoted to PCR plates followed by 10 µl of the terminated enzyme reaction described above. After through mixing of components the plates were sealed and placed in a thermocycler, programmed for 3 minutes at 95° C. to develop color, and then cooled to 30° C. Samples of 70 µL of the developed BCA reaction mixtures were transferred to a fresh plate and absorbance was measured at 562 nm in a spectrophotometer. Data acquired for three replicate plates were averaged.

Corn Starch Assay

Cargill Corn Starch material (flour or starch) was washed extensively with MilliQ water by repeated suspension and centrifugation prior to use in the assay. The washed corn starch was suspended in MilliQ water containing 0.005% sodium azide to obtain 20% (w/w) stock solutions, which were further diluted with a 20× stock buffer solution to 10.9% w/v corn flour and corn starch solutions (final buffer concentration of 55 mM KOAc, pH 5).

55 µL of the diluted corn flour or corn starch substrates were added to PCR microtiter plates along with 5 µL of 1:10 diluted enzyme samples using a bubble paddle reservoir. The plates were sealed and placed at 86° C. for 5 minutes followed by a ramp down to 45° C. The starch hydrolysis reaction was terminated by addition of 70 µL 0.1 N NaOH. The plates were sealed and centrifuged for 3 minutes at 1,610 RCF. The starch hydrolysis reaction products were analyzed by the BCA assay as described above.

Swelled Corn Starch (SCS) Assay

The SCS assay measures alpha-amylase activity on hydrated but intact ("swelled") starch granules. The overall number of enzymatic turnovers is assessed using the BCA reducing sugar assay, while the tendency of the enzyme to release large starch fragments into solution is assessed using iodine staining.

2% (w/w) swelled corn starch substrate was prepared by suspending 2 g of corn starch (Cargill Farms Organic Corn Starch) in 90 g of MilliQ water and heating in a submerged water bath set to 80° C. for 1 hour with regular swirling. After overnight cooling at room temperature, the volume was brought up to 100 mL with the addition of potassium acetate buffer, calcium chloride, sodium chloride and Tween-80 to give final concentrations of 50 mM KOAc (pH5.5), 0.125 mM CaCl$_2$), 2 mM NaCl, and 0.005% Tween-80.

55 µL of swelled corn starch substrate was dispensed into NUNC V-bottom polystyrene microtiter plates using a bubble paddle reservoir. The reaction was initiated by adding 5 µL of 12× enzyme solution to the plate to give a final enzyme concentration of ~0.03 ppm in reaction. The reaction plate was sealed with a Nunc seal and immediately placed in an iEMS incubator. Incubation occurred for 10 min at 25° C., or for 4 min at 60° C., while shaking at 1,150 RPM. After incubation, the reaction was terminated with the addition of 70 µL of 0.1 N NaOH. The plates were sealed and spun for 3 min at 3,000 RPM. Swelled corn starch reactions were done as a single plate, but assayed in triplicate for subsequent Iodine and BCA assays.

The BCA assay is described above. For the iodine reaction, 95 µL of Lugol's reagent (freshly diluted by 12-fold in water; Sigma-Aldrich L6146-1L) was added to 96-well Costar 9017 microtiter plates. 5 µL of supernatant sample was added to the plates and mixed six times by pipetting up and down. The plates were then shaken on a table top microtiter plate mixer for 1 minute at speed 6-7. Absorbance was read at 530 nm using a SpectraMax M5 spectrophotometer.

CS-26 Corn Starch Microswatch Assay

The assays were performed as described, above, except that 170 µl of potassium acetate buffer was added to each well of microswatch-containing MTP and subsequently 10 µL of diluted enzyme solution was added to each well resulting in a total volume of 180 µL/well. The MTP was sealed and incubated for 20 minutes at 1,150 rpm at 25° C.

Viscosity Analysis

Viscosity experiments were performed using a Rapid Visco Analyser (Newport Scientific) with 38 mm×68 mm plain washed cans (Part No. AA0384001) and a double-skirted paddle (Part no. NS101783). Data acquisition and analysis was performed with Thermocline for Windows (version 3.11). Immediately before each run, 33 g of 25% dry solids (ds) corn flour slurry was prepared in an RVA can as follows: 9.17 g corn flour (11.8% moisture content) was weighed out on an analytical balance and mixed with 23.83 g deionized water. The sample pH was adjusted with 0.0828 mL 1N sulfuric acid (for pH 5.7) or 0.285 mL 1N sulfuric acid (for pH 5.2). Enzyme was added at appropriate dose, and the can was placed in the viscometer. All runs were 10 minutes in length, with a temperature ramp to 85° C. or 95° C. over 80 seconds followed by a temperature hold at 85° C. or 95° C. for the remainder of the run.

Initial Screening Results

Mutations resulting in variants with expression greater than 250 µg/mL and at least 110% of the performance of CspAmy2-C18P in any one of the indicated assays in each assay were classified as performance-enhancing mutations. CspAmy2-C18P SEL variants with mutations at positions 6, 7, 8, 11, 14, 15, 20, 21, 23, 26, 27, 28, 37, 38, 39, 40, 42, 45, 46, 48, 49, 50, 51, 52, 53, 54, 58, 61, 62, 68, 70, 71, 72, 73, 79, 80, 81, 82, 84, 85, 87, 88, 89, 92, 93, 94, 95, 96, 97, 98, 101, 108, 111, 112, 113, 114, 115, 116, 117, 118, 120, 122, 123, 124, 126, 127, 129, 130, 131, 132, 133, 134, 136, 137, 138, 140, 142, 143, 144, 147, 148, 149, 150, 151, 152, 153, 154, 155, 156, 158, 159, 165, 167, 168, 170, 171, 172, 175, 176, 177, 180, 181, 182, 187, 190, 191, 193, 199, 200, 201, 203, 206, 208, 210, 211, 212, 214, 215, 216, 219, 221, 223, 225, 226, 227, 235, 238, 239, 240, 241, 242, 243, 245, 246, 247, 248, 249, 250, 252, 253, 254, 256, 257, 258, 260, 261, 262, 266, 267, 268, 269, 270, 271, 273, 276, 277, 279, 280, 282, 284, 285, 286, 288, 296, 299, 300, 301, 302, 303, 304, 307, 308, 310, 311, 312, 313, 316, 317, 318, 320, 321, 325, 327, 335, 338, 342, 348, 349, 352, 356, 357, 360, 362, 363, 368, 369, 377, 381, 382, 383, 384, 385, 388, 390, 392, 394, 395, 396, 397, 398, 400, 401, 402, 403, 404, 405, 407, 408, 410, 414, 415, 416, 418, 419, 420, 421, 422, 423, 424, 426, 428, 429, 430, 431, 434, 435, 436, 439, 441, 442, 444, 445, 446, 447, 448, 449, 450, 451, 454, 455, 457, 460, 461, 462, 463, 464, 465, 466, 467, 469, 470, 471, 473, 474, 475, 476, 477, 479, 480, 481, 482, 483, and 484 met this criteria. Specific performance-enhancing mutations included T6A, T6D, T6E, T6G, T6K, T6M, T6N, T6Q, T6S, M7A, M7V, M8C, M8F, M8I, M8L, M8Y, F11V, Y14A, Y14I, Y14Q, Y14T, Y14V, V15C, V15D, V15I, V15N, V15T, Q20A, Q20C, Q20D, Q20H, Q20K, Q20M, Q20N, Q20R, Q20S, Q20Y, Q21F, Q21W, N23A, N23C, N23D, N23E, N23H, N23K, N23Q, N23R, N23S, N23T, N23V, R26C, R26E, R26G, R26K, R26M, R26S, R26T, T27A, T27C, T27D, T27E, T27F, T27H, T27I, T27K, T27L, T27M, T27N, T27Q, T27R, T27S, T27V, T27Y, D28A, D28C, D28T, I37F, I37V, T38D, T38N, A39L, V40A, V40C, V40D, V40G, V40H, V40I, V40K, V40M, V40P, V40Q, V40R, V40S, V40T, V40W, V40Y, T42A, T42C, T42I, T42M, T42V, A45C, A45G, Y46F, G48A, T49I, S50A, S50C, S50E, S50G, S50K, S50M, S50N, S50Q, S50R, S50T, S50Y, Q51C, Q51D, Q51E, Q51S, Q51V, A52C, A52D, A52E, A52F, A52G, A52H, A52K, A52L, A52M, A52R, A52S, A52T, A52V, A52Y, D53E, V54N, V54T, P58A, P58C, P58H, P58I, P58S, P58T, P58V, L61M, L61V, Y62A, Y62C, Y62D, Y62F, Y62G, Y62H, Y62I, Y62K, Y62L, Y62M, Y62N, Y62P, Y62Q, Y62R, Y62S, Y62V, N68C, N68D, N68E, N68F, N68H, N68L, N68P, N68Q, N68R, N68S, N68V, N68W, N68Y, K70R, G71A, G71C, G71D, G71E, G71K, G71R, G71S, T72G, T72S, V73S, T79F, T79I, T79L, T79M, T79N, T79S, T79Y, K80A, K80C, K80D, K80F, K80H, K80I, K80M, K80N, K80Q, K80R, K80S, K80T, K80V, K80Y, G81A, G81D, G81E, G81F, G81H, G81I, G81K, G81N, G81P, G81R, G81S, G81T, E82A, E82D, E82M, E82Q, K84A, K84C, K84E, K84I, K84Q, K84R, K84S, K84T, K84Y, S85A, S85C, S85D, S85E, S85G, S85H, S85I, S85L, S85M, S85N, S85Q, S85R, S85T, S85V, S85Y, V87I, V87T, N88C, N88D, N88E, N88G, N88H, N88I, N88K, N88L, N88M, N88Q, N88R, N88S, N88T, N88V, N88W, N88Y, T89A, T89D, T89E, T89F, T89H, T89I, T89K, T89L, T89M, T89N, T89Q, T89R, T89S, T89Y, S92A, S92C, S92D, S92E, S92F, S92G, S92H, S92L, S92M, S92N, S92Q, S92R, S92T, S92W, S92Y, N93A, N93C, N93E, N93F, N93H, N93I, N93K, N93L, N93Q, N93S, N93T, N93Y, G94A, G94C, G94N, I95M, Q96A, Q96E, Q96H, Q96I, Q96K, Q96L, Q96M, Q96N, Q96R, Q96V, Q96Y, V97I, V97T, Y98F, Y98I, Y98L, Y98V, V101C, V101T, G108A, G108S, Y111D, Y111E, Y111L, Y111N, Y111S, Y111T, Y111V, T112A, T112F, T112H, T112I, T112K, T112L, T112M, T112N, T112P, T112R, T112V, T112W, E113D, E113N, E113Q, E113T, N114A, N114C, N114D, N114E, N114F, N114G, N114H, N114I, N114L, N114P, N114Q, N114R, N114S, N114T, N114V, N114W, N114Y, V115A, V115I, T116A, T116C, T116D, T116G, T116H, T116I, T116K, T116N, T116P, T116Q, T116R, T116S, A117C, A117I, A117S, A117V, V118A, V118C, V118E, V118F, V118H, V118I, V118L, V118M, V118N, V118Q, V118R, V118S, V118W, V118Y, V120A, V120C, V120I, V120M, V120T, P122A, P122D, P122E, P122G, P122H, P122N, P122R, P122S, P122T, P122W, S123A, S123C, S123G, S123K, S123L, N124A, N124D, N124F, N124G, N124L, N124R, N124S, N124V, Y126A, Y126C, Y126D, Y126E, Y126G, Y126H, Y126I, Y126K, Y126L, Y126M, Y126N, Y126Q, Y126R, Y126S, Y126T, Y126V, Y126W, Q127A, Q127C, Q127D, Q127E, Q127F, Q127H, Q127I, Q127K, Q127L, Q127M, Q127N, Q127R, Q127S, Q127T, Q127V, Q127W, Q127Y, T129A, T129C, T129D, T129E, T129F, T129G, T129I, T129K, T129L, T129M, T129N, T129Q, T129R, T129S, T129V, T129W, T129Y, S130A, S130G, S130I, S130K, S130L, S130M, S130N, S130P, S130R, S130T, S130V, S130W, G131A, G131C, G131D, G131F, G131H, G131I, G131K, G131L, G131M, G131P, G131Q, G131V, G131W, G131Y, E132A, E132C, E132D, E132F, E132G, E132H, E132I, E132K, E132L, E132M, E132N, E132P, E132Q, E132R, E132V, E132W, Y133A, Y133D, Y133E, Y133G, Y133K, Y133L, Y133M, Y133R, Y133S, Y133T, Y133W, N134A, N134D, N134F, N134G, N134H, N134I, N134K, N134L, N134M, N134R, N134S, N134V, N134W, N134Y, Q136A, Q136C, Q136D, Q136E, Q136F, Q136H, Q136K, Q136L, Q136M, Q136N, Q136R, Q136S, Q136T, Q136V, Q136W, Q136Y, A137S, A137T, A137V, W138F, W138Y, G140A, G140M, N142F, N142K, N142L, N142M, N142P, N142V, N142W, N142Y, F143H, F143Y, P144C, P144D, P144E, P144G, P144H, P144I, P144K, P144L, P144M, P144N, P144Q, P144S, P144T, P144Y, G147A, G147C, G147H, G147K, G147L, G147M, G147N, G147Q, G147R, T148A, T148D, T148E, T148F, T148I, T148K, T148L, T148R, T148S, T148V, T148W, T149A, T149C, T149D, T149E, T149F, T149H, T149K, T149L, T149M, T149N, T149Q, T149V, T149W, T149Y, Y150H, S151A, S151E, S151F, S151H, S151I, S151K, S151L, S151M, S151Q, S151R, S151V, N152A, N152C, N152D, N152E, N152G, N152H, N152K, N152M, N152P, N152Q, N152R, N152S, N152T, W153F, W153H, W153Q, W153R, W153T, W153Y, K154A, K154C, K154D, K154E, K154G, K154I, K154L, K154M, K154N, K154R, K154T, K154Y, W155P, Q156A, Q156D, Q156E, Q156F, Q156G, Q156H, Q156I, Q156L, Q156M, Q156N, Q156R, Q156S, Q156Y, F158C, F158D, F158K, F158L, F158M, F158N, F158P, F158Q, F158R, F158S, F158V, H159M, H159Y, W165C, W165D, W165E, W165F, W165H, W165I, W165K, W165L, W165M, W165Q, W165R, W165T, W165Y, Q167A, Q167D, Q167E, Q167G, Q167H, Q167K, Q167M, Q167N, Q167P, Q167S, Q167T, Q167V, S168A, S168D, S168F, S168H, S168I, S168K, S168M, S168N, S168Q, S168R, S168T, S168V, S168W, S168Y, S170A, S170C, S170D, S170E, S170F, S170L, S170M, S170N, S170Q, S170R, S170T, L171A, L171C, L171F, L171G, L171H, L171I, L171N, L171Q, L171R, L171T, L171V, L171W, L171Y, S172A, S172D, S172H, S172R, S172T, F175M, F175Y, K176I, K176T, F177L, F177V, F177W, D180A, D180C, D180F, D180G, D180H, D180I, D180L, D180M, D180N, D180Q, D180R, D180S, D180T, D180V, D180W, D180Y, G181A, G181C, G181D, G181E, G181F, G181H, G181K, G181L, G181M, G181N, G181Q, G181R, G181S, G181T, G181V, G181Y, K182A, K182P, E187D, E187I, E187K, E187M, E187N, E187P, E187R, E187S, E187T, E187V, E187Y, S190A, S190C, S190D, S190F, S190L, S190N, S190P, S190Q, E191A, E191C, E191F, E191G, E191H, E191I, E191K, E191N, E191Q, E191R, E191S, E191T, E191W, E191Y, G193A, G193C, G193D, G193E, G193F, G193H, G193K, G193L, G193M, G193N, G193Q, G193R, G193S, G193T, G193V, G193W, M199L, Y200F, A201M, Y203I, Y203L, Y203V, D206A, D206E, D206G, D206H, D206M, D206N, D206Q, D206R, D206S, D206T, P208A, P208E, P208F, P208I, P208K, P208L, P208T, P208V, P208Y, V210A, V210E, V210H, V210K, V210N, V210Q, V210R, V210S, V210T, V211A, V211E, V211H, V211I, V211Q, V211R, N212E, N212F, N212G, N212L, N212M, N212R, N212V, M214I, M214L, K215C, K215E, K215F, K215M, K215N, K215R, K215Y, K216F, V219I, V219T, Y221F, Y221I, Y221L, N223C, N223E, N223I, N223K, N223Q, N223R, N223S, N223T, N223V, N223W, N223Y, V225A, V225I, V225L, V225M, G226D, G226M, G226Q, G226R, G226S, L227F, L227I, L227W, L227Y, V235A, I238A, I238L, I238M, K239D, K239E, K239P, K239Q, K239R, K239S, K239T, F240K, F240L, F240M, F240Q, F240R, Q241A, Q241C, Q241D, Q241E, Q241G, Q241H, Q241K, Q241L, Q241M, Q241N, Q241P, Q241R, Q241S, Q241T, Q241V, Q241W, Q241Y, F242V, L243C, L243Y, D245A, D245C, D245E, D245G, D245L, D245M, D245N, W246F, V247I, V247L, D248E, D248H, D248N, D248T, D248V, N249A, N249E, N249G, N249H, N249Q, N249Y, A250M, A250S, A250V, A252C, A252D, A252E, A252G, A252H, A252I, A252K, A252L, A252M, A252N, A252Q, A252S, A252V, A252W, A252Y, A253E, A253I, A253K, A253L, A253M, A253Q, A253S, A253T, A253V, A253Y, T254F, T254K, T254S, K256A, K256M, K256N, K256S, E257Q, E257S, M258L, T260A, T260C, T260S, T260V, V261I, V261W, G262A, Q266A, Q266D, Q266E, Q266H, Q266I, Q266M, Q266N, Q266S, Q266T, Q266V, Q266Y, N267H, N267I, N267Q, N267R, N267S, N267T, N267V, N267Y, D268G, D268N, L269C, L269D, L269I, L269K, L269Q, L269S, L269T, L269Y, G270A, G270D, G270E, G270F, G270H, G270I, G270L, G270M, G270Q, G270T, G270V, G270Y, A271C, A271D, A271E, A271H, A271K, A271M, A271Q, A271R, A271S, A271T, A271V, A271Y, N273C, N273G, N273H, N273I, N273K, N273R, L276I, L276M, A277C, A277D, A277E, A277F, A277G, A277I, A277K, A277L, A277M, A277N, A277Q, A277R, A277S, A277T, A277V, A277W, A277Y, V279C, V279T, N280A, N282S, N282T, S284T, S284Y, L285A, L285C, L285I, L285V, F286M, A288C, A296C, A296D, A296E, A296F, A296G, A296H, A296I, A296L, A296M, A296N, A296Q, A296R, A296S, A296V, A296W, A296Y, T299A, T299D, T299E, T299F, T299G, T299K, T299L, T299M, T299R, T299S, T299V, T299W, G300A, G300C, G300D, G300E, G300F, G300H, G300K, G300M, G300Q, G300R, G300V, G300W, G301A, G301C, G301D, G301E, G301F, G301H, G301K, G301L, G301M, G301Q, G301R, G301S, G301T, G301V, G301W, G301Y, G302S, Y303A, Y303C, Y303D, Y303E, Y303F, Y303G, Y303H, Y303I, Y303K, Y303L, Y303M, Y303N, Y303Q, Y303R, Y303S, Y303T, Y303V, Y303W, Y304F, Y304K, Y304W, R307A, R307C, R307E, R307G, R307H, R307K, R307M, R307N, R307Q, R307S, R307T, N308C, N308D, N308E, N308G, N308L, N308M, N308T, N308V, L310A, L310C, L310D, L310E, L310H, L310I, L310M, L310P, L310W, L310Y, N311C, N311E, N311G, N311H, N311K, N311Q, N311R, N311S, N311V, N311W, N311Y, N312D, N312F, N312G, N312H, N312K, N312Q, N312R, T313A, T313S, A316D, A316E, A316G, A316H, A316K, A316Q, A316R, A316Y, S317C, S317D, S317G, S317H, S317K, S317L, S317N, S317Q, S317R, S317T, S317W, S317Y, N318A, N318C, N318F, N318G, N318I, N318K, N318L, N318M, N318Q, N318R, N318S, N318T, N318V, N318W, T320A, T320C, T320D, T320E, T320G, T320H, T320I, T320K, T320N, T320P, T320Q, T320R, T320V, T320W, T320Y, K321C, K321F, K321H, K321N, K321S, K321Y, L325A, L325C, L325F, L325I, L325M, L325Q, L325V, E327D, E327L, Q335C, Q335E, E338A, E338D, E338F, E338G, E338H, E338I, E338K, E338P, E338Q, E338R, E338T, E338V, E338Y, Q342A, Q342C, Q342G, Q342I, Q342M, Q342R, Q342S, Q342T, Q342V, Q342W, L348A, L348C, L348H, L348I, L348M, L348Q, L348S, L348T, A349G, A349R, F352I, F352L, F352M, F352T, F352V, R356Q, S357A, S357C, S357D, S357E, S357F, S357H, S357I, S357K, S357L, S357N, S357Q, S357T, S357V, S357W, S357Y, Y360F, Y360I, Y360L, Y360M, Y360V, S362A, S362C, S362E, S362I, S362T, S362V, V363I, V363L, M368F, M368I, M368L, M368Y, Y369A, Y369E, Y369I, Y369L, Y369N, Y369V, R377A, R377C, R377D, R377E, R377F, R377G, R377H, R377I, R377K, R377L, R377N, R377Q, R377S, R377T, R377V, R377W, R377Y, A381C, A381E, A381G, A381H, A381K, A381L, A381M, A381N, A381P, A381Q, A381V, A381W, A381Y, L382F, L382H, L382Q, L382S, K383A, K383C, K383D, K383E, K383H, K383I, K383L, K383M, K383N, K383Q, K383R, K383S, K383W, K383Y, S384A, S384C, S384D, S384F, S384G, S384H, S384I, S384L, S384N, S384R, S384V, S384Y, K385A, K385D, K385E, K385F, K385G, K385H, K385L, K385M, K385Q, K385R, K385T, K385V, K385Y, P388A, P388C, P388D, P388I, P388L, P388N, P388R, P388S, P388T, P388V, L390M, L390V, A392C, A392S, K394A, K394C, K394E, K394F, K394G, K394H, K394I, K394L, K394Q, K394R, K394S, K394T, K394V, K394W, K394Y, D395A, D395E, D395N, D395S, D395T, Y396A, Y396D, Y396F, Y396K, Y396M, Y396N, Y396Q, Y396T, Y396V, Y396W, A397D, A397E, A397H, A397K, A397M, A397N, A397Q, A397V, Y398A, Y398C, Y398F, Y398H, Y398I, Y398L, Y398W, T400A, T400C, T400D, T400F, T400G, T400I, T400K, T400L, T400M, T400N, T400Q, T400R, T400W, T400Y, Q401A, Q401C, Q401F, Q401H, Q401I, Q401L, Q401M, Q401N, R402C, R402D, R402F, R402K, R402L, R402M, R402N, R402Q, R402S, R402W, D403E, D403N, D403S, Y404E, Y404G, Y404K, Y404M, Y404N, Y404R, Y404W, I405C, I405F, I405L, I405M, I405V, N407A, N407C, N407D, N407E, N407G, N407K, N407M, N407Q, N407R, P408A, P408C, P408D, P408I, P408K, P408L, P408M, P408N, P408Q, P408V, P408W, V410A, V410C, V410D, V410E, V410F, V410H, V410I, V410L, V410M, V410N, V410Q, V410S, V410T, T414A, T414I, T414S, T414V, R415M, E416C, E416D, E416F, E416H, E416I, E416K, E416L, E416M, E416N, E416Q, E416R, E416T, E416V, E416W, E416Y, D418A, D418E, D418G, D418H, D418I, D418K, D418L, D418M, D418N, D418Q, D418S, D418T, D418V, D418W, S419A, S419C, S419E, S419G, S419L, S419M, S419N, S419R, S419V, S419W, S419Y, T420A, T420C, T420D, T420E, T420G, T420H, T420I, T420K, T420M, T420P, T420S, T420V, T420W, T420Y, K421A, K421D, K421E, K421H, K421I, K421L, K421M, K421N, K421P, K421Q, K421R, K421T, K421V, K421W, K421Y, A422C, A422D, A422E, A422F, A422G, A422I, A422L, A422N, A422P, A422Q, A422R, A422S, A422Y, K423A, K423D, K423E, K423F, K423H, K423I, K423L, K423M, K423N, K423Q, K423R, K423S, K423T, K423V, K423W, K423Y, S424A, S424C, S424G, S424K, S424N, S424Q, S424R, S424T, L426S, L426T, L426V, T428G, T428V, V429A, V429C, V429I, V429L, I430C, I430G, I430L, I430M, I430Q, I430V, T431A, T431C, T43iS, P434A, P434C, P434D, P434E, P434F, P434H, P434I, P434K, P434L, P434M, P434N, P434Q, P434R, P434S, P434V, P434Y, G435A, G435C, G435D, G435E, G435F, G435H, G435I, G435K, G435M, G435N, G435P, G435Q, G435R, G435S, G435T, G435W, G436F, G436I, G436M, G436N, G436Q, G436S, G436V, R439A, R439D, R439G, R439H, R439K, R439M, R439N, R439P, R439Q, R439S, R439V, R439W, R439Y, Y441A, Y441C, Y441D, Y441F, Y441G, Y441H, Y441K, Y441L, Y441M, Y441N, Y441P, Y441R, Y441S, Y441T, Y441W, V442A, V442C, V442I, V442T, T444C, T444D, T444E, T444F, T444G, T444H, T444I, T444K, T444L, T444M, T444N, T444P, T444R, T444S, T444W, S445A, S445C, S445E, S445G, S445H, S445K, S445L, S445M, S445N, S445T, S445V, N446A, N446C, N446H, N446K, A447C, A447D, A447F, A447H, A447L, A447M, A447N, A447Q, A447R, A447S, A447Y, G448A, G448C, G448D, G448E, G448H, G448K, G448L, G448M, G448N, G448Q, G448R, G448S, G448T, G448W, E449D, E449H, E449K, E449T, I450A, I450C, I450D, I450E, I450G, I450K, I450L, I450M, I450N, I450Q, I450S, I450T, I450W, I450Y, W451Y, L454A, L454I, L454K, L454M, L454W, T455A, T455I, T455L, T455S, N457H, N457K, N457R, N457T, N457V, N457Y, D460A, D460E, D460G, D460M, D460N, D460Q, D460S, D460V, K461C, K461H, K461L, K461M, K461N, K461Q, K461T, K461Y, I462A, I462L, I462M, I462Q, I462T, I462V, T463D, T463E, T463H, T463P, T463Q, T463R, T463V, T463Y, I464P, I464T, G465A, G465C, G465D, G465E, G465K, G465L, G465M, G465N, G465Q, G465W, G465Y, S466A, S466C, S466D, S466G, S466H, S466K, S466L, S466M, S466N, S466T, S466W, S466Y, D467E, D467G, D467L, Y469A, Y469D, Y469E, Y469I, Y469M, Y469N, Y469R, Y469S, Y469T, Y469V, Y469W, A470S, A470V, T471A, T471C, T471E, T471G, T471H, T471I, T471L, T471M, T471N, T471S, T471V, T471W, P473C, P473D, P473E, P473G, P473I, P473K, P473L, P473R, P473T, P473W, V474A, V474C, V474L, V474S, N475A, N475C, N475E, N475F, N475H, N475K, N475L, N475M, N475P, N475Q, N475R, N475S, N475T, N475V, G476A, G476D, G476E, G476F, G476H, G476I, G476L, G476M, G476N, G476P, G476Q, G476R, G476S, G476T, G476V, G476W, G476Y, G477A, G477D, G477F, G477H, G477I, G477K, G477L, G477M, G477Q, G477S, G477T, G477V, G477W, G477Y, V479C, V479D, V479E, V479F, V479H, V479I, V479N, V479P, V479Y, S480A, S480C, S480H, V481A, V481C, V481N, W482Y, V483A, V483G, V483I, V483K, V483L, V483M, V483R, V483Y, Q484A, Q484C, Q484F, Q484G, Q484H, Q484K, Q484L, Q484M, Q484P, Q484R, Q484T, and Q484Y.

Dose Response Screening Results

Figure 20:
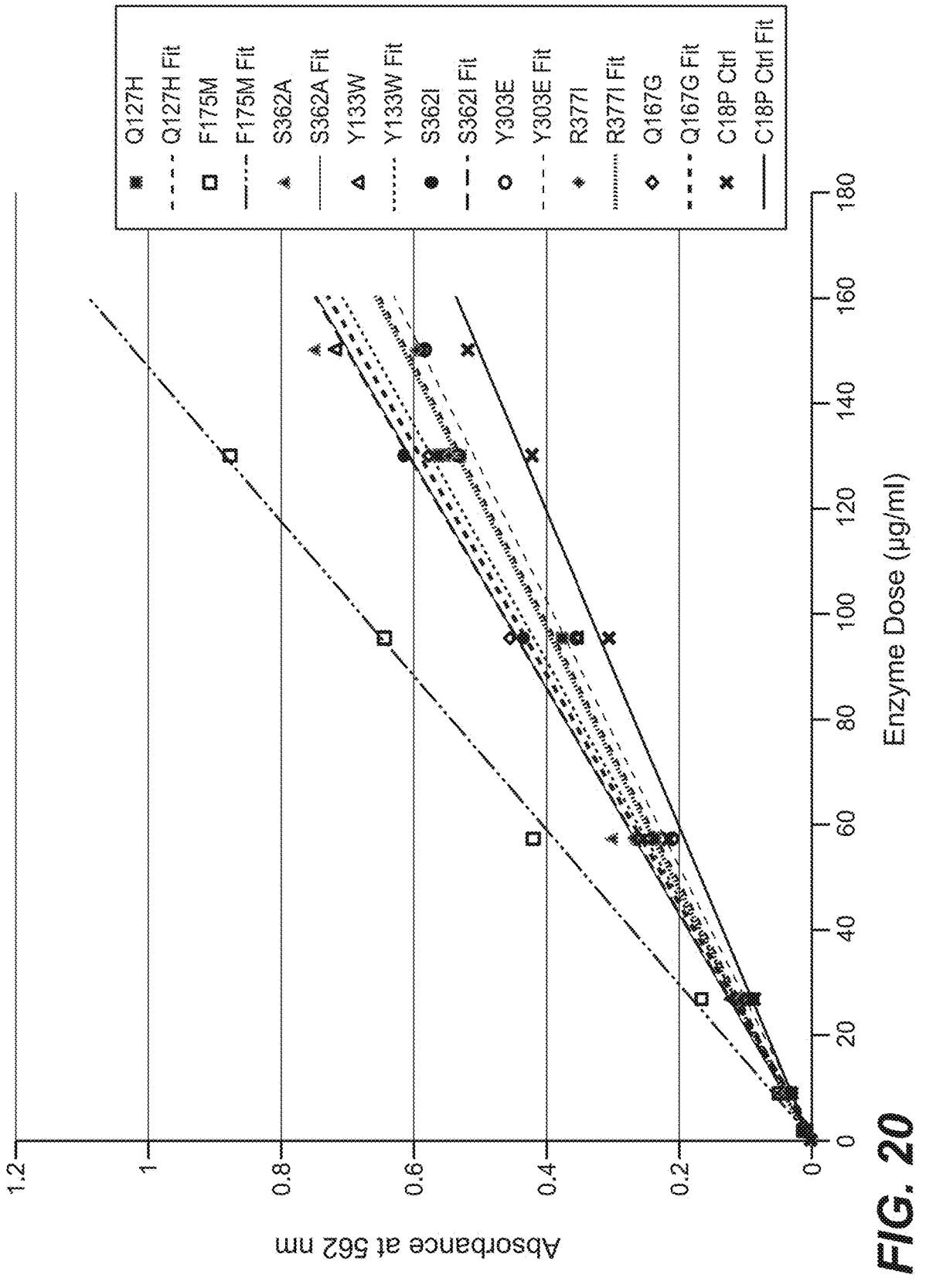
FIG. 20 is a graph showing examples of C18P variants demonstrating improved hydrolysis of corn starch at high temperatures. CspAmy2-C18P (N126Y+F153W+T180D+I203Y+S241Q) is shown as a reference.
Figure 21:
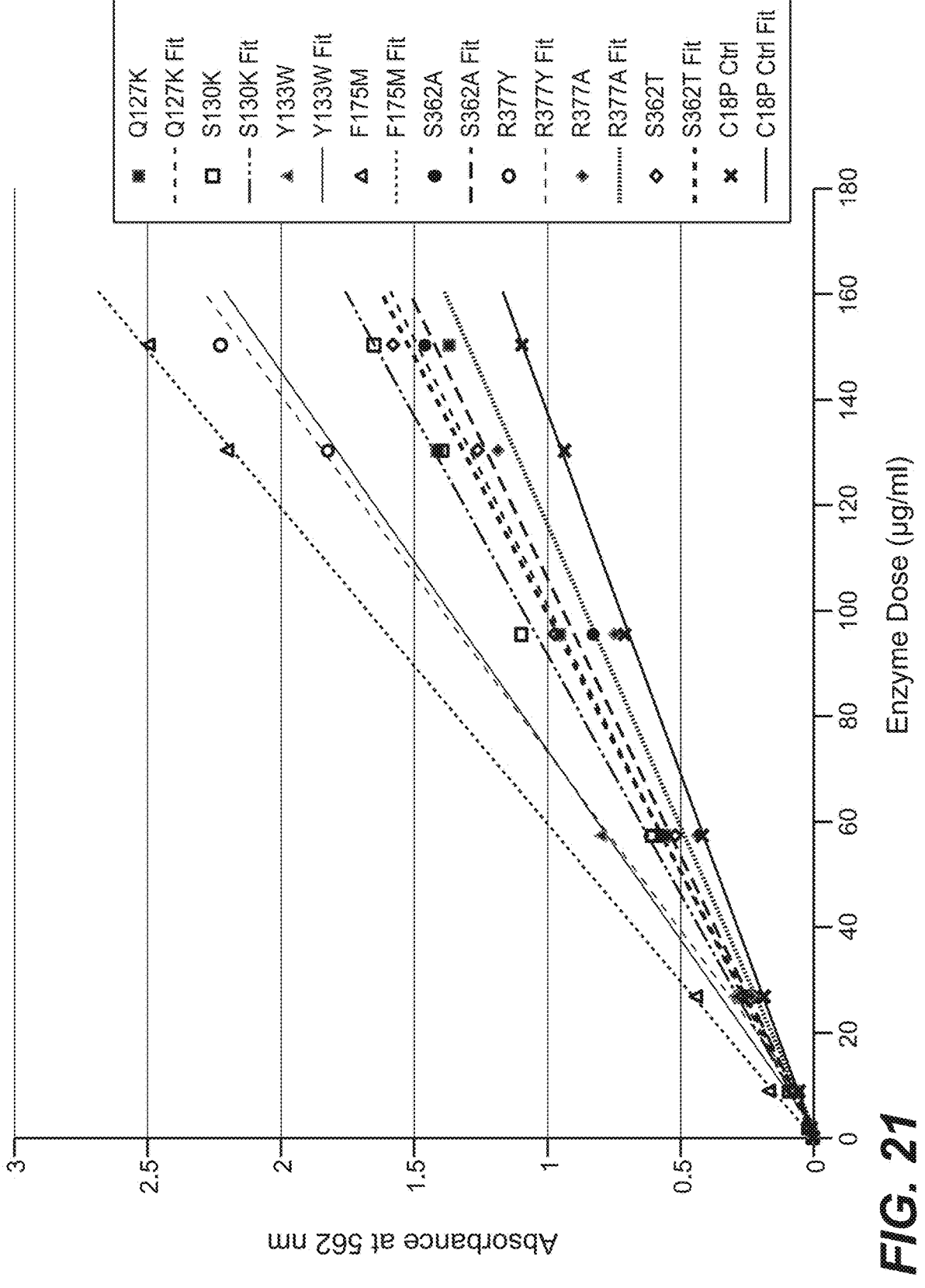
FIG. 21 is a graph showing examples of C18P variants demonstrating improved hydrolysis of amylopectin from corn. C18P is shown as a reference.
Figure 22:
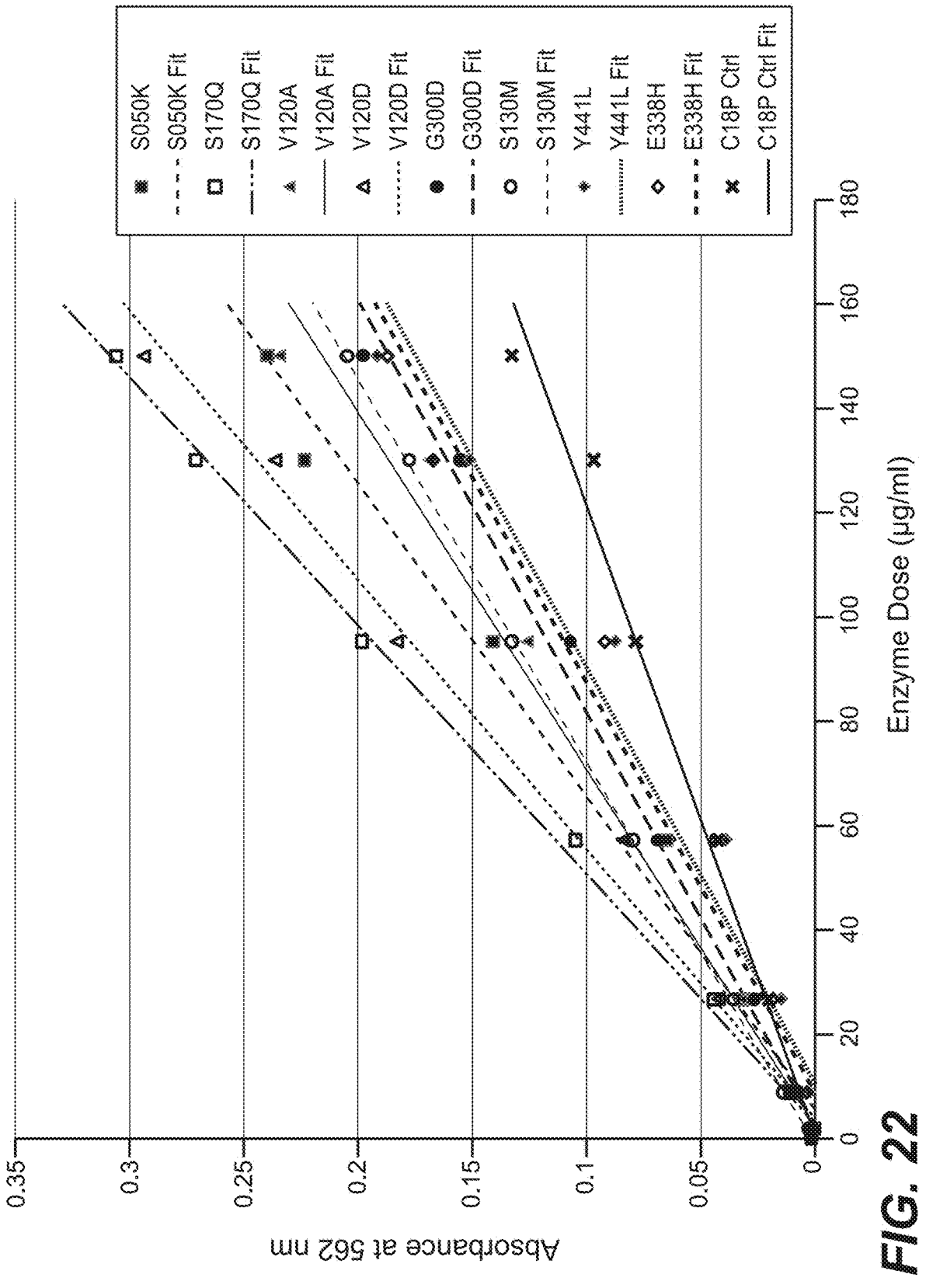
FIG. 22 is a graph showing examples of variants demonstrating improved generation of reducing sugars from starch. C18P is shown as a reference.
Figure 23:
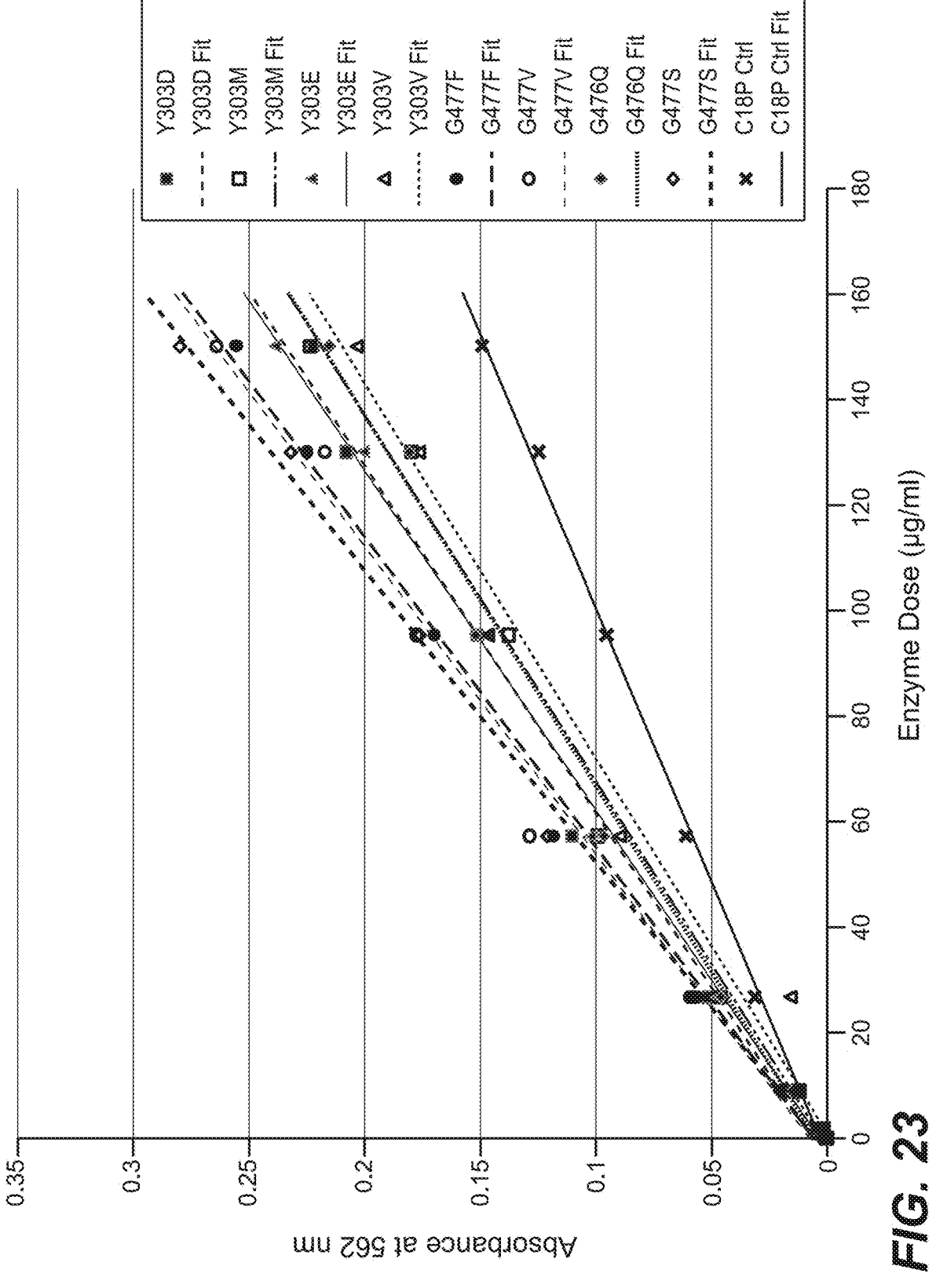
FIG. 23 is a graph showing examples of C18P variants demonstrating improved release of iodine staining material from starch. C18P is shown as a reference.
Figure 24:
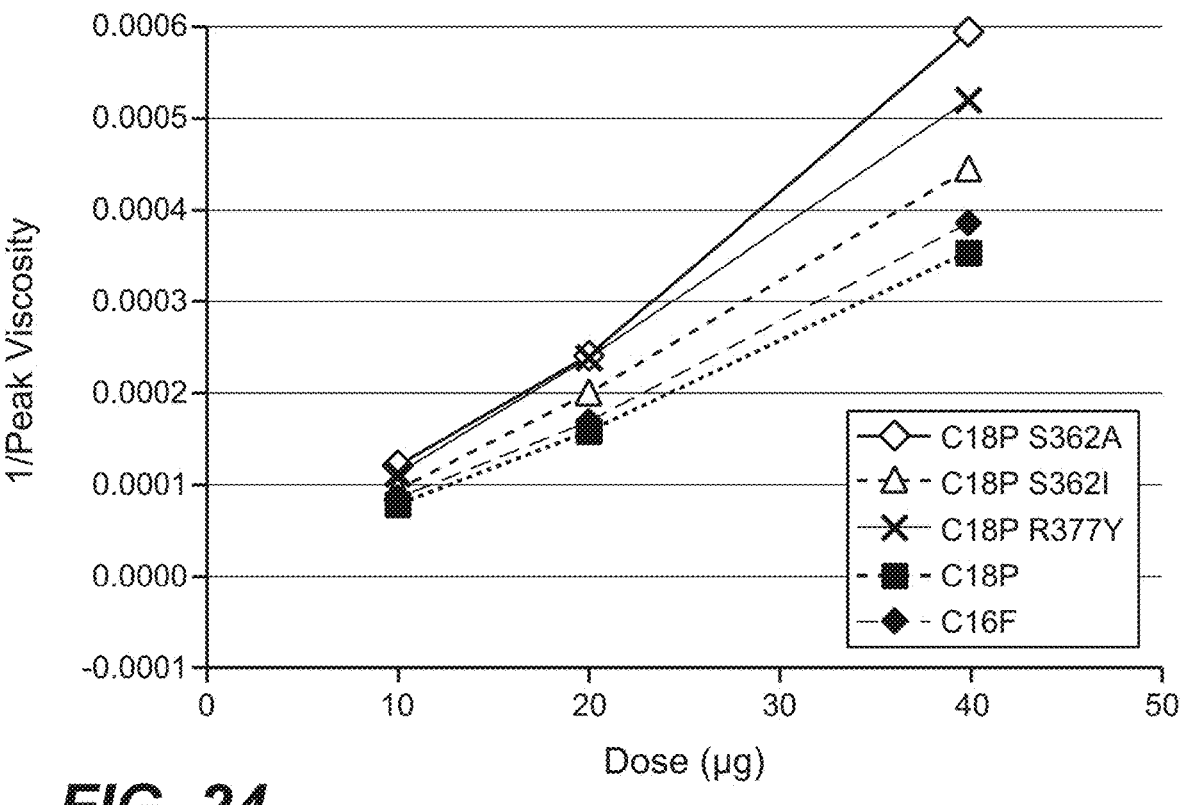
FIG. 24 is a graph showing the viscosity reduction of corn flour slurry produced by three C18P variants reported as fluidity (1/viscosity) versus dose of the variants (in pg). C18P and C16F are shown as references.

A subset of the variants with performance-enhancing mutations were tested more rigorously to demonstrate improved activity relative to wild type at multiple protein concentrations (i.e., improved specific activity). FIG. 20 shows examples of variants with improved hydrolysis of corn starch at high temperature. FIG. 21 shows examples of variants with improved hydrolysis of amylopectin from corn. FIG. 22 shows examples of variants with improved generation of reducing sugars from starch. FIG. 23 shows examples of variants with improved release of iodine staining material from starch. In FIGS. 20-23, the legends adjacent to the graphs indicate the mutations present in addition to those present to the control variant, CspAmy2-C18P. FIG. 24 shows examples of variants that demonstrate improved reduction of corn slurry viscosity compared to the CspAmy2-C18P control. CspAmy2-C16F is also included for comparison.

Example 15

Pair-Wise Combinations of Mutations at Positions 476 and 477

Site evaluation libraries were constructed and screened to determined the effect of pair-wise combinations of mutations at positions 476 and 477 in variant CspAmy2-C16F (CspAmy2 with the mutations N126Y, F153W, T180H, I203Y, and S241Q, and lacking R178 and G179). The matrix in FIG. 25 shows the PI values for CspAmy2-C16F position 476/477 variants compared to a CspAmy2-C16F control (with a PI value set at 1) in a CS-26 corn starch microswatch assay, as described, above. The amino acid residues at positions 476 and 477 are indicated on the left-side and top of the matrix, respectively. A "wild-type" revertant, i.e., G476G/G477G had an experimentally obtained PI score of 1.01, suggesting that the assay produces very reliable results. The absence of a number at a position in the matrix indicates poor expression of the particular variant or that the variant was not present among those tested. The matrix in FIG. 26 shows the PI values for the same variants in an amylose hydrolysis assay, as described, above. Again, a "wild-type" revertant, i.e., G476G/G477G had an experimentally obtained PI score corresponding to that of the control.

Remarkably, the results suggest that almost any combination of residues at positions 476 and 477, other the glycine pair that occurs in naturally in CspAmy2 (and in many α-amylases), increases the performance of the α-amylase in terms of improving the hydrolysis of insoluble amylopectin and improving the release of iodine staining material from hydrated starch. Without being bound to a theory, it is believed that the adjacent GG residues at the C-terminus of α-amylases contribute to starch-binding. While binding tightly to a substrate may be desirable in nature where substrate is limiting, in industrial applications it may be more desirable for the enzyme to release from one starch molecule after hydrolyzing it and find a different starch molecules to hydrolyze, rather than remaining associated with the first starch molecule and hydrolysing it processively.

Example 16

Additional C18P-Based Variants with Superior Performance in Secondary Liquefaction Site evaluation libraries (SELs) were constructed and screened to determined the effect of mutations at positions E132, Q167, A277, and T400 in CspAmy2-C18P. The residues present at these positions in the best tested variants are shown in Table 6.

TABLE 6

| Combinations of mutations tested | | | | |
| --- | --- | --- | --- | --- |
| Name | E132 | A277 | Q167 | T400 |
| C16F | E | A | Q | T |
| C25F | H | F | Q | T |
| C25B | H | F | E | T |
| C25A | H | F | E | K |

Figure 27:
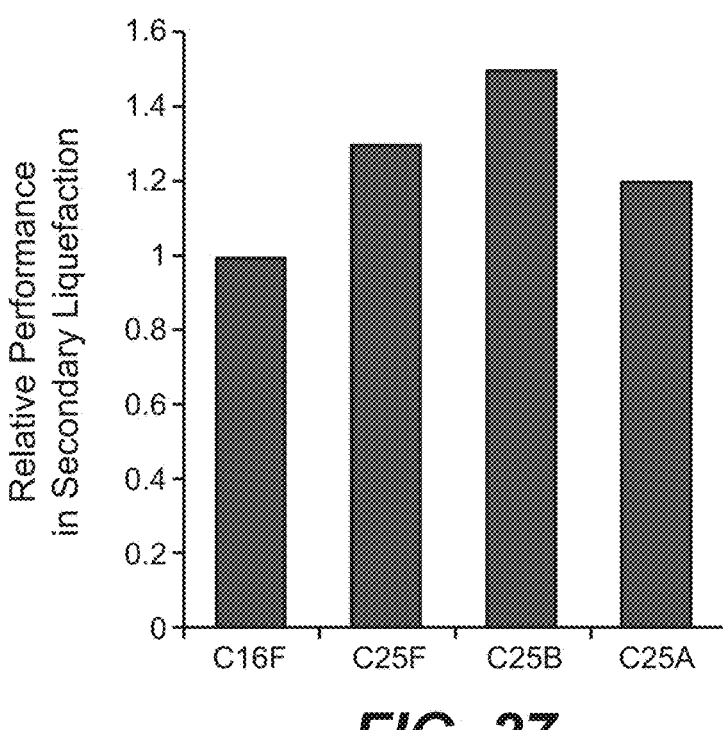
FIG. 27 is a graph showing the relative liquefaction performance of CspAmy2-C25F, B, and A compared to C16F.

The relative performance of CspAmy2-C25A, B, and F in a liquefaction assay compared to C18F is shown in FIG. 27. Mutations at positions 132 and 277 increase performance. Additional benefit is observed from mutations at positions 167. In further experiments, it was shown that C25B demonstrated superior liquefaction performance to C16F at pH 5.2 and 5.8, and with or without additional calcium. Variants CspAmy2-C25A, B, and F all outperformed variant CspAmy2-C18P (not shown).

The amino acid sequence of the mature CspAmy2-C25A amylase polypeptide is shown, below, as SEQ ID NO: 25 [the relevant substitutions are underlined]:

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRYQETS GHYNIQAWTG FNFPGRGTTY SNWKWQWFHF

DGTDWDESRS LSRIFKFDGK AWDWEVSSEN GNYDYLMYAD

YDYDHPDVVN EMKKWGVWYA NEVGLDGYRL DAVKHIKFQF

LKDWVDNARA ATGKEMFTVG EYWQNDLGAL NNYLFKVNYN

QSLFDAPLHY NFYAASTGGG YYDMRNILNN TLVASNPTKA

VTLVENHDTQ PGQSLESTVQ PWFKPLAYAF ILTRSGGYPS

VFYGDMYGTK GTTTREIPAL KSKIEPLLKA RKDYAYGKQR

DYIDNPDVIG WTREGDSTKA KSGLATVITD GPGGSKRMYV

GTSNAGEIWY DLTGNRTDKI TIGSDGYATF PVNGGSVSVW

VQQ
```

The amino acid sequence of the mature CspAmy2-C25B amylase polypeptide is shown, below, as SEQ ID NO: 26 [the relevant substitutions are underlined]:

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRYQETS GHYNIQAWTG FNFPGRGTTY SNWKWQWFHF

DGTDWDESRS LSRIFKFDGK AWDWEVSSEN GNYDYLMYAD

YDYDHPDVVN EMKKWGVWYA NEVGLDGYRL DAVKHIKFQF

LKDWVDNARA ATGKEMFTVG EYWQNDLGAL NNYLFKVNYN

QSLFDAPLHY NFYAASTGGG YYDMRNILNN TLVASNPTKA

VTLVENHDTQ PGQSLESTVQ PWFKPLAYAF ILTRSGGYPS

VFYGDMYGTK GTTTREIPAL KSKIEPLLKA RKDYAYGTQR

DYIDNPDVIG WTREGDSTKA KSGLATVITD GPGGSKRMYV

GTSNAGEIWY DLTGNRTDKI TIGSDGYATF PVNGGSVSVW

VQQ
```

The amino acid sequence of the mature CspAmy2-C25F amylase polypeptide is shown, below, as SEQ ID NO: 27 [the relevant substitutions are underlined]:

```
AATNGTMMQY FEWYVPNDGQ QWNRLRTDAP YLSSVGITAV

WTPPAYKGTS QADVGYGPYD LYDLGEFNQK GTVRTKYGTK

GELKSAVNTL HSNGIQVYGD VVMNHKAGAD YTENVTAVEV

NPSNRYQETS GHYNIQAWTG FNFPGRGTTY SNWKWQWFHF

DGTDWDQSRS LSRIFKFDGK AWDWEVSSEN GNYDYLMYAD

YDYDHPDVVN EMKKWGVWYA NEVGLDGYRL DAVKHIKFQF

LKDWVDNARA ATGKEMFTVG EYWQNDLGAL NNYLFKVNYN

QSLFDAPLHY NFYAASTGGG YYDMRNILNN TLVASNPTKA

VTLVENHDTQ PGQSLESTVQ PWFKPLAYAF ILTRSGGYPS
```

-continued

```
VFYGDMYGTK GTTTREIPAL KSKIEPLLKA RKDYAYGTQR

DYIDNPDVIG WTREGDSTKA KSGLATVITD GPGGSKRMYV

GTSNAGEIWY DLTGNRTDKI TIGSDGYATF PVNGGSVSVW

VQQ
```

Example 17

Additional CspAmy2-v5-Based Variants with Superior Performance in Cleaning Applications Additional CspAmy2-v5-based variants were made in an effort to further improve performance in cleaning applications. The variants and the mutations are shown in the Table 7. CspAmy2-v171 and CspAmy2-172 were previously described in Example 11. All variants included deletions at positions R178 and G179, indicated by "del (R178, G179)."

and 0.005% Tween-80) was added to each well for a final volume of 180 VL. The final enzyme concentrations ranged from 1 ppm down to 0.015 ppm. The plates were incubated at 25° C. with agitation at 1150 rpm for 15 minutes. Enzyme performance was judged by the amount of color released into the wash liquor. Color release was quantified spectrophotometrically at 488 nm by the transfer of 140 VL of the final wash solution to fresh medium-binding microtiter plates, and triplicate reads were blank-subtracted and averaged.

Figure 28:
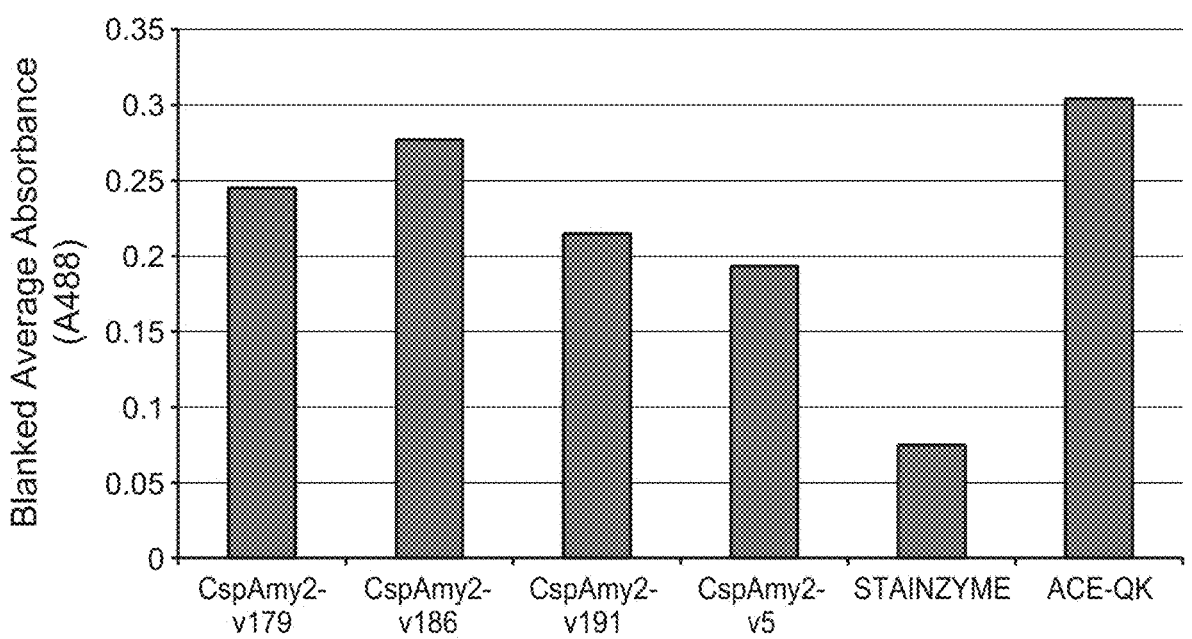
FIG. 28 is a graph showing the results of cleaning assays performed at 0.015 ppm with CspAmy2-v179, v186, and v191 compared to STAINZYME® and ACE-QK.

The results of the microswatch cleaning assays performed at 0.015 ppm enzyme are shown in FIG. 28. Variants CspAmy2-v179, v186, and v191 all demonstrated superior cleaning performance compared to CspAmy2-v5, and all CspAmy2 combinatorial variants were far superior to STAINZYME®. The results of the cleaning assays performed at all enzyme concentrations are shown in Table 8. All CspAmy2 demonstrated superior cleaning performance at lower concentrations compared to STAINZYME®.

TABLE 8

Results of the cleaning assays performed using CspAmy2 variants

| | Enzyme concentration (ppm) | | | | | | | | |
|---|---|---|---|---|---|---|---|---|---|
| Enzyme | 0.015 | 0.032 | 0.045 | 0.063 | 0.090 | 0.125 | 0.25 | 0.5 | 1.0 |
| CspAmy2-v179 | 0.25 | 0.31 | 0.32 | 0.35 | 0.35 | 0.37 | 0.37 | 0.36 | 0.38 |
| CspAmy2-v186 | 0.28 | 0.33 | 0.34 | 0.35 | 0.38 | 0.38 | 0.39 | 0.39 | 0.39 |
| CspAmy2-v191 | 0.22 | 0.30 | 0.31 | 0.35 | 0.37 | 0.38 | 0.39 | 0.39 | 0.40 |
| CspAmy2-v5 | 0.19 | 0.26 | 0.30 | 0.34 | 0.35 | 0.37 | 0.38 | 0.39 | 0.38 |
| STAINZYME ® | 0.07 | 0.12 | 0.14 | 0.19 | 0.19 | 0.25 | 0.30 | 0.34 | 0.38 |
| ACE-QK | 0.30 | 0.33 | 0.36 | 0.34 | 0.35 | 0.36 | 0.36 | 0.38 | 0.38 |

TABLE 7

Additional CspAmy2-v5-based variants

| Variant | Mutations |
|---|---|
| CspAmy2-v5 | del (R178, G179) + E187P + I203Y + G476K |
| CspAmy2-v171 | del (R178, G179) + T180D + E187P + I203Y + G476K |
| CspAmy2-v172 | del (R178, G179) + N126Y + T180D + E187P + I203Y + G476K |
| CspAmy2-v179 | del (R178, G179) + N126Y + T180D + E187P + I203Y + Y303D + G476T + G477E |
| CspAmy2-v180 | del (R178, G179) + N126Y + T180D + E187P + I203Y + Y303D + N475E + G477Q |
| CspAmy2-v181 | del (R178, G179) + N126Y + T180D + E187P + I203Y + Y303R + N475E + G476T + G477R |
| CspAmy2-v186 | del (R178, G179) + T38N + N88H + N126Y + T1291 + N134M + F153W + L171R + T180D + E187P + I203Y + G476K + G477E |
| CspAmy2-v191 | del (R178, G179) + N126Y + E132H + T180D + E187P + I203Y + Y303D + G476T + G477E |

The cleaning performance of the purified variants was analyzed in a microswatch cleaning assay performed essentially as described above. CFT CS-28 swatches were punched to form discs measuring 5.5 mm in diameter. Two discs were placed in each well of 3 each flat-bottom, non-binding 96-well assay plates. The CspAmy2 variants, STAINZYME®, and ACE-QK were each diluted to 0.5 mg/mL in dilution buffer (50 mM MOPS (pH 7.2) and 0.005% Tween), and then further diluted to 18 ppm in a microtiter plate. Several dilutions were made in the microtiter plates, down to 0.27 ppm. 10 μL of each of these samples were added to the three swatch plates, and 170 VL of HEPES buffer (25 mM HEPES, pH 8.0 with 2 mM CaCl₂

Figure 29:
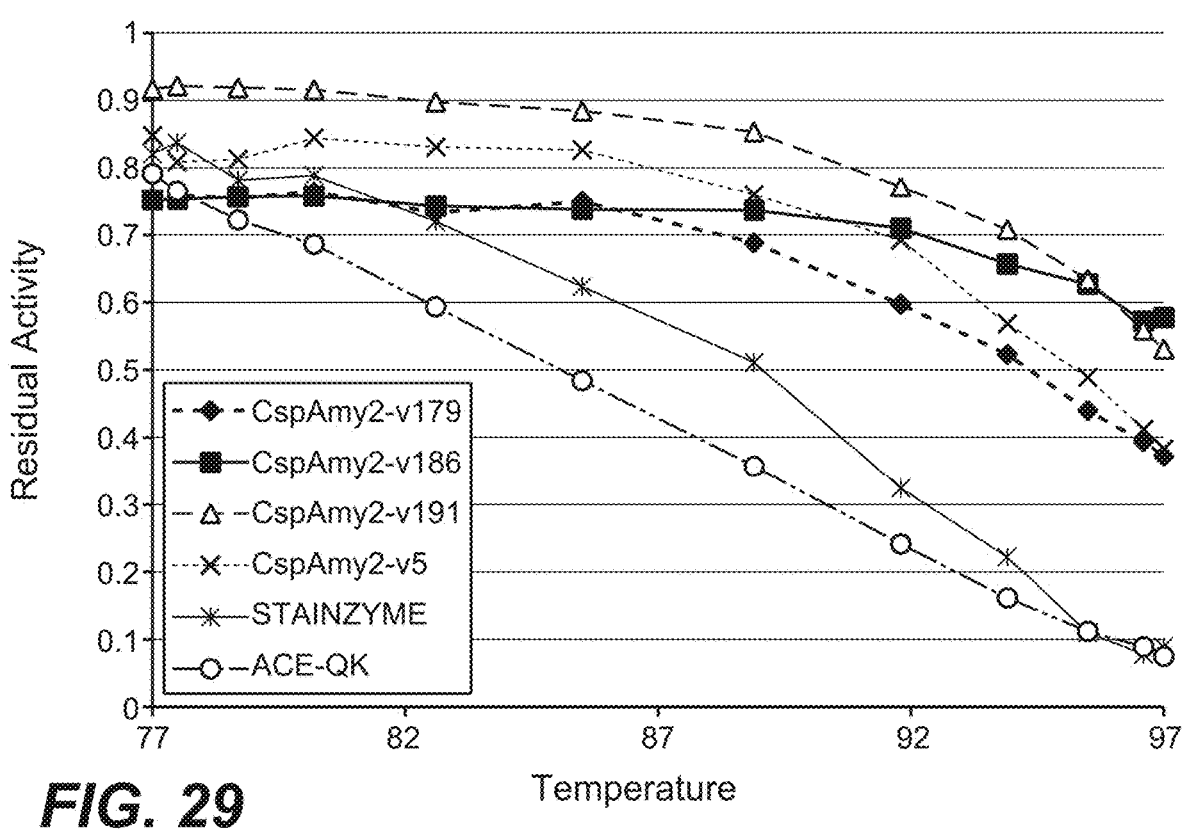
FIG. 29 is a graph showing the relative thermostability of CspAmy2 variants v5, v179, v186, and v191 compared to STAINZYME® and ACE-QK at temperatures ranging from 77° C. to 97° C.
Figure 30:
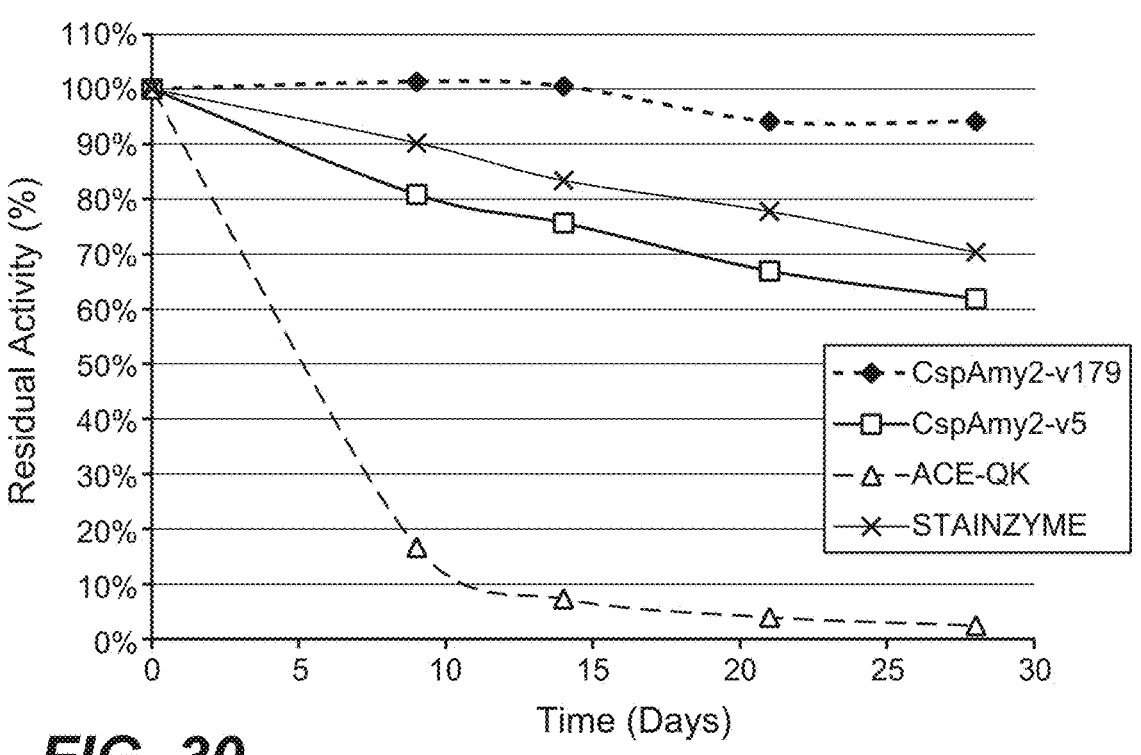
FIG. 30 is a graph showing the relative in-detergent storage stability of CspAmy2 variants v5 and v179 compared to STAINZYME® and ACE-QK in TIDE® regular HDL.
Figure 31:
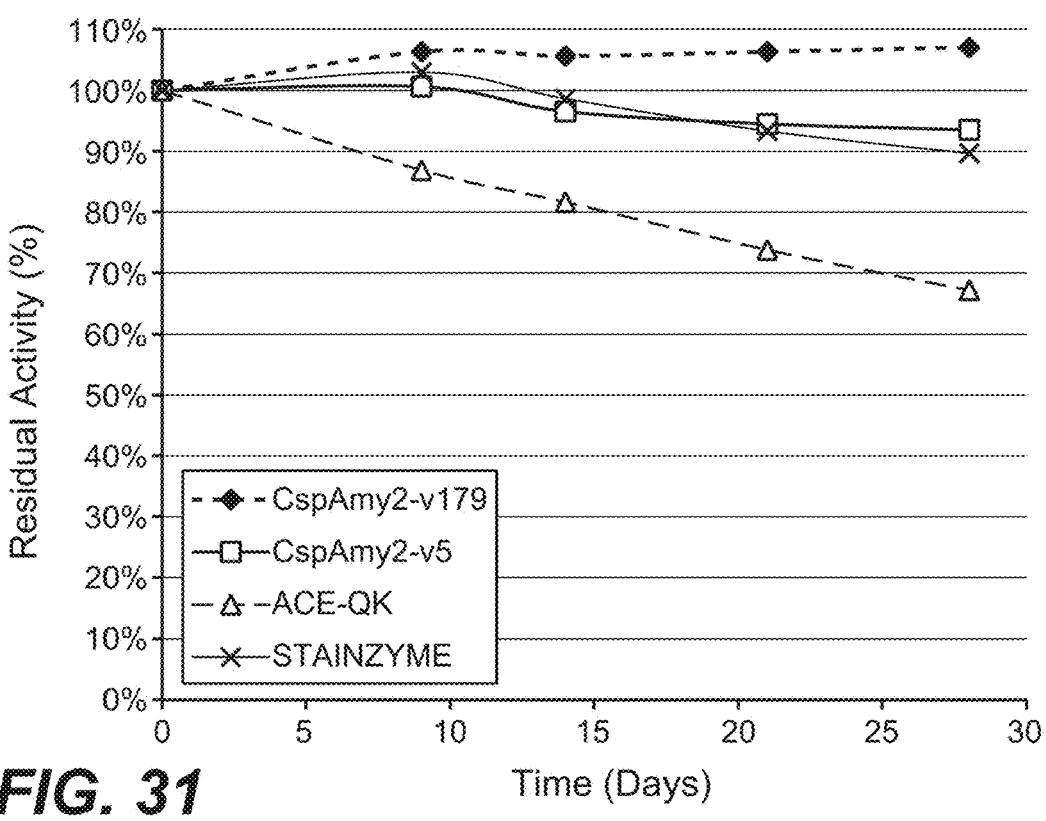
FIG. 31 is a graph showing the relative in-detergent storage stability of CspAmy2 variants v5 and v179 compared to STAINZYME® and ACE-QK in US TIDE® PODS™.
Figure 32:
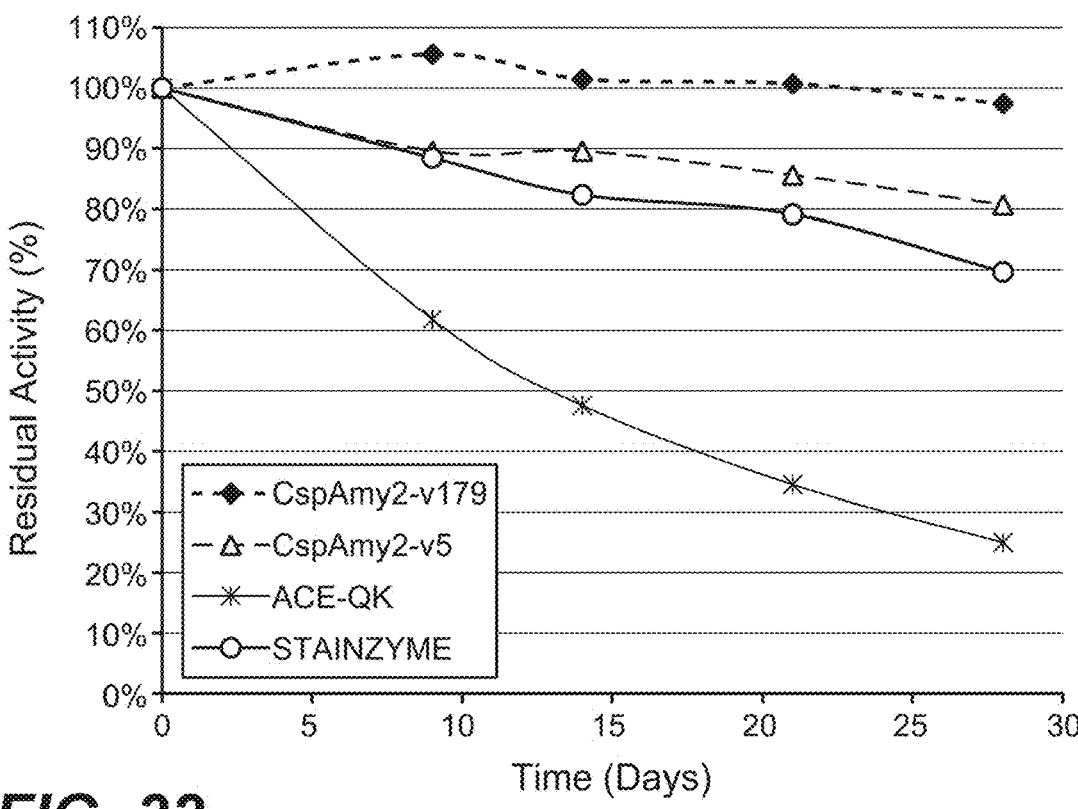
FIG. 32 is a graph showing the relative in-detergent storage stability of CspAmy2 variants v5 and v179 compared to STAINZYME® and ACE-QK in European ARIEL™ HDL.
Figure 33:
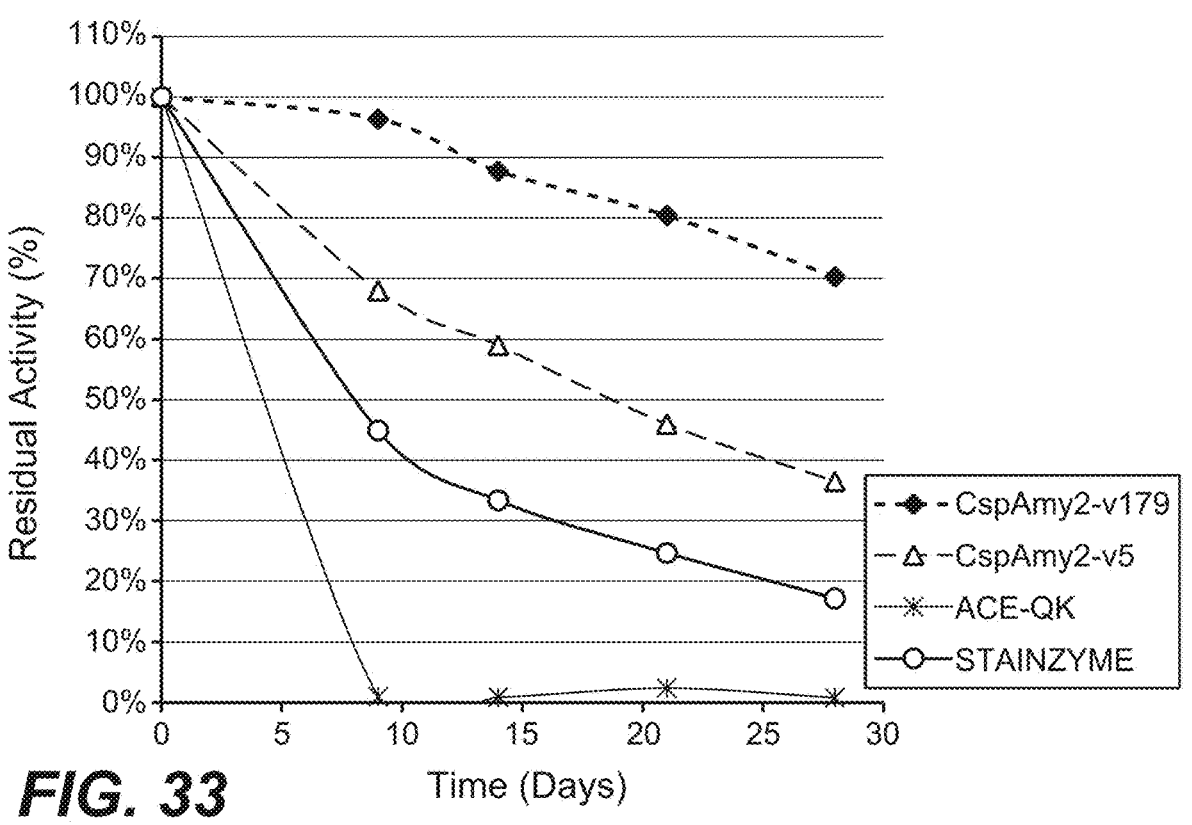
FIG. 33 is a graph showing the relative in-detergent storage stability of CspAmy2 variants v5 and v179 compared to STAINZYME® and ACE-QK in European OMO™ Color HDL.
Figure 34:
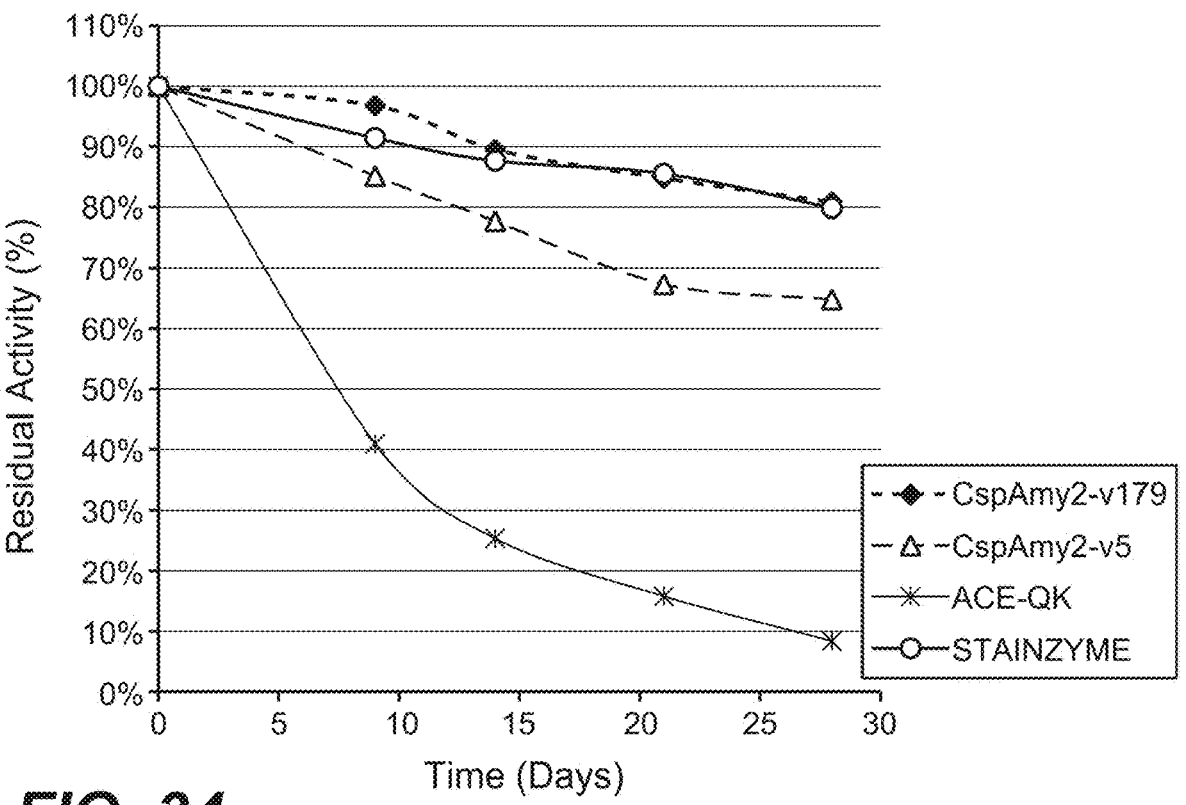
FIG. 34 is a graph showing the relative in-detergent storage stability of CspAmy2 variants v5 and v179 compared to STAINZYME® and ACE-QK in Chinese OMO™ Color HDL.
Figure 35:
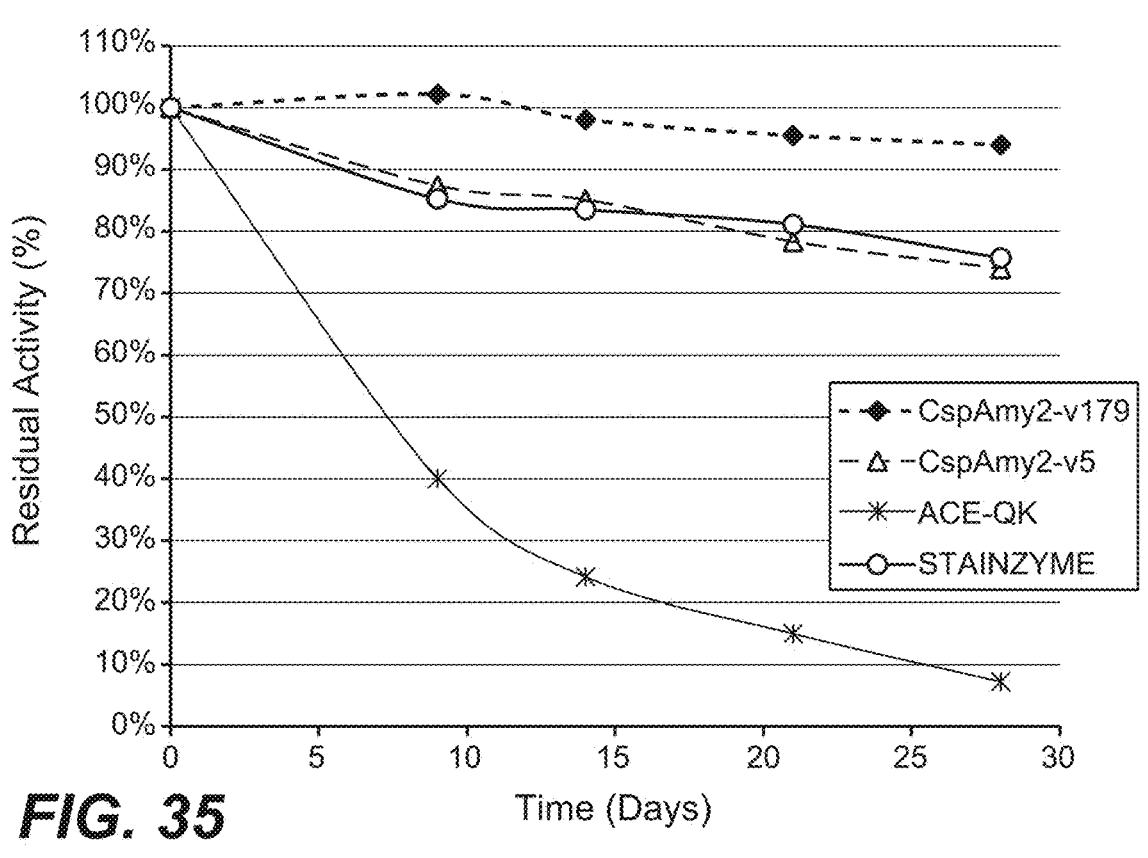
FIG. 35 is a graph showing the relative in-detergent storage stability of CspAmy2 variants v5 and v179 compared to STAINZYME® and ACE-QK in Chinese LIBY™ HDL.

Thermal stability assays were performed essentially as described. Stocks of CspAmy2 variants, STAINZYME®, and ACE-QK at 0.5 mg/mL were diluted to 5 ppm, 10 ppm, or 1 ppm, respectively, in dilution buffer (50 mM MOPS (pH 7.2) and 0.005% Tween) to account for their relative specific activities on the soluble substrate. 50 μL of each enzyme were added to each of 12 wells of PCR tubes and sealed. The "unstressed" samples were incubated at room temperature throughout the duration of the experiment. The other samples were incubated in a thermocycler in a gradient from 77° C. to 97° C. for 15 minutes. Samples were transferred to microtiter plates in triplicate, and alpha-amylase activity was measured on all unstressed and stressed samples using the Ceralpha reagent (Megazyme, Inc.). Residual activity was calculated by dividing the activity of each amylase after the thermal stress by the activity of that unstressed amylase. The results of the thermostability assay are shown in FIG. 29. Variants CspAmy2-v186 and v191 both demonstrated superior thermal stability compared to CspAmy2-v5. All the CspAmy2 variants demonstrated superior thermal stability compared to STAINZYME® and ACE-QK.

The in-detergent storage stability of the CspAmy2 variants was tested in a several commercial detergents, i.e., TIDE® regular HDL and TIDE® PODS™ (Procter & Gamble) for the USA market, ARIEL™ HDL (Procter & Gamble) and OMO Color HDL (Unilever) for the European market, and OMO™ (Unilever) and LIBY™ HDL (Liby) for the Chinese market. All detergents were heat inactivated at 90° C. for 4 hours to eliminate existing enzyme activities. Enzyme activity in the heat inactivated detergents was measured using the Suc-AAPF-pNA and Ceralpha assays for measuring protease and amylase activity, respectively.

To prepare the stability samples, 2% w/w protease (PURAFECT® Prime HA, DuPont Industrial Biosciences) and 0.5% w/w amylase were added to each detergent sample and mixed. Samples were stored in a $CO_2$ incubator (Sanyo) at 37° C. for 28 days. Aliquots were taken from each reaction sample at various time points, diluted in 50 mM MOPS (pH 7.15) buffer with 1% BSA added, and alpha-amylase activity was measured using the Ceralpha substrate (Megazyme, Inc). The activity for each sample was determined using an Arena 20XT Photometric Analyzer (Thermo Scientific) using a calibrated standard. The remaining activity after incubation for 28 days was reported as a percent of the total activity determined at time zero.

The amount of residual activity of the CspAmy2 variants compared to STAINZYME® and ACE-QK are shown in FIGS. 30-35. CspAmy2-v179 was particularly stable compared to other tested variants and the controls.

The amino acid sequence of mature CspAmy2-v179 is shown, below, as SEQ ID NO: 28:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

DYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNTESVSVWVQQ
```

The amino acid sequence of mature CspAmy2-v180 is shown, below, as SEQ ID NO: 29:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY

SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

DYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVEGQSVSVWVQQ
```

The amino acid sequence of mature CspAmy2-v181 is shown, below, as SEQ ID NO: 30:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGEYNIQAWTGFNFPGRGTTY
```

-continued
```
SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

DYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVETRSVSVWVQQ
```

The amino acid sequence of mature CspAmy2-v186 is shown, below, as SEQ ID NO: 31:

```
AATNGTMMQYFEWYVPNDGQQWNRLRTDAPYLSSVGINAVWTPPAYKGTS

QADVGYGPYDLYDLGEFNQKGTVRTKYGTKGELKSAVHTLHSNGIQVYGD

VVMNHKAGADYTENVTAVEVNPSNRYQEISGEYMIQAWTGFNFPGRGTTY

SNWKWQWFHFDGTDWDQSRSRSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

YYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNKESVSVWVQQ
```

The amino acid sequence of mature CspAmy2-v191 is shown, below, as SEQ ID NO: 32:

```
AATNGTMMQYFEWYVPNDGQQWNRLRTDAPYLSSVGITAVWTPPAYKGTS

QADVGYGPYDLYDLGEFNQKGTVRTKYGTKGELKSAVNTLHSNGIQVYGD

VVMNHKAGADYTENVTAVEVNPSNRYQETSGHYNIQAWTGFNFPGRGTTY

SNFKWQWFHFDGTDWDQSRSLSRIFKFDGKAWDWPVSSENGNYDYLMYAD

YDYDHPDVVNEMKKWGVWYANEVGLDGYRLDAVKHIKFSFLKDWVDNARA

ATGKEMFTVGEYWQNDLGALNNYLAKVNYNQSLFDAPLHYNFYAASTGGG

DYDMRNILNNTLVASNPTKAVTLVENHDTQPGQSLESTVQPWFKPLAYAF

ILTRSGGYPSVFYGDMYGTKGTTTREIPALKSKIEPLLKARKDYAYGTQR

DYIDNPDVIGWTREGDSTKAKSGLATVITDGPGGSKRMYVGTSNAGEIWY

DLTGNRTDKITIGSDGYATFPVNTESVSVWVQQ
```

Example 18

Combinatorial Variants of PcuAmy1

To determine whether equivalent combinatorial mutations resulted in similar performance gains in a different α-amylase molecule, equivalent mutations were made in an α-amylase from *Paenibacillus curdlanolyticus* (i.e., PcuAmy1). The amino acid sequence of the mature of PcuAmy1 polypeptide is shown, below (SEQ ID NO: 3):

ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRNVETTSTYQIQAWTQYDFPGRGNTYS

SFKWRWYHFDGVDWDQSRGLNRIYKLRGDGKDWDWEVDSEYGNYDYLMGA

DLDFNHPDVVNETKTWGKWFVNTVNLDGVRLDAVKHIKFDFMRDWVNNVR

STTGKNLFAVGEYWHYDVNKLNSYITKTNGTMSLFDVPLHFRFYDASNGG

GGYDMRNLLNNTLMSSNPMKAVTFVENHDTQPTQALQSTVQSWFKPLAYA

TILTREQGYPCVFYGDYYGTSDGKISSYKPIMDKLLNARKVYAYGTQRDY

FDHPDIVGWTREGDAAHAGSGLATLITDGPGGSKWMYVGTSKAGQVWTDK

TGNRSGTVTIDANGWGNFWVNGGSVSVWAK

Mutations were made at positions N125, F152, R177, G178, E186, G472, and G473 (using SEQ ID NO: 3 for numbering), corresponding to mutations at positions N126, F153, R178, G179, E187P, G476, and G477, respectively in CspAmy2 (SEQ ID NO: 1). A further mutation was introduced at position N205. Consistent with previous nomenclature "del (R177, G178)" refers to deletions, in this case at positions R177 and G178. In addition to the aforementioned mutations, the PcuAmy1 variants further included mutations at position T333, A335, and Q337E. These mutations, particularly at T333, impart protease resistance to PcuAmy1 but do not affect performance (see Example 19). The variants are shown in Table 9.

TABLE 9

Combinatorial variants of PcuAmy1 amylase

| Variant | Mutations |
| --- | --- |
| PcuAmy1-v1A | del (R177, G178) + N125Y + E186P + T333G + A335S + Q337E + G472K |
| PcuAmy1-v6 | del (R177, G178) + N125Y + F152W+ E186P + T333G + A335S + Q337E + G472K |
| PcuAmy1-v8 | del (R177, G178) + N125Y + F152W+ E186P + T333G + A335S + Q337E + G472R + G473R |
| PcuAmy1-v16 | del (R177, G178) + N125Y + F152W+ E186P + N205D + T333G + A335S + Q337E + G472K |

The codon-optimized nucleotide sequence of the PcuAmy1 gene is set forth as SEQ ID NO: 33:

GCCGACAACGGCACAATCATGCAGTATTTCGAGTGGTACCTGCCGAACGA

CGGAGCGCACTGGAACAGACTTAATAACGACGCACAAAACCTGAAAAATG

TGGGCATCACGGCAGTGTGGATTCCTCCGGCATACAAGGGCGGCAGCTCA

GCAGATGTTGGCTACGGAGTTTACGATACATACGACCTGGGCGAGTTCAA

TCAGAAAGGCACGGTCAGAACAAAGTACGGAACGAAGAGCGAACTGATTT

CAGCGGTCAACAATCTTCACGCAAAGGGCATTGCGGTTTACGGCGACGTG

GTCCTGAACCATAGAATGAATGCGGATGCAACGGAGCTTGTGGATGCGGT

TGAGGTGGATCCGAACAACAGAAACGTCGAGACGACAAGCACGTATCAGA

TCCAGGCATGGACGCAATACGATTTCCCGGGCAGAGGCAACACGTACAGC

AGCTTTAAATGGAGATGGTATCACTTCGACGGCGTCGACTGGGACCAGAG

CAGAGGCCTGAACAGAATCTATAAGCTGAGAGGCGATGGCAAGGATTGGG

-continued

ACTGGGAGGTCGACAGCGAGTACGGCAACTACGATTACCTGATGGGAGCG

GACCTGGACTTCAACCACCCGGATGTGGTTAACGAAACAAAGACATGGGG

CAAATGGTTTGTGAACACGGTGAACCTGGATGGCGTCAGACTGGACGCGG

TTAAGCACATCAAGTTCGACTTCATGAGAGACTGGGTGAACAACGTGAGA

AGCACGACGGGCAAGAACCTTTTCGCAGTTGGCGAGTATTGGCACTACGA

CGTGAACAAACTGAACAGCTACATCACGAAGACGAATGGCACGATGAGCC

TGTTCGACGTGCCGCTGCACTTTAGATTTTATGATGCAAGCAACGGCGGA

GGCGGCTACGACATGAGAAACCTGCTGAATAACACGCTGATGAGCAGCAA

CCCGATGAAGGCGGTTACATTCGTTGAGAACCATGACACACAACCGACGC

AGGCCCTGCAATCAACGGTCCAAAGCTGGTTTAAGCCGCTTGCGTATGCT

ACAATCCTGACGAGAGAGCAAGGCTACCCGTGCGTTTTCTACGGCGACTA

TTATGGAACAAGCGACGGCAAAATTAGCAGCTACAAGCCGATCATGGATA

AGCTTCTTAACGCGAGAAAGGTGTACGCCTACGGCACGCAGAGAGATTAC

TTCGATCATCCGGACATCGTTGGCTGGACAAGAGAAGGCGATGCAGCACA

TGCTGGCTCAGGACTGGCAACGCTTATCACAGATGGCCCTGGCGGAAGCA

AGTGGATGTATGTTGGAACGTCAAAGGCAGGCCAGGTCTGGACGGATAAA

ACAGGAAACAGAAGCGGAACGGTGACGATTGATGCCAATGGCTGGGGAAA

CTTTTGGGTTAATGGCGGATCAGTTAGCGTTTGGGCAAAATAA

The amino acid sequence of the mature of PcuAmy1-v1A polypeptide is shown below as SEQ ID NO: 34:

ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRYVETTSTYQIQAWTQYDFPGRGNTYS

SFKWRWYHFDGVDWDQSRGLNRIYKLDGKDWDWPVDSEYGNYDYLMGADL

DFNHPDVVNETKTWGKWFVNTVNLDGVRLDAVKHIKFDFMRDWVNNVRST

TGKNLFAVGEYWHYDVNKLNSYITKTNGTMSLFDVPLHFRFYDASNGGGG

YDMRNLLNNTLMSSNPMKAVTFVENHDTQPGQSLESTVQSWFKPLAYATI

LTREQGYPCVFYGDYYGTSDGKISSYKPIMDKLLNARKVYAYGTQRDYFD

HPDIVGWTREGDAAHAGSGLATLITDGPGGSKWMYVGTSKAGQVWTDKTG

NRSGTVTIDANGWGNFWVNKGSVSVWAK

The amino acid sequence of the mature of PcuAmy1-v6 polypeptide is shown below as SEQ ID NO: 35:

ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRYVETTSTYQIQAWTQYDFPGRGNTYS

SWKWRWYHFDGVDWDQSRGLNRIYKLDGKDWDWPVDSEYGNYDYLMGADL

DFNHPDVVNETKTWGKWFVNTVNLDGVRLDAVKHIKFDFMRDWVNNVRST

TGKNLFAVGEYWHYDVNKLNSYITKTNGTMSLFDVPLHFRFYDASNGGGG

YDMRNLLNNTLMSSNPMKAVTFVENHDTQPGQSLESTVQSWFKPLAYATI

LTREQGYPCVFYGDYYGTSDGKISSYKPIMDKLLNARKVYAYGTQRDYFD

-continued

```
HPDIVGWTREGDAAHAGSGLATLITDGPGGSKWMYVGTSKAGQVWTDKTG

NRSGTVTIDANGWGNFWVNKGSVSVWAK
```

The amino acid sequence of the mature of PcuAmy1-v8 polypeptide is shown below as SEQ ID NO: 36

```
ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRYVETTSTYQIQAWTQYDFPGRGNTYS

SWKWRWYHFDGVDWDQSRGLNRIYKLDGKDWDWPVDSEYGNYDYLMGADL

DFNHPDVVNETKTWGKWFVNTVNLDGVRLDAVKHIKFDFMRDWVNNVRST

TGKNLFAVGEYWHYDVNKLNSYITKTNGTMSLFDVPLHFRFYDASNGGGG

YDMRNLLNNTLMSSNPMKAVTFVENHDTQPGQSLESTVQSWFKPLAYATI

LTREQGYPCVFYGDYYGTSDGKISSYKPIMDKLLNARKVYAYGTQRDYFD

HPDIVGWTREGDAAHAGSGLATLITDGPGGSKWMYVGTSKAGQVWTDKTG

NRSGTVTIDANGWGNFWVNRRSVSVWAK
```

The amino acid sequence of the mature of PcuAmy1-v16 polypeptide is shown below as SEQ ID NO: 37:

```
ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRYVETTSTYQIQAWTQYDFPGRGNTYS

SWKWRWYHFDGVDWDQSRGLNRIYKLDGKDWDWPVDSEYGNYDYLMGADL

DFDHPDVVNETKTWGKWFVNTVNLDGVRLDAVKHIKFDFMRDWVNNVRST

TGKNLFAVGEYWHYDVNKLNSYITKTNGTMSLFDVPLHFRFYDASNGGGG

YDMRNLLNNTLMSSNPMKAVTFVENHDTQPGQSLESTVQSWFKPLAYATI

LTREQGYPCVFYGDYYGTSDGKISSYKPIMDKLLNARKVYAYGTQRDYFD

HPDIVGWTREGDAAHAGSGLATLITDGPGGSKWMYVGTSKAGQVWTDKTG

NRSGTVTIDANGWGNFWVNKGSVSVWAK
```

Figure 36:
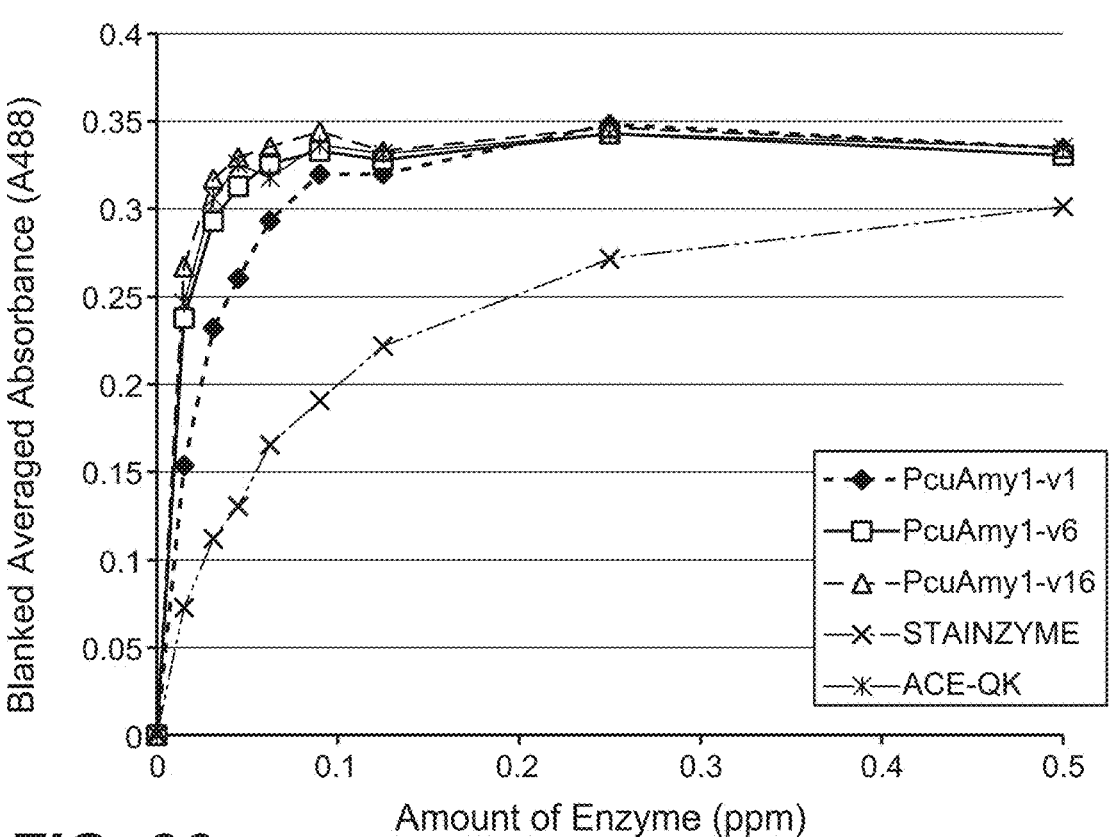
FIG. 36 is a graph showing the relative cleaning performance of PcuAmy1 variants v1, v6, v8, and v16 compared to STAINZYME® and ACE-QK in buffer at pH 8.0. Enzyme doses are noted on the x-axis.

The cleaning performance of PcuAmy1-v1, PcuAmy1-v6, and PcuAmy1-v16, compared to STAINZYME® and ACE-QK is shown in FIG. 36. The microswatch assay was performed as described in Example 17. PcuAmy1-v6 and PcuAmy1-v16 outperformed PcuAmy1-v1 and STAINZYME® at low doses (e.g., 0.1 ppm enzyme or less).

Figure 37:
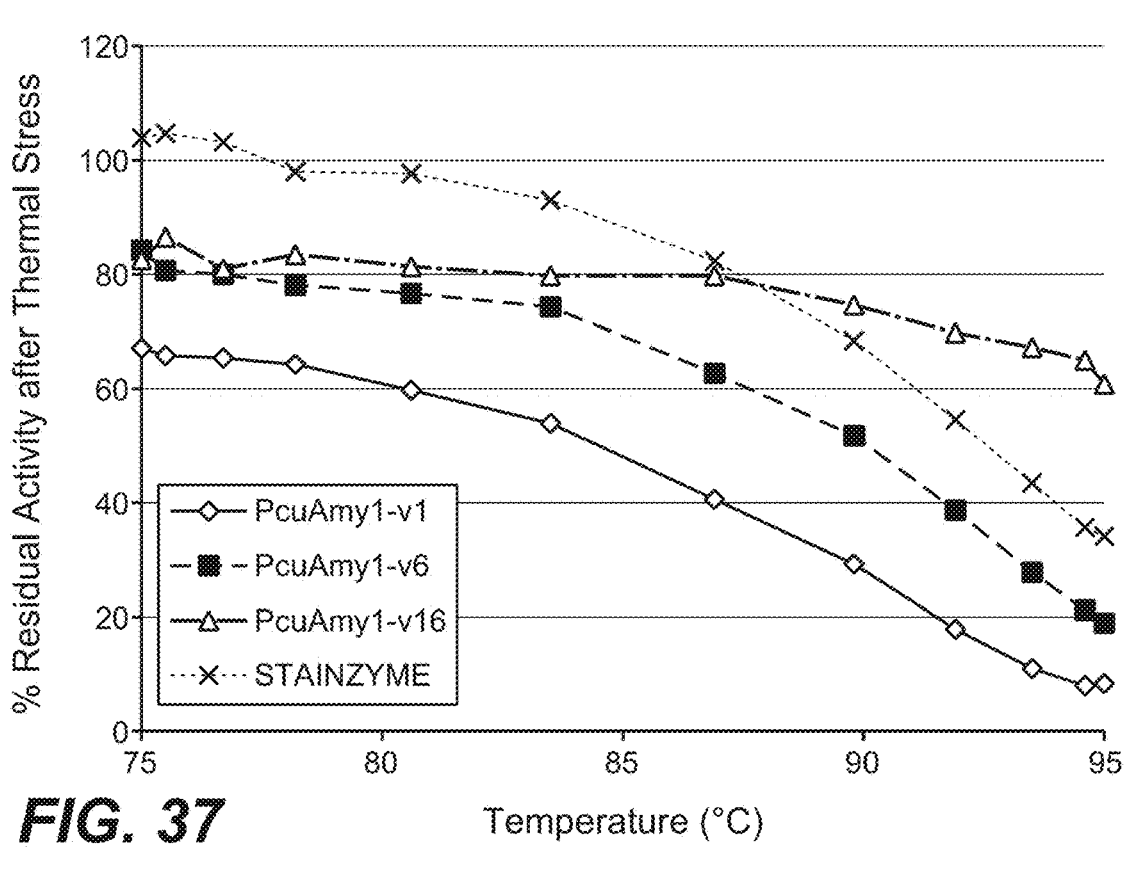
FIG. 37 is a graph showing the relative thermal stability of PcuAmy1 variants v1, v6, v8, and v16 compared to STAINZYME® in buffer at the temperatures indicated 5 ppm of PcuAmy1 variants and 10 ppm of STAINZYME® were used.

The thermal stability of PcuAmy1-v1, PcuAmy1-v6, and PcuAmy1-v16, compared to STAINZYME® is shown in FIG. 37. The assays were performed as described in Example 17. PcuAmy1-v16 were more thermostable than the other tested molecules using the same detergents and enzyme doses.

Example 19

Combinatorial Variants in BASE

As in Example 18, to determine whether equivalent combinatorial mutations resulted in similar performance gains in a different α-amylase molecule, equivalent mutations were made in an α-amylase derived from Bacillus sp. TS-23. The amino acid sequence of BASE, a C-terminaltruncated version of the Bacillus sp. TS-23 α-amylase (see, e.g., US20120045817 and WO2010/115028), is shown below as SEQ ID NO: 5:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYSFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK
```

The codon-modified nucleic acid sequence encoding the mature form of BASE (AmyTS23t), is set forth as SEQ ID NO: 38:

```
TCTGCAGCT TCAGCAAAC ACCGCGCCG ATTAACGAA

ACCATGATG CAGTATTTC GAATGGGAT CTGCCGAAC

GATGGCACC CTGTGGACC AAAGTGAAA AACGAAGCG

GCGAACCTG AGCAGCCTG GGCATTACC GCGCTGTGG

CTGCCGCCG GCATATAAA GGCACCAGC CAGAGCGAT

GTGGGCTAT GGCGTGTAT GATCTGTAC GATCTGGGC

GAATTTAAC CAGAAAGGC ACCATTCGT ACCAAATAT

GGCACCAAA ACCCAGTAT ATTCAGGCG ATCCAGGCG

GCGAAAGCG GCGGGTATG CAGGTGTAT GCGGATGTG

GTGTTTAAC CATAAAGCG GGTGCGGAT GGCACCGAA

TTTGTGGAT GCGGTGGAA GTGGATCCG AGCAACCGT

AACCAGGAA ACCAGCGGC ACCTATCAG ATTCAGGCG

TGGACCAAA TTTGATTTT CCCGGCCGT GGCAACACC

TATAGCAGC TTTAAATGG CGCTGGTAT CATTTTGAT

GGCACCGAT TGGGATGAA AGCCGTAAA CTGAACCGC

ATCTATAAA TTTCGTAGC ACCGGCAAA GCGTGGGAT

TGGGAAGTG GATACCGAA AACGGCAAC TATGATTAC

CTGATGTTC GCAGACCTG GATATGGAT CATCCGGAA

GTGGTGACC GAACTGAAA AACTGGGGC ACCTGGTAT

GTGAACACC ACCAACATT GATGGCTTT CGTCTGGAT

GCGGTGAAA CACATCAAA TACAGCTTT TTTCCGGAT

TGGCTGACC TATGTGCGT AACCAGACC GGCAAAAAC

CTGTTTGCG GTGGGCGAA TTTTGGAGC TATGATGTG

AACAAACTG CACAACTAC ATCACCAAA ACCAACGGC

AGCATGAGC CTGTTTGAT GCGCCGCTG CATAACAAC
```

-continued

```
TTTTATACC GCGAGCAAA AGCAGCGGC TATTTTGAT

ATGCGTTAT CTGCTGAAC AACACCCTG ATGAAAGAT

CAGCCGAGC CTGGCCGTG ACCCTGGTG GATAACCAT

GATACCCAG CCGGGCCAG AGCCTGCAA AGCTGGGTG

GAACCGTGG TTTAAACCG CTGGCCTAC GCGTTTATT

CTGACCCGT CAAGAGGGC TATCCGTGC GTTTTTTAT

GGCGATTAT TACGGCATC CCGAAATAT AACATTCCG

GGCCTGAAA AGCAAAATT GATCCGCTG CTGATTGCG

CGTCGTGAT TATGCGTAT GGCACCCAG CGTGATTAT

ATTGATCAC CAGGATATT ATTGGCTGG ACCCGTGAA

GGCATTGAT ACCAAACCG AACAGCGGC CTGGCCGCG

CTGATTACC GATGGCCCG GGTGGCAGC AAATGGATG

TATGTGGGC AAAAAACAT GCGGGCAAA GTGTTTTAT

GATCTGACC GGCAACCGT AGCGATACC GTGACCATT

AACGCGGAT GGCTGGGGT GAGTTTAAA GTGAACGGC

GGCAGCGTG AGCATTTGG GTGGCGAAA TAAGTTAAC

AGA
```

Mutations were made at positions N128, T134, F155, T182, R180, S181, E189, and G475 were made in BASE (using SEQ ID NO: 5 for numbering), which corresponds to mutations at positions N126, E132, F153, R178, G179, E187P, and G476, respectively in CspAmy2 (SEQ ID NO: 1). The variants are shown in Table 10.

TABLE 10

Combinatorial variants of BASE amylase

| Variant | Mutations |
|---|---|
| BASE-V28 | del (R180, G181) + N128Y + E189P + G475R |
| BASE-V29 | del (R180, G181) + F155W + E189P + G475R |
| BASE-V30 | del (R180, G181) + T134E + T182H + E189P + G475R |
| BASE-V31 | del (R180, G181) + N128Y + T134E + T182H + E189P + G475R |
| BASE-V32 | del (R180, G181) + N128Y + F155W + E189P + G475R |
| BASE-V33 | del (R180, G181) + T134E + F155W + T182H + E189P + G475R |
| BASE-V34 | del (R180, G181) + N128Y + T134E + F155W + T182H + E189P + G475R |
| BASE-V35 | del (R180, G181) + N128Y + T134H + F155W + T182D + E189P + G475R |
| BASE-V36 | del (R180, G181) + N128Y + T134E + F155W + T182G + E189P + G457R |
| ACE-QK | del (R180, G181) + S243Q + G475K |

The amino acid sequence of BASE-V28 is shown below as SEQ ID NO: 39:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGTYQIQAWTKFDFPGRGN

TYSSFKWRWYHFDGTDWDESRKLNRIYKFTGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS
```

-continued

```
SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK
```

The amino acid sequence of BASE-V29 is shown below as SEQ ID NO: 40:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSWKWRWYHFDGTDWDESRKLNRIYKFTGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK
```

The amino acid sequence of BASE-V30 is shown below as SE ID NO: 41:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGEYQIQAWTKFDFPGRGN

TYSSFKWRWYHFDGTDWDESRKLNRIYKFHGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK
```

The amino acid sequence of BASE-V30 is shown below as SE ID NO: 42:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGEYQIQAWTKFDFPGRGN

TYSSFKWRWYHFDGTDWDESRKLNRIYKFHGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY
```

-continued

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

The amino acid sequence of BASE-V32 is shown below as SEQ ID NO: 43:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGTYQIQAWTKFDFPGRGN

TYSSWKWRWYHFDGTDWDESRKLNRIYKFTGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

The amino acid sequence of BASE-V33 is shown below as SEQ ID NO: 44:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGEYQIQAWTKFDFPGRGN

TYSSWKWRWYHFDGTDWDESRKLNRIYKFHGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

The amino acid sequence of BASE-V34 is shown below as SEQ ID NO: 45:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGEYQIQAWTKFDFPGRGN

TYSSWKWRWYHFDGTDWDESRKLNRIYKFHGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

The amino acid sequence of BASE-V35 is shown below as SEQ ID NO: 46:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGHYQIQAWTKFDFPGRGN

TYSSWKWRWYHFDGTDWDESRKLNRIYKFDGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

The amino acid sequence of BASE-V36 is shown below as SEQ ID NO: 47:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRYQETSGEYQIQAWTKFDFPGRGN

TYSSWKWRWYHFDGTDWDESRKLNRIYKFGGKAWDWPVDTENGNYDYLMF

ADLDMDHPEVVTELKNWGTWYVNTTNIDGFRLDAVKHIKYSFFPDWLTYV

RNQTGKNLFAVGEFWSYDVNKLHNYITKTNGSMSLFDAPLHNNFYTASKS

SGYFDMRYLLNNTLMKDQPSLAVTLVDNHDTQPGQSLQSWVEPWFKPLAY

AFILTRQEGYPCVFYGDYYGIPKYNIPGLKSKIDPLLIARRDYAYGTQRD

YIDHQDIIGWTREGIDTKPNSGLAALITDGPGGSKWMYVGKKHAGKVFYD

LTGNRSDTVTINADGWGEFKVNRGSVSIWVAK

Figure 38:
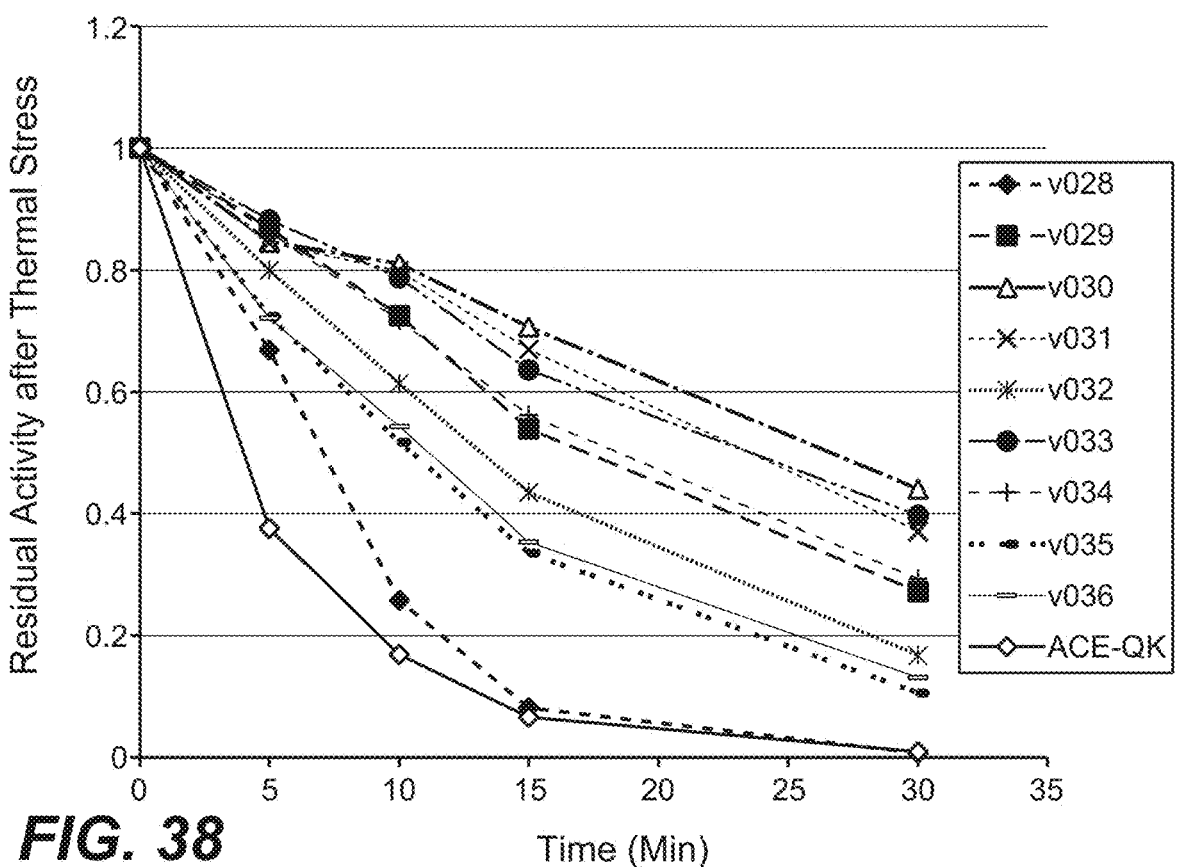
FIG. 38 is a graph showing the relative thermal stability of ARG BASE variants incubated for the indicated amounts of time at 95° C.

The thermal stability of BASE-V28, V29, V30, V31, V32, V33, V34, and V35, compared to ACE-QK (e.g., US20120045817 and WO2010/115028), is shown in FIG. 38. All the BASE variants were more stable than ACE-QK, although BASE-V28 was only marginally more stable.

Example 19

Interactions Between Residues in RG-Deletion Molecules

Figure 39:
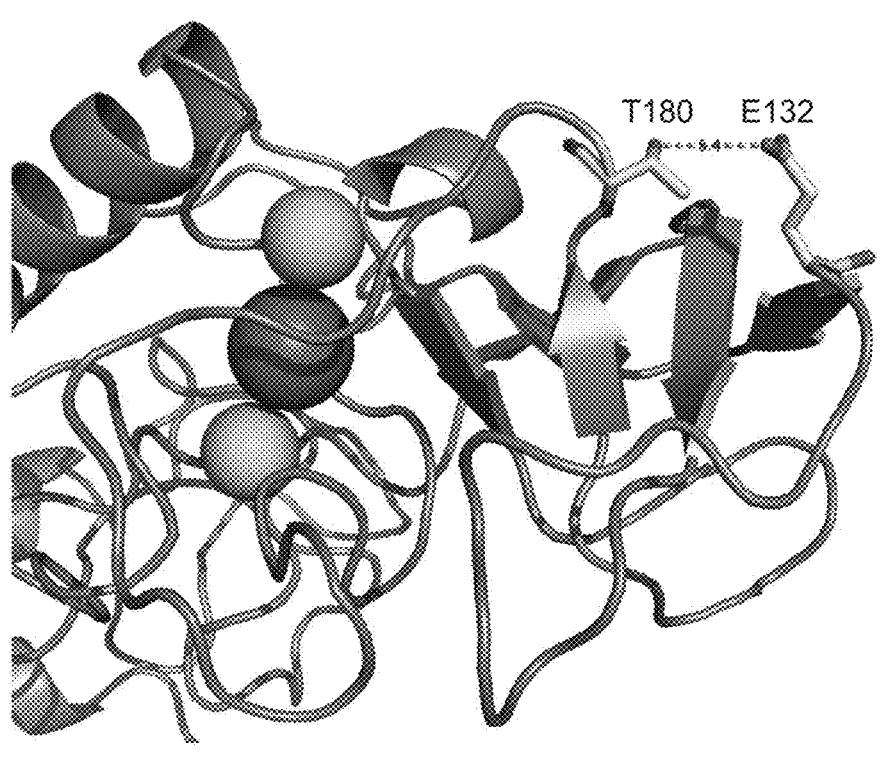
FIG. 39 shows a portion of the three-dimensional structure of CspAmy2-v1 highlighting the potential for interaction between a glutamate at position 132 and a threonine at position 180.
Figure 40:
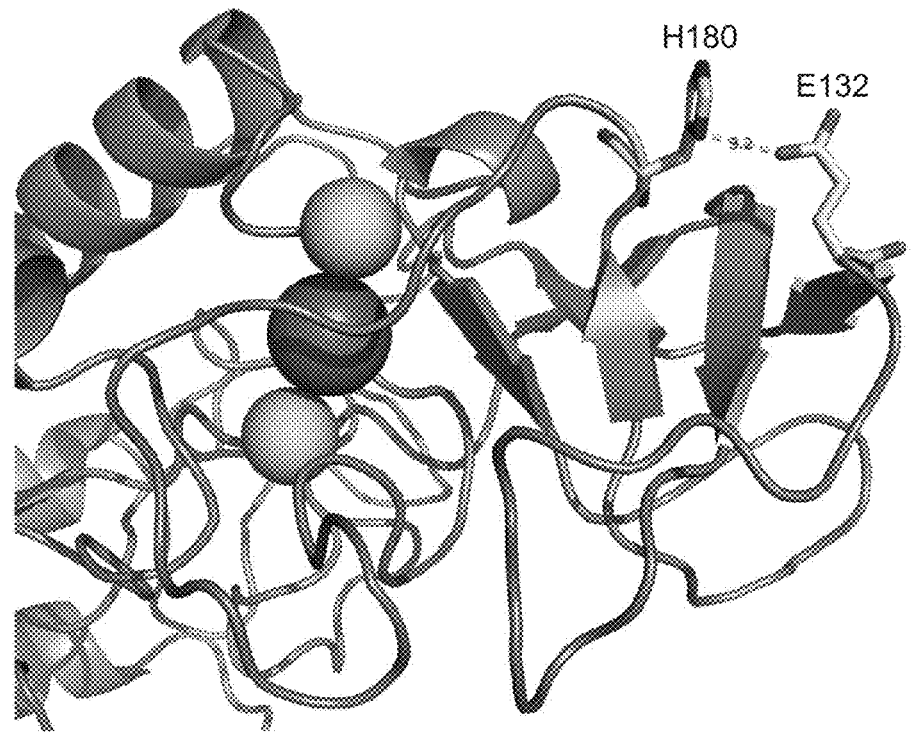
FIG. 40 shows a portion of the three-dimensional structure of CspAmy2-v1 highlighting the potential for interaction between a glutamate at position 132 and a histidine at position 180.

A structural interaction between residues 132 and 180 (refering to SEQ ID NO: 1 for numbering) explains the increased stability of some of the variants. Details of the crystal structure of CspAmy2-v1 are shown in FIGS. 39-42. As shown in FIG. 39, the naturally occurring glutamate side chain at position 132 is positioned towards the side chain of the naturally-occurring threonine at position 180. The distance of 5.4 Angstroms, however, is too great for the formation of any stabilizing interaction. As shown in FIG. 40, a T180H variant (e.g., CspAmy2-vC16C) has the histidine imidazole NH group in proximity to the E132 glutamate carboxylate. The distance of 3.2 Angstroms allows the formation of a stabilizing hydrogen bond. At pH of roughly 4.5 to 7.0, a favorable charge interaction (i.e., salt bridge) is also likely between these residues. Referring to, e.g., Examples 6 and 7 and FIGS. 8-10, the observations that CspAmy2-C16E is more stable than CspAmy2-C16C, CspAmy2-C16F is more stable than CspAmy2-C16D, CspAmy2-C16I is more stable than CspAmy2-C16G, and CspAmy2-C16J is more stable than CspAmy2-C16H, which pairs of variants differ only by the presence or absence of the mutation T180H, supports this hypothesis. Similarly, referring to, e.g., Examples 17 and FIG. 29, the observation that CspAmy2-v191 is more stable than CspAmy2-v179, which pair of variants differ only by the presence or absence of the mutation E132H, supports this hypothesis.

Figure 41:
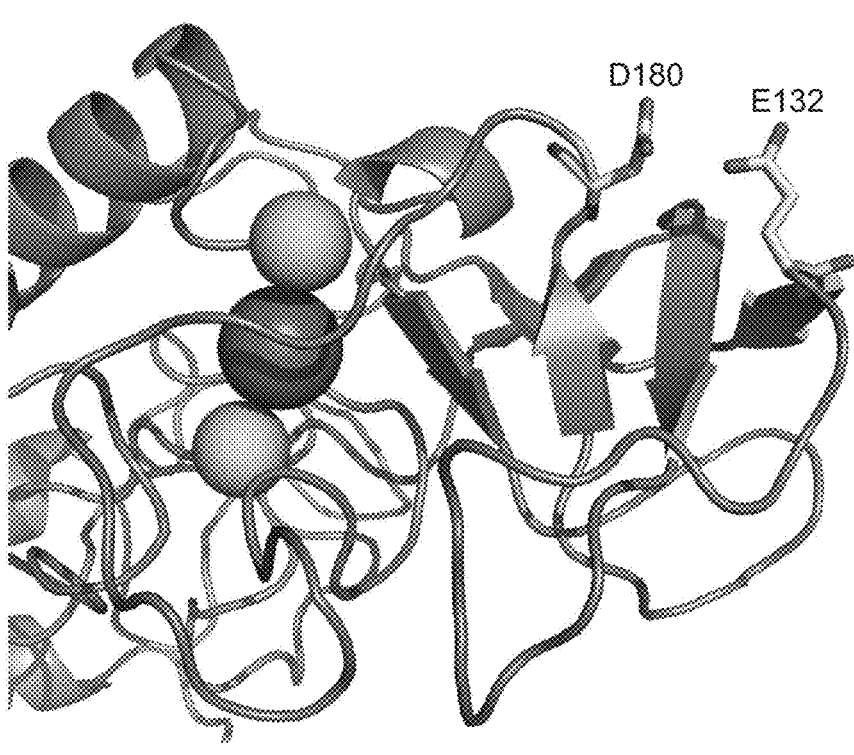
FIG. 41 shows a portion of the three-dimensional structure of CspAmy2-v1 highlighting the potential for interaction between a glutamate at position 132 and an aspartate at position 180.
Figure 42:
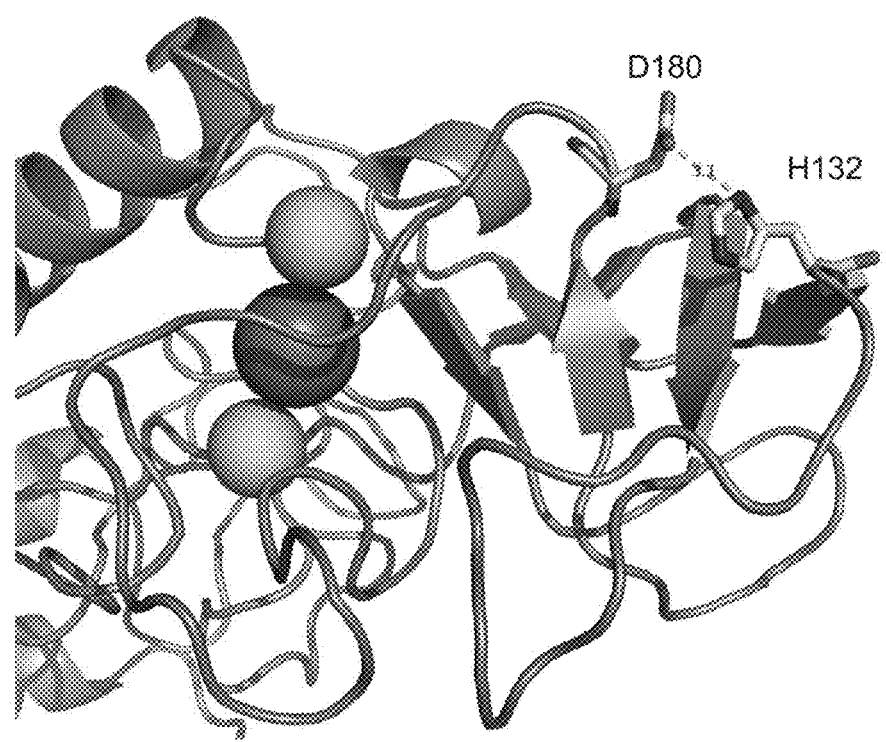
FIG. 42 shows a portion of the three-dimensional structure of CspAmy2-v1 highlighting the potential for interaction between a histidine at position 132 and an aspartate at position 180.

As shown in FIG. 41, an aspartic acid at position 180 may also be capable of hydrogen bonding with the glutamate at position 132, although hydrogen bonding may be overwhelmed by unfavorable like charge interactions. However, the presence of histidine at position 132, in combination with an aspartate at position 180, restores the possibility for a favorable interaction created by a T180D mutation (FIG. 42). The stabilizing effect of the E132H mutation in CspAmy2-v191 and CspAmy2-C25A, B, and F, which all have a T180D mutation, supports this hypothesis (e.g., Example 16 and FIG. 27).

In BASE, positon E132 corresponds to position T134 and position T180 corresponds to position T182. The observations that BASE-V31 is more stable than BASE-V28 and BASE-V33 is more stable than BASE-V29 further supports this hypothesis in the context of a different α-amylase. In both cases, the mutations T134E and T180H appear to work together to enable the formation of a stabilizing interaction, likely a salt bridge. Similarly, V34 is more stable than V36, because of the stabilizing interaction between the glutamate and histidine in V34, which does not occur between the glutamate and glycine in V36.

Although the position 132-180 interaction was demonstrated using an "RG" deletion, it can fully be expected to work in the context of an adjacent "DG" or TG" deletion. It will be appreciated that the conserved amino acid sequence motif $X_1G/S_1X_2G_2$ (SEQ ID NO: 48), as exemplified by RGTG (SEQ ID NO: 49) in CspAmy2 α-amylase (SEQ ID NO: 1), is adjacent to the calcium-binding loop in α-amylases. X1 is typically arginine. G/S$_1$ is most often glycine but is serine in the case of BASE. X2 varies but is commonly aspartate or threonine. G2 is highly conserved. Deleting the TG in CspAmy2 α-amylase, instead of RG, would mean that the remaining residues would be RG rather than TG. Although the arginine would be derived from position 178 as opposed to the threonine, which is derived from position 180, the three-dimensional structure of the resulting variant is indistinguishable from one having an RG deletion plus an R to G substitution, and stabilizing the resulting molecule is simply a matter of selecting a suitable residue at position 132 to form a stabilizing interaction with whatever residue is remaining at the equivalent position in the $X_1G/S_1X_2G_2$ motif, whether it originally corresponded to position 180 or position 178 in the patent molecule (using SEQ ID NO: 1 for numbering). For convenience, this residue may be referred to as the remaining non-G residue in the aforementioned motif.

Therefore, in general, if position 132 is negatively charged (i.e., D or E), then the remaining non-G residue should be positively charged (i.e., H, R, or K). If position 132 is positively charged (i.e., H, R, or K), then the remaining non-G residue should be negatively charged (i.e., D or E).

Example 19

Proteolytic Cleavage of PcuAmy1 and Variants

Figure 43:
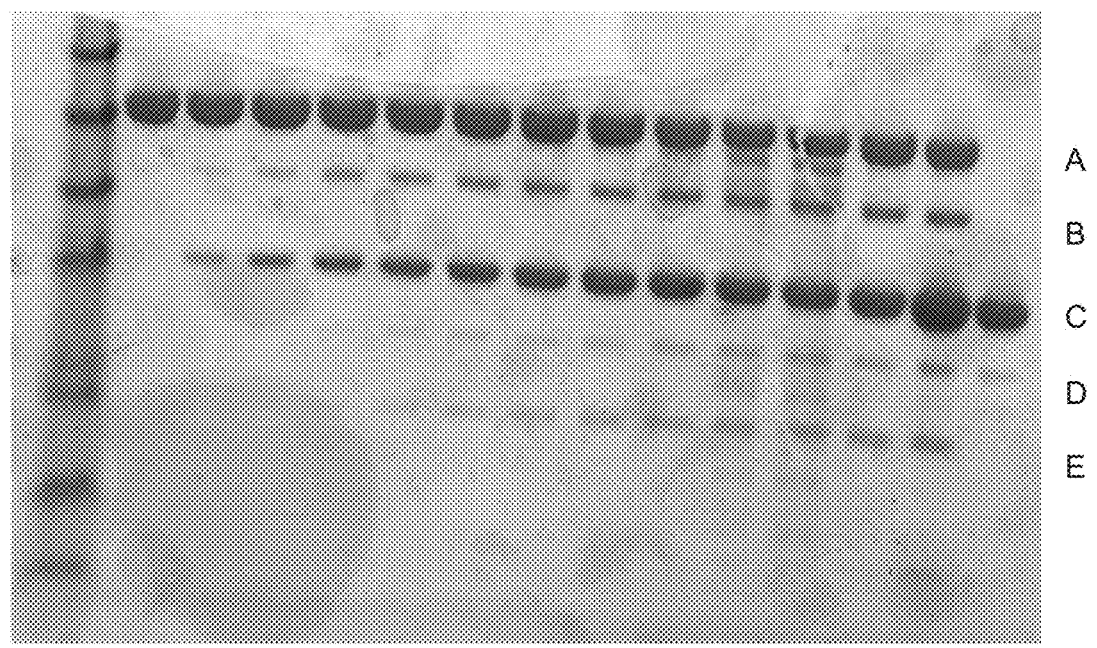
FIG. 43 is an image of an SDS/PAGE gel showing the cleavage of PcuAmy1-v1 in the presence of increasing amounts of GG36 protease. The letters on the right side of the gel indicate (A) intact full-length PcuAmy1-v1, (B) a first cleavage product of PcuAmy1-v1, (C) GG36 protease, (D) a contaminant in the GG36 protein preparation, and (E) a second cleavage product of PcuAmy1-v1.

Incubation of wild-type PcuAmy1 amylase, or the PcuAmy-v1 variant, with subtilisin proteases leads to cleavage of the proteins, as observed when the reaction products are subjected to SDS/PAGE electrophoresis. FIG. 43 is an image of an SDS/PAGE gel showing the cleavage of 20 g of PcuAmy1-v1 in the presence of increasing amounts of GG36 protease, (from 0 to 40 g as indicated above the gel). The letters on the right side of the gel indicate (A) intact full-length PcuAmy1-v1, (B) a first cleavage product of PcuAmy1-v1, (C) GG36 protease, (D) a contaminant in the GG36 protein preparation, and (E) a second cleavage product of PcuAmy1-v1. The main degradation products observed after incubation of PcuAmy-v1 amylase with a subtilisin protease have a molecular weight of about 38 and 16 kDa (B and E, respectively). The amount of proteolytic degradation is dependent on the concentration of protease used. This makes PcuAmy1 amylase suboptimal for inclusion in enzyme detergent formulations that contain commonly-used subtilisin proteases.

A sample of PcuAmy-v1 protein was incubated with GG36 protease (*Bacillus lentis* subtilisin) and the reaction products were analyzed by mass spectroscopy. The results were consistent with hydrolysis occurring between residues Q334 and L336 (not shown).

To determine whether protease-stable variants of PcuAmy could be engineered, PcuAmy1-v3 and further variants 3A to 3L were constructed and tested. PcuAmy1-v3 is a variant of PcuAmy1 with the mutations E186P, G472K and lacking R177 and G178 (using SEQ ID NO: 3 for numbering). The substitution E186P and the deletions at R177 and G178 increase the detergent stability of PcuAmy1. The substitution G472K improves cleaning performance. None of these mutations has any effect on protease sensitivity (data not shown). Therefore, including these mutations in variants made to explore the effect of other mutations on protease stability does not interfere with the results.

The mature form of PcuAmy1-v3 is shown, below, as (SEQ ID NO: 50):

ADNGTIMQYFEWYLPNDGAHWNRLNNDAQNLKNVGITAVWIPPAYKGGSS

ADVGYGVYDTYDLGEFNQKGTVRTKYGTKSELISAVNNLHAKGIAVYGDV

VLNHRMNADATELVDAVEVDPNNRNVETTSTYQIQAWTQYDFPGRGNTYS

SFKWRWYHFDGVDWDQSRGLNRIYKLDGKDWDWPVDSEYGNYDYLMGADL

DFNHPDVVNETKTWGKWFVNTVNLDGVRLDAVKHIKFDFMRDWVNNVRST

TGKNLFAVGEYWHYDVNKLNSYITKTNGTMSLFDVPLHFRFYDASNGGGG

YDMRNLLNNTLMSSNPMKAVTFVENHDTQPTQALQSTVQSWFKPLAYATI

LTREQGYPCVFYGDYYGTSDGKISSYKPIMDKLLNARKVYAYGTQRDYFD

HPDIVGWTREGDAAHAGSGLATLITDGPGGSKWMYVGTSKAGQVWTDKTG

NRSGTVTIDANGWGNFWVNKGSVSVWAK

To identify the reason for PcuAmy1 protease sensitivity, the amino acid sequence of PcuAmy1 was compared to that of other CAZy Family GH-13 amylases which show protease-resistance, such as PURASTAR® ST (*B. licheniformis* amylase or AmyL), SPEZYME® XTRA (*Geobacillus stearothermophilus* amylase or AmyS), ACE-QK (WO2010/115021), and STAINZYME® (Novozymes). Based on observed differences in sequence, PcuAmy1 variants PcuAmy1-v3A to PcuAmy1-v3L (i.e., 3A-3L) were designed and tested for protease resistance. The mutations present in each variant are listed in Table 11. They were introduced into PcuAmy1-v3 (SEQ ID NO: 49), using standard methods, many of which are described above.

113

TABLE 11

List of mutations introduced in PcuAmy1-v3 resulting in variants 3A to 3L

| Position | wt | 3A | 3B | 3C | 3D | 3E | 3F | 3G | 3H | 3I | 3J | 3K | 3L |
|---|---|---|---|---|---|---|---|---|---|---|---|---|---|
| 319 | M | | | | | | | | | | T | | |
| 333 | T | G | G | G | G | | | | | | | G | G |
| 335 | A | | S | S | S | | S | | | | | S | S |
| 337 | Q | | E | E | E | | | | E | | | | E |
| 339 | T | | | | | | | | | | | W | |
| 341 | Q | | | | | | | | | | | E | |
| 342 | S | | | P | P | | | | | P | | P | T |
| 351 | T | | | F | | | F | | | | W | | |

Figure 44:
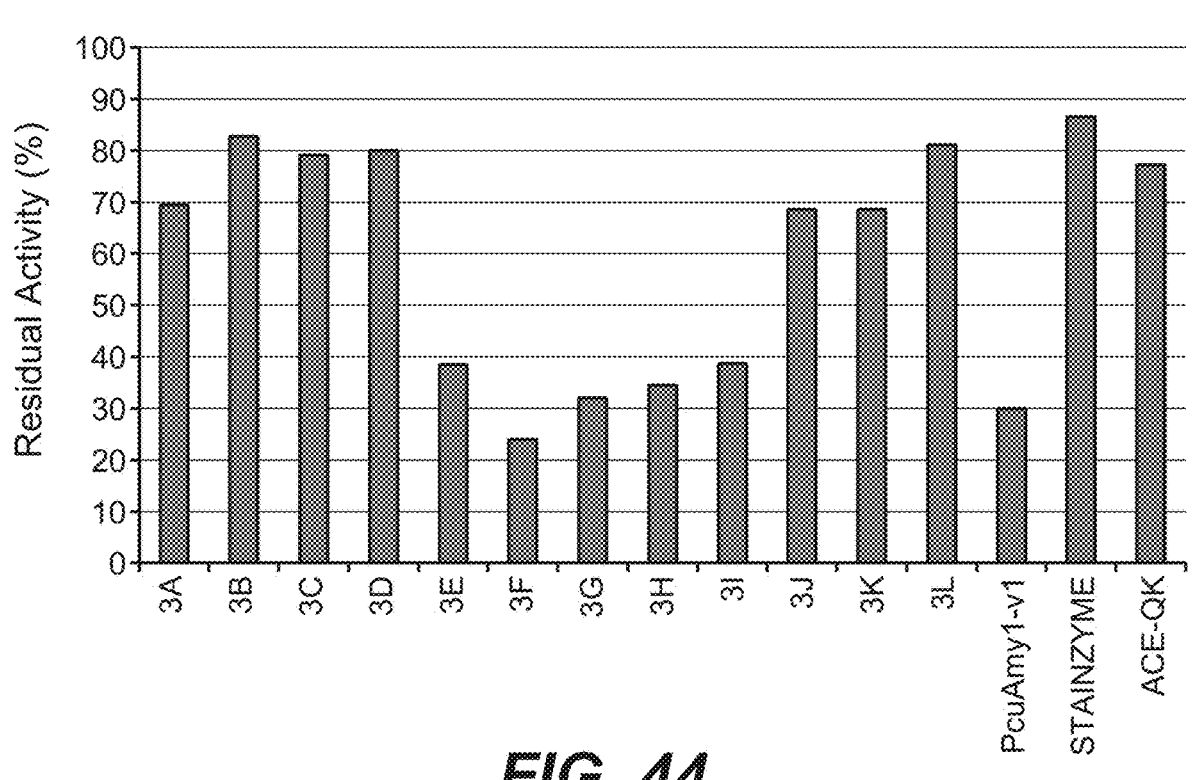
FIG. 44 is a graph showing the residual α-amylase activity of PcuAmy1 and several engineered variants following incubation with GG36 protease.
Figure 45:
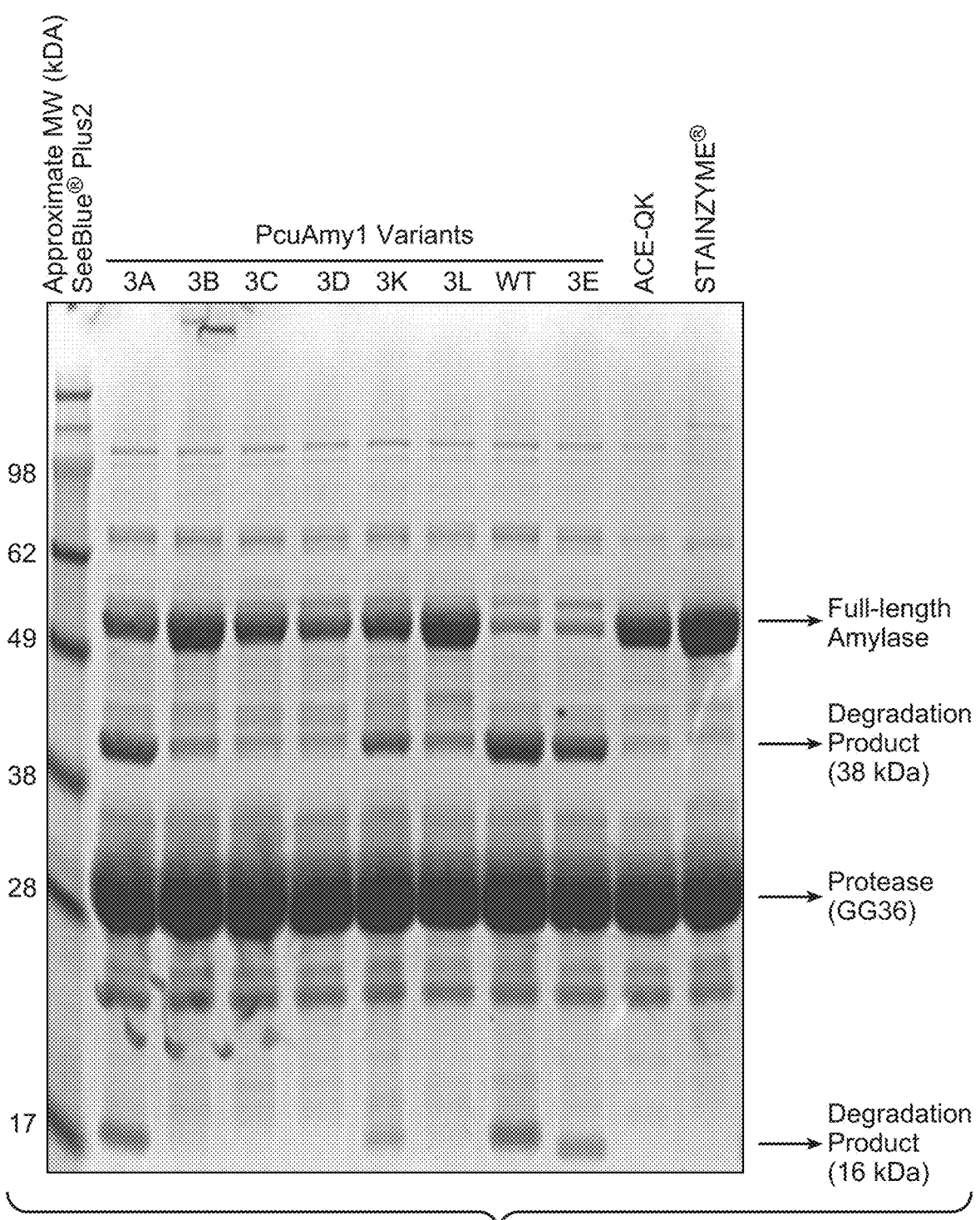
FIG. 45 is an image of an SDS/PAGE gel showing the proteolytic cleavage of PcuAmy1 and several engineered variants following incubation with GG36 protease.

The 12 PcuAmy1 variants were expressed in *B. subtilis* as described, above. 40 µL filtered supernatant from each PcuAmy1 variant culture broth was incubated with 100 µg GG36 protease for 6 hours at room temperature, and subsequently analyzed for remaining amylase activity using the Megazyme Ceralpha substrate assay (Megazyme International Ireland, Co. Wicklow, Ireland). Residual activity after protease incubation was compared to the amylase activity of each sample after incubation with buffer alone. The results are shown in FIG. 44. A subset of the samples was also analyzed by SDS-PAGE (FIG. 45), with the protein standard, SEEBLUE® Plus2 (Invitrogen). The commercially available amylases were included for comparison.

PcuAmy1 variants 3A, 3B, 3C, 3D, and 3L maintained >70% of their enzymatic activity after incubation with GG36 protease. PcuAmy1 variants 3J and 3K maintained >65% of their enzymatic activity after incubation with GG36 protease. PcuAmy1 variants 3E, 3F, 3G, 3H, and 3I did not show an appreciable increase of stability compared to the wild-type enzyme. Samples of the 3B, 3C, 3D and 3L incubations were analyzed by SDS/PAGE and showed significant reduction in degradation products when incubated with GG36 protease, confirming that the increase in residual amylase activity was due to decreased proteolytic cleavage.

These results of the small-scale experiment indicate that the introduction of a mutation at position T333 significantly reduces the proteolytic cleavage of PcuAmy1, and that additional mutations at A335, Q337, and S342 further reduce proteolytic cleavage. The T351W mutation but not the T351F mutation, also appears to reduce the proteolytic cleavage of PcuAmy1.

To better characterize the relative contributions of these mutations to protease resistance, the following additional variants were made:

PcuAmy1-v10: del (R177, G178)+E186P+T333G+Q337E+G472K

PcuAmy1-v11—: del (R177, G178)+E186P+T333G+A335S+G472K

PcuAmy1-v12: del (R177, G178)+E186P+A335S+Q337E+G472K

PcuAmy1-v13: del (R177, G178)+E186P+T333G+A335S+Q337E+T351W+G472K

Variants PcuAmy1-v10, PcuAmy1-v11, and PcuAmy1-v12 include pair-wise combination of mutations at positions T333, A335, and Q337. PcuAmy1-v3-v13 includes mutations at all the aforementioned positions and includes the additional mutation T351W. These variants were compared in a large scale detergent stability assay to the following previously-described variants:

PcuAmy1-v3B: del (R177, G178)+E186P+T333G+A335S+Q337E+G472K

PcuAmy1-v3L: del (R177, G178)+E186P+T333G+A335S+Q337E+S342T+G472K

114

The commercial detergents Total Color (MIFA Ag Frenkendorf, Switzerland) and Omo (Unilever, London, UK) were heat inactivated at 90° C. for 4 hours to eliminate existing enzyme activities. Enzyme activity in the heat inactivated detergents was measured using the Suc-AAPF-pNA and Ceralpha assays for measuring protease and amylase activity, respectively. To prepare the stability samples, 2% w/w protease (PURAFECT® Prime 4000L, Danisco US Inc.) and 0.5% w/w amylase were added to each detergent sample and mixed. Samples were stored in a C02 incubator (Sanyo) at 37° C. for 14 days. Aliquots were taken from each reaction sample at various time points, diluted in 50 mM MOPS, pH 7.15 buffer with 1% BSA added, and alpha-amylase activity was measured using the Ceralpha substrate (Megazyme, Inc). The activity for each sample was determined using a Arena 20XT Photometric Analyzer (Thermo Scientific) using a calibrated standard. The remaining activity at each time point was reported as a percent (%) of the total activity determined at time zero.

Figure 46:
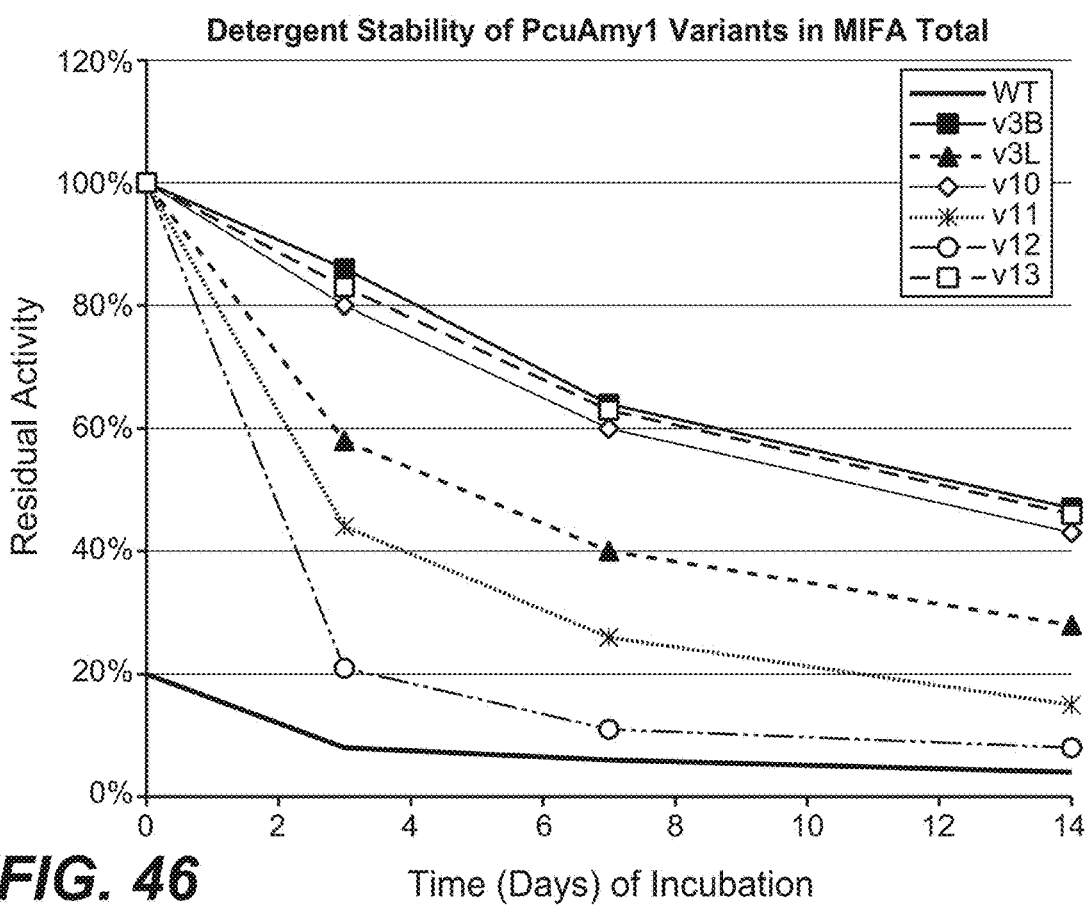
FIG. 46 is a graph showing the stability of PcuAmy1-v1 and several engineered variants following incubation with GG36 protease in MIFA Total detergent for up to 14 days at 37° C.
Figure 47:
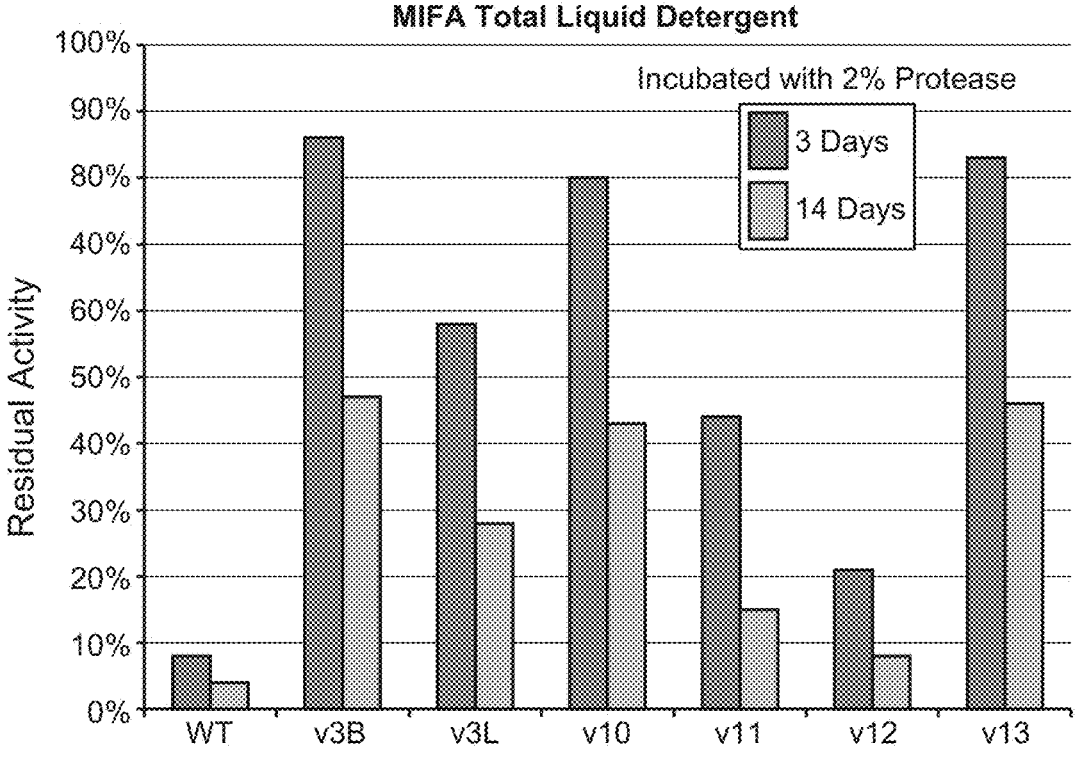
FIG. 47 is a graph showing the stability of PcuAmy1-v1 and several engineered variants following incubation with GG36 protease in MIFA Total detergent for 3 or 14 days at 37° C.
Figure 48:
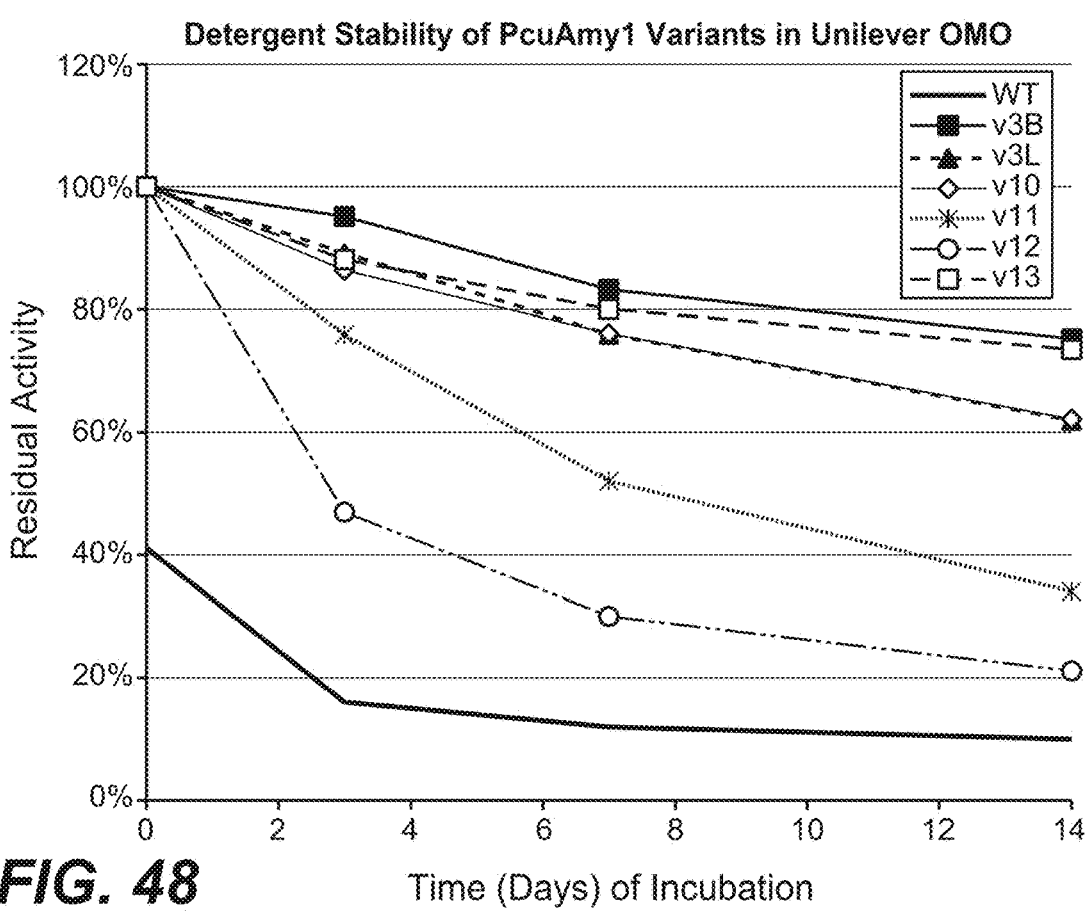
FIG. 48 is a graph showing the stability of PcuAmy1-v1 and several engineered variants following incubation with GG36 protease in Unilever Omo detergent for up to 14 days at 37° C.
Figure 49:
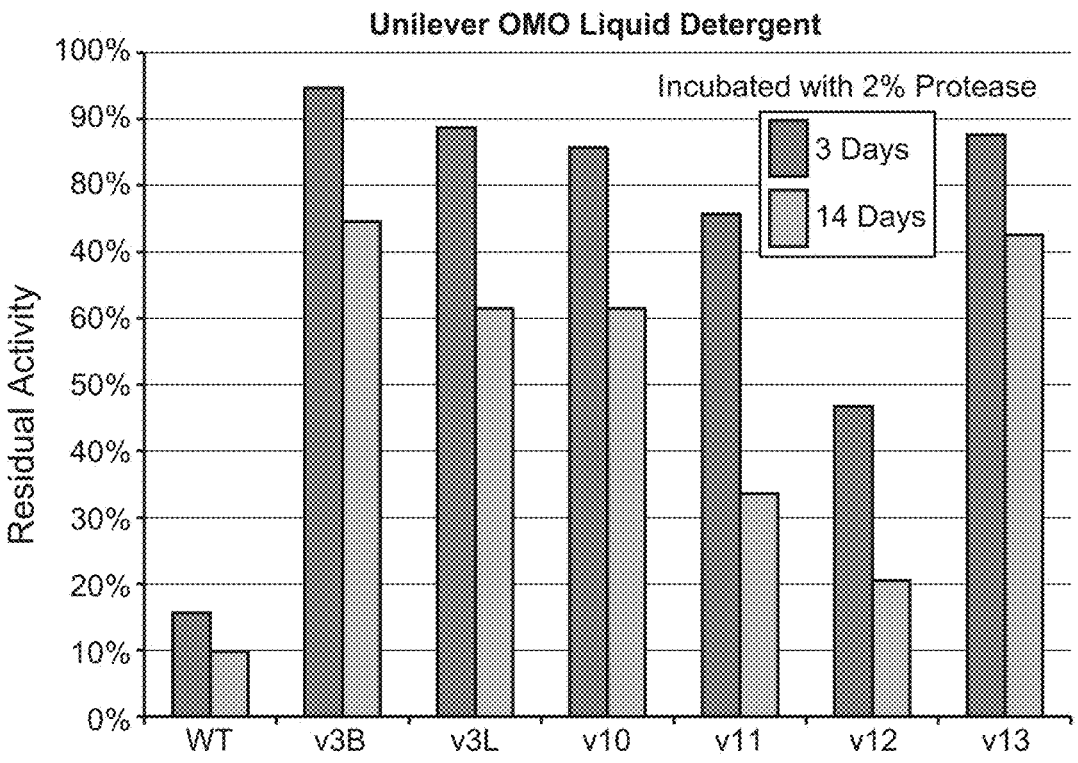
FIG. 49 is a graph showing the stability of PcuAmy1-v1 and several engineered variants following incubation with GG36 protease in Unilever Omo detergent for 3 or 14 days at 37° C.

The results of the detergent stability assays performed in MIFA Total (MIFA Ag Frenkendorf, Switzerland) and Unilever OMO (Unilever, London, UK) are shown in FIGS. 46-50. FIGS. 46 and 48 show the residual activity of PcuAmy1 variants over time in MIFA Total and Unilever Omo, respectively, supplemented with FNA protease. FIGS. 47 and 49 summarize the data for the 3 and 14 day time points. PcuAmy1 variants that include the T333 mutation, i.e., 3B, 3L, v10, v13, and to a lesser degree, v11 were the most stable. Variants that did not include the T333 mutation, i.e., V1 and v12, were the least stable. As evidenced by v10 and v11, the presence of a mutation at Q337E further improves stability.

The cleaning performance of purified PcuAmy1-v3B and PcuAmy1-v3L was analyzed in a microswatch cleaning assay. CFT CS-28 rice starch on cotton swatches (Center for Test materials, BV, Vlaardingen, Netherlands) containing an indicator dye bound to the starch were punched to form discs measuring 5.5 mm in diameter. Two discs were placed in each well of three flat-bottom non-binding 96-well assay plates.

Both enzymes and two commercial amylase products: PURASTAR® ST (alpha-amylase from *Bacillus licheniformis*; DuPont Industrial Biosciences, Palo Alto, California, USA), and STAINZYME® (Novozymes, Copenhagen, Denmark) were diluted to 0.5 mg/mL in dilution buffer (50 mM MOPS, pH 7.2, 0.005% Tween), and then further diluted to 2 ppm in a microtiter plate. 200 µL of these samples were transferred into the first row of each of three swatch plates. 100 µL of HEPES buffer (25 mM HEPES, pH 8.0 with 2 mM $CaCl_2$ and 0.005% Tween-80) was then added to each well of the next five rows of the swatch plates, and serial dilutions were made to result in final enzyme concentrations of 2, 1, 0.5, 0.25, and 0.125 ppm as well as a row of blank (buffer only) wells with 200 µL in every well. Plates were incubated at 25° C. with agitation at 1150 rpm for 15 minutes. The wash liquor was transferred to fresh microtiter plates and enzyme performance was judged by the amount of color released into the wash liquor. Color release was quantified spectrophotometrically at 488 nm, and triplicate reads were blank-subtracted and averaged.

Figure 50:
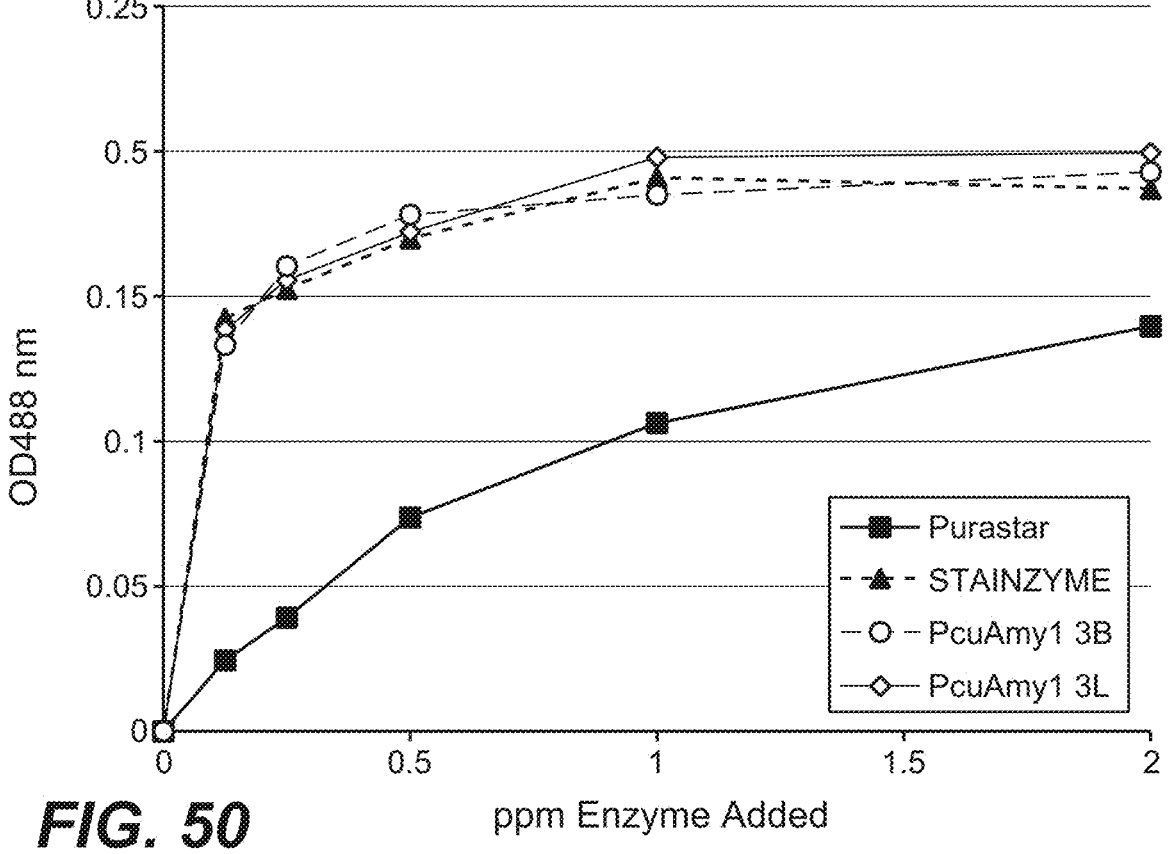
FIG. 50 is a graph showing the dose-dependent cleaning performance of PcuAmy1-3B and PcuAmy1-3L in buffer at pH 8.0 compared to two commercial benchmarks.

The results are shown in FIG. 50. Both PcuAmy1-v3B and PcuAmy1-v3L demonstrated excellent cleaning performance.

Commercial detergent Persil Universal Gel Gold (Henkel, Dusseldorf, Germany) was heat inactivated at 90° C. for 4 hours to eliminate existing enzyme activities. Following inactivation, enzyme activity in the heat inactivated detergents was measured using the Suc-AAPF-pNA substrate-based and Ceralpha assay (Megazyme, Wicklow, Ireland) to ensure that any protease and amylase activities, respectively, had been abolished. A 10% solution of detergent was then made in water.

100 µL of each of the enzyme stocks (at 0.5 mg/mL) were added to 400 µL of the 10% detergent solutions. The enzymes tested were PURASTAR®, STAINZYME®, PcuAmy1-v3B and PcuAmy-v3L. 50 µL of enzyme stock solution was added to PCR tubes and incubated at either 60, 70, 80, or 90° C. for 15 minutes. Prior to incubation, 10 µL was removed and incubated at room temperature throughout the duration of the experiment to serve as the "unstressed" samples. Following incubation, an additional 1:10 dilution of each sample was made in dilution buffer. Samples were then transferred to microtiter plates in triplicate, and alpha-amylase activity was measured on all unstressed and stressed samples using the Ceralpha assay. Residual activity was calculated by dividing the activity of each amylase after the thermal stress by the activity of the unstressed amylase.

Figure 51:
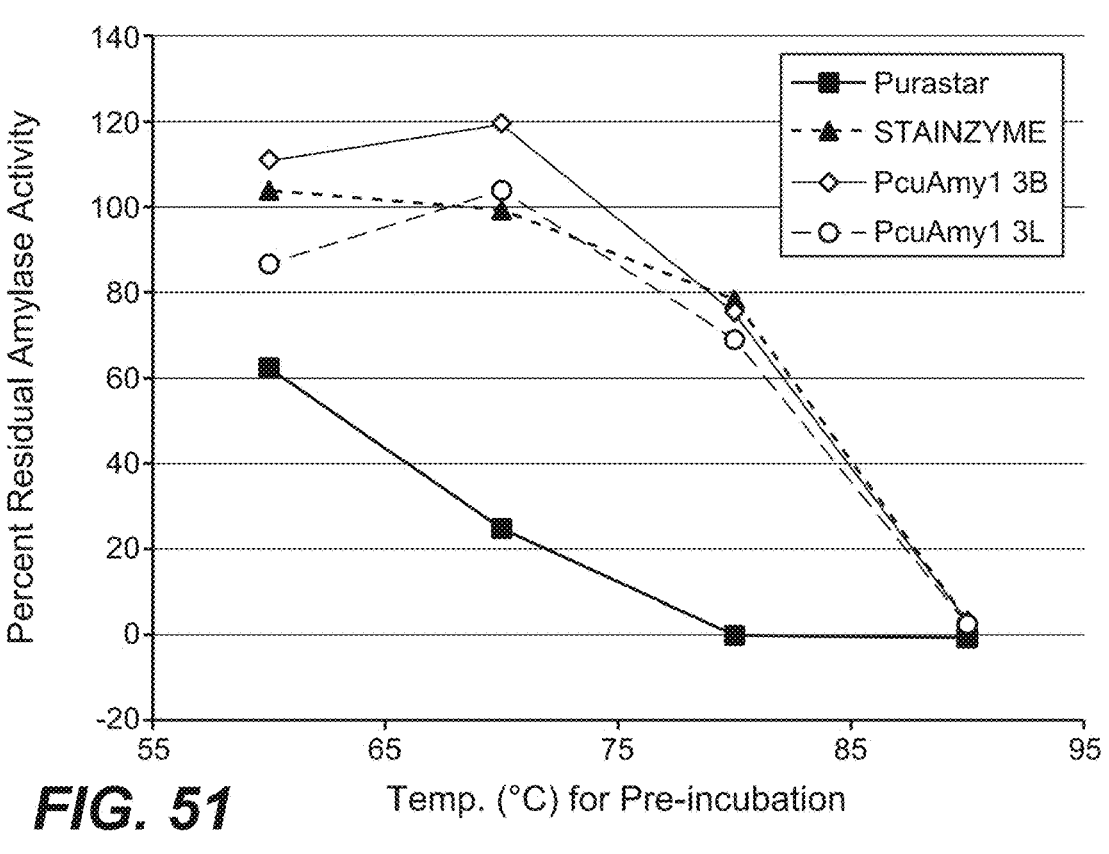
FIG. 51 is a graph showing the stability of PcuAmy1-3B and PcuAmy1-3L in Persil Universal Gel Gold detergent compared to two commercial benchmarks.
Figure 52:
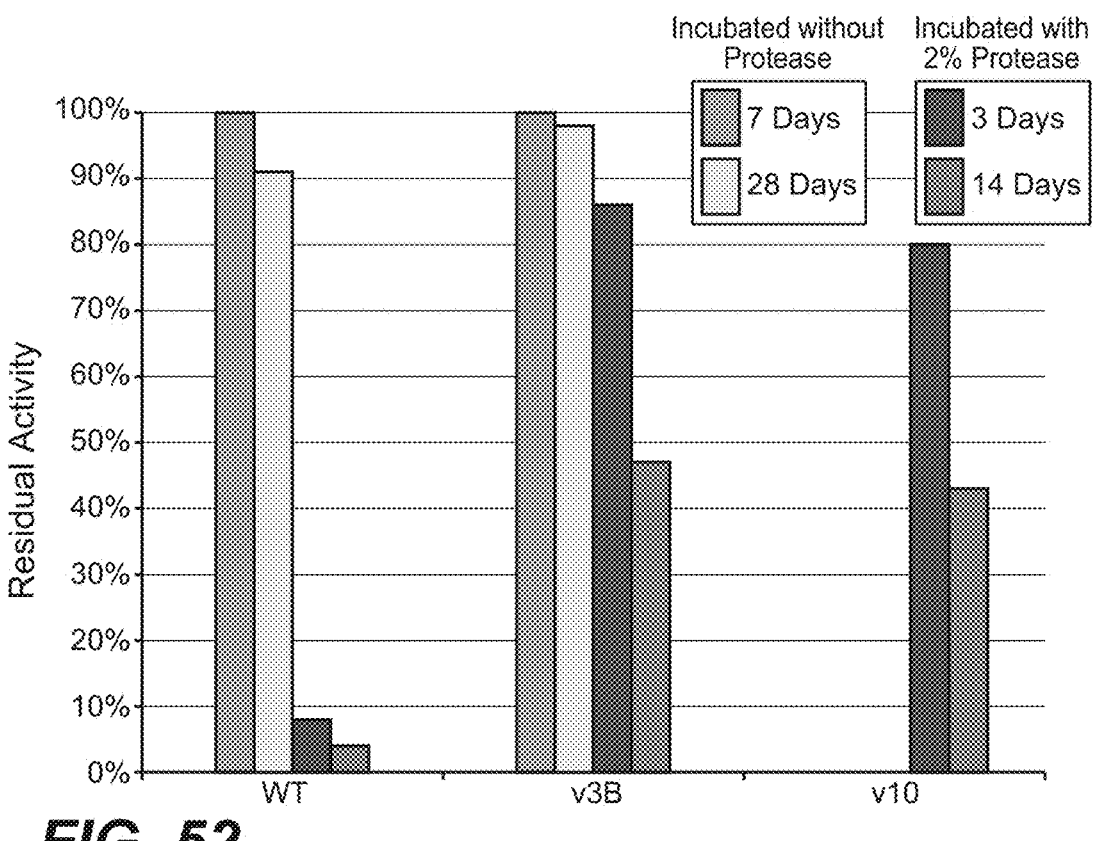
FIG. 52 is a graph showing the stability of PcuAmy1-v1 and several engineered variants following incubation with GG36 protease in MIFA Total detergent for 3 or 14 days at 37° C.

The results are shown in FIGS. 51 and 52. PcuAmy1-v3B and PcuAmy-v3L demonstrated similar thermostability compared to STAINZYME®, and significantly better stability than PURASTAR®.

Although the foregoing compositions and methods have been described in some detail by way of illustration and examples for purposes of clarity of understanding, it will be apparent to those skilled in the art that certain changes and modifications may be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

What is claimed is:

1. A recombinant variant of a parent α-amylase comprising:
a mutation at an amino acid residue corresponding to E187 or S241; and
at least one mutation at an amino acid residue corresponding to an amino acid residue selected from the group consisting of N126, Y150, F153, L171, T180, and, I203;
wherein the variant α-amylase has at least 95% amino acid sequence identity relative to SEQ ID NO: 1, which is used for numbering; and
wherein the variant has increased thermostability, detergent stability, starch liquefaction activity, and/or cleaning performance compared to the parent α-amylase or a reference α-amylase differing from the variant α-amylase only by the absence of the mutations.

2. The variant α-amylase of claim 1, further comprising deletions of amino acid residues corresponding to R178 and G179, or T180 and G181.

3. The variant α-amylase of claim 1, further comprising a mutation at an amino acid residue corresponding to G476 and/or G477, using SEQ ID NO: 1 for numbering.

4. The variant α-amylase of claim 1, comprising a combination of mutations corresponding to mutations selected from the group consisting of:

$E187P + I203Y + G476K$, $E187P + I203Y + G476K + R458N + T459S + D460T$, $T180D + E187P + I203Y + G476K$, $N126Y + T180D + E187P + I203Y + G476K$, $N126Y + T180D + E187P + I203Y + Y303D + G476T + G477E$, $N126Y + T180D + E187P + I203Y + Y303D + N475E + G477Q$, $N126Y + T180D + E187P + I203Y + Y303R + N475E + G476T + G477R$, $T038N + N088H + N126Y + T129I + N134M + F153W + L171R + T180D + E187P + I203Y + G476K + G477E$, $N126Y + E132H + T180D + E187P + I203Y + Y303D + G476T + G477E$, $N126Y + E187P + G476K$, $N126Y + F153W + E187P + G476K$, $N126Y + F153W + E187P + G4726 + G477R$, $N126Y + E187P + I203Y$, $N126Y + I203Y + S241Q$, $N126Y + T180H + E187P + I203Y$, $N126Y + T180H + I203Y + S241Q$, $N126Y + F153W + T180H + E187P + I203Y$, $N126Y + F153W + T180H + I203Y + S241Q$, $N126Y + Y150H + F153W + L171N + E187P + I203Y$, $N126Y + Y150H + F153W + L171N + I203Y + S241Q$, $N126Y + Y150H + F153W + L171N + T180H + E187P + I203Y$, $N126Y + Y150H + F153W + L171N + T180H + I203Y + S241Q$, and $N126Y + F153W + T180D + I203Y + S241Q$;

wherein the variant as increase thermostability, detergent stability, stability starch liquefaction activity, or cleaning performance compared to the parent.

5. The variant amylase of claim 1, comprising the combinations of mutations corresponding to N126Y+F153W+T180D+I203Y+S241Q and one or more mutations corresponding to mutations selected from the group consisting of E132H, Q167E, A277F, and T400K.

6. The variant amylase of claim 5, comprising the combinations of mutations corresponding to mutations selected from the group consisting of:

$N126Y + E132H + F153W + T180D + I203Y + S241Q + A277F$, $N126Y + E132H + F153W + Q167E + T180D + I203Y + S241Q + A277F$, and $N126Y + E132H + F153W + Q167E + T180D + I203Y + S241Q + A277F + T400K$.

7. The variant amylase of claim 1, wherein the parental α-amylase is from a *Cytophaga* species, a *Paenibacillus* species, or not from a *Bacillus* species.

8. The variant amylase of claim 1, wherein the variant α-amylase has at least 97% amino acid sequence identity to the amino acid sequence of SEQ ID NO: 1, SEQ ID NO: 3, or SEQ ID NO: 5.

9. A composition comprising the variant α-amylase of claim 1.

10. The composition of claim 9, further comprising one or more additional enzymes selected from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, ß-glucanase, arabinosidase, hyaluronidase, chondroitinase, laccase, metalloproteinase, amadoriase, glucoamylase, arabinofuranosidase, phytase, isomerase, transferase, and an amylase other than the amylase of claim 1.

11. The composition of claim 9, wherein the composition is for liquifying starch.

12. A method for saccharifying a composition comprising starch to produce a composition comprising glucose, wherein the method comprises:
   (i) contacting the solution comprising starch with effective amount of the variant amylase of claim 1; and
   (ii) saccharifying the solution comprising starch to produce the composition comprising glucose; wherein the variant amylase catalyzes the saccharification of the starch solution to glucose or other enriched carbohydrate syrups.

13. The method of claim 12, wherein the composition comprising starch comprises liquefied starch, gelatinized starch, granular starch, or starch heat-treated below its gelatinization temperature.

14. The method of claim 12, wherein the fermentation is a simultaneous saccharification and fermentation (SSF) reaction.

15. The method of claim 12, wherein the method further comprises contacting a mash and/or a wort with an amylase.

16. The method of claim 12, further comprising adding glucoamylase, hexokinase, xylanase, glucose isomerase, xylose isomerase, phosphatase, phytase, pullulanase, β-amylase, α-amylase that is not the variant α-amylase, protease, cellulase, hemicellulase, lipase, cutinase, isoamylase, redox enzyme, esterase, transferase, pectinase, alpha-glucosidase, beta-glucosidase, or a combination thereof, to the starch solution.

17. The method of claim 12, wherein the amylase is expressed and secreted by a host cell.

18. The method of claim 17, wherein the composition comprising starch is contacted with the host cell.

19. The method of claim 17, wherein the host cell further expresses and secretes one or more enzymes selected from the group consisting of glucoamylase, hexokinase, xylanase, glucose isomerase, xylose isomerase, phosphatase, phytase, pullulanase, β-amylase, α-amylase that is not the variant α-amylase, protease, cellulase, hemicellulase, lipase, cutinase, isoamylase, redox enzyme, esterase, transferase, pectinase, alpha-glucosidase, and beta-glucosidase.

20. The method of claim 17, wherein the host cell further expresses and secretes a glucoamylase.

21. The method of claim 17, wherein the host cell is capable of fermenting the composition.

\* \* \* \* \*